US012661471B2

(12) United States Patent (10) Patent No.: US 12,661,471 B2
Tatkov et al. (45) Date of Patent: Jun. 23, 2026

(54) RESPIRATORY INTERFACE

(71) Applicant: Fisher & Paykel Healthcare Limited, Auckland (NZ)

(72) Inventors: Stanislav Tatkov, Auckland (NZ); Andrew Paul Maxwell Salmon, Auckland (NZ); Maximilian Ichabod Pinkham, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 800 days.

(21) Appl. No.: 17/309,578

(22) PCT Filed: Dec. 10, 2019

(86) PCT No.: PCT/IB2019/060589
§ 371 (c)(1),
(2) Date: Jun. 7, 2021

(87) PCT Pub. No.: WO2020/121177
PCT Pub. Date: Jun. 18, 2020

(65) Prior Publication Data
US 2022/0023570 A1 Jan. 27, 2022

Related U.S. Application Data

(60) Provisional application No. 62/910,702, filed on Oct. 4, 2019, provisional application No. 62/826,529, filed (Continued)

(51) Int. Cl.
*A61M 16/06* (2006.01)
(52) U.S. Cl.
CPC .... *A61M 16/0666* (2013.01); *A61M 16/0616* (2014.02); *A61M 16/0683* (2013.01)

(58) Field of Classification Search
CPC ................ A61M 15/08; A61M 15/085; A61M 16/0066; A61M 16/06; A61M 16/0605;
(Continued)

(56) References Cited

U.S. PATENT DOCUMENTS 1,125,542 A 1/1915 Humphries
4,273,124 A * 6/1981 Zimmerman ..... A61M 16/0666
128/207.18
(Continued)

FOREIGN PATENT DOCUMENTS

AU 2007205140 8/2012
AU 2009317882 5/2015
(Continued)

OTHER PUBLICATIONS

International Search Report and Written Opinion of PCT/IB2019/060589, Dated Mar. 3, 2020 in 17 pages.

*Primary Examiner* — Joseph D. Boecker
*Assistant Examiner* — Brian T Khong
(74) *Attorney, Agent, or Firm* — VIA LLP

(57) ABSTRACT

A respiratory interface (100) for delivering gases to a single nare of a patient; comprises of a gases delivery assembly having a single sealing nasal prong (200) configured to seal with one of the nares of a patient, a conduit (300), a conduit connector (400) and a support (500) with headgear strap clips (503). The prong slides relative to the support to be interchangeable such that it can engage and seal with either nari. A cuff (250, 1250) is connected to slider members (501, 1501). In another embodiment (FIGS. 33-49), the headgear strap (2600) is coupled directly to the prong; the strap (2600) is received between includes cutouts (2241) of the prong (2200) and a cuff (2250).

18 Claims, 69 Drawing Sheets

Related U.S. Application Data on Mar. 29, 2019, provisional application No. 62/777, 721, filed on Dec. 10, 2018.

(58) Field of Classification Search
CPC .......... A61M 16/0616; A61M 16/0666; A61M 16/0672; A61M 16/0683; A61M 16/0688; A61M 16/08; A61M 16/0816; A61M 16/0875; A61M 16/16; A61M 2205/0216; A61M 2206/10; A61M 2210/0618
See application file for complete search history.

(56) References Cited

U.S. PATENT DOCUMENTS

| | | | | |
|---|---|---|---|---|
| 4,660,555 | A | * | 4/1987 | Payton .............. A61M 16/0497 |
| | | | | 128/207.18 |
| 4,742,824 | A | * | 5/1988 | Payton .............. A61M 16/0666 |
| | | | | 128/207.18 |
| 4,773,448 | A | | 9/1988 | Francis |
| 4,782,832 | A | | 11/1988 | Trimble et al. |
| 5,724,965 | A | | 3/1998 | Handke et al. |
| 6,431,172 | B1 | | 8/2002 | Bordewick |
| 7,318,463 | B2 | | 1/2008 | Tanaka et al. |
| 7,556,043 | B2 | | 7/2009 | Ho et al. |
| 8,636,007 | B2 | | 1/2014 | Rummery et al. |
| 9,539,404 | B2 | | 1/2017 | McAuley et al. |
| 9,550,038 | B2 | | 1/2017 | McAuley et al. |
| 9,884,160 | B2 | | 2/2018 | McAuley et al. |
| 9,962,512 | B2 | | 5/2018 | Cipollone et al. |
| 2002/0014241 | A1 | | 2/2002 | Gradon et al. |
| 2005/0011524 | A1 | * | 1/2005 | Thomlinson ...... A61M 16/0825 |
| | | | | 128/207.18 |
| 2005/0121037 | A1 | | 6/2005 | Wood |
| 2007/0175480 | A1 | | 8/2007 | Gradon et al. |
| 2008/0223375 | A1 | * | 9/2008 | Cortez .............. A61M 16/0688 |
| | | | | 128/207.18 |
| 2012/0204870 | A1 | * | 8/2012 | McAuley ......... A61M 16/0666 |
| | | | | 128/207.18 |
| 2012/0222678 | A1 | * | 9/2012 | Colbaugh ........ A61M 16/0683 |
| | | | | 128/205.25 |
| 2013/0319421 | A1 | | 12/2013 | Hitchcock et al. |
| 2014/0261434 | A1 | | 9/2014 | Ng et al. |
| 2015/0007817 | A1 | * | 1/2015 | Longest ........... A61M 16/1095 |
| | | | | 128/203.14 |
| 2016/0030696 | A1 | * | 2/2016 | Klenner ........... A61M 16/0003 |
| | | | | 128/207.18 |
| 2016/0158476 | A1 | | 6/2016 | Tatkov |
| 2016/0346495 | A1 | * | 12/2016 | Payton ............. A61M 16/0683 |
| 2018/0001045 | A1 | | 1/2018 | Cortez, Jr. et al. |
| 2018/0064899 | A1 | | 3/2018 | Ewers et al. |
| 2018/0221613 | A1 | | 8/2018 | McAuley et al. |

FOREIGN PATENT DOCUMENTS

| | | | | |
|---|---|---|---|---|
| EP | 3150246 | | 10/2018 | |
| EP | 3030299 | | 7/2020 | |
| JP | 2007-506480 | | 3/2007 | |
| JP | 2016509953 | | 4/2016 | |
| WO | WO 2004/030736 | | 4/2004 | |
| WO | WO 2011/059346 | | 5/2011 | |
| WO | WO 2011/141841 | | 11/2011 | |
| WO | WO 2015/009172 | | 1/2015 | |
| WO | WO 2015/151019 | | 10/2015 | |
| WO | WO 2015/164921 | | 11/2015 | |
| WO | WO 2016/157103 | | 10/2016 | |
| WO | WO 2017/160166 | | 9/2017 | |
| WO | WO 2017/182987 | | 10/2017 | |
| WO | WO-2017182987 A1 * | 10/2017 | ........ A61M 16/0611 |
| WO | WO-2018220535 A1 * | 12/2018 | ........ A61M 16/0666 |

* cited by examiner

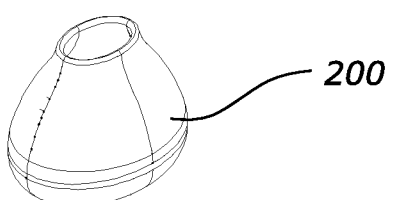
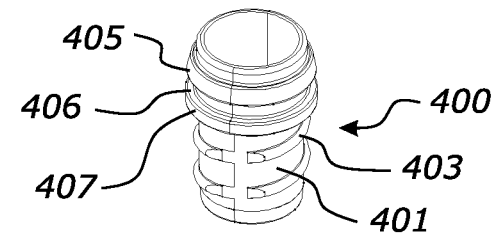
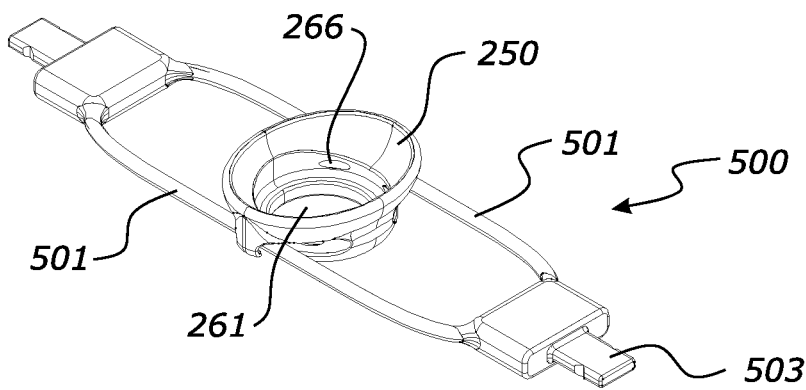
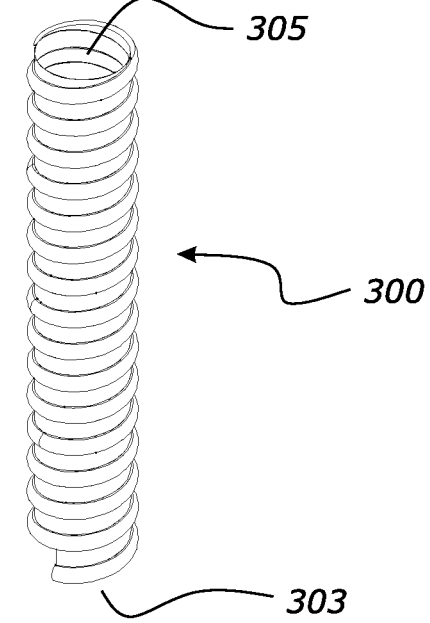
*FIG. 9A*

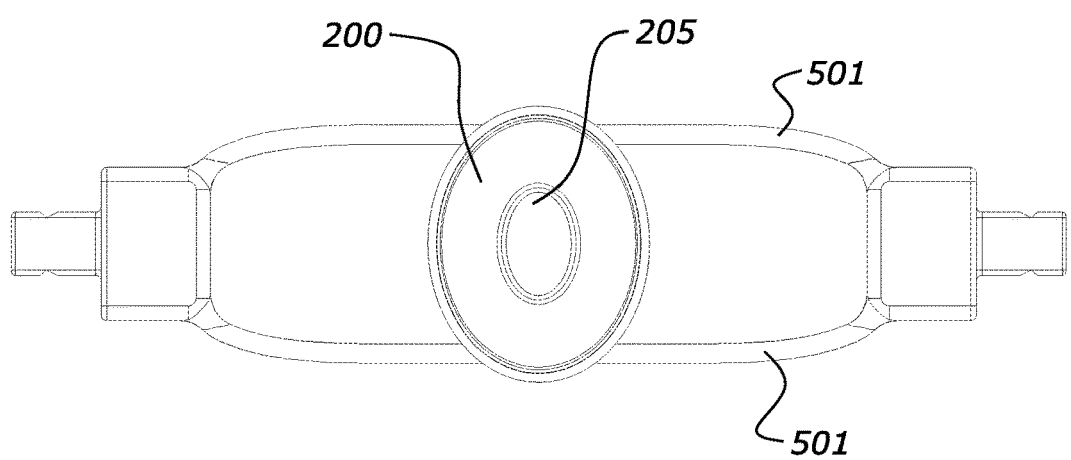
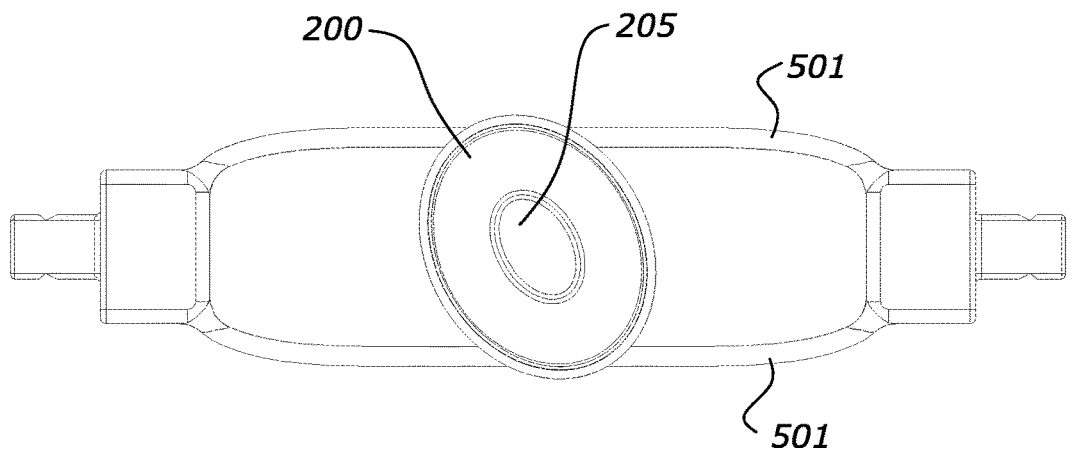
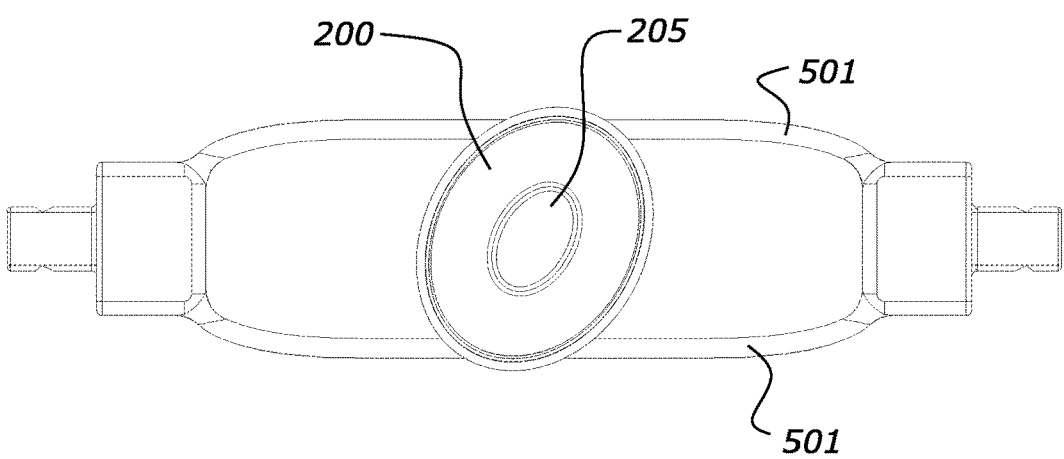
*FIG. 16*

FIG. 47
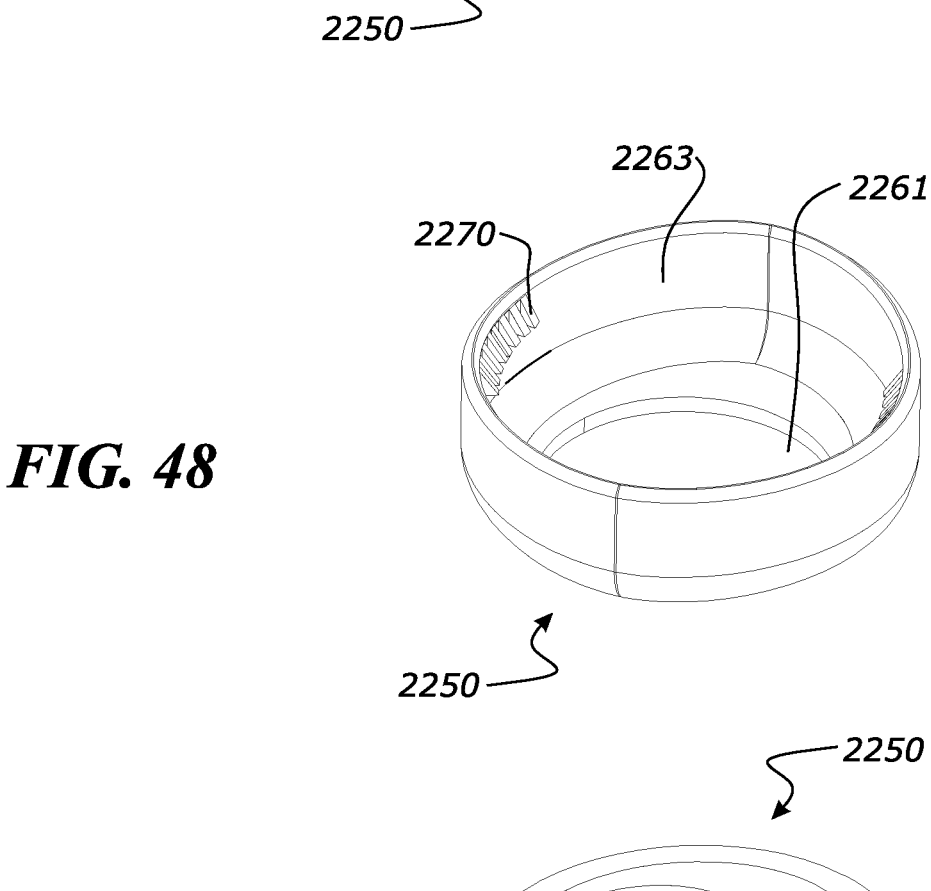
FIG. 48
FIG. 49
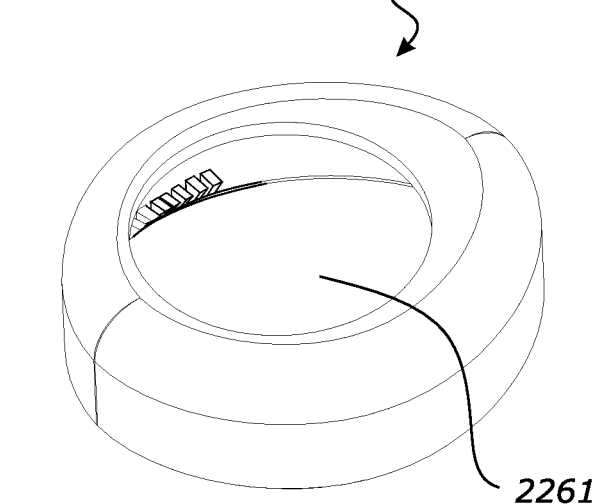

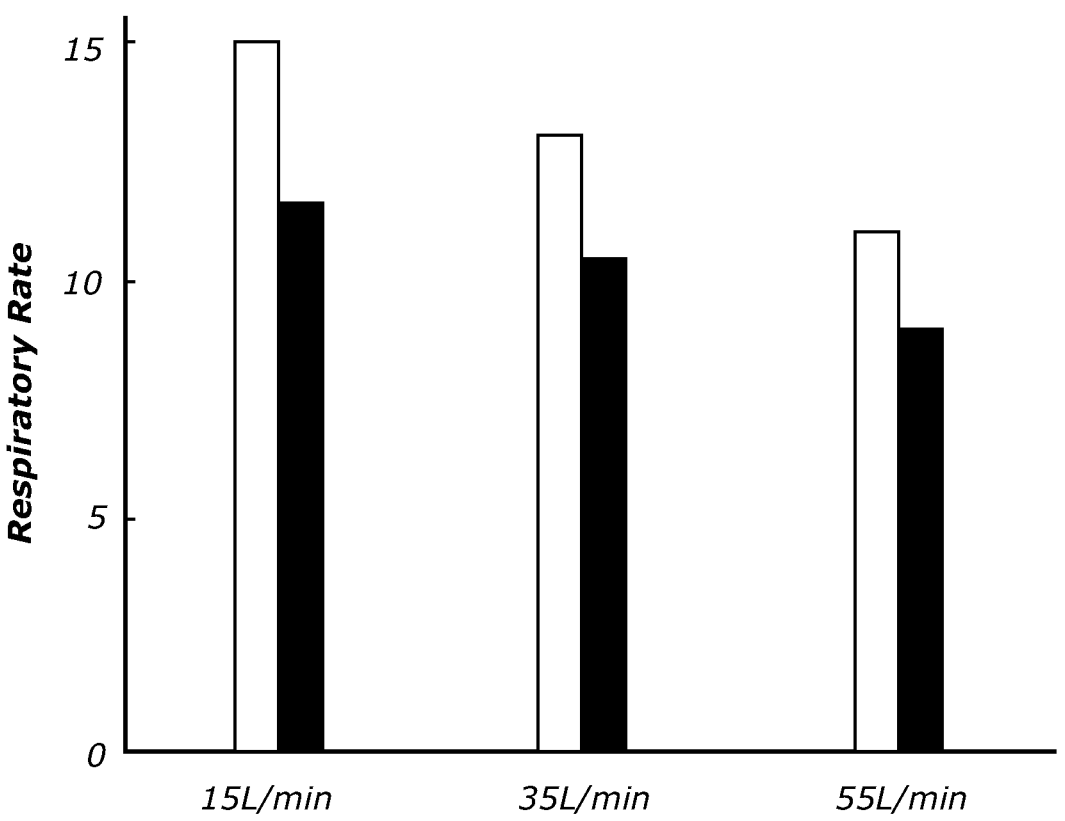
FIG. 61A
FIG. 61B
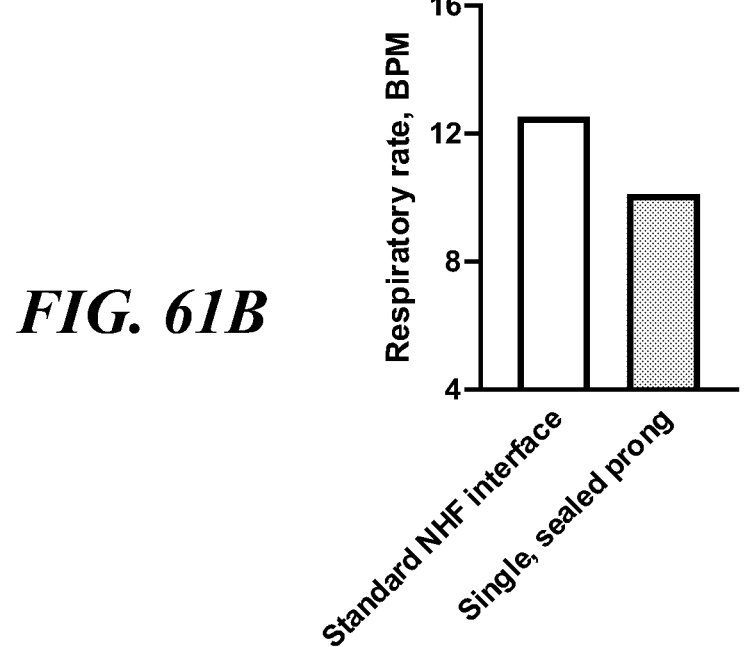

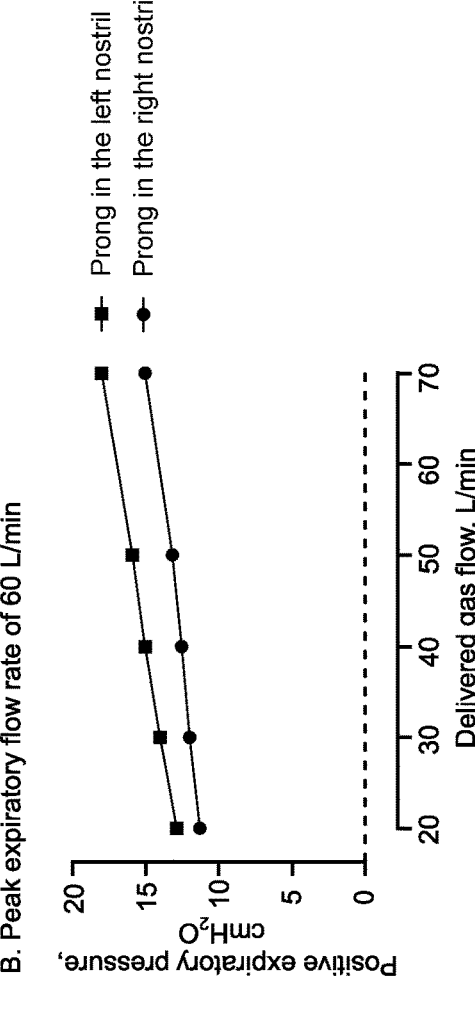
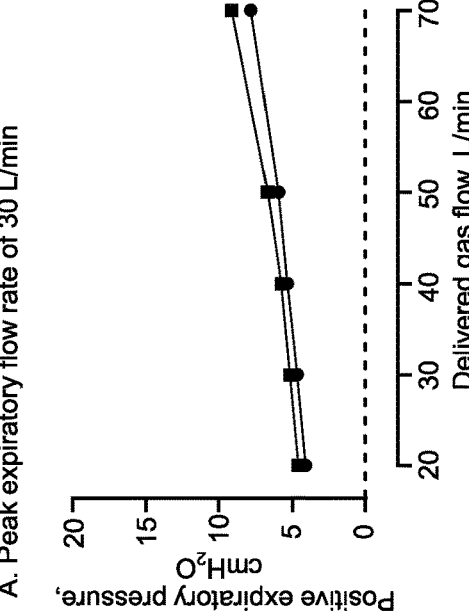
*FIG. 61C*

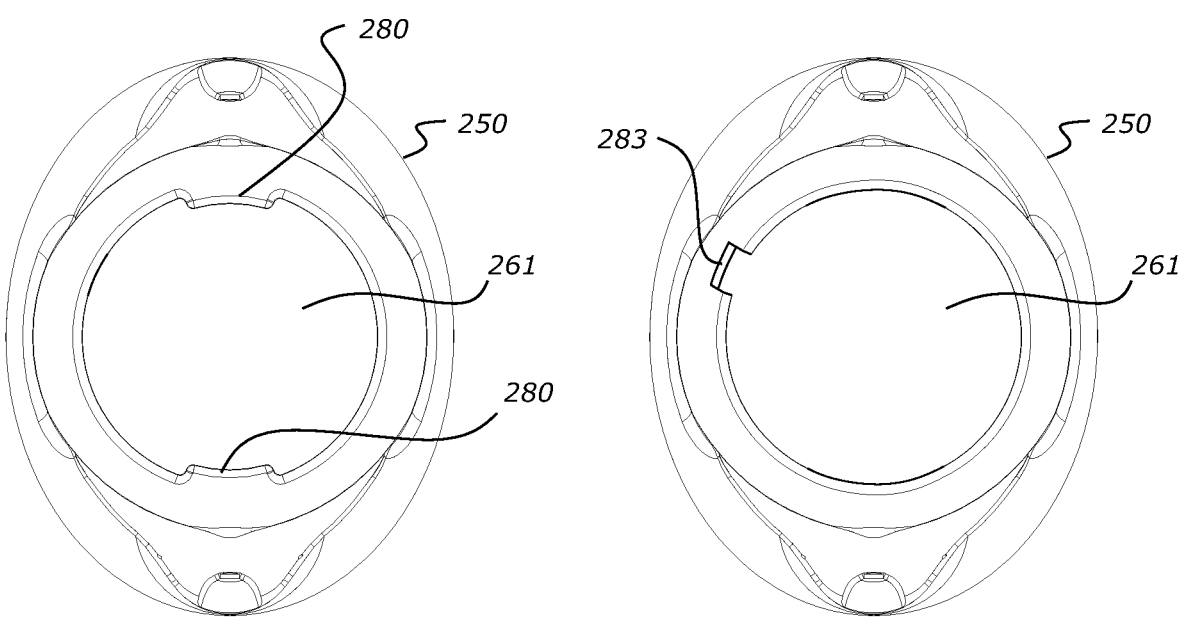
FIG. 67A                    FIG. 67B
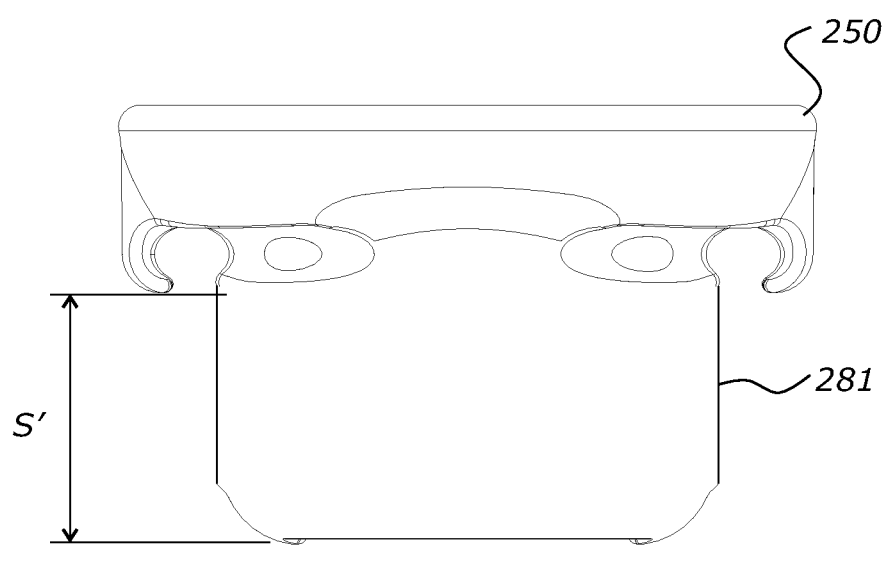
FIG. 68

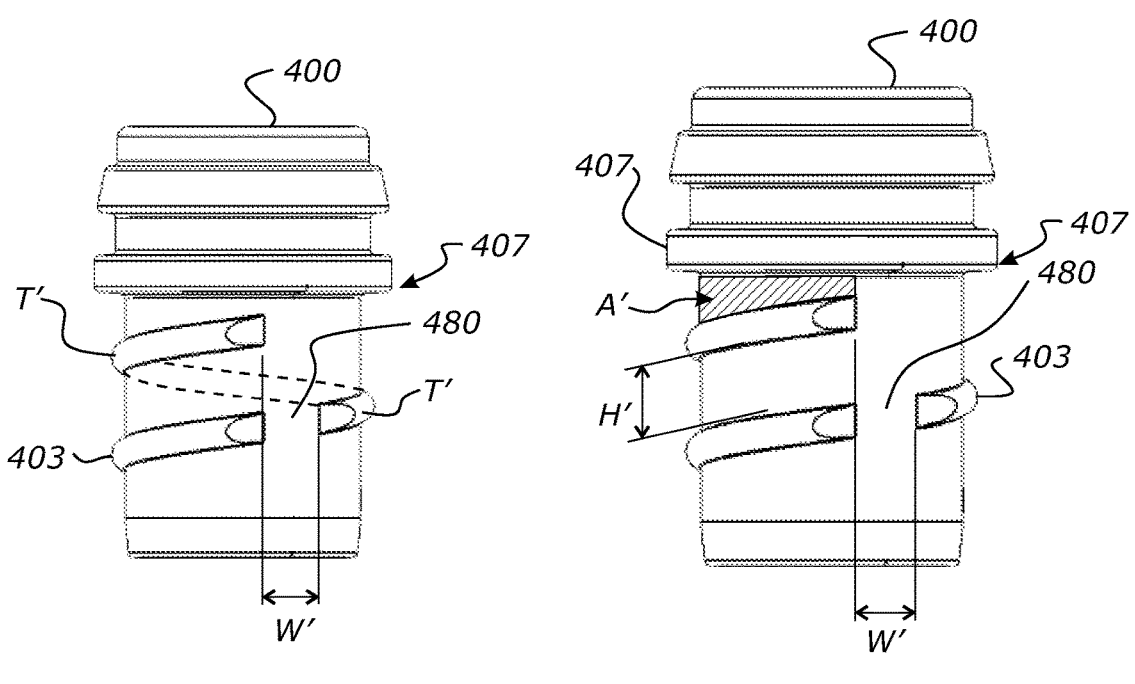
FIGURE 69
FIGURE 70A
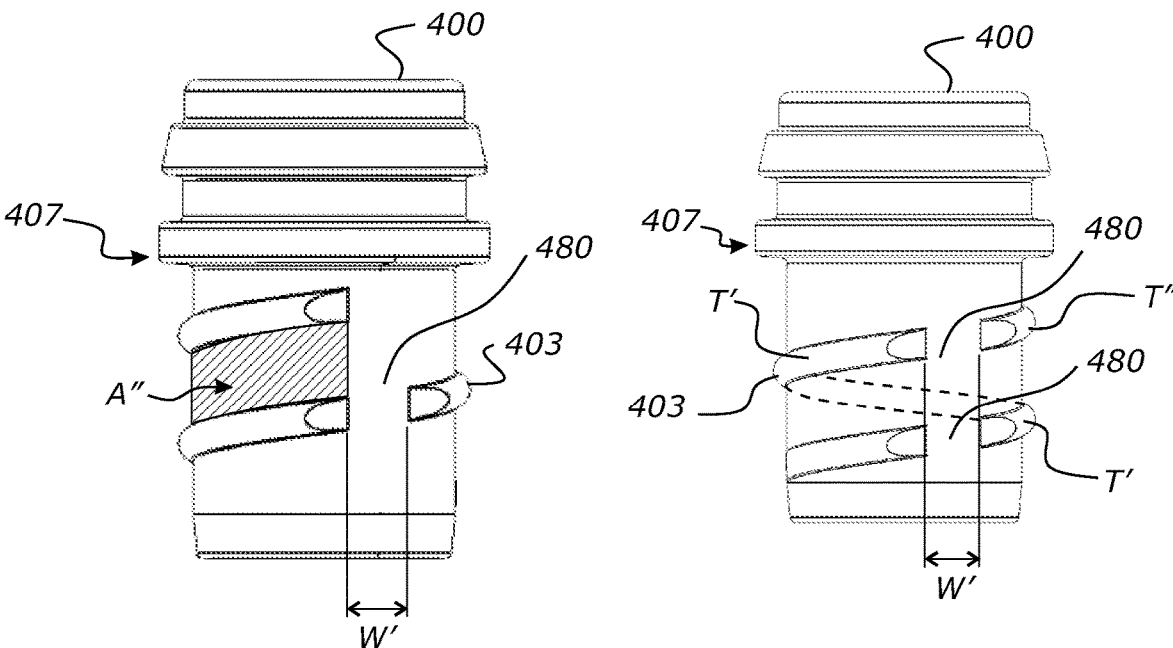
FIGURE 70B
FIGURE 71

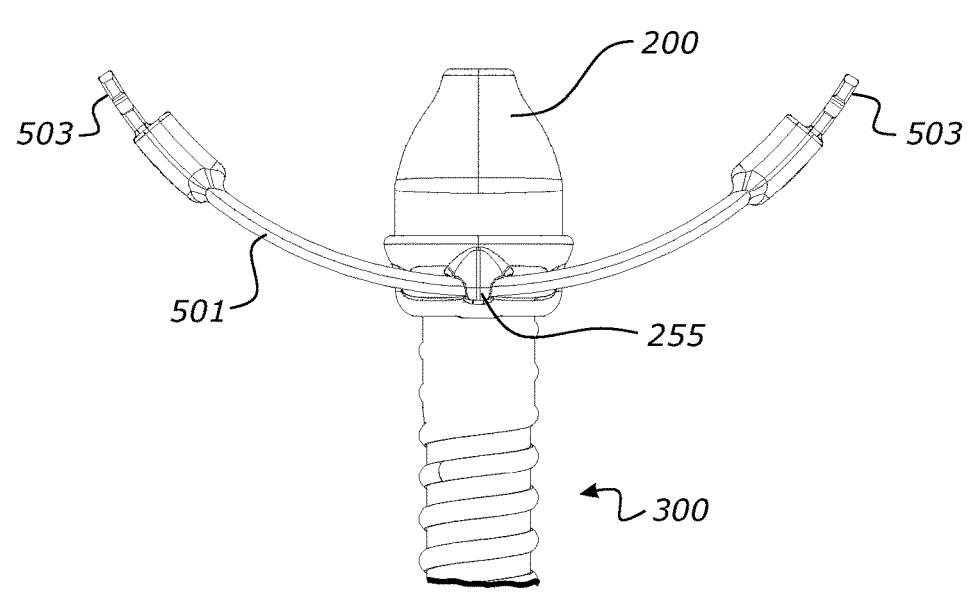
FIG. 73
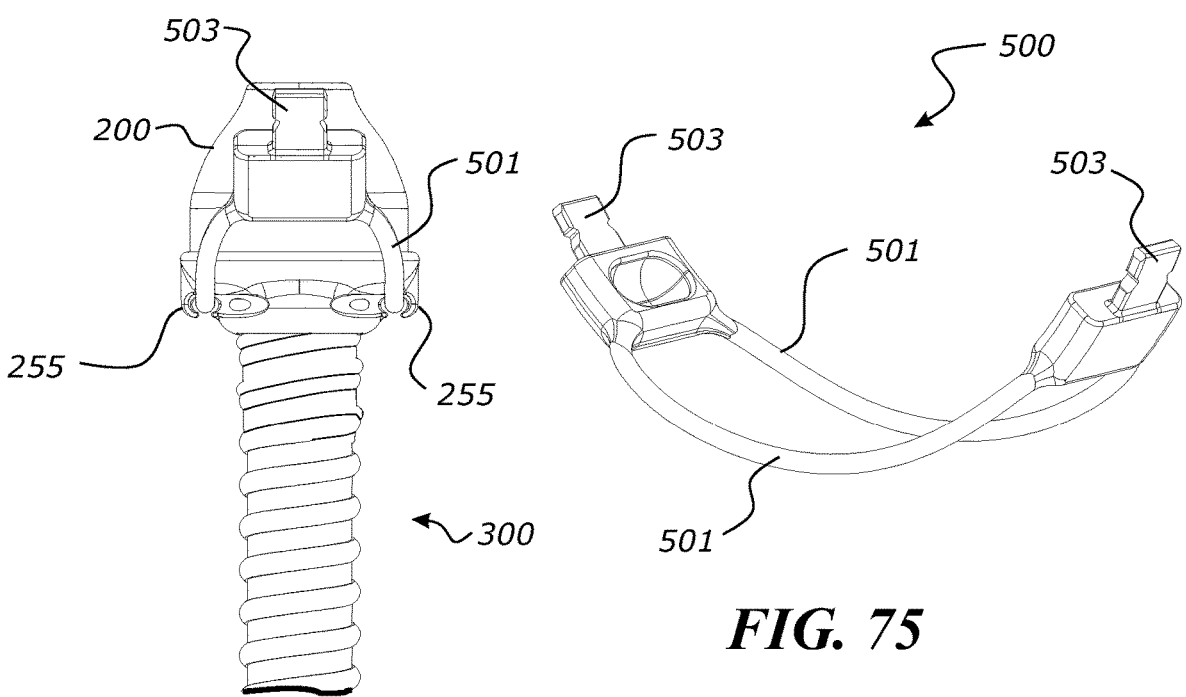
FIG. 74
FIG. 75

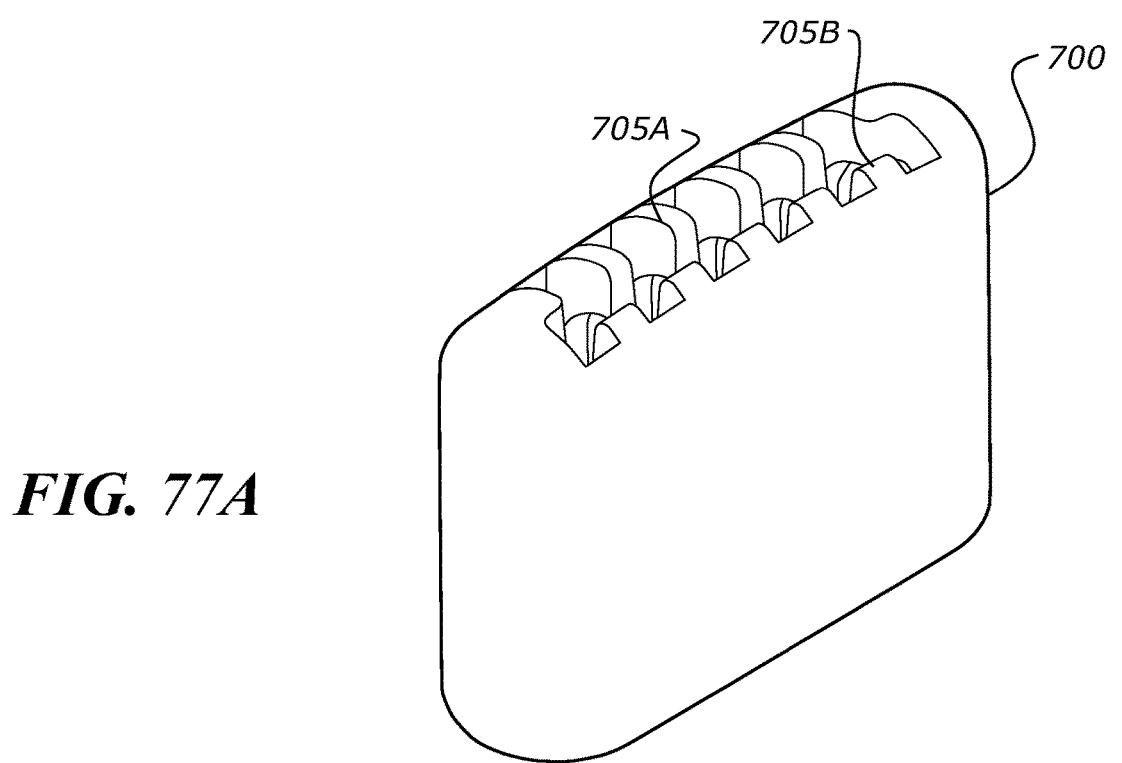
FIG. 77A
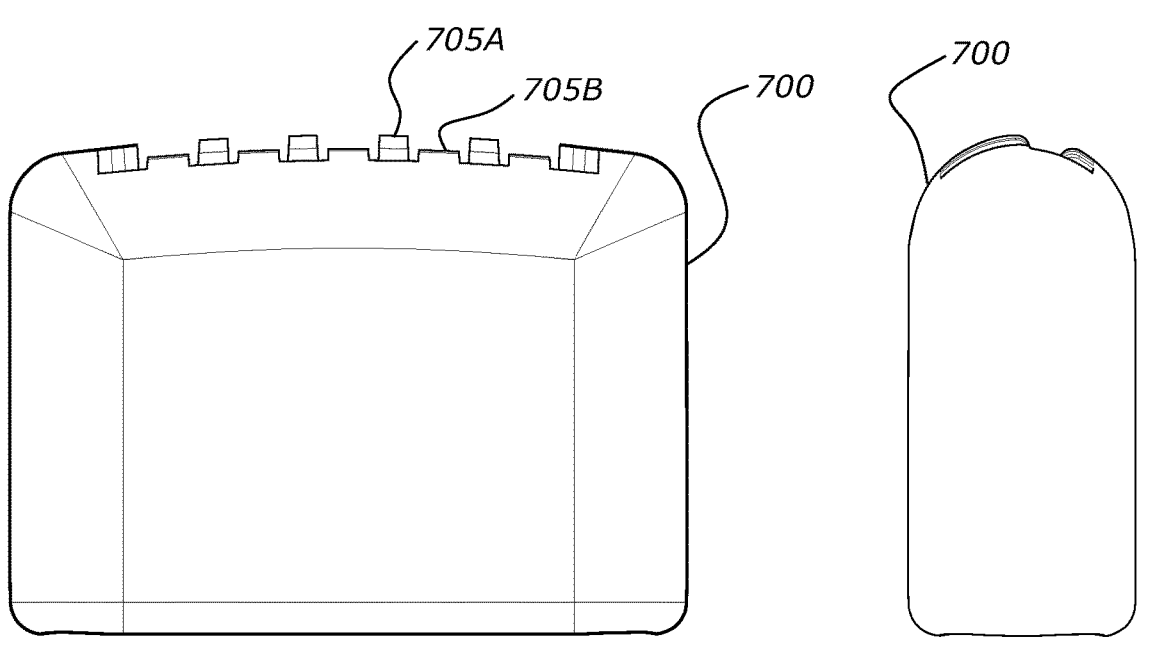
FIG. 77B               FIG. 77C

RESPIRATORY INTERFACE

TECHNICAL FIELD

The present disclosure relates to a respiratory interface, in particular a respiratory patient interface to provide gases or fluids to a patient.

BACKGROUND

Breathing assistance apparatuses are used in various environments such as hospital, medical facility, residential care, or home environments to deliver a flow of gases to users or patients. A breathing assistance or respiratory therapy apparatus (collectively, 'respiratory apparatus' or 'respiratory devices') may be used to deliver a flow of gases e.g. air and/or supplementary oxygen or other gases to a user. Respiratory devices may also comprise a humidification apparatus to deliver heated and humidified gases. A respiratory apparatus may allow adjustment and control over characteristics of the gases flow, including flow rate, temperature, gases concentration, humidity, pressure, etc. Sensors, such as flow sensors and/or pressure sensors are used to measure characteristics of the gases flow.

SUMMARY

There is provided a respiratory interface for delivering gases to a single nare of a patient, the respiratory interface comprising:

a single sealing nasal prong, the single sealing nasal prong comprising:

a seal body configured to seal with one of the nares of a patient, the seal body having or comprising substantially opposing front and rear surfaces, and substantially opposing left and right surfaces, the substantially opposing front and rear surfaces being substantially symmetrical to each other, an inlet configured to receive gases, an outlet configured to supply the gases to the patient, the outlet located in a generally central location between the left and right surfaces such that the single sealing nasal prong can seal either one of the patient's nares, wherein the seal body and the outlet of the single sealing nasal prong are arranged such that one of the patient's nares is substantially sealed and gases are supplied to that nare from the outlet while the other of the patient's nares is unsealed and is free from direct gases supply from the outlet.

There is provided a respiratory interface for delivering gases to a single nare of a patient, the respiratory interface comprising:

a single sealing nasal prong, the single sealing nasal prong comprising:

a seal body configured to seal with one of the nares of a patient, the seal body having or comprising substantially opposing front and rear surfaces, and substantially opposing left and right surfaces, the substantially opposing left and right surfaces being substantially symmetrical to each other, an inlet configured to receive gases, an outlet configured to supply the gases to the patient, the outlet located in a generally central location between the left and right surfaces such that the single sealing nasal prong can seal either one of the patient's nares, wherein the seal body and the outlet of the single sealing nasal prong are arranged such that one of the patient's nares is substantially sealed and gases are supplied to that nare from the outlet while the other of the patient's nares is unsealed and is free from direct gases supply from the outlet.

Optionally, the substantially opposing front and rear surfaces are substantially symmetrical to each other.

Optionally, the respiratory interface further comprises a gases delivery assembly, the gases delivery assembly comprising the single sealing nasal prong.

Optionally, the gases delivery assembly further comprises a conduit connected to, or connectable to the single sealing nasal prong.

Optionally, the respiratory interface further comprises headgear connected to, or connectable to, the gases delivery assembly.

There is provided a respiratory interface for delivering gases to a single nare of a patient, the respiratory interface consisting of:

a gases delivery assembly having:

a single sealing nasal prong with a seal body configured to seal with one of the nares of a patient, an inlet configured to receive gases, and an outlet configured to supply the gases to the patient, a conduit directly coupled to the single sealing nasal prong and in fluid communication with the single sealing nasal prong, and headgear connected to, or connectable to, the gases delivery assembly.

There is provided a respiratory interface for delivering gases to a single nare of a patient, the respiratory interface comprising:

a gases delivery assembly, the gases delivery assembly consisting of:

a single sealing nasal prong having a seal body configured to seal with one of the nares of a patient, an inlet configured to receive gases, and an outlet configured to supply the gases to the patient;

a conduit directly coupled to the single sealing nasal prong and in fluid communication with the single sealing nasal prong, and headgear connected to, or connectable to, the gases delivery assembly.

There is provided a respiratory interface for delivering gases to a single nare of a patient, the respiratory interface comprising:

a frameless gases delivery assembly comprising:

a single sealing nasal prong having a seal body configured to seal with one of the nares of a patient, the single sealing nasal prong having an inlet configured to receive gases, and an outlet configured to supply the gases to the patient;

a conduit in fluid communication with the single sealing nasal prong; and headgear connected to, or connectable to, the gases delivery assembly.

Optionally, the headgear is directly connected to the gases delivery assembly.

Optionally, the headgear is directly connected to the single sealing nasal prong.

Optionally, the headgear is directly connected to the conduit.

Optionally, the seal body comprises a wall defining the inlet, the outlet and the seal body.

Optionally, the wall thickness is about 0.7 mm to about 0.8 mm.

Optionally, the respiratory interface further comprises an adjuster configured to decouple the single sealing nasal prong from tension when it is moved from one nare to the other while still allowing the headgear to maintain the headgear retention force.

Optionally, the adjuster comprises a support.

Optionally, the support is, or comprises, one or more sliding members.

Optionally, the support or a strap is, or comprises, a flexible portion.

Optionally, the adjuster is coupled to a cuff that supports the single sealing nasal prong, in between, or as an intermediate component of, the headgear arrangement.

Optionally, the respiratory interface further comprises a clip configured to removably fasten the conduit to another item associated with patient.

Optionally, the outlet is located in a generally central location between the front and rear surfaces.

Optionally, the opposing left and right surfaces are substantially symmetrical to each other.

Optionally, the single sealing nasal prong is pivotable about an axis such that it is orientable to fit either of the patient's nares.

Optionally, the single sealing nasal prong comprises a rigid portion connected to, or connectable to, the gas flow assembly.

Optionally, the rigid portion provides stability for the single sealing nasal prong relative to the gas flow assembly.

Optionally, a wall thickness of the rigid portion is about 1.5 mm to about 4 mm.

Optionally, the single sealing nasal prong comprises a supple portion configured to substantially conform to shape of the patient's nare.

There is provided a respiratory interface for delivering gases to a single nare of a patient, the respiratory interface comprising:

a single sealing nasal prong having a seal body configured to seal with one of the nares of a patient, an inlet configured to receive gases, and an outlet configured to supply the gases to the patient;

a conduit having an outlet configured to supply the gases to the single sealing nasal prong, the conduit being coupled with, or couplable with, the single sealing nasal prong such that the conduit outlet is coaxial with the single sealing nasal prong inlet.

Optionally, a cross-sectional area of the conduit outlet is similar to a cross-sectional area of the prong inlet.

Optionally, a ratio of the width of the single sealing nasal prong to the length of the single sealing nasal prong is about 0.4 to about 0.9.

Optionally, a ratio of a cross sectional area of the prong outlet to a cross sectional area of a conduit outlet 305 is about 0.72.

Optionally, a ratio of a cross sectional area of the prong outlet to a cross-sectional area of a base of the seal is about 0.33.

Optionally, the prong outlet is generally centred in relation to the conduit outlet.

Optionally, the single sealing nasal prong comprises a supple sealing portion.

Optionally, the single sealing nasal prong comprises a rigid coupling portion.

Optionally, the rigid coupling portion is integral to the single sealing nasal prong.

Optionally, the seal body comprises a wall defining the inlet, the outlet and the seal body.

Optionally, the wall thickness is about 0.7 mm to about 0.8 mm.

Optionally, the respiratory interface further comprises a cuff having a prong coupling portion, wherein the single sealing nasal prong is received by, or receivable by, the prong coupling portion of the cuff.

Optionally, the rigid coupling portion is coupled with the cuff.

Optionally, the rigid coupling portion comprises the single sealing nasal prong inlet.

Optionally, a gases path from the conduit to the prong outlet is substantia linear.

Optionally, the single sealing nasal prong and the conduit assembly form a continuous gases pathway.

Optionally, the single sealing nasal prong and the conduit assembly form a direct fluid coupling.

Optionally, the conduit assembly includes a conduit and conduit connector that facilitates coupling between the conduit and the cuff.

Optionally, an inner surface of the rigid portion comprises an undercut or recess and the cuff comprises a complementary groove, the undercut or recess and the complementary groove interacting with each other to couple the prong to the conduit.

Optionally, the cuff comprises a headgear attachment hook.

Optionally, the rigid portion comprises cut outs or recesses configured to receive a portion of a headgear strap.

Optionally, the cuff comprises teeth configured to grip and retain a portion of a headgear strap.

Optionally, the conduit and prong arrangement are configured to reduce resistance to flow.

There is provided a respiratory interface for delivering gases to a single nare of a patient, the respiratory interface comprising:

a single sealing nasal prong having a seal body configured to seal with one of the nares of a patient, an inlet configured to receive gases, and an outlet configured to supply the gases to the patient;

an adjuster configured to allow the single sealing nasal prong to be removable from first nare and positioned in the patient's other nare to seal with the other nare without the single sealing nasal prong being detached from the respiratory interface.

Optionally, the respiratory interface further comprises headgear, wherein the headgear comprises the adjuster.

Optionally, the headgear comprises a single strap or a bifurcated strap.

Optionally, the headgear comprises a stretchable portion.

Optionally, the headgear comprises a non-stretchable portion.

Optionally, the non-stretchable portion has a stretchable portion on each side.

Optionally, the adjuster comprises a sliding member that allows prong adjustment independently from the headstrap.

Optionally, the single sealing nasal prong is a movable prong.

Optionally, the single sealing nasal prong is movable between two positions.

Optionally, the single sealing prong is rotatable from a first location in which the prong seals with a first nare of a patient to a second location in which the prong seals with a second nare of a patient.

Optionally, the single sealing nasal prong is rotatable about a pivot point or rotatable about a vertical axis.

Optionally, the pivot point is located between the first location and the second location.

Optionally, the first location is on a first region of a manifold and the second location is on a second region of the manifold.

Optionally, the first location on a first region of a manifold and the second location are on the same region of the manifold.

Optionally, the prong outlet extends at a first angle to correspond to the angle of the first nare when in the first location and the prong outlet extends at a second angle to correspond to the angle of the second nare when in the second location.

Optionally, the manifold comprises a first outlet corresponding to the first location of the prong and a second outlet corresponding to the second location of the prong.

Optionally, the respiratory interface further comprises a bung configured to seal the second opening when the single sealing nasal prong is in the first location and seal the first opening when the single sealing nasal prong is in the second location.

Optionally, the bung is integral with the prong and is configured to rotate as the prong rotates.

Optionally, the respiratory interface further comprises a tether that couples the bung to the respiratory interface.

Optionally, the seal body has opposing left and right surfaces and the prong outlet is located in a generally central location between the left and right surfaces such that the single sealing nasal prong can seal either one of the patient's nares.

Optionally, the seal body has opposing front and rear surfaces and the prong outlet is located in a generally central location between the front and rear surfaces such that the single sealing nasal prong can seal each of the patient's nares independently of vertical orientation.

There is provided a respiratory interface for delivering gases to a single nare of a patient, the respiratory interface comprising:
    a body with a pair of side arms configured to provide
        stability for the interface on the cheeks of the patient;
    a single sealing nasal prong;
    a manifold having a single sided inlet to receive gases
        from a gas source, and an outlet that delivers gases to
        the single sealing nasal prong;
    wherein the single sealing nasal prong is arranged such
        that one of the patient's nares is substantially sealed
        and gases are supplied to that nare from the outlet while
        the other of the patient's nares is unsealed and is free
        from direct gases supply from the outlet.

Optionally, the manifold is a separate part from the side arms, the side arms being couplable to, or coupled with, the manifold.

Optionally, the sides arms comprise a headgear attachment feature.

Optionally, a conduit clip engages with, or is engageable with, a conduit.

There is provided a respiratory interface for delivering gases to a single nare of a patient, the respiratory interface comprising:
    a single sealing nasal prong having a seal body configured
        to seal with one of the nares of a patient, an inlet
        configured to receive gases, and an outlet configured to
        supply the gases to the patient;
    a support for the single sealing nasal prong strap, the
        single sealing nasal prong being translatable relative to
        the support to be interchangeably received by the
        patient's nares, the single sealing nasal prong remaining coupled to the support; and
    headgear connected to, or connectable to, the support.

Optionally, the support comprises a sliding member.

Optionally, the support comprises two sliding members.

Optionally, the sliding member(s) is/are formable or conformable such that the sliding member(s) substantially follow or accommodate a contour of a patient's face.

Optionally, the sliding member(s) comprise a pre-formed profile.

Optionally, said pre-formed profile comprises a pre-curve or radiused profile comprising a curve or a profile that substantially follows or accommodates a contour of a patient's face or wherein said curve or profile is substantially convex with respect to a patient's face.

Optionally, the pre-formed profile comprises one or more of: a radius of about 120° of a circle, about one third of a circle, an arc-shaped configuration.

Optionally, the pre-formed profile comprises a radius length and/or pre-curve length of about 70 mm to about 110 mm.

Optionally, the pre-curved or radiused profile comprises a radius length or pre-curve length of about 90 mm.

Optionally, the respiratory interface further comprises clips at end portions of sliding member(s) coupled to, or couplable with, headgear.

Optionally, the strap(s) are coupled to, or couplable to, the single sealing nasal prong.

Optionally, the straps are removably coupled to the single sealing nasal prong.

Optionally, the headgear is a single strap or a bifurcated strap.

Optionally, at least one terminal end of the headgear comprises a strap attachment.

Optionally, the strap attachment comprises: a substantially hollow body comprising of internal walls to define a channel therebetween, the substantially hollow body comprising of a mouth end and a terminal end, the mouth end defining an opening into the channel and for receiving a free end of a headstrap, and the terminal end defining an end of the channel substantially distal of the mouth end, the channel providing for a pathway extending between the mouth end and the terminal end through which said headstrap is to be threaded, at least one first projection extending from a base attached to said internal wall to a tip in a direction substantially towards an opposing internal wall or into the channel defined by at least an opposing side wall, wherein the tip is configured to engage at least a portion or a surface of a headstrap to be received within said channel, said tip configured to substantially permit the headstrap to be thread in a direction into the channel and along the pathway from the mouth end to the terminal end and said tip configured to substantially resist the headstrap from being removed or withdrawn from the channel in a direction extending from the terminal end towards the mouth end of said substantially hollow body, and wherein the tip of the at least one first projection is disposed so as to be spaced off from said opposing internal wall by a pre-determined distance, said pre-determined distance being a function of a thickness of a headstrap to be received within the channel.

Optionally, the strap attachment comprises: two or more walls defining a channel, the channel configured to receive an end of a headstrap, a first projection set comprising at least one first projection extending from a first wall of the strap attachment and substantially towards or into the channel, the first projection comprising a distal end configured to engage a portion of the headstrap and prevent the end of the headstrap received in the channel, from being removed from the channel, wherein the distal end of the first projection is spaced at a distance from a second opposing wall of the channel, and wherein the distance is provided as a function of a thickness of the headstrap to be received in the channel.

Optionally, the strap attachment comprises: two or more walls defining a channel, the channel configured to receive an end of a headstrap, a first projection set comprising at least one first projection, a second projection set comprising at least one second projection, and wherein the first projection set and the second projection set extend from opposing walls of the strap attachment into the channel, wherein the at least one first projection of the first projection set and the at least one second projection of the second projection set comprise distal ends configured to engage a portion of a headstrap and prevent removal of an end of the headstrap received in the channel, and wherein the distal ends of the at least one first and second projections taper to, or comprise of, a pointed end or apex.

Optionally, the strap attachment comprises: two or more walls defining a channel, the channel configured to receive an end of a headstrap, a first projection set comprising at least one first projection, a second projection set comprising at least one second projection, and wherein the first and second projection sets define a curved or tortuous path through which the end of the headstrap is to be received, wherein the at least one first projection of the first projection set and the at least one second projection of the second projection set comprise a distal end to engage a portion of the headstrap and prevent removal of an end of the headstrap received in the channel, and wherein the distal ends of the at least one first and second projections taper to, or comprise of, a pointed end or apex.

Optionally, the strap attachment comprises a strap termination, or a ferrule.

Optionally, the at least one terminal end of the headgear is received within a channel of the strap attachment, and wherein, once received, the at least one terminal end of the headgear follows a defined pathway, optionally such as a substantially tortuous path, within the channel of the strap attachment.

Optionally, the strap attachment comprises a plurality of projections, the plurality of projections comprising a first projection set and a second projection set, and wherein the first and second projection sets are arranged on opposing sides of the channel.

Optionally, the first projection set and second projection set are arranged to be offset, optionally such as being laterally offset, from each other in an opposing configuration.

Optionally, the projections are configured to extend towards an end of the strap attachment opposite a headstrap insertion end of the strap attachment.

Optionally, at least one projection tapers towards a pointed end or tip or apex.

Optionally, said strap attachment comprises of a mouth through which said headgear is to be inserted into said channel.

Optionally, said mouth comprises lead-in features.

Optionally, said lead-in features comprises substantially rounded lips for accommodating or receiving said headgear.

Optionally, the seal body has opposing left and right surfaces, and the prong outlet is centred between the left and right surfaces such that the single sealing nasal prong can be adjusted to seal in either one of the nares providing therapy to the patient.

Optionally, the seal body has opposing front and rear surfaces, and the prong outlet is centred between the front and rear surfaces such that the single sealing nasal prong can be inserted independently of vertical orientation.

There is provided a respiratory interface for delivering gases to a single nave of a patient, the respiratory interface comprising:

a single sealing nasal prong having a seal body configured to seal with one of the nares of a patient, an inlet configured to receive gases, and an outlet configured to supply the gases to the patient;

a cuff comprising a prong coupling portion;

wherein the single sealing nasal prong is received by, or receivable by, the prong coupling portion of the cuff.

Optionally, the cuff comprises a conduit coupling portion coupled with, or couplable with, a conduit assembly.

Optionally, single sealing nasal prong comprises an undercut or recess and the cuff comprises a complementary groove.

Optionally, a portion of the single sealing nasal prong received by, or receivable by, the cuff is a rigid portion.

Optionally, a portion of the conduit s threaded for engagement with the cuff.

Optionally, the single sealing nasal prong coupling portion and conduit coupling portion of the cuff are integral to the cuff.

Optionally, the single sealing nasal prong coupling portion and conduit coupling portion of the cuff are separate parts.

Optionally, the prong coupling portion of the cuff comprises a shape that generally corresponds to the shape of the single sealing nasal prong.

Optionally, the prong coupling portion of the cuff is substantially elliptical or oval shaped.

Optionally, the conduit outlet is aligned with the cuff opening, which in turn aligns with the prong inlet and the prong outlet to maintain a substantially linear gases path from the conduit to the single sealing nasal prong.

Optionally, the conduit outlet, the cuff opening, and the prong inlet have a similar diameter.

Optionally, the headgear attachment comprises a ring mounted on the cuff.

Optionally, an inner surface of the single sealing nasal prong has one or more cut outs to receive a portion of the headstrap.

Optionally, the headgear attachment comprises one or more teeth on an inner surface of the cuff.

Optionally, the headstrap held in place via friction fit.

Optionally, the headstrap coupled to prong via glue, welding, protrusion(s), and/or clips.

Optionally, the headgear includes a sliding member.

Optionally, the sliding member is coupled to, or couplable to, the cuff via a clip.

Optionally, the sliding member is removably coupled to, or removably couplable to, the cuff.

Optionally, the sliding member decouples movement of the single sealing nasal prong from the headgear.

Optionally, the sliding member comprises headgear attachment regions at or near each end.

Optionally, the sliding member is a single sliding member or pair of sliding members.

Optionally, the sliding member(s) is/are formable or conformable such that the sliding member(s) substantially follow or accommodate a contour of a patient's face.

Optionally, the sliding member(s) comprise a pre-formed profile.

Optionally, said pre-formed profile comprises a pre-curve or radiused profile comprising a curve or a profile that substantially follows or accommodates a contour of a patient's face or wherein said curve or profile is substantially convex with respect to a patient's face.

Optionally, the pre-formed profile comprises one or more of: a radius f about 120° of a circle, about one third of a circle, an arc-shaped configuration.

Optionally, the pre-formed profile comprises a radius length and/or pre-curve length of about 70 mm to about 110 mm.

Optionally, the pre-curved or radiused profile comprises a radius length or pre-curve length of about 90 mm.

Optionally, the headgear comprises a single strap, or a bifurcated strap.

Optionally, at least one terminal end of the headgear comprises a strap attachment.

Optionally, the strap attachment comprises: a substantially hollow body comprising of internal walls to define a channel therebetween, the substantially hollow body comprising of a mouth end and a terminal end, the mouth end defining an opening into the channel and for receiving a free end of a headstrap, and the terminal end defining an end of the channel substantially distal of the mouth end, the channel providing for a pathway extending between the mouth end and the terminal end through which said headstrap is to be threaded, at least one first projection extending from a base attached to said internal wall to a tip in a direction substantially towards an opposing internal wall or into the channel defined by at least an opposing side wall, wherein the tip is configured to engage at least a portion or a surface of a headstrap to be received within said channel, said tip configured to substantially permit the headstrap to be thread in a direction into the channel and along the pathway from the mouth end to the terminal end and said tip configured to substantially resist the headstrap from being removed or withdrawn from the channel in a direction extending from the terminal end towards the mouth end of said substantially hollow body, and wherein the tip of the at least one first projection is disposed so as to be spaced off from said opposing internal wall by a pre-determined distance, said pre-determined distance being a function of a thickness of a headstrap to be received within the channel.

Optionally, the strap attachment comprises: two or more walls defining a channel, the channel configured to receive an end of a headstrap, a first projection set comprising at least one first projection extending from a first wall of the strap attachment and substantially towards or into the channel, the first projection comprising a distal end configured to engage a portion of the headstrap and prevent the end of the headstrap received in the channel, from being removed from the channel, wherein the distal end of the first projection is spaced at a distance from a second opposing wall of the channel, and wherein the distance is provided as a function of a thickness of the headstrap to be received in the channel.

Optionally, the strap attachment comprises: two or more walls defining a channel, the channel configured to receive an end of a headstrap, a first projection set comprising at least one first projection, a second projection set comprising at least one second projection, and wherein the first projection set and the second projection set extend from opposing walls of the strap attachment into the channel, wherein the at least one first projection of the first projection set and the at least one second projection of the second projection set comprise distal ends configured to engage a portion of a headstrap and prevent removal of an end of the headstrap received in the channel, and wherein the distal ends of the at least one first and second projections taper to, or comprise of, a pointed end or apex.

Optionally, the strap attachment comprises: two or more walls defining a channel, the channel configured to receive an end of a headstrap, a first projection set comprising at least one first projection, a second projection set comprising at least one second projection, and wherein the first and second projection sets define a curved or tortuous path through which the end of the headstrap is to be received, wherein the at least one first projection of the first projection set and the at least one second projection of the second projection set comprise a distal end to engage a portion of the headstrap and prevent removal of an end of the headstrap received in the channel, and wherein the distal ends of the at least one first and second projections taper to, or comprise of, a pointed end or apex.

Optionally, the strap attachment comprises a strap termination, or a ferrule.

Optionally, the at least one terminal end of the headgear is received within a channel of the strap attachment, and wherein, once received, the at least one terminal end of the headgear follows a defined pathway, optionally such as a substantially tortuous path, within the channel of the strap attachment.

Optionally, the strap attachment comprises a plurality of projections, the plurality of projections comprising a first projection set and a second projection set, and wherein the first and second projection sets are arranged on opposing sides of the channel.

Optionally, the first projection set and second projection set are arranged to be offset, optionally such as being laterally offset, from each other in an opposing configuration.

Optionally, the projections are configured to extend towards an end of the strap attachment opposite a headstrap insertion end of the strap attachment.

Optionally, at least one projection tapers towards a pointed end or tip or apex.

Optionally, said strap attachment comprises of a mouth through which said headgear is to be inserted into said channel.

Optionally, said mouth comprises lead-in features.

Optionally, said lead-in features comprises substantially rounded lips for accommodating or receiving said headgear.

There is provided a respiratory interface for delivering gases to a single nare of a patient, the respiratory interface comprising:

a single sealing nasal prong comprising:

an inlet configured to receive gases;

an outlet configured to supply the gases to the patient;

a seal body having a wall defining an exterior of the single sealing nasal prong;

the seal body and the outlet of the single sealing nasal prong being arranged such that one of the patient's nares is substantially sealed and gases are supplied to that nare from the outlet while the other of the patient's nares is unsealed and is free from direct gases supply from the outlet;

wherein the respiratory interface is configured to provide respiratory flow therapy to the patient through the single sealing nasal prong, wherein the respiratory flow causes flushing of the airways to clear dead space within airways.

Optionally, the wall having an at-rest shape and being configured to substantially maintain the at-rest shape upon insertion into a patient's nare.

Optionally, gases flowing through the gases passage causes the exterior of the single sealing nasal prong to seal with one of the nares of a patient. The gases flowing through the prong may cause the wall of the prong to inflate to seal against the nare of the user.

Optionally, the wall defines the inlet, the outlet and the seal body.

Optionally, the wall thickness is about 0.7 mm to about 0.8 mm.

Optionally, a cross-section of the prong outlet is generally oval.

Optionally, the cross-section of the prong outlet is elliptical.

Optionally, the cross-section of the outlet has a semi-minor radius of about 1 mm to about 3 mm and a semi-major radius of about 4 mm to about 24 mm.

Optionally, the cross-section of the outlet has a semi-minor radius of about 1 mm to about 3 mm and a semi-major radius of about 5 mm to about 10 mm.

Optionally, the semi-minor radius is about 2 mm and the semi-major radius is about 7 mm.

Optionally, the seal body tapers inwardly from the inlet towards the outlet.

Optionally, a cross-sectional area of the prong outlet is smaller than a cross-sectional area of the prong inlet.

Optionally, the single sealing nasal prong is configured to provide expiratory pressure between 3.5 cmH2O and 16 cmH2O.

Optionally, the single sealing nasal prong is configured to provide expiratory pressure between 3.5 cmH2O and 20 cmH2O.

Optionally, an exterior of the seal body tapers inwardly from an inlet end toward an outlet end.

Optionally, an exterior of the seal body is outwardly curved.

Optionally, the flow rate is controlled to generate desired pressures on inspiration and expiration.

Optionally, the flow rate is lowered upon expiration to lower the expiratory pressure.

Optionally, the respiratory interface is configured such that the expiratory pressure is about 5-6 cmH2O.

Optionally, the respiratory interface is configured such that the expiratory airway pressure is about 5-8 cmH2O.

Optionally, the outlet is configured such that gases delivered front the outlet causes washout of dead space gases through the unsealed nare.

Optionally, the single nasal prong is interchangeable between nares.

Optionally, the respiratory interface further comprises one or more sliding members that allows prong adjustment independently from headstrap adjustment.

Optionally, the respiratory interface further comprises a conduit configured to deliver gases directly to the single sealing nasal prong without passing through another component.

Optionally, cross section of the prong inlet is substantially similar to a cross section of the conduit outlet.

Optionally, a cross section of the inlet is substantially similar to a cross section of the conduit proximal to the patient.

Optionally, a gases path from the conduit to the prong outlet is substantially linear.

Optionally, the single sealing nasal prong and the conduit form a continuous gases pathway.

Optionally, the single sealing nasal prong and the conduit form a direct fluid coupling.

There is provided a single sealing nasal prong comprising:
an inlet configured to receive gases;
an outlet configured to supply the gases to the patient, the outlet having a generally oval cross-section;
a seal body having a wall defining an exterior of the single sealing nasal prong, the exterior of the single sealing nasal prong being outwardly curved and tapering inwardly from an inlet end toward an outlet end;
the wall defining a gases passage between the inlet and the outlet;
wherein gases flowing through the gases passage causes the exterior of the single sealing nasal prong to seal with one of the nares of a patient.

Optionally, the other nostril is left

Optionally, a cross-sectional area of the prong outlet is smaller than a cross-sectional area of the prong inlet.

Optionally, the seal body and the outlet of the single sealing nasal prong are arranged such that one of the patient's nares is substantially sealed and gases are supplied to that nare from the outlet while the other of the patient's nares is unsealed and is free from direct gases supply from the outlet.

Optionally, the seal body comprises a wall defining the inlet, the outlet and the seal body.

Optionally, the wall thickness is about 0.7 mm to about 0.8 mm.

Optionally, the prong has a sealing portion and a coupling portion.

Optionally, the coupling portion is more rigid than the sealing portion.

Optionally, the coupling portion has a lip engaged with, or engageable with, the conduit cuff.

Optionally, the lip has an undercut to receive the groove from the conduit part.

Optionally, the prong outlet is positioned relative to the prong body such that the prong can be adjusted to seal in either one of the nares providing therapy to the user.

Optionally, the single sealing nasal prong is interchangeable between the user's nares.

Optionally, the single sealing nasal prong is configured to provide expiratory pressure between 3.5 cmH2O and 16 cmH2O.

Optionally, a cross section of the prong inlet is substantially similar to a cross section of the conduit outlet.

Optionally, a ratio of the length of the single sealing nasal prong to the width of the single sealing nasal prong is about 1.52 to about 1.59.

Optionally, a ratio of a cross sectional area of the prong outlet to a cross sectional area of a conduit outlet 305 is about 0.72.

Optionally, a ratio of a cross sectional area of the prong outlet to a cross-sectional area of a base of the seal is about 0.33.

Optionally, the prong outlet is generally centred in conduit outlet.

Optionally, the single sealing nasal prong comprises a supple sealing portion.

Optionally, the single sealing nasal prong comprises a rigid coupling portion.

Optionally, a wall thickness of the rigid coupling portion is about 1.5 mm to about 4 mm.

Optionally, the prong outlet is centred in the prong body in a horizontal orientation such that the prong can be adjusted to seal in either one of the nares providing therapy to the user.

Optionally, the prong outlet is centred in the prong body in both a horizontal and vertical orientation such that the prong can be inserted independently of vertical orientation.

Optionally, the seal body is substantially symmetrical about a vertical axis.

Optionally, the seal body is substantially symmetrical about a horizontal axis.

There is provided a respiratory interface for providing a gases flow at a flow rate to clear dead space, the respiratory interface consisting of:

There is provided a respiratory interface for delivering gases to a single nare of a patient, the respiratory interface comprising:

a gases delivery assembly, the gases delivery assembly consisting of:

only a single sealing nasal prong having a seal body configured to seal with one of the nares of a patient, an inlet configured to receive gases, and an outlet configured to supply the gases to the patient;

a conduit directly coupled to the single sealing nasal prong and in fluid communication with the single sealing nasal prong, and headgear connected to, or connectable to, the gases delivery assembly.

The gas delivery assembly further includes a support, the support comprising a pair of opposed clips to connect to corresponding clips attached to the headgear.

Advantageously, the technology as disclosed herein provides for a single nasal prong gases delivery member to deliver a gases therapy to a patient. The single nasal prong can be incorporated as part of a respiratory interface which can be worn by, or is supported upon, a patient.

The single nasal prong may be of a sealing or partially sealing configuration with the patient or the nare to which the nasal prong is to be associated with.

Whether the nasal prong should be a sealing or partially sealing configuration may depend upon a gases therapy which is intended to be delivered to the patient. The extent of sealing or partial sealing may depend upon other patient comfort features which may be provisioned as part of the nasal prong design or shape or other comfort or fit or therapy type characteristics. The prong provides some sealing to increase expiratory pressure as compared to unsealed prongs.

A respiratory interface for delivering gases to a single nare of a patient. The respiratory interface comprising one or a pair of side arms which may be integral with, attachable to, or removably connectable with, a headgear member. The respiratory interface further comprising a frame or bridging member to locate or support a single nasal prong. The frame or bridging member to be substantially locatable in a region beneath the patient's septum, or substantially provided so as to provide for the single nasal prong to be, operatively, provisioned to deliver gases to a nare of a patient.

The frame or bridging member configured to allow for the translation, rotation or other positioning of said single nasal prong relative to the patient's nare or nares, such that said single nasal prong can be adjustably locatable about said frame or bridging member so as to be positioned for delivery of gases to a single nare, or positioned as to be moveable from one of said patient's nares to the other of said patient's nares.

The single nasal prong may be translated along or about said frame or bridging member, or may be rotatable with respect to said frame or bridging member, so as to adjust the orientation of said nasal prong with respect to the patient and each of the patient's nares.

A respiratory interface comprising a base frame and a nasal prong (and optionally a headgear or a connectable or attachable headgear), wherein said nasal prong is laterally adjustable with respect to said base frame.

A method of configuring the output location of gases from a respiratory interface so as to provide for a supply of gases to a patient, the output provided by a gases delivery member in the form of a nasal prong, wherein said nasal prong is adjustable between a substantially left and a substantially right position with respect to a patient's nares, and relative in location to the remainder of a respiratory interface to which it is in fluid communication.

In some configurations, a respiratory interface comprises a single sealing nasal prong the single sealing nasal prong comprises a seal body configured to seal with one of the nares of a patient. The seal body may have opposing front and rear surfaces, and opposing left and right surfaces. The opposing front and rear surfaces may be substantially symmetrical to each other. When viewed from the top, the opposing front and rear surfaces may be symmetrical about a vertical plane. The single sealing nasal prong 2 may have the inlet configured to receive gases and the outlet configured to supply the gases to the patient. The inlet of the prong may be distal to the nostril and the outlet may be proximal when the prong is positioned in an operational position. The outlet may be located in a generally central location between the left and right surfaces such that the single sealing nasal prong can seal either one of the patient's nares. The central location of the single sealing nasal prong may be a location in which the centre of the outlet is equidistant from an outer circumferential surface of the prong. The outer circumferential surface may be considered at the widest circumferential region of the prong. Explained another way the outlet of the prong may be in the centre of the outer circumferential surface of the prong body when viewed from the top. The outlet may be positioned such that the prong may be symmetrical about at least two perpendicular vertical planes passing through the prong.

The location of the prong outlet may allow the single sealing nasal prong to be used independently of nostril orientation and may allow the prong to seal with either nostril. Human nostrils are angled toward each other and the current prong may be shaped and configured to seal with either nostril. The seal body and the outlet of the single sealing nasal prong may be arranged such that one of the patient's nares is substantially sealed and gases are supplied to that nare from the outlet while the other of the patient's nares is unsealed and is free from direct gases supply from the outlet or gases supply from a respiratory system to which the respiratory interface is part of. The outlet being centrally located helps to allow the prong to engage and seal against either the left or right nostril of the user. The prong may be shaped to fit into and substantially occlude either the right or left nostril of the user. For example, the prong can be positioned or located on the patient's face in two different orientations. That is, the interface could itself be rotated 180 degrees and still appropriately fit the patient for suitable prong engagement with a patient's nare. The central prong outlet location can also allow the interface to be suitably fitted for engagement in or with the nare when rotated about 180 degrees and as such can be considered to be orientation-independent when being positioned on the patient's face, provided the sliding member or members (e.g. item 501, 1501) extend in a substantially horizontal manner, or plane, across the face. In some configurations, the prong may be configured to allow the interface to be suitably fitted for engagement in or with the nare when rotated about 180 degrees and as such can be considered to be orientation-independent when being positioned on the patient's face while remaining attached to a support (e.g. support 500) or without being disconnected, detached or decoupled from a support (e.g. support 500). In some configurations, the prong or interface may be configured to allow the prong to be interchangeably fitted in or with a left or right nare of a patient while allowing the prong to remain attached to a support (e.g. support 500) or without being detached from a support (e.g. support 500), for example the prong is translatable relative to the support or if the prong is located in a fixed position relative to the support, the interface can be flipped to position the prong in or with the desired nare.

The respiratory interface as described herein may comprise a conduit to transport gases to a prong. The conduit may be an unheated, breathable conduit. The conduit may allow some water vapour to escape through the walls of the conduit. The breathable conduit may allow excess water vapour to escape from the gases flow to prevent condensation within the conduit. The conduit may comprise a breathable wall or may comprise breathable sections within the wall of the conduit.

In an alternative configuration the conduit may comprise a heater wire positioned within the conduit. The heater wire may be located in the lumen of the conduit or alternatively may be integrated into the wall of the conduit. The heater wire is configured to heat the gases within the conduit.

In one aspect, there is provided a respiratory interface for providing gases to a user, the respiratory interface comprising:

a single nasal prong, the single nasal prong comprising a seal body configured to seal with one of the nostrils (i.e. nares) of the user, the seal body comprising an arcuate wall defining a gases passage, an inlet configured to receive gases into the seal body, an outlet configured to supply gases to the nostril of the user, the inlet and the outlet defined in the seal body, the outlet located in a central location on the seal body when viewed from the top of the interface.

The respiratory interface comprises a headgear, the headgear configured to mount the interface on a user's head in an operation position, and the respiratory interface comprises a gases supply conduit in fluid communication with the single nasal prong to provide gases to the prong. The operation position of the interface is when the single prong is inserted into a nostril of the user.

The outlet located in a central location relative to the outer profile of the prong when viewed from the top.

The outlet is positioned in a central location relative to a left surface, a right surface, front surface and rear surface of the seal body.

The outlet is symmetrical about a vertical plane extending from front to back of the prong, and extending through the outlet. The outlet is symmetrical about a vertical plane extending from left to right of the prong and extending through the outlet.

The outlet may be symmetrical about a vertical and a horizontal axis of the prong.

The outlet being centrally located allows the prong to be independent of nostril directionality or orientation. The outlet being centrally located on the seal body allows the prong to be used with a left nostril or right nostril of the user. As noted previously, the prong can be positioned or located on the patient's face in two different orientations, That is, the interface could itself be rotated 180 degrees and still appropriately fit the patient for suitable prong engagement with a patient's nare.

The arcuate wall comprises a supple region and a stiff region, the supple region extending away from the stiff region and the supple region of the arcuate wall configured to flex or elastically deform to conform to a user's nostril to form a seal with the nostril.

The respiratory interface comprises a cuff and the prong being connected to the cuff.

The respiratory interface comprising a conduit and a conduit connector, the conduit being coupled to the conduit connector, the cuff connected to the conduit connector and the prong.

The cuff is configured to facilitate fluid coupling between the conduit connector and the prong such that gases flow from the conduit to the prong through the conduit connector.

The respiratory interface comprises a support, the prong being supported by the support configured to allow the prong to translate along the support relative to the nostrils of the user.

The support comprises one or more sliding members and a clip arranged at either end of the sliding member. The headgear clip configured to engage with a corresponding clip coupled to a headgear strap. The headgear strap is used to mount the interface on a user's face in an operative position. Alternatively, the support comprises one or more sliding members and the headgear strap may be directly attached or connected to an end of the sliding member. For example, the headgear strap may be welded or adhered or otherwise attached directly to the sliding member, or threaded directly into the buckle without clips.

The one or more sliding members extend laterally. In one form, the support comprises a pair of sliding members, the pair of sliding members arranged parallel to each other. The sliding members terminate in a headgear clip at opposing ends of the sliding members.

The cuff is engaged to the support and moveable along the support relative to the support. In use, the cuff is moveable relative to the nose and/or face of the user.

In one aspect there is provided a respiratory interface comprising:

a single nasal prong configured to engage and at least partially occlude a nostril of a user, a conduit in fluid communication with the single nasal prong to provide respiratory gases to the single nasal prong, a cuff, the cuff connected to the prong and connected to the conduit, a headgear configured to mount the interface onto the head of the patient, wherein the interface provides respiratory gases at a flow rate that causes dead space clearance within the user's airways and creates an expiratory airway pressure within the airways of the patient.

The respiratory interface is configured to provide respiratory gases at a flow rate where the respiratory gases flush carbon dioxide or expired gases from within the airways of the patient.

The respiratory interface is configured to provide respiratory gases at a flow rate such that the respiratory gases reach the nasopharynx and/or the oropharynx. The flow of respiratory gases being delivered through a single nostril while the other nostril remains unoccluded and provides an expiratory gases pathway to allow expired gases to escape as they are flushed out.

The respiratory interface is configured to provide gases at a flow rate that equals or exceeds peak inspiratory demand. Alternatively, the respiratory interface provides gases at a flow rate that is less than the peak inspiratory demand of the user, while still providing flushing, dead space clearance and some expiratory airway pressure.

In another aspect, there is provided a medical tube component comprising a conduit connector and a cuff, said conduit connector comprising a thread, said thread comprising at least one region of discontinuity, and wherein said cuff comprises at least one protrusion configured to interact with said region of discontinuity when brought into engagement with said conduit in a first direction, and said at least one protrusion is configured to engage with at least a portion of said thread beyond, or away from, said region of discontinuity when brought into engagement with said thread in a second direction.

The first direction may be provided by application of a first force or first movement.

The said second direction may be provided by application of a second force or second movement.

The first and second directions may be different.

The first and second directions may be substantially transverse with respect to each other.

The first direction may be substantially aligned with an axial direction of the conduit connector.

The second direction may be substantially transverse to said axial direction of the conduit connector.

The second direction may be a rotation for engaging said at least one protrusion upon said thread.

The second direction may be an axial rotation of the cuff with respect to the axial direction of said conduit.

The protrusion may engage or becomes engaged with said thread once moved in said second direction.

The protrusion may be configured to engage with said thread to at least partially restrain or lock the cuff to or upon the conduit connector upon application of a force or movement in the second direction.

Once engaged, the protrusion may substantially restrain or inhibit relative axial movement or displacement of the cuff and conduit connector with respect to each other.

The cuff may be rotated greater than about 5° from said region of discontinuity.

The cuff may be rotated greater than about 10° from said region of discontinuity.

The cuff may be rotated from about 10° to about 160° from said region of discontinuity.

The cuff may be rotated about 90° from said region of discontinuity.

The cuff may be rotated greater than about 170° from said region of discontinuity.

An opening of said cuff may be of an inner diameter that is greater than an outer diameter of said conduit connector.

The cuff may comprise a plurality of said protrusions.

The cuff may comprise two or more protrusions.

The thread may comprise of a plurality of said discontinuous regions.

The thread may comprise two or more, or a plurality of said discontinuous regions.

The number of discontinuous regions and the number of protrusions may be matched or equal to each other.

The cuff may be rotated about 90° from said discontinuous regions.

A nasal prong may be connectable to said conduit connector.

A nasal prong may be connected to said conduit connector.

The cuff may abut or contact a portion of said nasal prong when said cuff is substantially engaged with said thread.

The nasal prong or a part thereof may be formed of a relatively soft or substantially compliant material.

The cuff may at least partially compress a portion of said nasal prong when said cuff is engaged with said thread.

A portion of said nasal prong may be at least partially compressed upon engagement of said cuff with said thread.

A friction-fit type engagement of said cuff with said nasal prong may be provided upon engagement of said cuff with said thread.

The cuff may be removably attached to said conduit connector.

The cuff may be detachable from said conduit connector.

The cuff may be engageable with a first thread of said conduit connector.

The cuff may be engageable with a first thread portion and a second thread portion of said conduit connector.

The protrusion(s) may engage said thread portion distal from a terminal end of the conduit connector.

The protrusion(s) may engage with a portion of said thread proximal to an end of the conduit connector connectable with the nasal prong.

The protrusion(s) may engage a portion of the thread closest to, or substantially adjacent to, the nasal prong such that said conduit is thread mountable or thread connectable with the conduit connector threads adjacent the cuff.

The protrusion may be a tab.

The protrusion may be a substantially radially inwardly extending projection.

The discontinuity region may provide for a predetermined width of discontinuity sufficient to receive or accommodate a width of a protrusion, such that the width of the protrusion is less than the width of the discontinuity.

The thread may be a substantially helical thread.

A conduit may be substantially engaged with said conduit connector by rotating or winding of said conduit upon said thread.

The conduit may be substantially engaged with said conduit connector subsequent to said cuff being brought into engagement with said thread.

The protrusion once engaged with said thread, may be brought into thread engagement by locating of said protrusion to within a region between adjacent winds of said thread, or a region adjacent to a wind of said thread and a flange of said conduit connector.

The flange may be a stopping flange.

The flange may act as a barrier to the cuff being overwound or for the cuff to be brought to bear upon said flange.

The cuff may provide for a shank portion upon which said protrusion(s) are located radially inwardly thereof of an inner wall of said cuff, said shank portion being of a longitudinal length sufficient to locate said protrusion(s) in a region adjacent to a wind of said thread or within a region between adjacent winds of said thread.

The cuff may be held in a predetermined orientation or position by a compression fit between each of:

i) a terminal end of said conduit once said conduit is substantially engaged with said thread of said conduit connector, and ii) by a base of said nasal prong once said nasal prong is substantially engaged with said cuff.

There is provided a strap attachment for terminating a headstrap, the strap attachment comprising: a substantially hollow body comprising of internal walls to define a channel therebetween, the substantially hollow body comprising of a mouth end and a terminal end, the mouth end defining an opening into the channel and for receiving a free end of a headstrap, and the terminal end defining an end of the channel substantially distal of the mouth end, the channel providing for a pathway extending between the mouth end and the terminal end through which said headstrap is to be threaded, at least one first projection extending from a base attached to said internal wall to a tip in a direction substantially towards an opposing internal wall or into the channel defined by at least an opposing side wall, wherein the tip is configured to engage at least a portion or a surface of a headstrap to be received within said channel, said tip configured to substantially permit the headstrap to be threaded in a direction into the channel and along the pathway from the mouth end to the terminal end and said tip configured to substantially resist the headstrap from being removed or withdrawn from the channel in a direction extending from the terminal end towards the mouth end of said substantially hollow body, and wherein the tip of the at least one first projection is disposed so as to be spaced off from said opposing internal wall by a pre-determined distance, said pre-determined distance being a function of a thickness of a headstrap to be received within the channel.

Optionally, a ratio of pre-determined distance to the thickness of the headstrap ranges from 1:4 to 1:1.

Optionally, the pre-determined distance is less than the thickness of the headstrap to be received within the channel.

Optionally, the tip comprises a substantially pointed end or an apex.

Optionally, the at least one first projection comprises a leading side and a trailing side, the leading side and trailing side extending from the base to the tip of the at least one first projection, and positioned in a direction substantially along the pathway from the mouth end to the terminal end.

Optionally, the leading side and trailing side are configured such that the at least one first projection forms a substantially hook shaped projection.

Optionally, the trailing side comprises an acute angle with respect to the internal wall.

Optionally, the acute angle is about 40 degrees to about 80 degrees.

Optionally, further comprising at least one second projection, extending from the opposing internal wall into the channel.

Optionally, further comprising a plurality of first projections forming a first projection set, and a plurality of second projections forming a second projection set.

Optionally, projections of the first projection set are substantially aligned with projections of the second projection set.

Optionally, wherein projections of the first projection set are substantially non-aligned or offset with projections of the second projection set.

Optionally, projections of the first projection set and projections of the second projection set are substantially laterally offset from each other with respect to a lateral direction across the width of said channel, said width direction being substantially perpendicular to an insertion direction of said headstrap.

Optionally, projections of the first projection set and projections of the second projection set are substantially alternating in extend of length.

Optionally, the projections of the first and second projection sets form teeth.

Optionally, the mouth end comprises lead-in features.

Optionally, said lead-in features comprise substantially rounded lips for accommodating or receiving said headstrap.

Optionally, said lead-in features provide a guide or guides for receiving said headstrap and directing said headstrap into said channel.

Optionally, said terminal end is defined by an occlusion of the channel.

Optionally, said terminal end is a closed or blocked end of said channel, or is a substantially closed end of said channel.

Optionally, said terminal end comprises one or a plurality of protrusions which extend into or substantially across said channel, from either the internal wall or the opposing internal wall.

Optionally, protrusions extending from the internal wall are substantially aligned with protrusions extending from the opposing internal wall of said channel.

Optionally, protrusions extending from the internal wall are substantially non-aligned with protrusions extending from the opposing internal wall of said channel.

Optionally, the one or more protrusions are substantially aligned with opposing projections of the first projection set and/or second projection set.

Optionally, the protrusions are offset from the first projection set and/or the second projection set in a direction to which the channel is configured to receive the headstrap.

There is provided a strap attachment for terminating a headstrap, the strap attachment comprising: two or more walls defining a channel, the channel configured to receive an end of a headstrap, a first projection set comprising at least one first projection extending from a first wall of the strap attachment and substantially towards or into the channel, the first projection comprising a distal end configured to engage a portion of the headstrap and prevent the end of the headstrap received in the channel, from being removed from the channel, wherein the distal end of the first projection is spaced at a distance from a second opposing wall of the channel, and wherein the distance is provided as a function of a thickness of the headstrap to be received in the channel.

Optionally, a ratio of the distance to the thickness of the headstrap ranges from 1:4 to 1:1.

Optionally, the distance is less than the thickness of the headstrap to be received in the channel.

Optionally, the distal end of the first projection comprises a substantially pointed end or an apex.

Optionally, the at least one first projection comprises a leading side and a trailing side positioned in a direction substantially along which the channel is configured to receive the headstrap, and wherein the leading side and trailing side are configured such that the at least one first projection forms a substantially hook shaped projection.

Optionally, the trailing side comprises an acute angle with respect to the first wall of the strap attachment.

Optionally, the acute angle is about 40 degrees to about 80 degrees

Optionally, further comprising a second projection set, the second projection set comprising at least one second projection.

Optionally, the second projection set is configured to extend from the second opposing wall of the strap attachment into the channel.

Optionally, the first projection set and the second projection set comprise a plurality of projections, optionally wherein the projections are teeth.

Optionally, projections of the first projection set are substantially aligned with projections of the second projection set.

Optionally, projections of the first projection set are substantially non-aligned or offset with projections of the second projection set.

Optionally, projections of the first projection set and projections of the second projection set are substantially laterally offset from each other with respect to a lateral direction across the width of said channel, said width direction being substantially perpendicular to an insertion direction of said headstrap.

Optionally, projections of the first projection set and projections of the second projection set are substantially alternating in extend of length.

Optionally, a mouth defines an entry into said channel.

Optionally, said mouth comprises lead-in features.

Optionally, said lead-in features comprise substantially rounded lips for accommodating or receiving said headstrap.

Optionally, said lead-in features provide a guide or guides for receiving said headstrap and directing said headstrap into said channel.

Optionally, at an opposing end of said channel from said mouth, said channel terminates at a terminal end.

Optionally, said terminal end is defined by an occlusion of the channel.

Optionally, said terminal end comprises one or a plurality of protrusions which extend into or substantially across said channel.

Optionally, said terminal end is a closed or blocked end of said channel, or is a substantially closed end of said channel.

Optionally, further comprising one or more protrusions extending from the first wall and/or the second opposing wall, such that said one or more protrusions extend into or substantially across said channel.

Optionally, protrusions extending from the first wall are substantially aligned with protrusions extending from the second opposing wall of said channel.

Optionally, protrusions extending from the first wall are substantially non-aligned with protrusions extending from the second opposing wall of said channel.

Optionally, the one or more protrusions are substantially aligned with opposing projections of the first projection set and/or second projection set.

Optionally, the protrusions are offset from the first projection set and/or the second projection set in a direction to which the channel is configured to receive the headstrap.

There is provided a strap attachment for terminating a headstrap, the strap attachment comprising: two or more walls defining a channel, the channel configured to receive an end of a headstrap, a first projection set comprising at least one first projection, a second projection set comprising at least one second projection, and wherein the first projection set and the second projection set extend from opposing walls of the strap attachment into the channel, wherein the at least one first projection of the first projection set and the at least one second projection of the second projection set comprise distal ends configured to engage a portion of a headstrap and prevent removal of an end of the headstrap received in the channel, and wherein the distal ends of the at least one first and second projections taper to, or comprise of, a pointed end or apex.

Optionally, the distal ends of the first and second projection sets are spaced apart at a first distance along a plane parallel to a plane extending between and through the ends of the channel of the strap attachment.

Optionally, the first distance comprises about 4-8 mm

Optionally, the first projection set extends into the channel from a wall proximal to an end of the strap attachment through which the end of the headstrap is to be received.

Optionally, the ends of the first and second projection sets are spaced apart at a second distance along a plane transverse to a plane extending between and through the ends of the channel of the strap attachment.

Optionally, the second distance comprises about 0.5 mm to about 2 mm.

Optionally, a height of the second projection set between the respective channel wall and distal end is less than a height of the first projection set between the respective channel wall and distal end.

Optionally, a distance from the distal end of the first projection set and/or second projection set to the respective opposing wall is provided as a function of a thickness of the headstrap.

Optionally, the distance is less than the thickness of a headstrap that is to be received within the channel of the strap attachment.

Optionally, a ratio of the distance to the thickness of the headstrap ranges from 1:4 to 1:1.

Optionally, a distance from the distal end of the first projection set to the opposing wall is about 1 mm to about 1.5 mm.

Optionally, a distance from the end of the second projection set to the opposing wall is about 1 mm to about 2 mm.

Optionally, projections of the first projection set are substantially aligned with projections of the second projection set.

Optionally, projections of the first projection set are substantially non-aligned or offset with projections of the second projection set.

Optionally, projections of the first projection set and projections of the second projection set are substantially laterally offset from each other with respect to a lateral direction across the width of said channel, said width direction being substantially perpendicular to an insertion direction of said headstrap.

Optionally, projections of the first projection set and projections of the second projection set are substantially alternating in extend of length.

Optionally, a mouth defines an entry into said channel.

Optionally, said mouth comprises lead-in features.

Optionally, said lead-in features comprise substantially rounded lips for accommodating or receiving said headstrap.

Optionally, said lead-in features provide a guide or guides for receiving said headstrap and directing said headstrap into said channel.

Optionally, at an opposing end of said channel from said mouth, said channel terminates at a terminal end.

Optionally, said terminal end is defined by an occlusion of the channel.

Optionally, said terminal end comprises one or a plurality of protrusions which extend into or substantially across said channel.

Optionally, said terminal end is a closed or blocked end of said channel, or is a substantially closed end of said channel.

Optionally, further comprising one or more protrusions extending from the first wall and/or the second opposing wall, such that said one or more protrusions extend into or substantially across said channel.

Optionally, protrusions extending from the first wall are substantially aligned with protrusions extending from the second opposing wall of said channel.

Optionally, protrusions extending from the first wall are substantially non-aligned with protrusions extending from the second opposing wall of said channel.

Optionally, the one or more protrusions are substantially aligned with opposing projections of the first projection set and/or second projection set.

Optionally, the protrusions are offset from the first projection set and/or the second projection set in a direction to which the channel is configured to receive the headstrap.

There is provided a strap attachment for terminating a headstrap, the strap attachment comprising: two or more walls defining a channel, the channel configured to receive an end of a headstrap, a first projection set comprising at least one first projection, a second projection set comprising at least one second projection, and wherein the first and second projection sets define a curved or tortuous path through which the end of the headstrap is to be received, wherein the at least one first projection of the first projection set and the at least one second projection of the second projection set comprise a distal end to engage a portion of the headstrap and prevent removal of an end of the headstrap received in the channel, and wherein the distal ends of the at least one first and second projections taper to, or comprise of, a pointed end or apex.

Optionally, the at least one first projection extends from a wall of the strap attachment into the channel, and the at least one second projection extends from an opposing wall of the strap attachment into the channel.

Optionally, the one or more projections of the first and second projection sets are offset relative to one another along at least one plane.

Optionally, a first plane comprises a plane parallel to a plane extending between and through ends of the channel of the strap attachment.

Optionally, a second plane comprises a plane transverse to a plane extending between and through ends of the channel of the strap attachment.

Optionally, the at least one first projection and the at least one second projection comprise a plurality of projections.

Optionally, the projections are teeth.

Optionally, projections of the first projection set are substantially aligned with projections of the second projection set.

Optionally, projections of the first projection set are substantially non-aligned or offset with projections of the second projection set.

Optionally, projections of the first projection set and projections of the second projection set are substantially laterally offset from each other with respect to a lateral direction across the width of said channel, said width direction being substantially perpendicular to an insertion direction of said headstrap.

Optionally, projections of the first projection set and projections of the second projection set are substantially alternating in extend of length.

Optionally, a mouth defines an entry into said channel.

Optionally, said mouth comprises lead-in features.

Optionally, said lead-in features comprise substantially rounded lips for accommodating or receiving said headstrap.

Optionally, said lead-in features provide a guide or guides for receiving said headstrap and directing said headstrap into said channel.

Optionally, at an opposing end of said channel from said mouth, said channel terminates at a terminal end.

Optionally, said terminal end is defined by an occlusion of the channel.

Optionally, said terminal end comprises one or a plurality of protrusions which extend into or substantially across said channel.

Optionally, said terminal end is a closed or blocked end of said channel, or is a substantially closed end of said channel.

Optionally, further comprising one or more protrusions extending from the first wall and/or the second opposing wall, such that said one or more protrusions extend into or substantially across said channel.

Optionally, protrusions extending from the first wall are substantially aligned with protrusions extending from the second opposing wall of said channel.

Optionally, protrusions extending from the first wall are substantially non-aligned with protrusions extending from the second opposing wall of said channel.

Optionally, the one or more protrusions are substantially aligned with opposing projections of the first projection set and/or second projection set.

Optionally, the protrusions are offset from the first projection set and/or the second projection set in a direction to which the channel is configured to receive the headstrap.

There is provided a headgear for a patient interface comprising, at least one headstrap, and at least one strap attachment according to any of the above statements, engaged with an end of the headstrap.

Optionally, the headgear is releasably attachable to a patient interface.

Optionally, the patient interface comprises a single sealing nasal prong.

Optionally, the patient interface comprises a support on which the single sealing nasal prong is slidable.

There is provided a respiratory interface for delivering gases to a single nare of a patient, the respiratory interface comprising a single sealing nasal prong having a seal body configured to seal with one of the two nares of a patient, a prong inlet configured to receive gases, and a prong outlet configured to supply the gases to the patient, a support for the single sealing nasal prong, and a conduit directly coupled to the single sealing nasal prong and in fluid communication with the single sealing nasal prong, wherein the single sealing nasal prong and/or the respiratory interface is configured to allow the prong to interchangeably seal in or with a left or right nare of the patient.

Optionally, the prong and/or respiratory interface is configured to allow the prong to interchangeably seal in or with a left or right nare of a patient while allowing the prong to remain attached to the support or without being detached from the support.

Optionally, the prong is located in a fixed position relative to the support.

Optionally, the prong is translatable relative to the support.

Optionally, the support is outside of or separate from or does not form a part of the conduit or gases being supplied to the single sealing nasal prong.

Optionally, the conduit is fluidly separated from the support, or wherein the support does not form a part of a gas path of gases being supplied to the single sealing nasal prong.

Optionally, the conduit is only in fluid communication with the single sealing nasal prong.

Optionally, the conduit comprises a single conduit.

Optionally, the respiratory interface further comprises a gases path from the conduit to the prong outlet, wherein the gases path is substantially linear.

Optionally, a conduit outlet of the conduit is directly coupled to the prong inlet of the single sealing nasal prong, and wherein the conduit outlet and the prong outlet share a substantially common substantially central axis.

Optionally, the respiratory interface further comprises a headgear removably connectable to the support.

Optionally, the respiratory interface further comprises a cuff, the single sealing nasal prong configured to couple with the cuff.

Optionally, the respiratory interface further comprises a conduit connector, the conduit configured to couple with the conduit connector.

Optionally, the conduit connector and the cuff are separate or integral components.

Optionally, the single sealing nasal prong comprises a substantially supple or substantially compliant material and the conduit connector and/or cuff comprises a substantially rigid material.

There is provided a method of providing respiratory therapy to a patient, providing a gas at substantially high flow rates to a patient via a patient interface with single sealing prong provided on a support, the single sealing prong configured to substantially seal with and deliver the gases to one of the patient's nares while the other of the patient's nares is substantially unsealed and free from the gases provided by the gases supply, adjusting the single sealing prong to substantially seal with either of the two nares of the patient based on a patient pressure.

Optionally, adjusting the single sealing prong depends on the nasal cycle of the patient.

Optionally, the patient pressure comprises the peak expiratory pressure (PEP).

Optionally, adjusting the single sealing prong comprises increasing or decreasing the PEP of the patient.

Optionally, adjusting comprises sliding and/or rotating the single sealing prong on a support.

Optionally, high flow rates comprise at least 20 L/min.

Optionally, the method further comprises humidifying the gas.

There is provided a respiratory support system, comprising a gases flow source configured to provide a gases flow at a high flow rate to a patient, and a patient interface comprising a single sealing nasal prong configured to deliver the gases flow at the high flow rate to the patient, and wherein the single sealing nasal prong is adapted to substantially seal with a single nare of two nares of the patient.

Optionally the respiratory support system further comprises a humidifier configured to heat and humidify the gases flow to be provided to the patient.

Optionally the humidifier comprises a humidification chamber removably connected to a humidifier base unit.

Optionally the humidification chamber is configured to be filled with a humidification liquid such as water for the humidification of the gases flow to the patient.

Optionally the humidification chamber comprises a heat conductive base and the humidifier base unit comprises a heater plate, and the heat conductive base allows the heating of the humidification liquid in the chamber when in contact with the heater plate of the humidifier base unit.

Optionally the flow source and humidifier base unit are integral.

Optionally, the patient interface is configured to increase expiratory pressure in the patient's airway.

Optionally, the single sealing nasal prong comprises a seal body configured to seal the single nare of a patient, the seal body having opposing front and rear surfaces, and opposing left and right surfaces, the opposing front and rear surfaces being substantially symmetrical to each other, an inlet configured to receive gases, an outlet configured to supply the gases to the patient, the outlet located in a generally central location between the left and right surfaces such that the single sealing nasal prong can seal either one of the patient's nares, and wherein the seal body and the outlet of the single sealing nasal prong are arranged such that one of the patient's nares is substantially sealed and gases are supplied to that nare from the outlet while the other of the patient's nares is unsealed and is free from direct gases supply from the outlet.

Optionally, the respiratory support system further comprises a gases delivery assembly having the single sealing nasal prong with a seal body configured to seal with the single nare of a patient, an inlet configured to receive gases, and an outlet configured to supply the gases to the patient, a conduit directly coupled to the single sealing nasal prong and in fluid communication with the single sealing nasal prong, and headgear connected to, or connectable to, the gases delivery assembly.

Optionally, the respiratory support system further comprises a gases delivery assembly, the gases delivery assembly consisting of the single sealing nasal prong having a seal body configured to seal with the single nare of a patient, an inlet configured to receive gases, and an outlet configured to supply the gases to the patient, a conduit directly coupled to the single sealing nasal prong and in fluid communication with the single sealing nasal prong, and headgear connected to, or connectable to, the gases delivery assembly.

Optionally, the respiratory support system further comprises a frameless gases delivery assembly comprising the single sealing nasal prong having a seal body configured to seal with the single nare of a patient, the single sealing nasal prong having an inlet configured to receive gases, and an outlet configured to supply the gases to the patient, a conduit in fluid communication with the single sealing nasal prong, and headgear connected to, or connectable to, the gases delivery assembly.

Optionally, the respiratory support system further comprises a respiratory interface for delivering gases to a single nare of a patient, the respiratory interface comprising the single sealing nasal prong having a seal body configured to seal with the single nare of a patient, an inlet configured to receive gases, and an outlet configured to supply the gases to the patient, and a conduit having an outlet configured to supply the gases to the single sealing nasal prong, the conduit being coupled with, or couplable with, the single sealing nasal prong such that the conduit outlet is coaxial with the single sealing nasal prong inlet.

Optionally, the respiratory support system further comprises a respiratory interface for delivering gases to a single nare of a patient, the respiratory interface comprising the single sealing nasal prong having a seal body configured to seal with the single nare of a patient, an inlet configured to receive gases, and an outlet configured to supply the gases to the patient, and an adjuster configured to allow the single sealing nasal prong to be removable from first nare and positioned in the patient's other nare to seal with the other nare without the single sealing nasal prong being detached from the respiratory interface.

Optionally, the respiratory support system further comprises a respiratory interface for delivering gases to a single nare of a patient, the respiratory interface comprising a body with a pair of side arms configured to provide stability for the interface on the cheeks of the patient, the single sealing nasal prong, a manifold having a single sided inlet to receive gases from a gas source, and an outlet that delivers gases to the single sealing nasal prong, wherein the single sealing nasal prong is arranged such that one of the patient's nares is substantially sealed and gases are supplied to that nare from the outlet while the other of the patient's nares is unsealed and is free from direct gases supply from the outlet.

Optionally, the respiratory support system further comprises a respiratory interface for delivering gases to a single nare of a patient, the respiratory interface comprising the single sealing nasal prong having a seal body configured to seal with the single nare of a patient, an inlet configured to receive gases, and an outlet configured to supply the gases to the patient, a support for the single sealing nasal prong, the single sealing nasal prong being translatable relative to the support, the single sealing nasal prong to be interchangeably received by the patient's nares, the single sealing nasal prong remaining coupled to the support, and headgear connected to, or connectable to, the support.

Optionally, the respiratory support system further comprises a respiratory interface for delivering gases to a single nare of a patient, the respiratory interface comprising the single sealing nasal prong having a seal body configured to seal with the single nare of a patient, an inlet configured to receive gases, and an outlet configured to supply the gases to the patient, and a cuff comprising a prong coupling portion, wherein the single sealing nasal prong is received by, or receivable by, the prong coupling portion of the cuff.

Optionally, the single sealing nasal prong comprises an inlet configured to receive gases, an outlet configured to supply the gases to the patient, the outlet having a generally oval cross-section, a seal body having a wall defining an exterior of the single sealing nasal prong, the exterior of the single sealing nasal prong being outwardly curved and tapering inwardly from an inlet end toward an outlet end, the wall defining a gases passage between the inlet and the outlet, wherein gases flowing through the gases passage causes the exterior of the single sealing nasal prong to seal with the single nare of a patient.

Optionally, the humidifier comprises a humidification chamber, the humidification chamber comprising a gases inlet to receive the gases flow from the gases flow source, and a gases outlet to deliver humidified gases flow to the patient interface.

Optionally, the respiratory support system further comprises an inspiratory conduit located between the humidifier and the patient interface, the inspiratory conduit configured to deliver the humidified gases flow to the patient interface.

Optionally, the inspiratory conduit is a heated inspiratory conduit.

Optionally, the respiratory support system further comprises a patient conduit located between the inspiratory conduit and the patient interface.

Optionally, the patient conduit is formed of breathable material.

Optionally, the high flow rate comprises a gases flow to be delivered to the patient of at least 20 L/min.

Optionally, the high flow rate comprises a gases flow to be delivered to the patient of up to about 70 L/min.

Optionally, the gases flow comprises a set gas flow rate.

Optionally, the respiratory support system further comprises a headgear retain the patient interface on the patient's face.

Optionally, the respiratory support system further comprises a respiratory interface for delivering gases to a single nare of a patient, the respiratory interface comprising the single sealing nasal prong further comprising an inlet configured to receive gases, an outlet configured to supply the gases to the patient, and a seal body having a wall defining an exterior of the single sealing nasal prong, the seal body and the outlet of the single sealing nasal prong being arranged such that one of the patient's nares is substantially sealed and gases are supplied to that nare from the outlet while the other of the patient's nares is unsealed and is free from direct gases supply from the outlet, and wherein the respiratory interface is configured to provide respiratory flow therapy to the patient through the single sealing nasal prong, and wherein the respiratory flow causes flushing of the airways to clear dead space within the airways.

Optionally the wall defines the inlet, the outlet and the seal body.

Optionally, a wall thickness is about 0.7 mm to about 0.8 mm.

Optionally, a cross-section of the prong outlet is generally oval.

Optionally, the cross-section of the prong outlet is elliptical.

Optionally, the cross-section of the outlet has a semi-minor radius of about 1 mm to about 3 mm and a semi-major radius of about 5 mm to about 1.0 mm.

Optionally, the semi-minor radius is about 2 mm and the semi-major radius is about 7 mm.

Optionally, the seal body tapers inwardly from the inlet towards the outlet.

Optionally, a cross-sectional area of the prong outlet is smaller than a cross-sectional area of the prong inlet.

Optionally, the single sealing nasal prong is configured to provide expiratory pressure between 3.5 cmH2O and 20 cmH2O.

Optionally, an exterior of the seal body tapers inwardly from an inlet end toward an outlet end.

Optionally, an exterior of the seal body is outwardly curved.

Optionally, the gases flow rate is controlled to generate desired pressures on patient inspiration and expiration.

Optionally, the gases flow rate is lowered upon patient expiration to lower the expiratory pressure.

Optionally, the system is configured such that the expiratory airway pressure is about 5-8 cmH2O.

Optionally, the outlet is configured such that gases delivered from the outlet causes washout of dead space gases through the unsealed nare.

Optionally, the single nasal prong is interchangeable between nares.

Optionally, the respiratory support system further comprises one or more sliding members, the sliding members configured to allow nasal prong adjustment independently from headstrap adjustment.

Optionally, the respiratory support system further comprises a conduit configured to deliver gases directly to the single sealing nasal prong without passing through another component.

Optionally, a cross section of the prong inlet is substantially similar to a cross section of the conduit outlet.

Optionally, a cross section of the inlet is substantially similar to a cross section of the conduit proximal the patient.

Optionally, a gases path from the conduit to the prong outlet is substantially linear.

Optionally, the single sealing nasal prong and the conduit form a continuous gases pathway.

Optionally, the single sealing nasal prong and the conduit form a direct fluid coupling.

There is provided a kit comprising a humidification chamber with a humidification inlet configured to couple to a flow source and a humidification outlet, an inspiratory conduit with an inspiratory conduit inlet configured to couple to the humidification outlet and an inspiratory conduit outlet, and a single sealing nasal prong configured to couple to the inspiratory conduit outlet.

Optionally, the humidification chamber is configured to be filled with a humidification liquid such as water for the humidification of the gases flow to the patient.

Optionally, the humidification chamber is removably connectable to a humidifier base unit.

Optionally the humidifier base unit is integral with the flow source.

Optionally, the humidification chamber comprises a heat conductive base and the humidifier base unit comprises a heater plate, and the heat conductive base allows the heating of the humidification liquid in the chamber when in contact with the heater plate of the humidifier base unit Optionally, the single sealing nasal prong is that of any of the aspects or embodiments described above.

Optionally, the single sealing nasal prong further comprises a patient conduit, the patient conduit comprising an inlet configured to couple to the inspiratory conduit outlet.

Optionally, the patient conduit is formed of a breathable material.

Optionally, the inspiratory conduit is heated.

Optionally, the kit further comprises a conduit clip configured to secure the inspiratory conduit to a patient or the surroundings of a patient.

Features from one or more embodiments or configurations may be combined with features of one or more other embodiments or configurations.

The term 'comprising' as used in this specification means 'consisting at least in part of'. When interpreting each statement in this specification that includes the term 'comprising', features other than that or those prefaced by the term may also be present. Related terms such as 'comprise' and 'comprises' are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

It should be understood that alternative embodiments or configurations may comprise any or all combinations of two or more of the parts, elements or features illustrated, described or referred to in this specification.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth. This invention may also be said broadly to consist in the parts, elements and features referred to or indicated in the specification of the application, individually or collectively, and any or all combinations of any two or more said parts, elements or features.

BRIEF DESCRIPTION OF THE DRAWINGS

Specific embodiments and modifications thereof will become apparent to those skilled in the art from the detailed description herein having reference to the figures that follow, of which:

FIG. 9A is an exploded view of the respiratory interface of FIG. 2.

FIG. 16 is a series of top views showing a pivotable prong,

FIG. 37 is a front view of the respiratory interface of FIG. 33.

FIG. 38 is a rear view of the respiratory interface of FIG. 33,

FIG. 47 is a front perspective view of the cuff of the respiratory interface of FIG. 33.

FIG. 48 is a rear perspective view of the cuff of FIG. 47,

FIG. 49 is a rear perspective view of the cuff of FIG. 47,

FIGS. 61A and 61B show graphs with results of testing respiratory rate comparing standard respiratory interfaces having two nasal prongs and a respiratory interface according to a configuration of the invention.

FIG. 61C shows graphs with results of testing peak expiratory flow rate comparing a left and right nare of a user with a respiratory interface according to a configuration of the invention.

FIGS. 6613 and 66C illustrate the cuff configuration of FIGS. 65, 66A and showing a protrusion width P'.

FIG. 67A illustrates a bottom view of a cuff configuration with a pair of protrusions.

FIG. 67B illustrates a bottom view of a cuff configuration provided with a notch feature.

FIG. 68 illustrates a side view of a cuff configuration with an elongated or lengthened shank being of a height S'.

FIG. 69 illustrates a conduit connector comprising of a thread with a region of discontinuity, provided with a first thread portion T'.

FIG. 70A illustrates the conduit connector of FIG. 69 indicating a region A' into which a protrusion of a cuff may become engaged therein.

FIG. 70B illustrates the conduit connector of FIG. 69 indicating a region A" into which a protrusion of a cuff may become engaged therein.

FIG. 71 illustrates a cuff connector comprising of a first thread portion T' and a second thread portion T".

FIG. 73 illustrates a front view of a sliding member provided as a pre-formed shape or bent configuration.

FIG. 74 illustrates the arrangement of FIG. 73 from a side view.

FIG. 75 illustrates a sliding member provided as a pre-formed shape or bent configuration.

FIGS. 77A, 77B and 77C illustrate perspective, front, and side views of an example embodiment of a strap attachment.

DETAILED DESCRIPTION

Figure 1A:
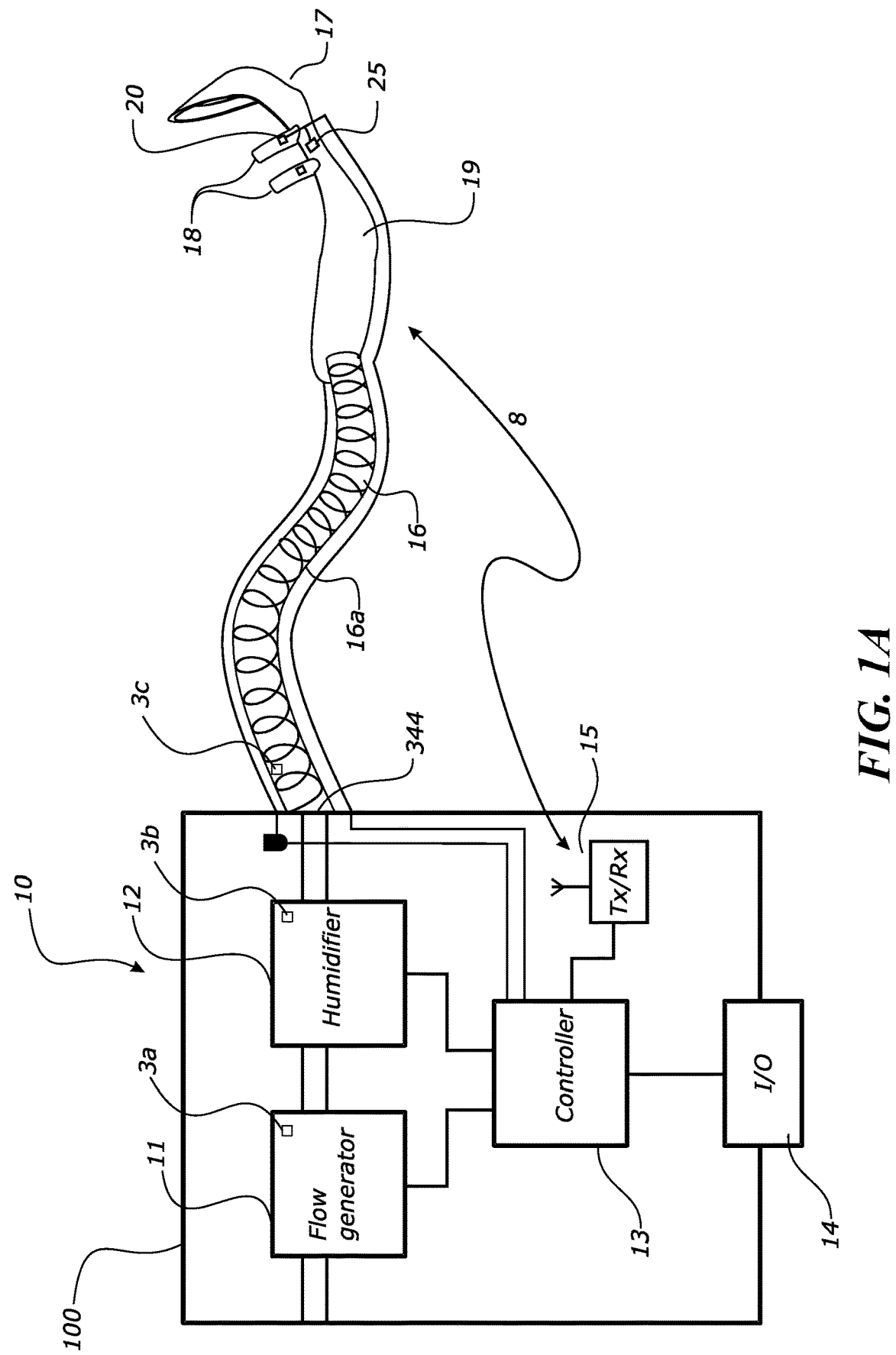
FIG. 1A shows in diagrammatic form a breathing assistance apparatus.

A breathing assistance apparatus 10 for delivering a flow of gas (which may contain one or more gases) to a patient is shown in FIG. 1. The apparatus 10 could, for example, be a CPAP apparatus or a high flow apparatus. An exemplary CPAP apparatus is described in WO 2011/056080. The contents of that specification are incorporated herein in their entirety by way of reference.

In general terms, the apparatus 10 comprises a main housing 100 that contains a flow generator 11 in the form of a motor/impeller arrangement, a humidifier 12, a controller 13, and a user I/O interface 14 (comprising, for example, a display and input device(s) such as button(s), a touch screen, or the like). The controller 13 is configured or programmed to control the components of the apparatus, including operating the flow generator 11 to create a flow of gas (gas flow) for delivery to a patient, operating the humidifier 12 to humidify and/or heat the generated gas flow, receive user input from the user interface 14 for reconfiguration and/or user-defined operation of the apparatus 10, and output information (for example on the display) to the user. The user could be a patient, healthcare professional, or anyone else interested in using the apparatus.

A patient breathing conduit 16 is connected to a gas flow output or patient outlet port 30 in the housing 100 of the breathing assistance apparatus 10, and is connected to a respiratory interface 17 (i.e. patient interface 17) such as a nasal cannula with a manifold 19 and nasal prongs 18. Additionally, or alternatively, the patient breathing conduit 16 could be connected to a face mask. Additionally, or alternatively, the patient breathing conduit could be connected to a nasal pillows mask, and/or a nasal mask, and/or a tracheostomy interface, or any other suitable type of respiratory interface. The gas flow, which may be humidified, that is generated by the breathing assistance apparatus 10 is delivered to the patient via the patient breathing conduit 16 through the respiratory interface 17. The patient breathing conduit 16 can have a heater wire 16a to heat gas flow passing through to the patient. The heater wire 16a is under the control of the controller 13. The patient breathing conduit 16 and/or respiratory interface 17 can be considered part of the breathing assistance apparatus 10, or alternatively peripheral to it. The breathing assistance apparatus 10, breathing conduit 16, and respiratory interface 17 may together form a breathing assistance system or, in some configurations, a flow therapy system.

General operation of an exemplary breathing assistance apparatus 10 will be known to those skilled in the art, and need not be described in detail here. However, in general terms, the controller 13 controls the flow generator 11 to generate a gas flow of the desired flow rate, controls one or more valves to control the mix of air and oxygen or other alternative gas, and controls the humidifier 12 to humidify the gas flow and/or heat the gas flow to an appropriate level. The gas flow is directed out through the patient breathing conduit 16 and respiratory interface 17 to the patient. The controller 13 can also control a heating element in the humidifier 12 and/or the heating element 16a in the patient breathing conduit 16 to humidify and/or heat the gas to a desired temperature that achieves a desired level of therapy and/or comfort for the patient. The controller 13 can be programmed with, or can determine, a suitable target temperature of the gas flow.

Operation sensors 3a, 3b, 3c, 20, and 25, such as flow, temperature, humidity, and/or pressure sensors, can be placed in various locations in the breathing assistance apparatus 10 and/or the patient breathing conduit 16 and/or respiratory interface 17. Output from the sensors can be received by the controller 13, to assist it to operate the breathing assistance apparatus 10 in a manner that provides optimal therapy. In some configurations, providing optimal therapy includes meeting a patient's inspiratory demand. The apparatus 10 may have a transmitter and/or receiver 15 to enable the controller 13 to receive signals 8 from the sensors and/or to control the various components of the breathing assistance apparatus 10, including but not limited to the flow generator 11, humidifier 12, and heater wire 16a, or accessories or peripherals associated with the breathing assistance apparatus 10. Additionally, or alternatively, the transmitter and/or receiver 15 may deliver data to a remote server or enable remote control of the apparatus 10.

The breathing assistance apparatus 10 may be any suitable type of apparatus to deliver respiratory flow therapy i.e. a flow of gases to a user. Respiratory flow therapy involves providing a flow of gases at a desired flow rate. The apparatus 10 is preferably a flow-controlled device that is controlled to deliver a pre-set or predetermined flow rate. The flow of gases is humidified using a humidifier in order to make the flow of gases more comfortable and tolerable for the user.

In some configurations, the apparatus 10 may deliver a high gas flow or high flow therapy (of e.g. air, oxygen, other gas mixture, or some combination thereof) to a patient to assist with breathing and/or treat breathing disorders. In some configurations, the gas is or comprises oxygen. In some configurations, the gas comprises a blend of oxygen and ambient air. As used herein, 'high flow' therapy refers to administration of gas to the airways of a patient at a relatively high flow rate that generally meets or exceeds the peak inspiratory demand of the patient, or which generally meets or exceeds the inspiratory flow of the patient. The flow rates used to achieve 'high flow' may be any of the flow rates listed below. For example, in some configurations, for an adult patient 'high flow therapy' may refer to the delivery of gases to a patient at a flow rate of greater than or equal to about 10 litres per minute (10 LPM), such as between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, car between about 45 LPM and about 65 LPM, or between about 50 LPM and about 60 LPM. In some configurations, for a neonatal, infant, or child patient 'high flow therapy' may refer to the delivery of gases to a patient at a flow rate of greater than 1 LPM, such as between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and 25 LPM. A high flow therapy apparatus with an adult patient, a neonatal, infant, or child patient, may deliver gases to the patient at a flow rate of between about 1 LPM and about 100 LPM, or at a flow rate in any of the sub-ranges outlined above. In some instances, neonates (i.e. infants) can be provided with a gas flow rate of 2 L per min per kg based on the mass of the neonate. Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

During high flow therapy the delivered gas flow may generally meet or exceed the patient's inspiratory demand, which may increase oxygenation of the patient and/or reduce the work of breathing. Additionally, high flow therapy may generate a flushing effect in the nasopharynx such that the anatomical deadspace of the upper airways is flushed by the high incoming gas flows. This creates a reservoir of fresh gas available for each and every breath, while minimising re-breathing of carbon dioxide, nitrogen, etc.

An alternative form breathing assistance apparatus may be a standalone humidifier apparatus comprising a main housing and a humidifier 12. A stand-alone humidifier apparatus comprises a base unit including a heater plate and receptacle for a humidification chamber. A humidification chamber having a conductive base is also configured to hold a volume of humidification fluid e.g. water can be removably positioned on the humidifier apparatus, such that the conductive base of the humidification chamber is brought into contact with the heater plate. The heater plate heats the contents of the humidification chamber to humidify gases as they pass through the humidification chamber. The heater plate is controlled based on one or more sensors incorporated in the humidifier. The humidifier connects to a conduit that transports the humidified gases. The conduit includes a heater wire that extends the length of the conduit. The conduit may also include a sensor at the end of the conduit that is used in feedback control of at least the heater wire in the conduit and may also be used in controlling the heater plate operation. The stand-alone humidifier can be used with any suitable gases flow source e.g. a wall gases source, a ventilator or compressed gases. An exemplary standalone humidifier apparatus is described in WO 2015/038013. The contents of that specification are incorporated herein in their entirety by way of reference. The respiratory interface described herein can be used with a stand-alone humidifier.

The respiratory interface 17 may be a non-sealing interface to prevent barotrauma (e.g. tissue damage to the kings or other organs of the respiratory system due to difference in pressure relative to the atmosphere). The respiratory interface may be a nasal cannula with a manifold and nasal prongs, and/or a face mask, and/or a nasal pillows mask, and/or a nasal mask, and/or a tracheostomy interface, or any other suitable type of respiratory interface (i.e. patient interface).

As described below, the breathing assistance apparatus 10 has various features to assist with the functioning, use, and/or configuration of the breathing assistance apparatus 10.

The description below relates to a respiratory interface that can be used with a breathing assistance apparatus as described earlier to provide respiratory. The current respiratory interface can be used on neonates, children or adults. The prong can be sized for the different patient populations.

The respiratory interface described can be used for treating a number of different patient groups that require respiratory support e.g. COPD sufferers, people with acute respiratory illnesses etc. The respiratory interface can be used in hospitals or for in home care. The respiratory interface as described herein can be used to deliver respiratory flow rates that may be within the range of the high flow therapy as described earlier.

The various configurations of a respiratory interface described herein deliver gases and/or are for providing gas flow to a patient. The gases may be humidified gases or gases that have not been humidified. Further, each of the configurations described herein are also suitable for providing fluids comprising a mixture of gases and liquid(s) to a patient.

The various configurations of the respiratory interface are used to deliver respiratory gases to a user e.g. a patient. Examples of respiratory gases may be air, oxygen or a mixture of gases.

The various configurations of respiratory interface as described herein is used to deliver respiratory flow of gases to a patient. The respiratory flow rate may be similar to a flow rate as described earlier as high flow therapy i.e. the magnitude of the respiratory flow of gases delivered by the interface described herein may in the range as described with reference to "high flow therapy" or "nasal high flow". The respiratory interface as described herein may provide gases at a flow rate that equals or exceeds a user's peak inspiratory demand, thereby reducing or preventing entrainment of ambient air. Alternatively, the various configurations of respiratory interface as described herein can be used to deliver respiratory flow rates having a magnitude as described above but may not exceed peak inspiratory demand or may entrain some ambient air. The respiratory flow of gases delivered by the respiratory interface described herein may or may not be humidified.

The respiratory interface described herein can be used to provide a flow of gases similar to the flow rates as described earlier as "high flow therapy" due to one side (i.e. one nostril) being unsealed and the other nostril being sealed. The unsealed nostril reduces the chance of barotrauma in the patient (i.e. user) since there is one un-occluded airway, which allows a user to expire and/or provide enough leak to prevent barotrauma.

In the following description, proximal refers to being proximal to the patient's nostril, when in use, and distal refers to being distal to the patient's nostril, when in use.

The following is a general description of features of respiratory interfaces (i.e. patient interfaces) of the present disclosure for delivering gases to a single nare of a patient.

With reference to FIGS. 2 to 16, a first configuration of a respiratory interface 100 for delivering gases to a single nare of a patient will now be described. FIGS. 2 to 8 show various views of an assembled respiratory interface 100 and FIG. 9A shows an exploded respiratory interface 100. The respiratory interface 100 comprises a gases delivery assembly including a prong 200, a conduit 300, a conduit connector 400, and a support 500, Each of those components and their interaction with each other will be described in more detail below.

In the illustrated configuration, the prong is a single sealing nasal prong 200. The single nasal prong is interchangeable between nares such that it can engage either nare and seal with either of the nares. The single sealing prong substantially seals (i.e. substantially occludes) one nare (i.e. nostril) of a user when the respiratory interface is in an operative position.

Figure 10A:
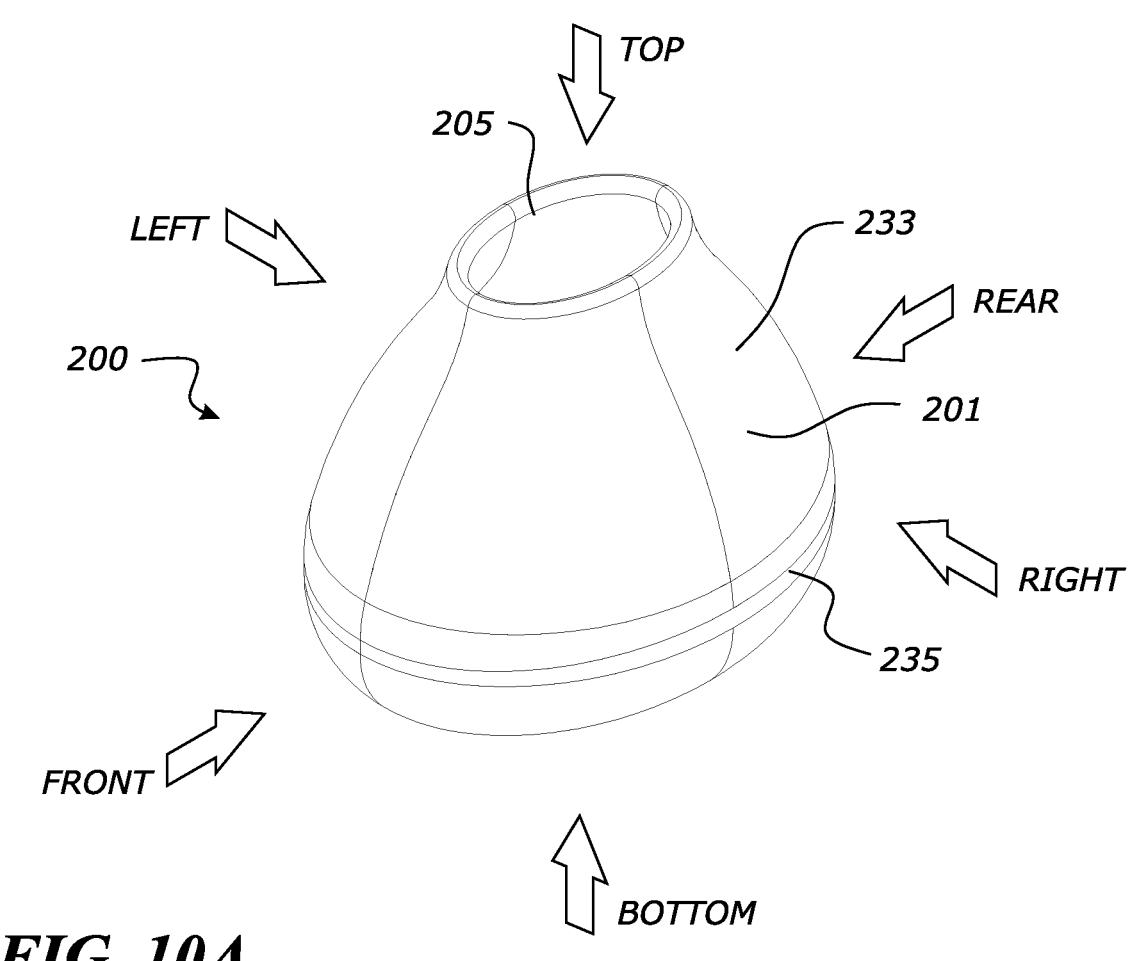
FIG. 10A is a front perspective view of the nasal prong of the respiratory interface of FIG. 2.
Figure 10B:
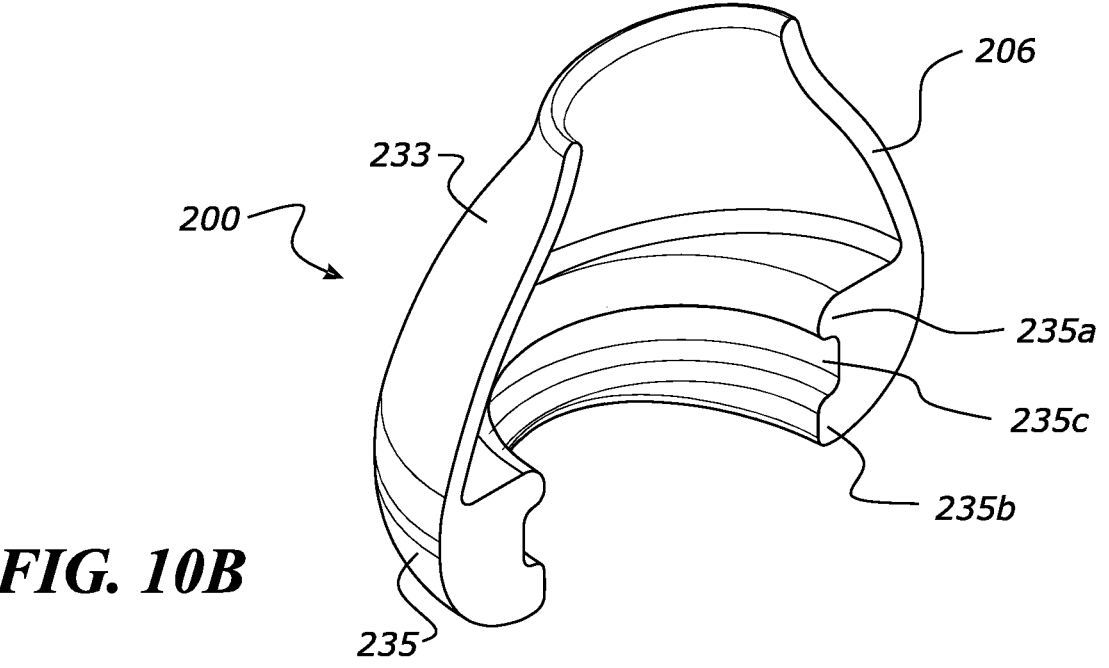
FIG. 10B is a cross-section through the nasal prong of the respiratory interface of FIG. 2.

The single sealing nasal prong 200 has a front surface and an opposing rear surface, a left surface and opposing right surface, a top surface and an opposing bottom surface. The surfaces are indicated in FIG. 10A. The single sealing nasal prong 200 comprises a seal body 201, an inlet 203, a gas passage 204, and an outlet 205. The seal body 201 is configured to seal with one of the nares of a patient. The cross-section illustrated in FIG. 10B shows the single sealing nasal prong 200 has a wall 206 defining an exterior of the single sealing nasal prong 200. The wall 206 also defines the gases passage 204 between the inlet 203 and the outlet 205.

The prong inlet 203 is configured to receive gases from a gases supply element e.g. a conduit. The prong inlet 203 is generally circular. The prong inlet 203 is located in the centre of the prong 200, when viewed from below. A cross section of the prong inlet 203 is substantially similar to a cross section of the conduit outlet 305 (FIG. 9A). The shape of the prong inlet 203 is substantially similar to the shape of the conduit outlet 305. The size of the prong inlet 203 is also substantially similar to the size of the conduit outlet 305. In the first illustrated configuration, the conduit outlet 305 is received within the prong inlet 203 to connect the single sealing nasal prong 200 to the conduit 300. The similar size and shape between the prong inlet 203 and the conduit outlet 305 means that there is minimal resistance to flow between the conduit 300 and the single sealing nasal prong 200 because there are no flow restrictions. This arrangement means that the delivered gases are not jetting, which improves delivery of a substance such as a nebulised gas. Further, the changes in gas velocity are minimised because there are no flow restrictions, such as sharp corners, edges, or other protrusions.

This configuration provides stability due to the conduit being coaxial with the prong. The conduit being coaxial causes a low bending moment on the interface from the tube. The low bending moment is because the tube hangs substantially vertically downward and does not extend to one side of the interface. The low bending moment improves stability of the interface when it is on the user's face.

Figure 2:
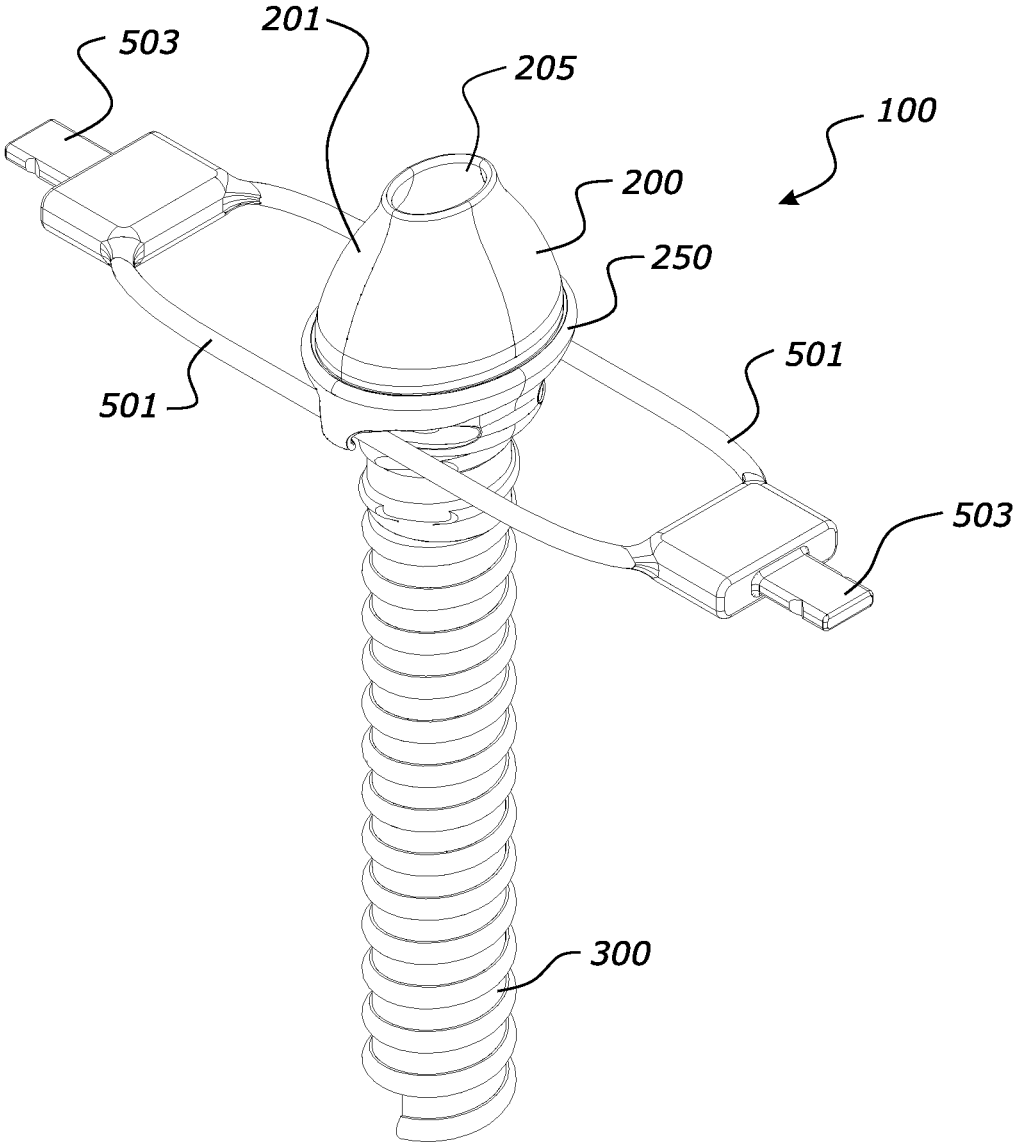
FIG. 2 is a front perspective view of one configuration of a respiratory interface.
Figure 3:
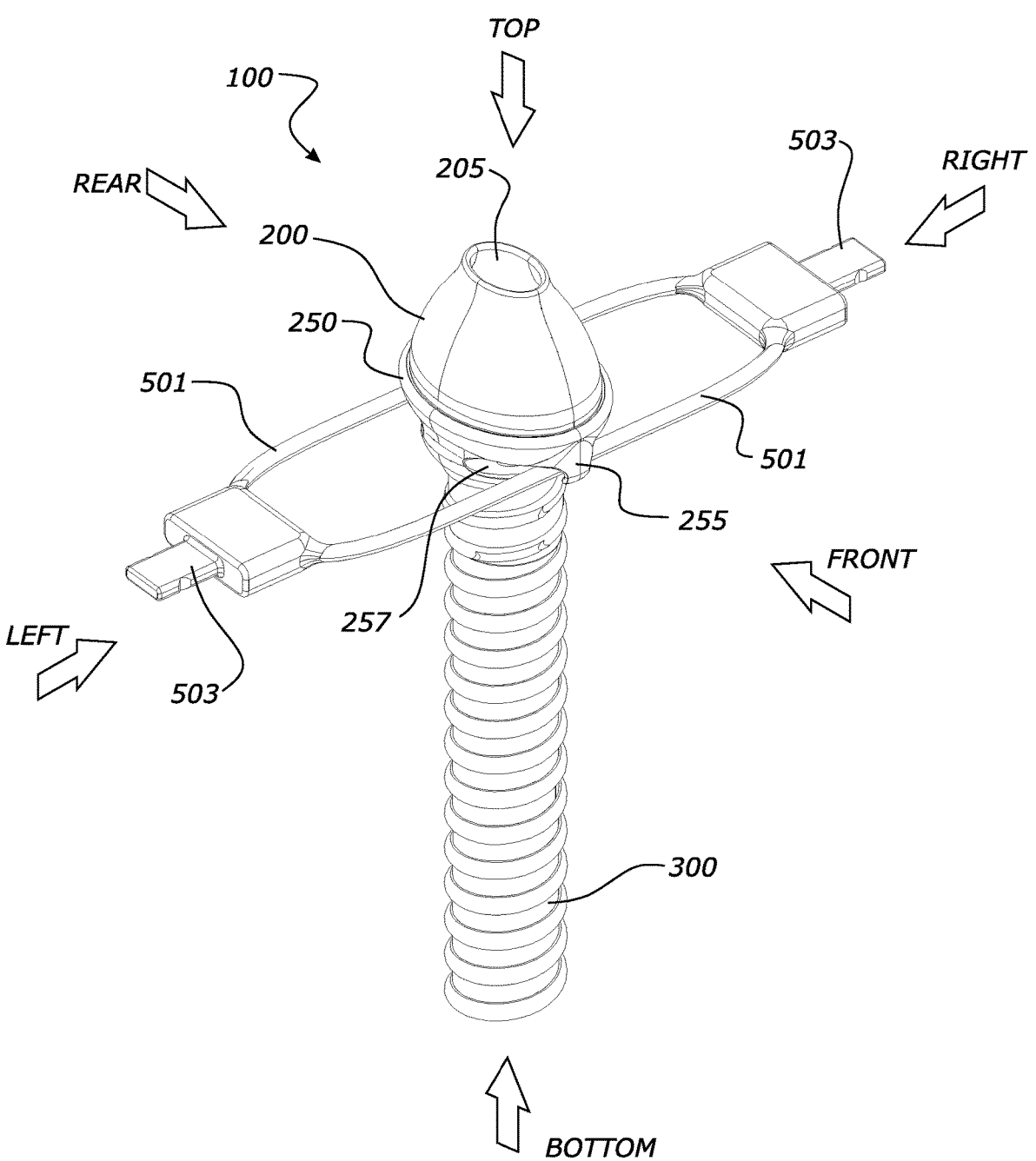
FIG. 3 is a rear perspective view of the respiratory interface of FIG. 2.

As shown in FIG. 2, there is a minimal change in direction through the conduit in the lead up to the single sealing nasal prong 200. The benefits of this arrangement include a flow path that is relatively straight and contains less cross-sectional restrictions than flow paths with bends and turns, resulting in less noise and less pressure drop.

The conduit 300 and prong 200 are configured to reduce the resistance to flow from a gas source to the nare, That is, there are no flow restrictions within or between the conduit 300 and the single sealing nasal prong 200. The conduit and prong arrangement do not include turns, bends, sharp corners, or features extending into the flow path. It will be appreciated that there will be some resistance to flow from the conduit and the prong itself; however, there are not additional flow restrictions.

The directly coupled conduit 300 to the prong 200 provides a direct connection without any change in direction of the gases. The prong inlet and conduit outlet are co-axial, which allows the gases to travel straight through the conduit into the prong and then out of the prong.

The prong outlet 205 is configured to supply the gases to the patient. With reference to the orientation of the single sealing nasal prong 200 in FIG. 13, the prong outlet 205 is located in a generally central location between the left surface and the right surface. In one example the prong outlet 205 is located in a generally central location between the left and right surface as well as the front and back surfaces. The generally central location allows the single sealing nasal prong to seal either one of the patient's nares when it is inserted in either nare (i.e. nostril).

As the single sealing nasal prong 200 has left and right symmetry and the prong outlet 205 is substantially in the centre, the single sealing nasal prong 200 is directionally independent. That is, the single sealing nasal prong 200 can be used with either nostril. The prong 200 is nostril orientation independent, meaning the prong outlet is symmetrical such that it can be used with either nostril and achieve a similar with each nostril of a user.

Also, the vertical orientation of the single sealing nasal prong can be changed, With reference to FIG. 1b that shows an orientation of the interface 100 when used with a patient, the front surface of the single sealing nasal prong is positioned below the rear surface. That is, the front surface is closer to the patient's lips and the rear surface is closer to the patient's nose. The symmetry of the single sealing nasal prong described above allows the single sealing nasal prong 200 to be used with front surface above the rear surface, or the rear surface above the front surface to still achieve a substantial seal with the nostril.

The prong outlet 205 and the prong inlet 203 of the illustrated configuration are concentric. That is, the prong outlet 205 and the prong inlet 203 have a common centre. In other words, the prong outlet 205 and prong inlet 203 are co-axial, as they have a common central axis. The prong inlet 203 is substantially circular in shape and the prong outlet 205 is elliptical in shape. The shape of the passage 204 changes from a circular shape adjacent the prong inlet 203 to an elliptical shape adjacent the prong outlet 205.

Alternatively, the prong outlet 205 and prong inlet may be offset from each other. That is, the centre of the prong inlet 203 and the prong outlet 205 may be offset from each other. In this alternative, the wall connecting the prong inlet 203 and the prong outlet 205 still defines a gases passage from the prong inlet 203 to the prong outlet 205.

Alternatively, the prong inlet 203 may be elliptical. In some configurations, the major axis of the prong inlet 203 and the major axis of the prong outlet 205 may be transverse, for example perpendicular, when viewed upwardly from the prong inlet 203. In some configurations, the major axis of the prong inlet 203 and the major axis of the prong outlet 205 may be parallel, for example co-planar, when viewed upwardly from the prong inlet 203.

The prong outlet 205 is smaller than the prong inlet 203. In particular, a cross-sectional area of the prong outlet 205 is smaller than a cross-sectional area of the prong inlet 203. A radius of the prong outlet 205 is smaller than a radius of the prong inlet 203.

The seal body 201 and the prong outlet 205 of the single sealing nasal prong 200 of the illustrated configuration are arranged such that one of the patient's nares is substantially sealed and gases are supplied to that nare from the prong outlet 205 while the other of the patient's nares is unsealed and is free from direct gases supply from the outlet. Gas is provided directly to the sealed nare from the single sealing nasal prong 200. The other nare may receive some of the gases, but the gas will be received indirectly. The other nare is not inhibited by the single sealing nasal prong 200 such that the patient can breathe normally through the other nare.

When using the respiratory interface 100, the patient's nose is about 50% sealed because the single sealing nasal prong 200 blocks one of the patient's nares and the other nare is unblocked. The patient will expire majority of exhaled gases via the path of least resistance, which is through the unsealed nare. The illustrated respiratory interface 100 is configured to seal at least 50% of the nostril the interface is engaged with. Preferably the respiratory interface 100 is shaped and configured to seal at least 75% of the nostril the interface is engaged with.

Figure 14:
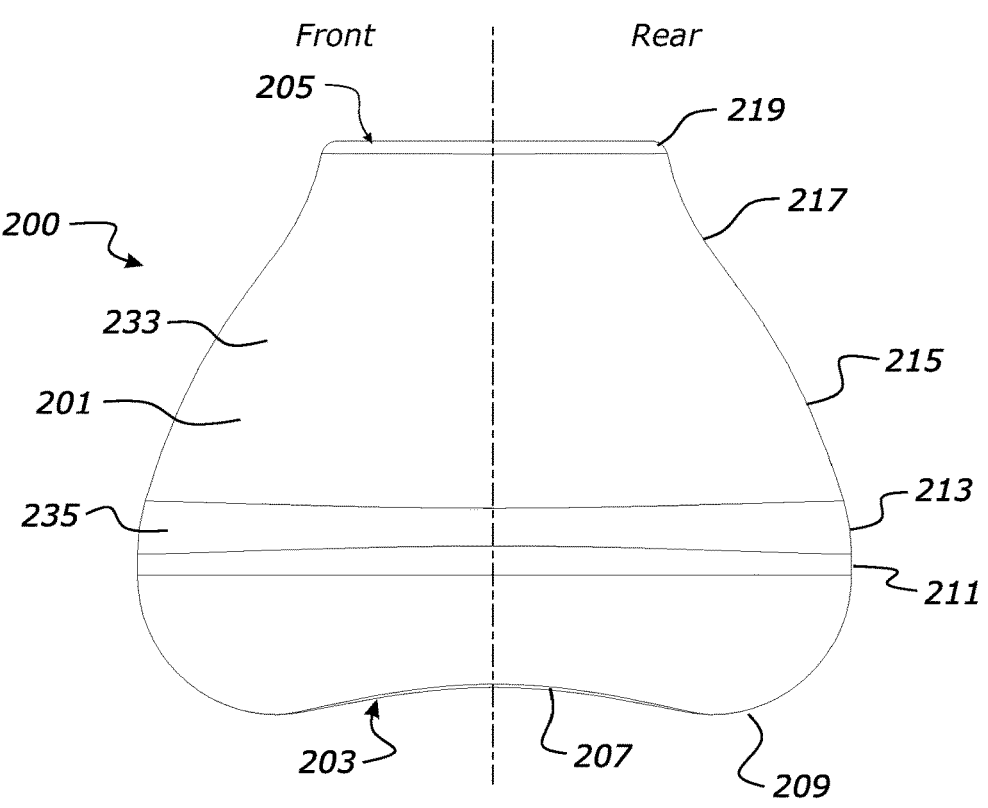
FIG. 14 is a side view of the nasal prong of FIG. 11A.
Figure 15:
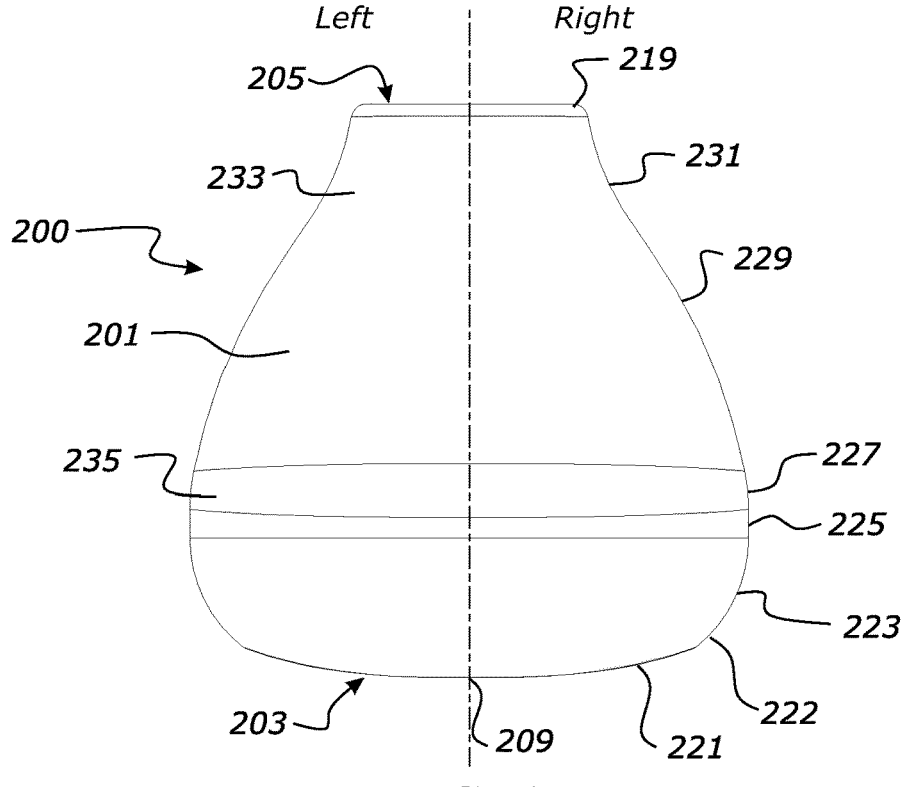
FIG. 15 is a front or rear view of the nasal prong of FIG. 11A.

With reference to FIGS. 14 and 15, the sealing prong 200 is bulbous shaped or globular shaped. The seal body 201 tapers inwardly from the inlet towards the outlet. In one configuration the sealing prong 200 is dome shaped. The single sealing nasal prong may have other similar shapes such as a raindrop shape, an ovoid shape, or an egg shape.

The single sealing nasal prong 200 has a relatively wider base region, which includes the prong inlet 203 and the coupling region, and a relatively narrower tip region, which includes the prong outlet 205. Between the base region and the tip region is a transition region.

The base region includes an outwardly extending wall. The wall extends outwardly and includes a substantially convex shape. The base region also defines a coupling region of the prong to couple to gases delivery conduit.

The tip region includes an upstanding wall defining the prong outlet. The wall is inwardly angled and upwardly extending wall. The tip region can be considered a frusto-conical shape.

The transition region includes a wall that connects the base region and the tip region. The transition region includes multiple transition regions. In particular, the transition region comprises an outwardly curved region that tapers toward an outlet. The diameter or major axis of the gas passage in the transition region reduces. The transition region may include an inflection region adjacent the tip region, more particularly at the intersection of the tip region and the transition region. In the inflection zone/region the curvature of the wall moves from an outwardly curved to a straight/slightly inwardly curved portion. The inflection region is the blend between the transition region to the tip region.

In one optional configuration where the inlet is circular and outlet is oval, the transition region may also comprise a shape change from a circular cross section at the base region to an oval/elliptical shape in the tip region.

The exterior of the single sealing nasal prong 200 is generally convexly curved. That is, the overall shape of the exterior is curved, and is curved outwardly. The exterior of the single sealing nasal prong 200 tapers inwardly from inlet end toward the outlet end—the inlet end is larger than the outlet end.

The wall thickness of the prong may be between 0.5 mm to 1.5 mm. In a further example the wall thickness of the prong is about 0.7 mm to about 0.8 mm. The wall 206 comprises a supple or compliant material. The material is a supple non-resilient material. A suitable material is silicone. Alternatively, the prong may be made of a biocompatible plastics material.

The single sealing nasal prong 200 maintains the shape shown in FIGS. 10 to 15 due to a combination of the supple material and the dome shape of the single sealing nasal prong 200. The single sealing nasal prong 200 maintains the shape when gas is flowing through the gas passage 204 and when gas is not flowing through the gas passage 204. Alternatively, the material may be a resilient material and the single sealing nasal prong maintains the shape shown in FIGS. 10 to 15 due to a combination of the supple material, the dome shape, and the resilient material. In this alternative configuration, the resilient material in combination with the dome shape of the single sealing nasal prong 200 assists the single sealing nasal prong to maintain the shape shown. The coupling comprising thickened walls to create a more rigid structure at the coupling region 235.

The wall 206 of the single sealing nasal prong 200 should be strong enough to not collapse i.e. the wall doesn't buckle, yet flexible so that it flexes or elastically deforms to the shape of the nares. The portion of the single sealing nasal prong 200 between the base region and the tip region has a constant wall thickness that allows the prong to flex and seal with the nares while preventing buckling. For example, in some configurations, the outlet end of the seal body 201 may have a relatively thinner wall thickness compared to the remainder of the wall, A thinner wall thickness may increase comfort for a patient. In other configurations, the wall thickness at the outlet end may be similar to the wall thickness of the remainder of the wall. A thicker wall may prevent collapse of the wall when the single sealing nasal prong 200 is inserted into the patient's nare.

Once placed in one of the nares of a patient, the exterior of the single sealing nasal prong 200 seals with the internal surface of that nare. The sealing surface is the outer surface of the wall defining the single sealing nasal prong 200. The single sealing nasal prong 200 seals against the tissue of the nare. The single sealing nasal prong seals with the nare when gas is flowing through the gas passage 204 and when gas is not flowing through the gas passage 204. The seal body 201 and the outlet 205 of the single sealing nasal prong 200 are arranged such that one of the patient's nares is substantially sealed and gases are supplied to that nare from the outlet while the other of the patient's nares is unsealed and is free from direct gases supply from the outlet. The single sealing nasal prong 200 is interchangeable between the patient's nares. The single sealing nasal prong seals with the other nare as it is inserted into that nare.

The interface has a single prong 200 and, in some configurations, does not have a manifold. in these configurations, the other nare is completely free of the interface. As can be seen in FIG. 1B, the interface interacts with only one of the patient's nares, and does not engage the other of the patient's nares. The other nare does not engage, or otherwise interact with a prong, manifold, or any other feature of the interface. The interface can be positioned on the patient's face such that one nare is not receiving gases from the conduit 300.

When not sealing with the patient's nare, the single sealing nasal prong 200 may have the shape shown in FIGS. 10 to 15, In use, the single sealing nasal prong 200 may flex and elastically deform to conform to the shape of the patient's nare to form a seal with the nare. The single sealing nasal prong 200 may conform exactly to the patient's nare. In this case, the single sealing nasal prong may seal completely with the patient's nare. As described earlier, the patient's nose is at least 50% sealed because the single sealing nasal prong 200 blocks one of the patient's nares and the other nare is unblocked. More specifically at least 50% of a nostril is sealed when in use. The prong 200 occludes 75% or more of the nostril. More preferably in use the prong is sized such that 90% or more of one nostril is occluded.

The patient's nose is about 50% sealed because the single sealing nasal prong 200 substantially blocks one of the patient's nares and the other nare is unblocked. The patient will breathe, in particular expire, via the path of least resistance, which is through the unsealed nare.

The elliptical shape of the prong outlet allows the prong to conform because the major axis compresses as the prong is inserted into the nare (the length of the major axis plays a role in the suppleness of the opening), while the minor axis provides structural support to prevent the prong from buckling. Hence, the prong can fit a variety of different nose shapes/sizes.

An elliptical shape also more closely matches the shape of the nasal cavity and opening, which means gases can be delivered more effectively and efficiently to the patient.

Alternatively, the single sealing nasal prong 200 may conform to a shape that is generally the same as the shape of the patient's nare, but with one or more differences. In this case, the single sealing nasal prong may partly seal with the patient's nare. Thus, the single sealing nasal prong may partially conform to the shape of the patient's nare.

With reference to the above description of the sealing provided by the prong, it will be appreciated that it is the body of the prong which enables such sealing, that being provided by the seal body 201.

Figure 4:
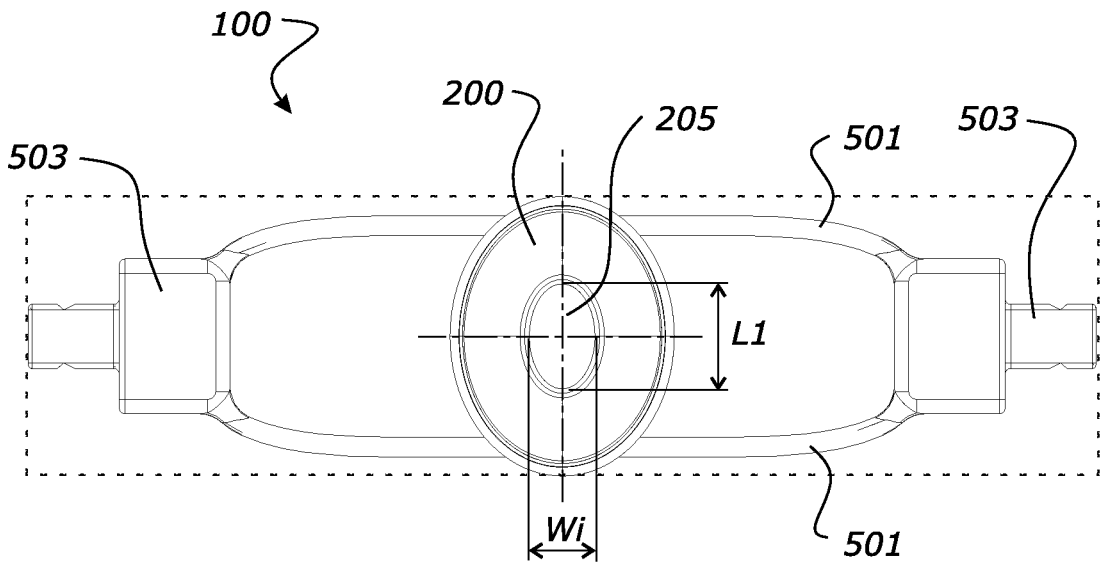
FIG. 4 is a top view of the respiratory interface of FIG. 2.
Figure 5:
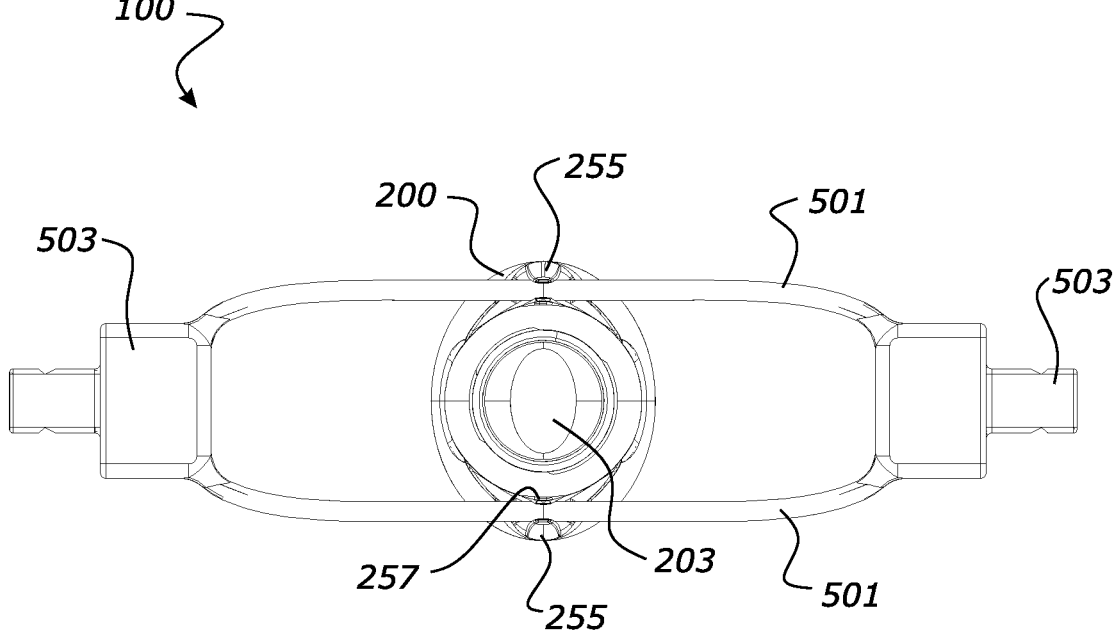
FIG. 5 is a bottom view of the respiratory interface of FIG. 2.

With reference to FIG. 4, the prong outlet 205 has a length L1, which is the longest dimension of the prong outlet 205.

The prong outlet 205 also has a width W1, which is the widest dimension of the prong outlet 205. A ratio of the width of the prong outlet 205 to the length of the prong outlet 205 is about 0.4 to about 0.9. The ratio may be about 0.4 to about 0.6, about 0.6 to about 0.8, about 0.8 to about 0.9, about 0.4 to about 0.5, about 0.5 to about 0.6, about 0.6 to about 0.7, or about 0.7 to about 0.8, for example.

The length of the prong outlet may be between 4 mm to 15 mm, Preferably the length is between 6 mm to 11 mm. The width of the prong outlet may be between 1.5 mm to 13.5 mm. Preferably the width of the prong outlet is between 3.5 mm to 6.5 mm. The length of the illustrated prong outlet 205 design shown is 9.48 mm and the width is 5.94 mm. The ratio of the prong outlet 205 to conduit outlet 305 is 0.72. The ratio of the cross-sectional area of the prong outlet 205 to cross-sectional area of the base of seal is 0.33. The cross-sectional area of the base is indicated with grey shading in FIG. 13.

The length of the single sealing nasal prong 200 is greater than the width of the single sealing nasal prong 200. A ratio of the length to width of the single sealing nasal prong 200 may be between 1.01 to 2, preferably between 1.4 to 1.6, more preferably 1.50 to 1.55.

The prong 200 may be provided in different sizes, such as small, medium, and large. In the illustrated configuration, the dimension for the minor axis vs. major axis of the ellipse are: Small: 5.3 mm by 7.7 mm, Medium: 5.9 mm by 9.4 mm, Large: 6.7 mm by 11.5 mm, with an approximate ratio for each size being: S: 0.69, M: 0.63, L: 0.58.

The relationship between the width and the length of the prong outlet 205 provides flexibility to the opening such that it can fit a variety of nare shapes. The length of the prong outlet 205 allows the prong outlet to be formed or distorted to match the user's nare, At the same time, the width of the prong outlet 205 provides some structural support.

A ratio of a cross sectional area of the prong outlet 205 to a cross sectional area of a conduit outlet 305 is about 0.2 to about 1, Preferably the ratio is about 0.5 to about 0.8. More preferably, the ratio is about 0.7 to about 0.8. In the illustrated configuration, the ratio is about 0.72, A ratio of a cross sectional area of the prong outlet 205 to a cross-sectional area of a base of the seal (indicated with grey shading in FIG. 13) is about 0.33.

With reference to FIGS. 10 to 15, the overall shape of the seal gently tapers from a wider distal portion at the inlet 203 to a narrower region at the prong outlet 205; that is, the seal tapers in a proximal direction.

The size of the prong inlet 203 opening is larger than the prong outlet 205. The taper includes a convex curvature ending in a protruding prong outlet 205. The curvature in combination with the thin wall allows the seal wall to conform and gently press against the internal surface of the nare forming a seal.

The single sealing nasal prong 200 comprises a supple sealing portion 233, which is provided by the wall 206. The supple portion 233 is configured to flex to substantially conform to shape of the patient's nare. The wall thickness of the supple portion 233 is about 0.7 mm to about 0.8 mm.

The thinner wall thickness of the wall 233 as compared to the wall thickness of the coupling portion 235 provides suppleness to the wall 233. The wall 233 can flex and elastically deform to conform to the shape of the nostril and seal with the nostril due to the thinner wall thickness of the wall 233 as compared to the coupling portion 235.

Figure 12:
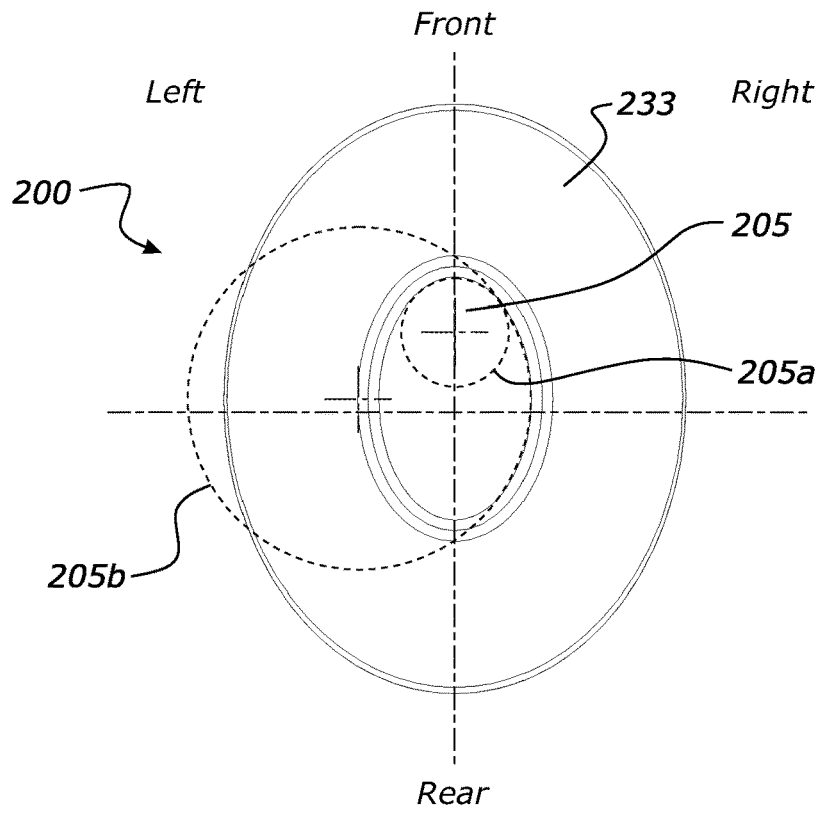
FIG. 12 is a top view of the nasal prong of FIG. 11A.
Figure 13:
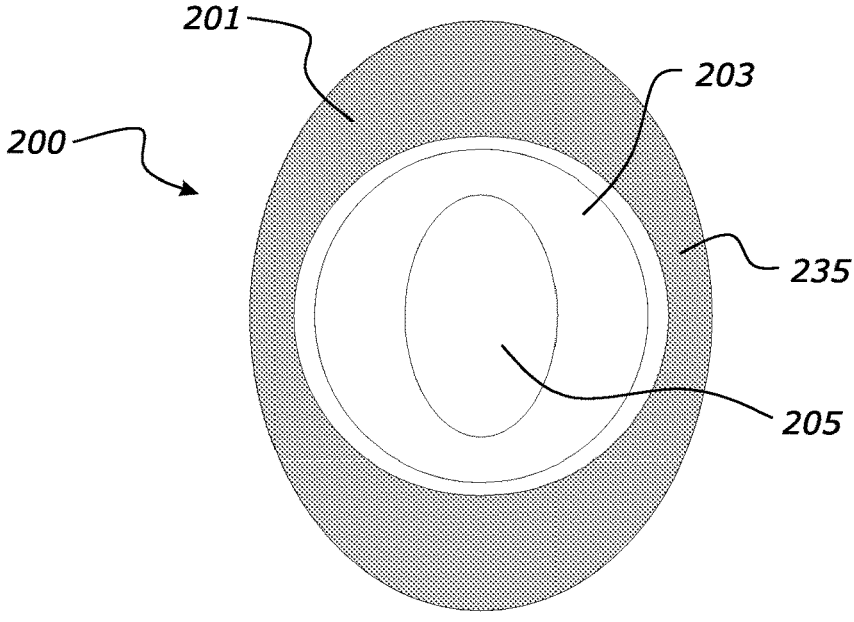
FIG. 13 is a bottom view of the nasal prong of FIG. 11A.

FIG. 12 shows the seal body 201 is substantially symmetrical between the left and right sides—the left surface is a mirror image of the right surface, With reference to the orientation of the single sealing nasal prong 200 in FIG. 12, the seal body 201 is also substantially symmetrical between the front and rear surfaces—the front surface is a mirror image of the rear surface, when viewed from above.

With reference to the orientation of the single sealing nasal prong 200 in FIG. 12, the prong outlet 205 is centred in the prong body 201 between the left and right surfaces. The central horizontal location allows the prong to be adjusted to seal in either one of the nares providing therapy to the patient. The central location of the prong outlet 205 together with the symmetry of the single sealing nasal prong 200, allows the single sealing nasal prong 200 to be changed from one nostril to the other during use. The prong seals equally well with either nostril due to the location of the prong outlet 205 and the shape of the prong outlet 205. The configuration of FIG. 12 also shows the prong outlet 205 centred in the prong body 201 between the front and rear surfaces such that the prong can be inserted with either the front surface above the rear surface or vice versa. In some alternative configurations, the outlet may be offset (not co-linear nor co-incident) from the horizontal axis, offset from the vertical axis, or offset from both the vertical axis and the horizontal axis.

The outlet 205 of the single sealing nasal prong 200 is centred in relation to the seal body 201, when viewed from above, With reference to the orientation of the single sealing nasal prong 200 in FIG. 12, the outlet is centred between the left and right surfaces and between the front and rear surfaces—the outlet is centred concentrically relative to the seal body. When assembled with the conduit 300, the prong outlet 205 is centred in the conduit outlet 305. The central axis of the single sealing nasal prong is aligned with a central axis of the conduit outlet 305.

The outlet 205 has a generally oval cross-section, With reference to FIG. 12, the prong outlet 205 of the illustrated configuration has an elliptical cross-section. The ellipse has a major axis that extends between the front and rear surfaces and a minor axis that extends between the left and right surfaces. The elliptical cross-section has a semi-minor radius or small chordal radius (represented by circle 205a) and a semi-major radius or large chordal (represented by circle 205b). In the illustrated configuration, the semi-minor radius is about 2 mm and the semi-major radius is about 7 mm. The cross-section of the outlet may have a semi-minor radius of about 1 mm to about 3 mm. The semi-minor radius may be about 1.5 mm, or about 2.5 mm. The cross-section of the outlet may have a semi-major radius of about 4 mm to about 24 mm. The semi-major radius may be about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, or about 23 mm. The semi-minor radius 205a defines the curvature of a front region and a rear region of the prong outlet 205. The semi-major radius 205b defines the curvature of the left and right region of the prong outlet 205.

The oval shape of the prong outlet 205 allows the prong outlet 205 to conform to a variety of different nose shapes, That is because the semi-major radius of the opening allows the outlet 205 to deform more readily than a circular outlet, which increases conformation with different nose shapes.

In some configurations, the single sealing nasal prong 200 has a sealing portion, which seals with the user's nare, and a coupling portion, which couples with the support and/or conduit. The relatively thin sealing portion and relatively thick coupling portions are shown in cross-section in FIG. 10B. Those portions are supple and rigid relative to each other—the supple portion is supple compared to the rigid portion and vice versa, but the rigid portion has some softness, compliance, or suppleness. In the illustrated configuration, the single sealing nasal prong is constructed from a supple or compliant material and the rigidity of the rigid portion is due to the relative thickness of the rigid portion compared to the supple portion. The supple portion seals with the user's nare and the rigid portion couples with the support and/or conduit. The single sealing nasal prong 200 also comprises the rigid coupling portion 235. The rigid coupling portion 235 is connected to, or connectable to, the gas flow assembly. The rigid coupling portion is also provided by the wall. The rigid coupling portion 235 provides stability for the single sealing nasal prong 200. The rigid coupling portion 235 is rigid compared to other portions of the single sealing nasal prong 200. In the configuration shown, the rigid coupling portion 235 is rigid by having a relatively thicker wall. For example, a wall thickness of the rigid coupling portion is about 1.5 mm to about 4 mm. The wall thickness may be about 2 mm, about 2.5 mm, about 3 mm, or about 3.5 mm. Alternatively, the rigid or less supple regions can be formed of a different material that is more rigid than the material of the supple portion. The rigid coupling portion 235 has two inwardly extending flanges 235a and 235b. The flange 235b closest to the inlet is a lip 235. The flange 235a is an undercut, which is formed by an undercut in the mould tool. The single sealing nasal prong 200 has a groove or recess 235c between the lip 235b and the undercut 235a. When assembled, the recess 235c receives the flange 405 from the connector 400.

The supple section 233 is supple compared to the relatively rigid coupling portion 235 because it has a thinner wall 233 compared to the thickness of the coupling portion 235. The wall of the supple region 233 can flex and elastically deform to conform to the shape of the nostril and seal with the nostril. The single sealing nasal prong 200 may experience localised flexing or elastic deformation or both. The supple region 233 having a thinner wall section allows some parts of the supple region to flex i.e. localised flexion or localised deformation. This localised flexion allows for improved sealing with a wide range of different nose shapes. The localised flexing allows for prong to conform to the nostril shape.

As described above, the prong inlet 203 is circular and the prong outlet 205 is elliptical. The transition between the prong inlet 203 and the prong outlet 205 is determined by the prong wall 206 shown in FIG. 10B. With reference to the cross-section shown in FIG. 10B, the wall thickness of the supple sealing portion remains generally constant. The shape of the gas passage corresponding to the supple sealing portion has a similar shape to the exterior of the single sealing nasal prong 200. With reference to FIGS. 10A and 100, the gas passage through the coupling portion is a cylindrical passage.

Figure 10C:
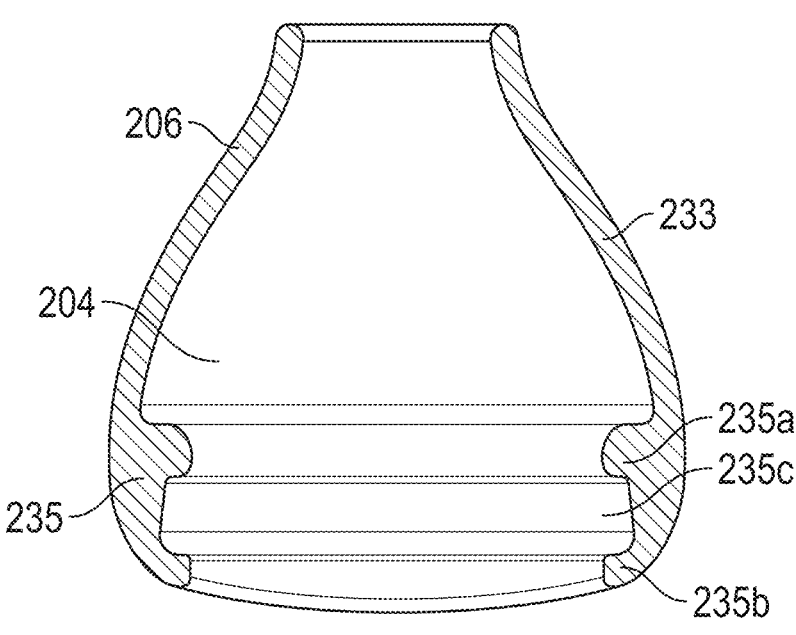
FIG. 10C is a cross-section through the nasal prong of the respiratory interface of FIG. 2.
Figure 10D:
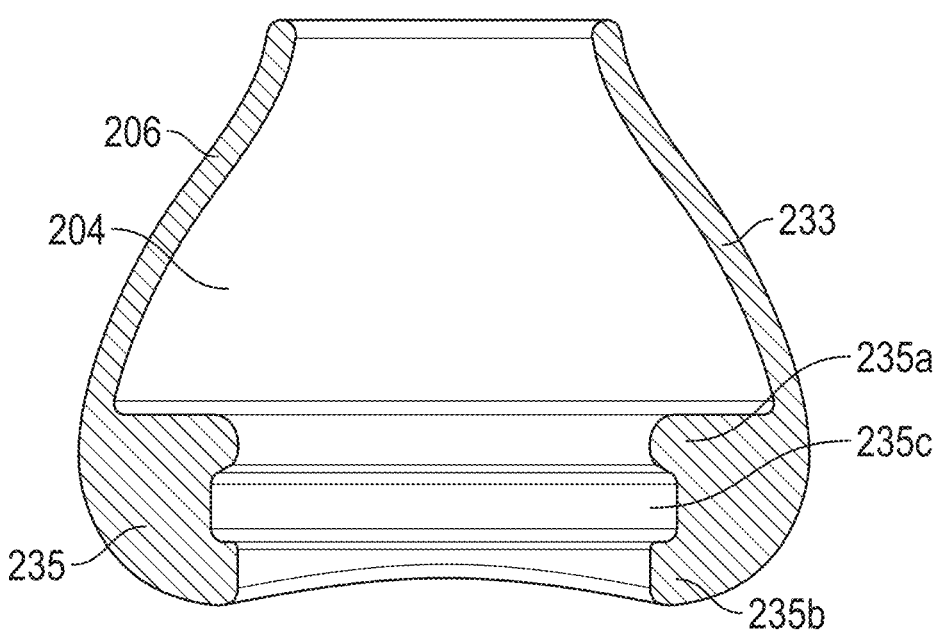
FIG. 10D is another cross-section through the nasal prong of the respiratory interface of FIG. 2.
Figure 11A:
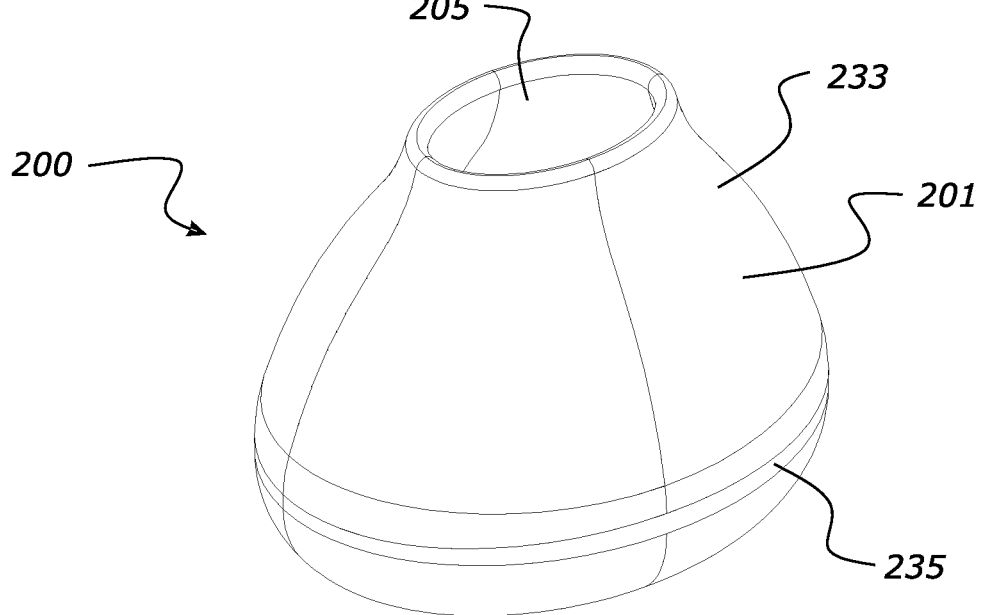
FIG. 11A is a rear perspective view of the nasal prong.

FIGS. 10C and 10D show cross-sections through the single sealing nasal prong 200. FIG. 10C shows a cross section through the plane indicated with a horizontal line in FIG. 4. FIG. 10D shows a cross section through the plane indicated with a vertical line in FIG. 4. Comparing FIGS. 10C and 10D, it can be seen that the supple section 233 is of approximately similar wall thickness, whilst the relatively rigid coupling portion 235 is greater in FIG. 10D relative to FIG. 10C, whilst at the same time the relatively rigid coupling portion 235 with its associated flanges 235a and 235b and the associated recess 235c provide for the same dimensioned or shaped region to receive the flange 405 from the connector 400, In this way, different sized or configured prongs 200 can be put into connection with the same connector 400. This provides a single interface which can be used with different sized or configured prongs 200 depending on the patient, Accordingly, the different sized or configured prongs are provided with the same fit capability for being fitted with the same, or a single, interface connector 400.

FIG. 14 shows the single sealing nasal prong 200 from the left side. The right side of the single sealing nasal prong is identical to the left side of the single sealing nasal prong. Starting from the inlet 203, the base region includes the bottom surface 207 of the single sealing nasal prong 200, which is concave or curved inwardly. The adjacent and lowermost surface 209 of the single sealing nasal prong 200 is curved outwardly to form a lobe. The lobe extends around the circumference and can be seen in both FIGS. 14 and 15. The surface of the lobe transitions into the transition region, which includes a relatively short generally vertical surface (when viewed as a profile shown in FIG. 14), which transitions into a gentle outwardly curved surface 213 i.e. a shallow outwardly curved surface. A central surface of the single sealing nasal prong 200 is a relatively planar surface that tapers inwardly. The tip includes a rim 219, and an inwardly curved surface 217 between the central surface 215 and the rim 219. The transitions between each surface are smooth transitions. The top edge 219 of the single sealing nasal prong 200 also forms the rim of the outlet 205.

FIG. 15 shows the single sealing nasal prong 200 from the front. The rear of the single sealing nasal prong is identical to the front of the single sealing nasal prong. Starting from the inlet 203, the base region includes the bottom surface 209 of the single sealing nasal prong 200, which is outwardly curved. The lobe can be seen in this view as a surface 223. The surface of the lobe is curved outwardly and the surface of the lobe extends upwardly. The curved surfaces 221 and 223 meet at a point 222 that provides a mildly sharp transition. That is, surface 223 transitions from an arc of a first radius to an arc of a second radius defining surface 221. The second radius is greater than the first radius. The transition from surface 223 to 221 defines a change in curves and directions of the surface. The transition region may define a fillet i.e. a rounded edge.

Moving upwards, the transition region includes a surface 225 that is relatively planar and extends in a vertical direction. The following surface also extends generally vertically, but has a slight outwards curve. The centre of the single sealing nasal prong 200 is a relatively planar surface 229 that tapers inwardly. In the view shown in FIG. 15, the tip includes the rim 219 and an inwardly curved surface 231 between the central surface 229 and the rim 219. The transitions between each surface, except the transition between surfaces 221 and 223, are smooth transitions. The regions 235, 227, 225 may be more rigid than the other surfaces. These surfaces are stiffer than the surface 233. These regions form the stiffer coupling portion of the prong. The regions 223, 208, 221 may be suppler than 235, 227, 225 but stiffer than 233 in order to allow the bottom of the prong to flex when received into a cuff.

When FIGS. 14 and 15 are compared, it can be seen that the surfaces of the left side correspond to surfaces of the front. For example, surface 211 of FIG. 14 corresponds to surface 225 of FIG. 15, In the illustrated configuration, surfaces 211 and 225 have a smooth transition between each other. This flat surface 225 transitions into surface 211 shown in FIG. 14.

In the illustrated configuration, the opposing front and rear surfaces are substantially symmetrical to each other.

The front and rear surfaces are symmetrical about a vertical plane. The opposing left and right surfaces are also substantially symmetrical to each other. The left and right surfaces are symmetrical about a vertical plane. As a result of the symmetry of all sides, the outlet 205 is located centrally between the front and rear surfaces and located centrally between the left and right surfaces. This allows the single sealing nasal prong 200 to be inserted into the nostril in any orientation because the symmetrical nature of the single sealing nasal prong 200 allows the single sealing nasal prong 200 to conform to and seal with either nostril. This makes it easier for a patient or clinician to insert the prong, and also makes it easier to move the prong from one nare to the other. Although a patient's nare does not have a corresponding symmetrical shape, these configurations will provide a seal with the patient's nare.

The single sealing nasal prong 200 has been described herein as sealing the patient's nare, Sealing occurs as the seal body 201 contacts the internal surface of the patient's nares rather than due to distension in the presence of pressure. Sealing occurs due to the seal body contacting the outer edge of the nostril. In some instances, the seal body may also contact the inner regions of nostril adjacent the nostril opening.

A single sealing nasal prong will be considered to substantially seal if it provides over 50% occlusion, and preferably over 70% occlusion of the patient's nare. The prong occludes 90% or more of the nostril when positioned in an operational position. In some configurations, the single sealing nasal prong 200 will substantially seal. The illustrated configuration almost completely seals. It will be appreciated that there will be some leak, but the leak is small enough to be negligible. In other configurations, the single sealing nasal prong 200 will not substantially seal the patient's nare. The amount of sealing controls how much pressure is delivered to the patient and how much dead space clearance occurs.

In an alternative configuration the sealing surface may expand/distend due to the gas flow creating pressure within the single sealing nasal prong 200. The seal body 201 may inflate to seal with the internal surface of the nostril of the patient. The prong may have a thin region wall 233 that may completely collapse in the absence of pressure or gas flow or may partially collapse in the absence of pressure or gas flow. In the presence of a gas flow and pressure, the prong wall 233 can expand or inflate and seal against the nostrils of the patient.

Referring back to FIGS. 1 to 9, other features of gases delivery assembly of the respiratory interface 100 will now be described. In addition to the single sealing nasal prong 200 described above, the gases delivery assembly further comprises a conduit 300. The conduit has an inlet 303, which receives a gases flow from a gas supply, and an outlet 305, which delivers gases to the single sealing nasal prong 200.

In the illustrated configuration, the outlet 305 of the conduit 300 is connected to, or connectable to the single sealing nasal prong 200. The connection is a direct connection—there are no other parts or features between the outlet of the conduit and the inlet of the prong. The single sealing nasal prong 200 and the conduit assembly form a continuous gases pathway. Alternatively, the conduit connector 400 may be placed between the outlet of the conduit and the inlet of the prong. A cross section of the prong inlet 203 is substantially similar to a cross section of the conduit outlet 305 proximal the patient. The shape of the prong inlet 203 is substantially similar to the shape of the conduit outlet 305.

The size of the prong inlet 203 is also substantially similar to the shape of the conduit outlet 305. The gases path from the conduit to the prong outlet 205 may be substantially linear.

In another configuration, the outlet 305 of the conduit 300 is connected to, or connectable to the single sealing nasal prong 200. The connection is a connection between an assembly of a cuff 250, 1250 with a conduit connector 400 (upon which a conduit 300, 1300 is also to be connected thereto). The cuff 250, 1250 is also to be connected to a slider member or members 501, 1501 to facilitate the movement of the cuff with each of the aforementioned components attached thereto along the slider member for suitable orientation or positioning of the prong (which is attached to a terminal end of the conduit connector) for engagement with a patient's nare.

In another configuration, the outlet 305 of the conduit 300 is connected to, or connectable to the single sealing nasal prong 200. The connection is a connection between an assembly of a cuff 250, 1250 with a prong 200. That is, the conduit can be connected to the cuff 250, 1250 and the prong can be held in place by an assembly of adjacently arranged prong and cuff and conduit outlet. In this manner, such an assembly may be provided through a friction-fit type arrangement for holding or retaining the prong in place against the cuff. In such configurations, a conduit connector 400 may be absent.

In another configuration, the outlet 305 of the conduit 300 is connected to, or connectable to the single sealing nasal prong 200. The connection is a direct connection—there are no other parts or features between the outlet of the conduit and the inlet of the prong. The single sealing nasal prong 200 and the conduit assembly form a continuous gases pathway. Alternatively, the conduit connector 400 may be placed between the outlet of the conduit and the inlet of the prong. A cross section of the prong inlet 203 is substantially similar to a cross section of the conduit outlet 305 proximal the patient. The shape of the prong inlet 203 is substantially similar to the shape of the conduit outlet 305, The size of the prong inlet 203 is also substantially similar to the shape of the conduit outlet 305. As a result, a gases path from the conduit to the prong outlet 205 may be substantially linear.

In some configurations, the single sealing nasal prong 200 and the conduit assembly form a direct fluid coupling and gases flow through the tube and directly into the prong. The conduit is configured to deliver gases directly to the single sealing nasal prong without passing through another component. There is no component (such as a manifold) between the outlet of the conduit 305 and the inlet 203 of the single sealing nasal prong 200. The reduced number of components compared to conventional interfaces reduces the size of the interface and also reduces friction/resistance to flow. The direct coupling of the tube to the prong allows a majority, i.e. almost all the flow, to be provided to the prong. The reduced resistance to flow provides a quieter (i.e. less noisy) interface and reduces pressure drops within the interface.

Figure 1B:
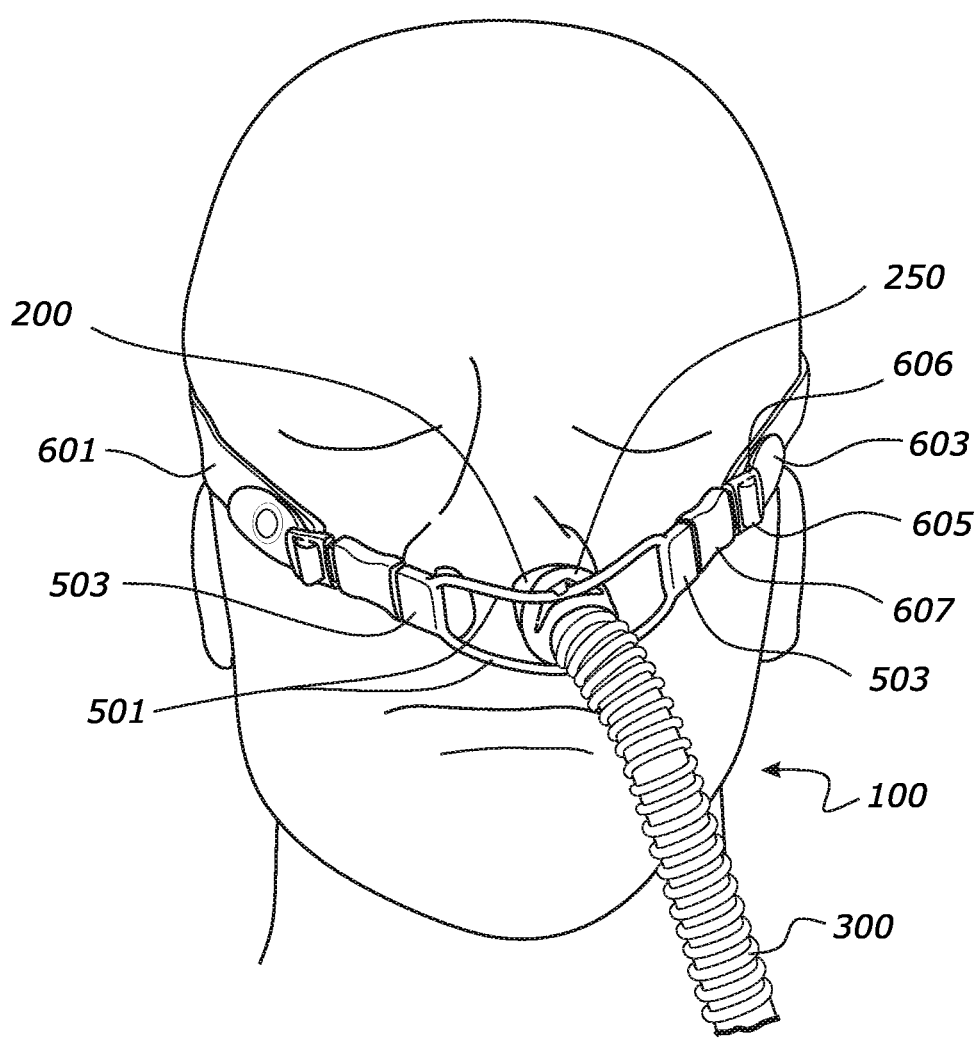
FIGS. 1B to 1D show a respiration interface on a patient.

As shown in FIGS. 1B and 2, there is a minimal change in direction through the conduit in the lead up to the single sealing nasal prong 200. The conduit 300 is directly coupled to the single sealing nasal prong 200. The single sealing nasal prong 200 and the conduit 300 have a common axis, more specifically the conduit outlet 305 and the inlet of the single sealing nasal prong 200 are coaxial (i.e. share a common axis). In the illustrated configuration, the prong outlet also is positioned to share a common axis with the prong inlet and the conduit outlet. The benefits of this arrangement include a flow path that is relatively straight and contains less cross-sectional restrictions than flow paths with bends and turns, resulting in less noise and less pressure drop. In some configurations, the support is outside of, or is separate from, or does not form a part of, the conduit or gases being supplied to the single sealing nasal prong. For example, the conduit may be fluidly separated from the support, or the support does not form a part of a gas path of gases being supplied to the single sealing nasal prong. In further configurations, the conduit 300 is only provided to be in fluid communication with the single sealing nasal prong 200 (and cuff 250). In some configurations, the conduit 300 is not in fluid communication with the support 500. In some configurations, the conduit 300 is separate from, and/or is not coupled or directly coupled to the support 500.

The conduit 300 and prong 200 are configured to reduce the resistance to flow from a gas source to the nare. That is, there are low flow restrictions within or between the conduit 300 and the single sealing nasal prong 200. The conduit and prong arrangement do not include turns, bends, sharp corners, or features extending into the flow path. It will be appreciated that there will be some resistance to flow as the gas flows through the conduit and the prong itself; however, there are not additional flow restrictions.

As described earlier, the conduit 300 is directly coupled to the single sealing nasal prong 200. In the illustrated configuration, the conduit outlet 305 is received within the prong inlet 203 to connect the single sealing nasal prong 200 to the conduit 300. The directly coupled conduit 300 to the prong 200 provides a direct connection without any change in direction of the gases. The prong inlet and conduit outlet are co-axial, which allows the gases to travel straight through the conduit 300 into the single sealing nasal prong 200 and then out of the single sealing nasal prong.

In addition, the conduit outlet 305, the cuff opening 261, and the prong inlet 203 have a similar diameter. The conduit outlet 305 is aligned with the cuff opening 261 (i.e. cuff inlet 261), which in turn aligns with the prong inlet 203 and the prong outlet 205 to maintain a substantially linear gases path from the conduit to the single sealing nasal prong 200.

In some configurations, the conduit assembly includes a conduit connector 400 that facilitates coupling between the conduit 300 and a cuff 250. The conduit connector 400 is a sleeve that is received in, or receivable in, the conduit at, or near, the conduit outlet 305. The connector 400 has an external thread and the conduit 300 has an internal thread. The threads can be wound together, connecting the connector and the conduit together. The conduit 300 and conduit connector 400 may be connected in other ways. For example, they may be glued together or have other complementary engagement features such as clips and recesses or may be moulded to the conduit or may include an overmould that couples the connector 400 to the conduit 300.

The arrangement of the conduit 300 and prong 200 improves patient comfort. In configurations in which the single sealing nasal prong 200 seals the patient's nare, some of the support pressure is provided by the contact of the prong at the patient's nare. The pressure on the patient's upper lip would be reduced when compared with a regular cannula because the support pressure is provided by the contact of the prong at the patient's nare.

Features of the support 500 for the single sealing nasal prong 200 will now be described.

FIGS. 2 to 8 show the support or adjuster 500. The support 500 provides an arrangement through which the prong outlet 205 can be adjusted to seal in either one of the nares providing therapy to the patient. Variations of respiratory interfaces having adjustable prongs are described in more detail below.

The support 500 includes a pair of sliding members 501, a cuff 250 for receiving the single sealing nasal prong and engaging with the members 501, and clips 503 that are connectable to headgear. Corresponding clips 607 are disposed on the headgear straps. The headgear straps are removably coupled to the sliding members 501 via the clips 503. The clips 503 form a male coupling element and are received into the corresponding clips 607 that are disposed on the headgear straps. Each of those components is described in more detail below.

The support 500 of this configuration has two sliding members 501. Each sliding member 501 has a generally circular cross-section and is an elongate member. The sliding members 501 extend generally parallel to each other and are connected together at each end, forming a loop as shown in FIGS. 2 to 8. Each sliding member 501 is relatively rigid (compared to the single sealing nasal prong, for example) but is sufficiently flexible such that it can bend to suit the face of the patient.

In another configuration, for example as illustrated in FIGS. 72-75, the support 500 (whether there are two sliding members 501 or a single sliding member 501), may be of a pre-formed shape or configuration or curvature.

In an example embodiment, the support 500 comprising sliding members 501 and/or 502 may comprise a pre-curve or radiused profile that substantially follows or accommodates a contour of a patient's face.

Alternatively, or in addition, the sliding members 501 and/or 502 may be formable or conformable such that, once formed, the sliding members 501 and/or 502 may substantially follow or accommodate a contour of a patient's face. In an example embodiment, the support may be formed from a wire or a material with a low deformable temperature or another malleable or mouldable material such that it can be shaped to a patient's face shape and/or size.

In an example embodiment the support 500 comprises a curve or profile of sliding members 501 and/or 502 such that said support 500 is substantially convex with respect to a patient's face.

Figure 17:
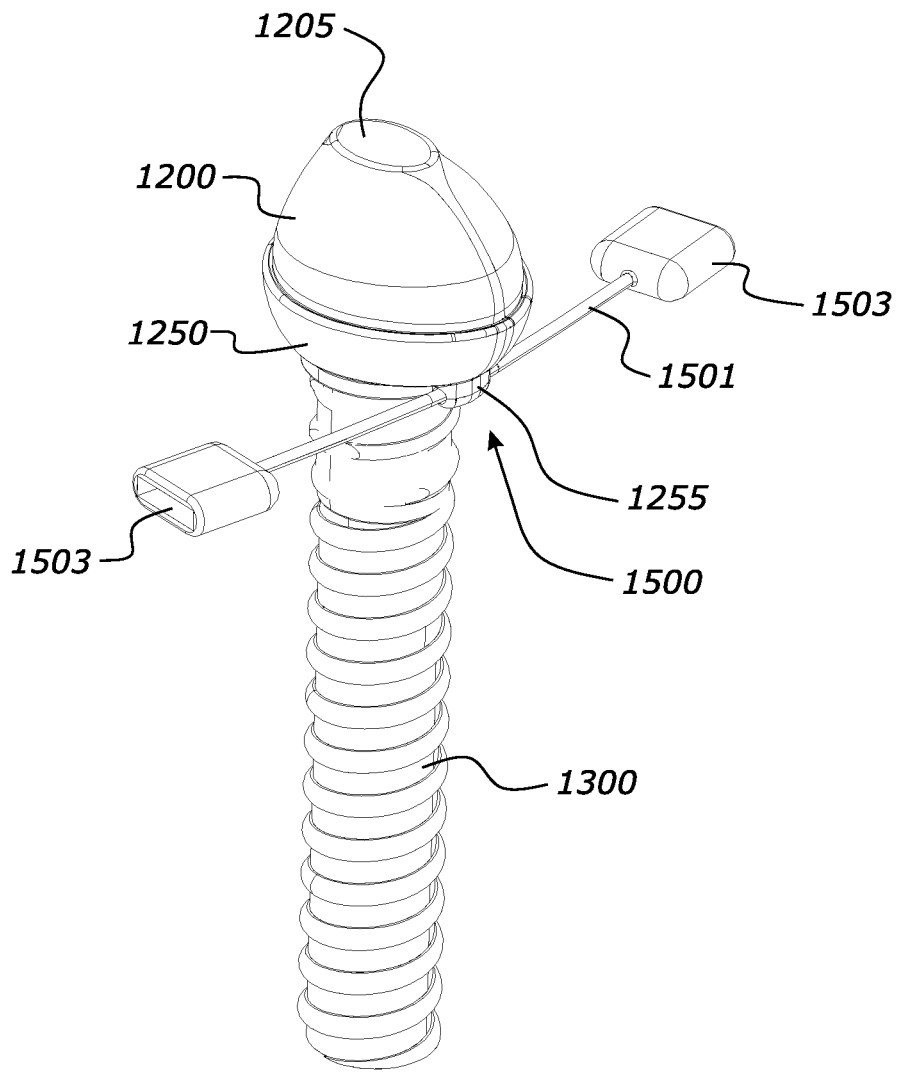
FIG. 17 is a front perspective view of another configuration of a respiratory interface.
Figure 18:
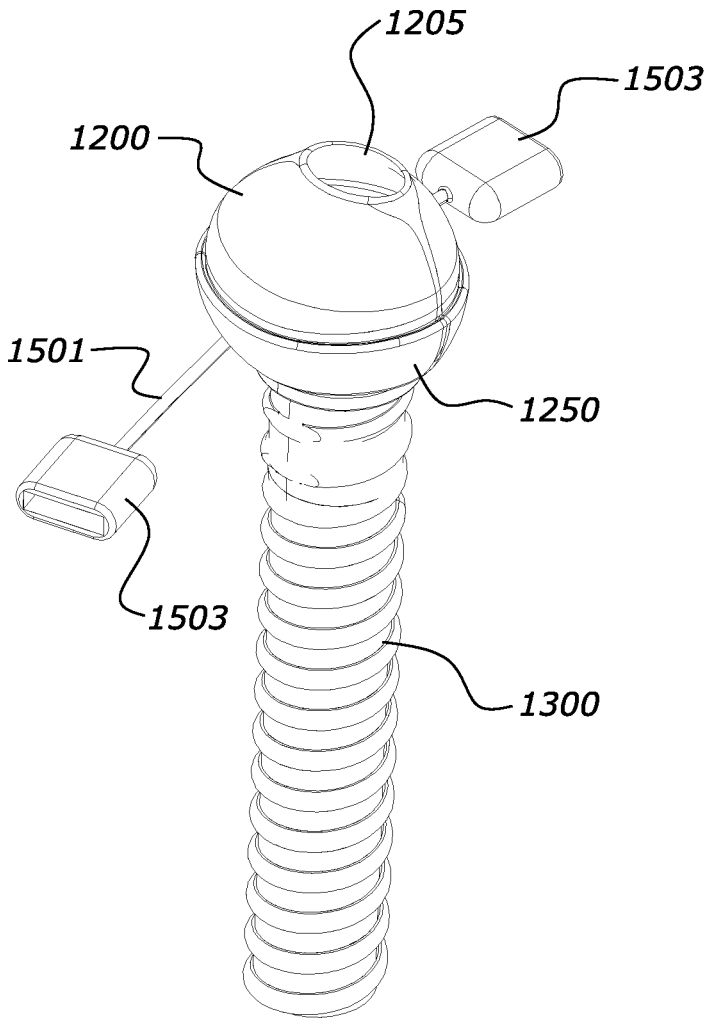
FIG. 18 is a rear perspective view of the respiratory interface of FIG. 17.

The pre-formed shape or configuration or curvature can be provided with a pre-determined radius of curvature, and may for example provide for about 120° of a circle or about one third of a circle or may be an arc shaped configuration. The pre-formed profile may comprise a radius length or pre-curve length of about 70 mm to about 110 mm, or about 90 mm. Such a pre-formed shape can facilitate particular ergonomics of positioning or angling of a prong 200 outlet for suitable engagement with either nare of the patient. In such a configuration, the sliding members 501 may be a single member (such as for example as illustrated in FIGS. 17-18, but where the sliding member 501 is of a pre-formed shape or configuration or is otherwise formed as bent shape), or may be a pair of sliding members 501, to provide for a pair of rails or pair of sliding members along which the cuff 250 can be traversed.

The sliding members 501, are constructed of a material having low coefficient of friction. The sliding members 501 may also have a smooth surface. The low coefficient of friction allows the cuff 250 to readily slide, pivot, or slide and pivot relative to the sliding members 501 with very little resistance. Suitable materials include nylon-based derivatives. In a configuration, the material of the sliding member is polyacetal (Delrin 500P NC010), or a cellulosic thermoplastic. In addition to being constructed from a material with a low coefficient of friction, the sliding members 501 are formed using injection moulding techniques to give a polished finish.

In some alternative configurations the sliding members 501 may include a soft material that encases the rigid members e.g. an overmoulded thermoplastic.

Figure 9B:
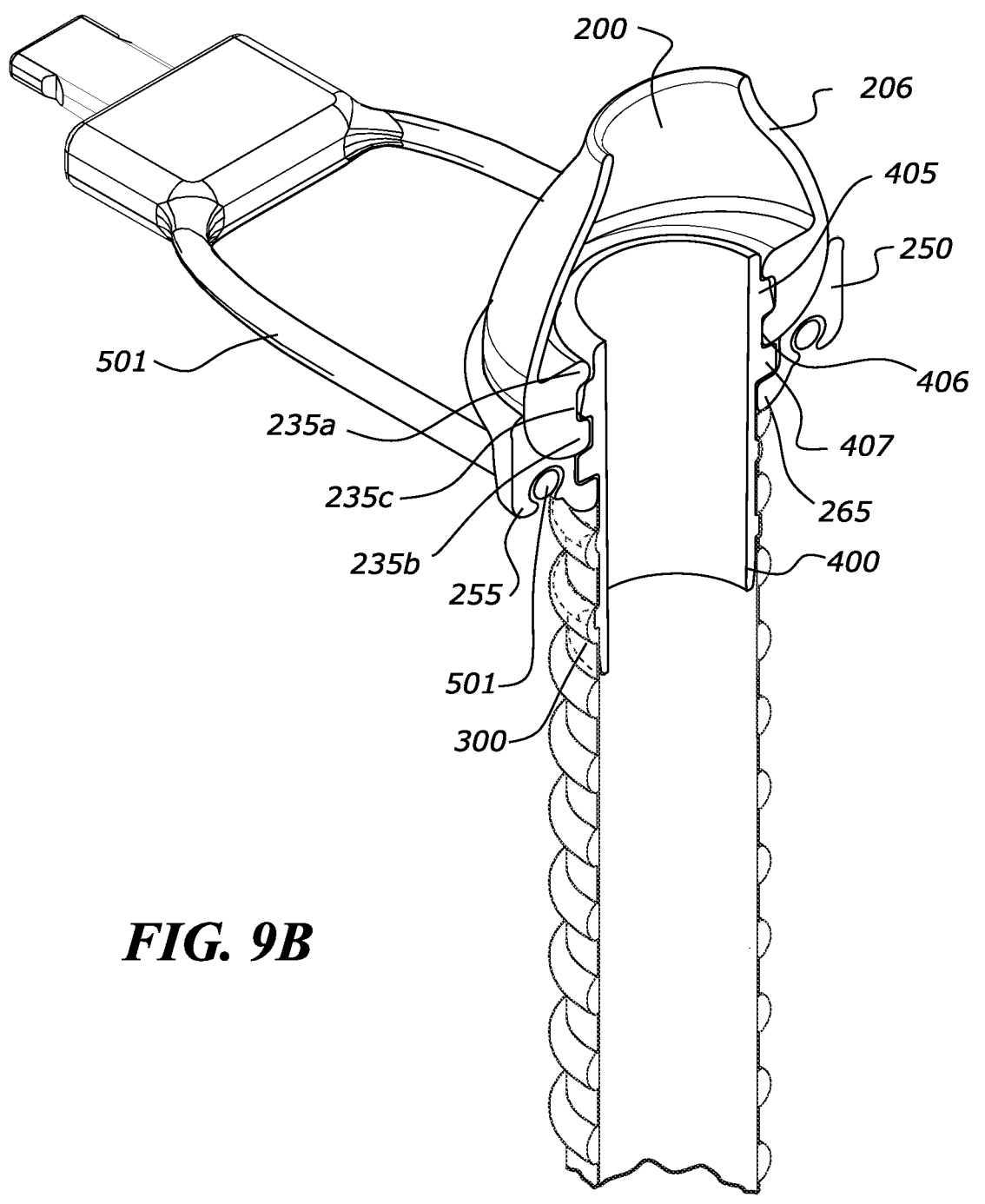
FIG. 9B is a cross section of the respiratory interface of FIG. 2.

FIG. 2 shows the cuff 250 connects the single sealing nasal prong 200 to the conduit, and also connects those components to the support 500. The sliding member(s) 501 are coupled to, or couplable to, the single cuff 250, and the cuff 250 is coupled with the single sealing nasal prong 200. FIG. 9B shows a cross-section of the single sealing nasal prong 200, cuff 250, and sliding members 501 of the support 500.

The sliding members 501 are able to flex. The sliding members 501 bend or flex the sliding members 501 toward the face of the user when the headgear is positioned in the operative position and coupled to the sliding members. An upward force is exerted on the prong (and support) in order to form a seal with the nostrils. The bend in the sliding members 501 causes a resultant force on the sliding members 501 due to resilience of the sliding members 501. The resultant force pulls the sliding members 501 away from the users. The sliding members and clips are held off the face when the mask is in an operative position. Only the prong and portions of the headgear straps are in contact with the face, and the support (including the sliding members) does not contact the face when in use.

The single sealing prong is advantageous because it can be disconnected from the support 500 without needing to remove the headgear. This allows the user to change the size of the sealing prong or replace the sealing prong without needing to adjust their headgear settings.

With reference to FIG. 9B, the cuff 250 secures the conduit 300, the conduit connector 400 and the single sealing nasal prong 200 together. The cuff 250 has an aperture 261 through which the conduit 300 and the connector 400 extend. The conduit connector 400 is secured to the cuff 250 via a conduit coupling portion 265 of the cuff 250. The cuff 250 has a prong coupling portion 263. The single sealing nasal prong 200 is received within, or receivable within, the prong coupling portion 263. A portion of the single sealing nasal prong 200 received by, or receivable by, the cuff 250 is a rigid portion of the single sealing nasal prong 200.

The recess 235c interacts with a first flange 405 of the conduit connector 400. The conduit connector 400 has a second flange 407 that abuts the inner surface of the cuff 250, preventing the conduit connector from being pulled out from the cuff 250, and the cuff receive the prong.

The single sealing nasal prong 200 is received within the prong coupling portion 263 such that the recess 235c of the single sealing nasal prong 200 couples with the flange 405 in the conduit coupling portion 265 as it protrudes through cuff opening 261 to interact with the single sealing nasal prong 200. The single sealing nasal prong coupling portion 263 is held in place via this interaction between the prong 200 and the conduit coupling portion 265.

In an alternative configuration, the conduit connector 400 part may be integral with the cuff 250 such that they are a single part. In this configuration, the prong undercut would interact directly with the cuff.

The prong coupling portion 263 and conduit coupling portion of the cuff 250 are integral. Alternatively, the prong coupling portion 263 and conduit coupling portion of the cuff 250 may be separate parts. If they are separate parts, they can be connected together by fasteners, clips, or adhesive, for example.

The prong coupling portion 263 of the cuff 250 comprises a shape that generally complements the shape of the single sealing nasal prong 200. The prong coupling portion is bowl-shaped with an elliptical or oval cross-section when viewed from above. The conduit assembly includes the conduit 300 and a conduit connector 400.

In an alternative form, the cuff 250 may include a plurality of cuff flanges that engage with the flanges on the connector (i.e. threads) on the outer surface of the connector body to couple the cuff 250 to the connector 400. The inner region of the single sealing nasal prong 200 may not include flanges and the connector 400 may be friction fitted into the single sealing nasal prong 200, or the single sealing nasal prong 200 includes projections to allow a snap fit between the single sealing nasal prong 200 and the connector 400.

The conduit connector 400 of the illustrated configuration is a sleeve, which has a much shorter length than the conduit 300. The conduit 300 and conduit connector 400 may have complementary threaded portions. In the illustrated configuration, the threads of the conduit connector are partial threads—they do not extend fully around the perimeter of the sleeve. Alternatively, the threads may extend around the perimeter of the sleeve. The conduit connector 400 has two outwardly extending flanges 405, 407, with a space defined between the flanges. The flanges 405, 407 are near the outlet of the conduit connector 400. The flanges 405, 406 extend around the entire perimeter of the sleeve. The conduit 300 and connector may be connected with other mechanical connections, including recesses, protrusions, clips, press fits, adhesives, and/or welding.

In an alternative configuration, the threads may be on the internal surface of the conduit connector 400, which then receives the conduit 300. In this configuration, threads on the exterior of the conduit 300 interact with the threads 403 of the connector 400.

A variety of different arrangements between the single sealing nasal prong 200, the cuff 250, and the conduit connector 400 are possible. For example, the single sealing nasal prong 200, the cuff 250, and the conduit connector 400 can be separate and disconnectable components, which is the configuration illustrated above.

In a further alternative configuration, as for example shown by way of reference to FIGS. 62-71, there is provided a medical tube component comprising a conduit connector 400 and a cuff 250, where the conduit connector 400 itself comprises a thread 403. The thread 403 comprises at least one region of discontinuity 480. The cuff 250 comprises at least one protrusion 280 configured to interact with the region of discontinuity 480 when brought into engagement with the conduit 300 in a first direction (as for example shown by arrow D' in FIG. 63A). The at least one protrusion 280 is further configured to engage with at least a portion of the thread 403 beyond, or away from, the region of discontinuity 480 when brought into engagement with the thread 403 in a second direction (as for example shown by the arrow D" in FIG. 63B).

In respect of the protrusion to interact with the region of discontinuity, the protrusion is to be received or inserted into, or accommodated within the region of discontinuity. In this manner, the region of discontinuity is configured in size or shape or both to accept the protrusion(s) to allow the cuff to be placed upon the conduit connector and moved (e.g. slid) into a particular place or position, before a second direction of force or movement is applied.

Figure 63C:
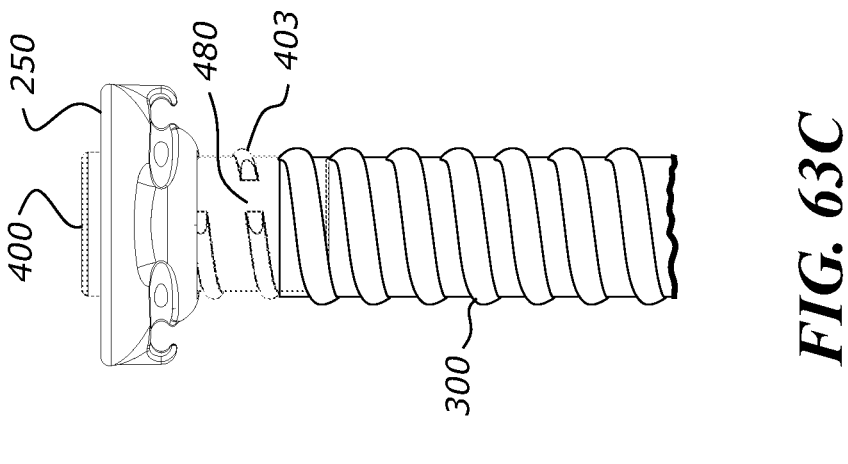
FIG. 63C exemplifies the completed assembly of the cuff with the conduit connector and conduit engaged upon the conduit connector also.
Figure 63B:
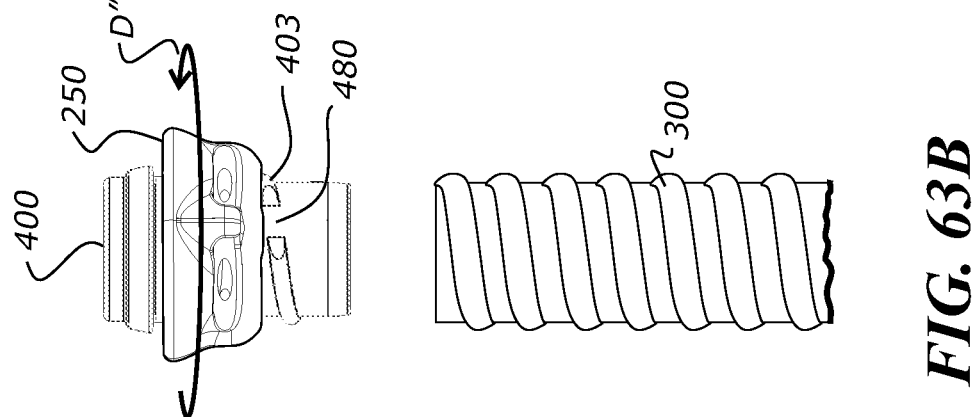
FIG. 63B exemplifies the second direction for engaging the cuff onto the conduit connector.
Figure 63A:
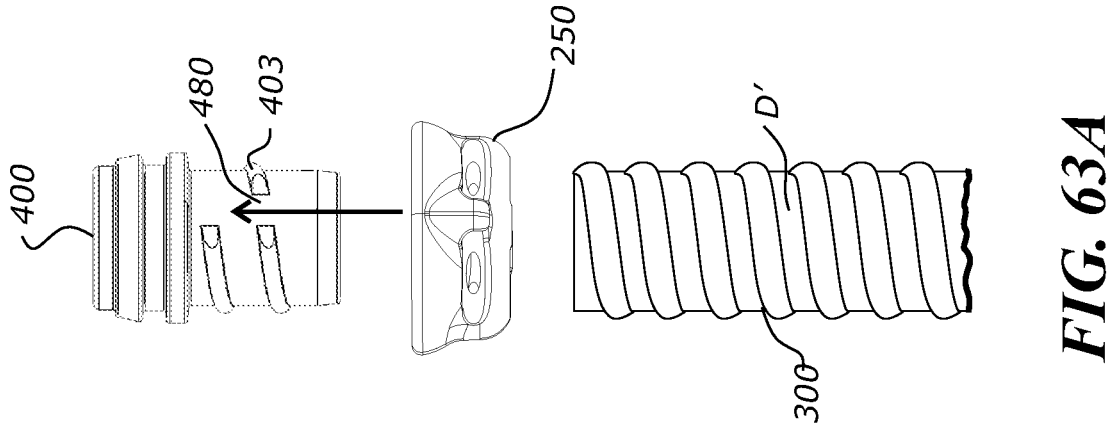
Figure 64:
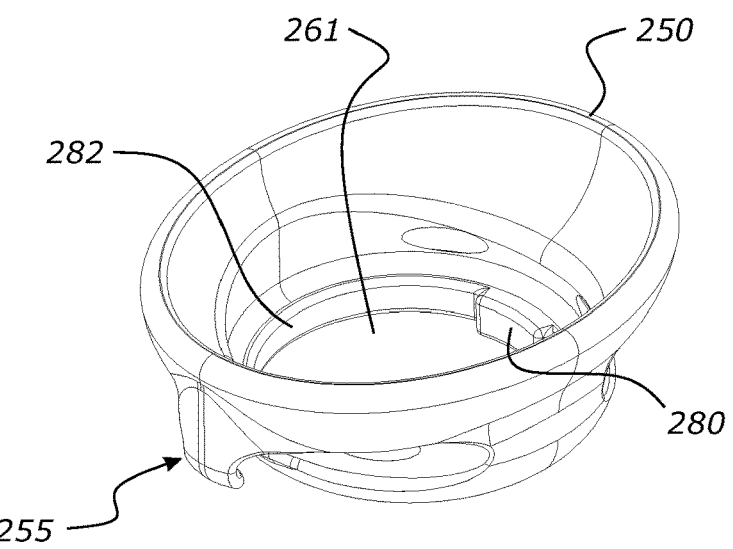
FIG. 64 illustrates a cuff configuration provided with a single protrusion.
Figure 65:
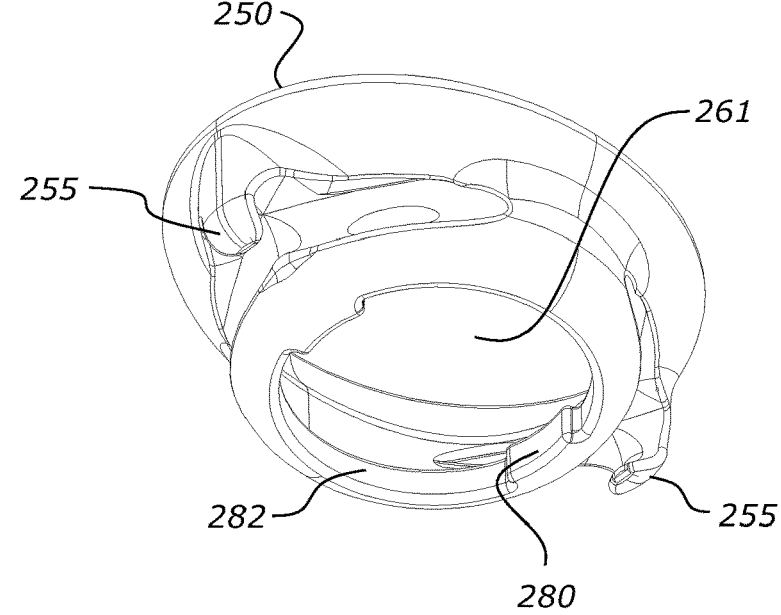
FIGS. 65, 66A illustrate a cuff configuration provided with two protrusions.
Figure 66A:
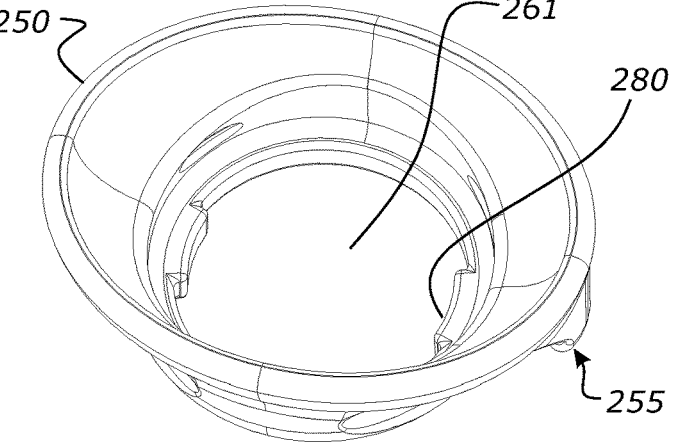
Figure 66B:
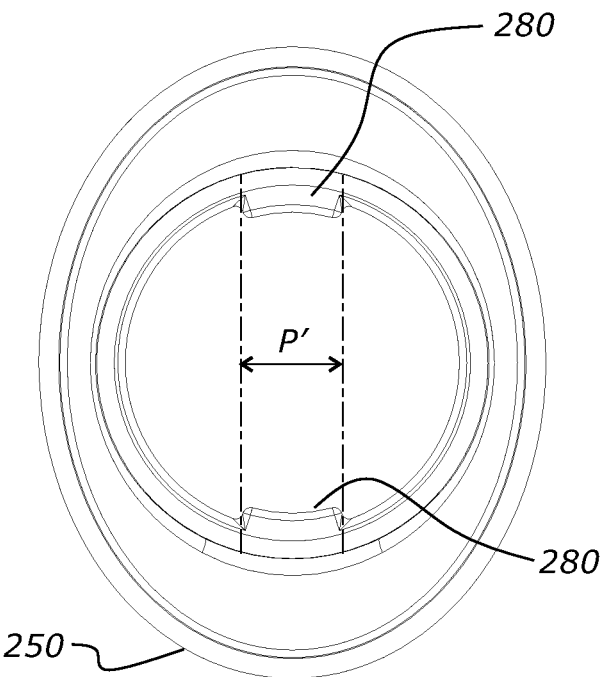
Figure 66C:
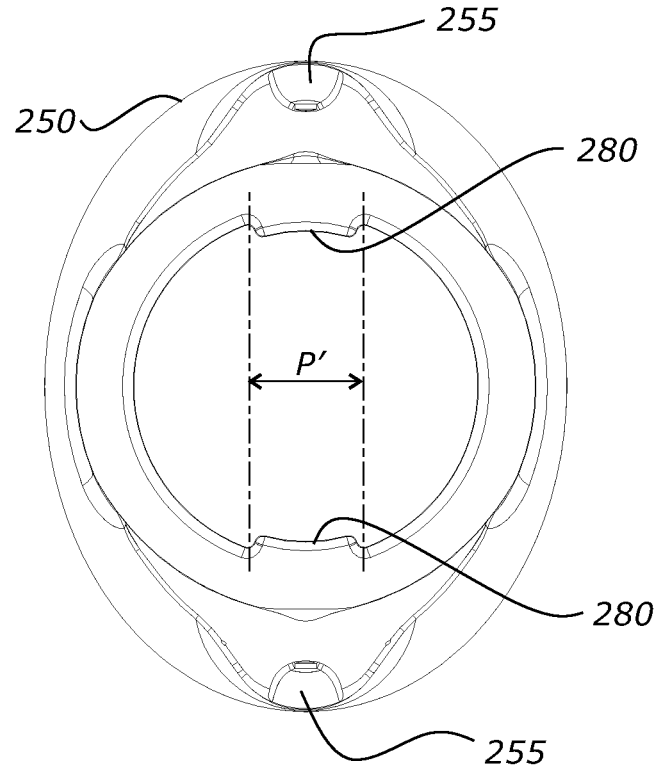
Figure 66D:
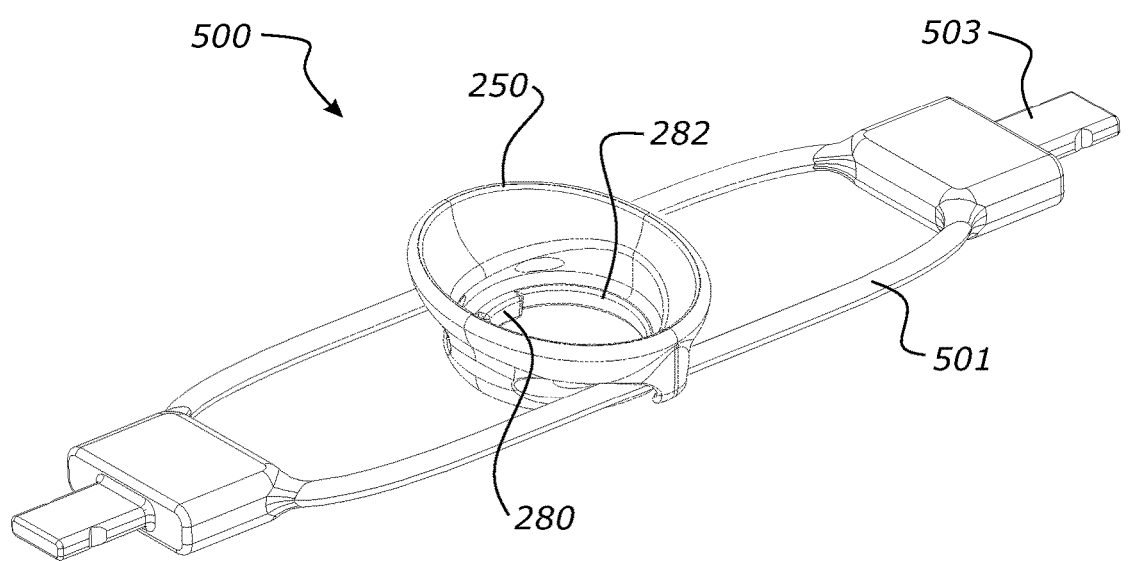
FIG. 66D illustrates a cuff configuration with a single protrusion on a pair of sliding members.
Figure 66E:
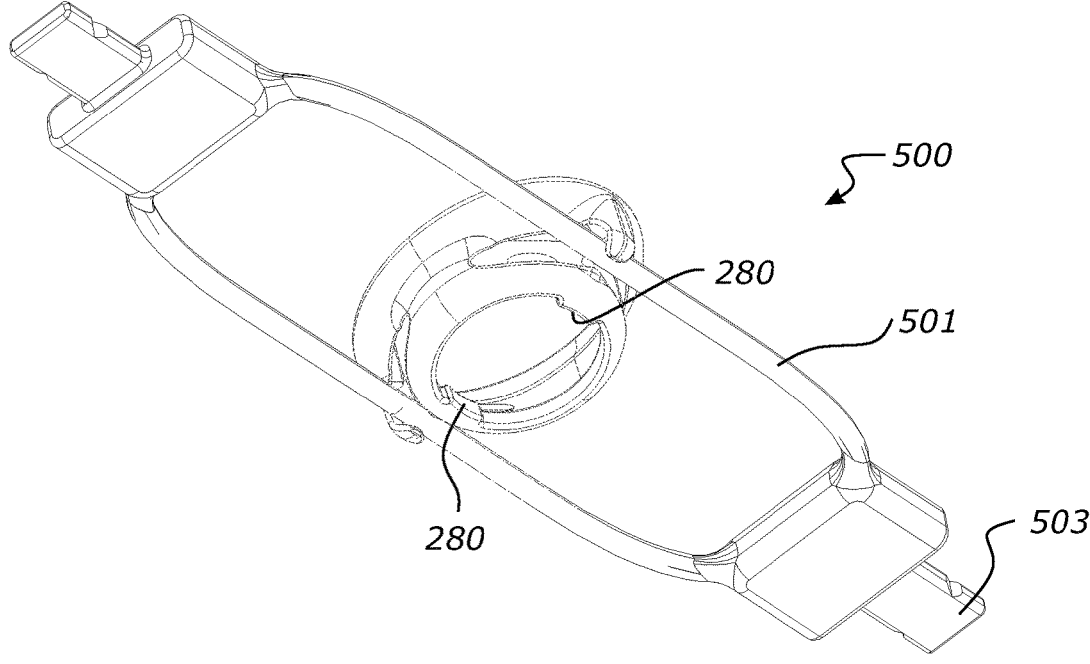
FIG. 66E illustrate a cuff configuration with a pair of protrusions on a pair of sliding members.
Figure 72:
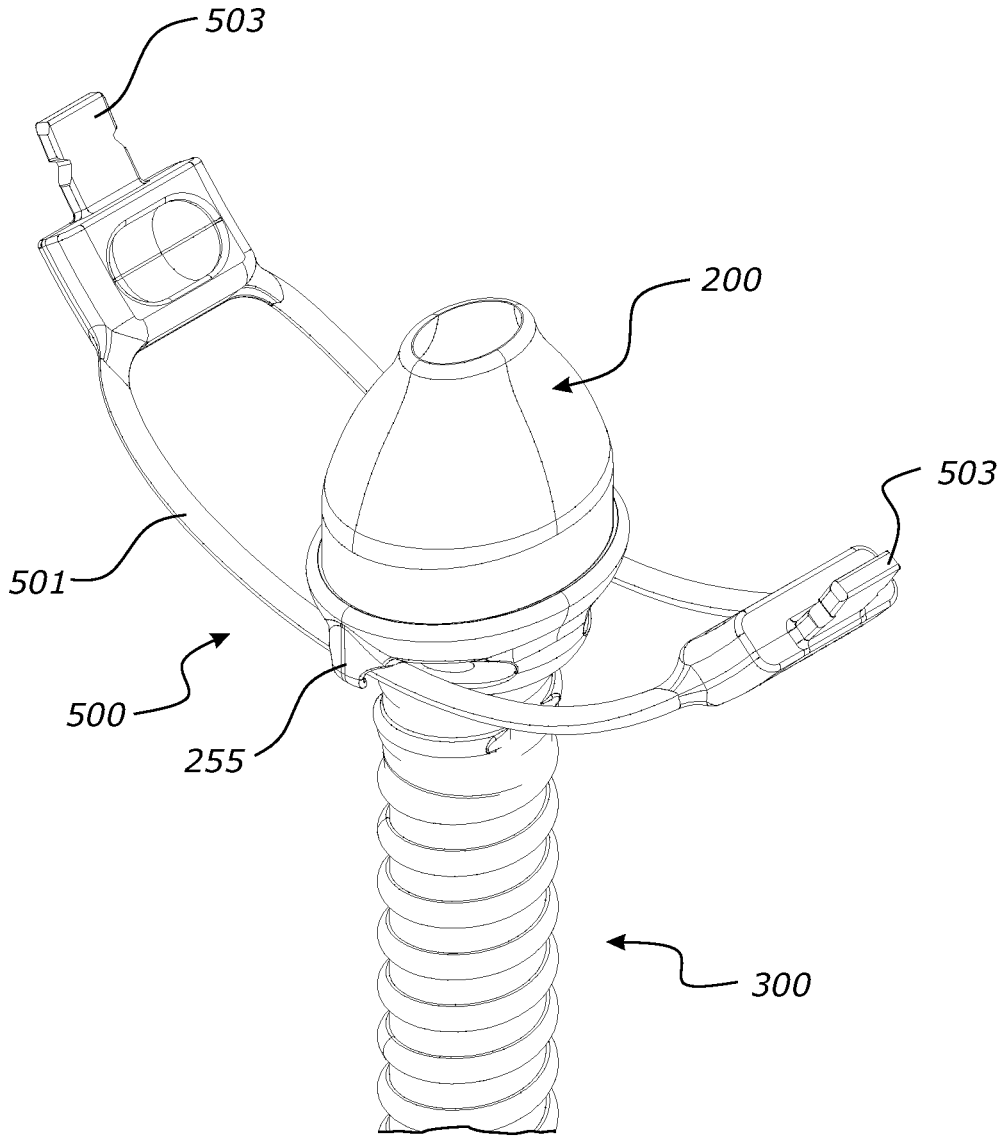
FIG. 72 illustrates a top perspective view of a pre-formed shape or bent configuration of a sliding member with a cuff engaged thereon.

FIG. 63A illustrates the separate component parts of the conduit 300, the cuff 250 and the conduit connector 400 as an intervening or intermediate component for making the assembly of the cuff 250 and the conduit 300, FIG. 63B illustrates the initial engagement of the cuff 250 upon the conduit connector 400, FIG. 63C illustrates the final assembly made and with the conduit 300 also having been put into engagement or connection with the conduit connector.

Figure 76:
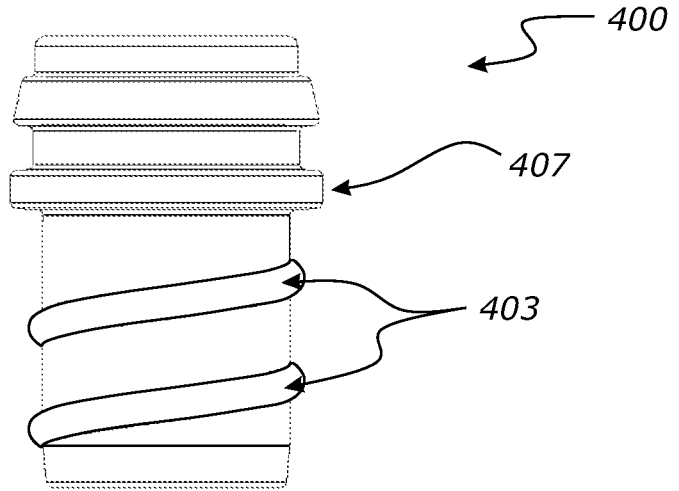
FIG. 76 illustrates a conduit connector provided with a single continuous thread portion.

FIG. 76 illustrates a further configuration in which the conduit connector 400 is provided with a continuous thread enabling the cuff 250 to be wound on to the conduit connector directly.

The first direction is provided by application of a first force or first movement. For example, see FIG. 63A illustrating a first direction as indicated by the arrow D'.

The second direction is provided by application of a second force or second movement. For example, see FIG. 638 illustrating a second direction as indicated by the arrow D".

As illustrated, the first and second directions are different from each other, in this way, a connection between the cuff 250 and the conduit connector 400 is made as a two-part movement so as to provide for a relatively secure connection which is substantially free from accidental or inadvertent disconnection. That is, disconnection or detachment of the cuff 250 and the conduit connector 400 requires a series of positive (and different) directional movements to free these parts from their connection or attachment with each other.

With respect to the two different directions, the first and second directions may be substantially transverse with respect to each other, or provide for a first axial direction and a second rotational direction.

The first direction is generally or substantially aligned with an axial direction of the conduit connector 400, while the second direction is generally or substantially transverse to the axial direction of the conduit connector 400, More particularly, the second direction can be a rotation for engaging the at least one protrusion 280 of the cuff 250 upon or with the thread 403 of the conduit connector 400. For example, the second direction can be an axial rotation of the cuff 250 with respect to the axial direction of the conduit 300.

The protrusion or protrusions 280 provided by the cuff 250 can engage with or become engaged with the thread 403 or portions of the thread 403 once the cuff 250 (with the protrusions 280) is moved or rotated in the second direction.

The protrusion(s) 280 is/are configured to substantially engage with the thread 403 or portions of the thread 403 of the conduit connector 400 to at least partially restrain or lock the cuff 250 to or upon the conduit connector 400 upon application of a force or movement in the second direction. In this manner, the cuff 250 and the conduit connector 400 may be substantially further inhibited from disconnection or detachment from each other, without applying a reversing of the second direction and of the first direction, in a reverse (i.e. detaching or disconnecting) manoeuvre. Accordingly, once engaged, the protrusion(s) 280 acts to substantially restrain or inhibit relative axial movement or displacement of the cuff 250 and conduit connector 400 from or with respect to each other.

Where more than one protrusion is provided, such protrusions may be axially offset from each other at suitable distances to account for the pitch of the thread on the conduit connector 400, such that each protrusion is then able to be located or accommodated within a region adjacent between two turns or windings or runs of the thread 403 or at least a first protrusion is able to be located or accommodated within a region between a run or winding of the thread 403 and a flange 407 of the connector 400. Accordingly, the protrusions may be positioned upon the cuff to achieve the above, and may be located or arranged about the cuff at spaced intervals, whether in an equidistant manner or a non-equidistant manner.

The protrusions 280 may act to achieve such locking or restraint upon rotating the cuff through greater than about 5°, or greater than about 10°, from the region of discontinuity. Alternatively, this may be achieved by rotating the cuff 250 (with protrusion's 280) through about 90° from said region of discontinuity 480. In a further alternative, the cuff 250 may be rotated greater than about 170° from said region of discontinuity, for example in a configuration where there is a single discontinuous thread 403 on the conduit connector 400 and a single protrusion 280 on the cuff.

It will be appreciated that depending on the placement or positioning of the region or regions of discontinuity 480, once the protrusion(s) 280 have been substantially inserted into the region or regions of discontinuity 480, the second direction should be executed in a manner sufficient to provide for an engagement of the protrusion(s) 280 with or adjacent (such as A') to the thread 403 or into a region between adjacent windings or runs of the thread (such as A"). For example, see FIGS. 70A and 70B which illustrated hatched areas A' and A" to indicate potential regions which may accommodate the engagement with the protrusion(s) 280.

An opening 261 of the cuff 250 has an inner diameter that is greater than an outer diameter of the conduit connector 400. In this manner, the conduit connector 400 is to be received with the opening 261 of the cuff 250. In this manner, the conduit connector 400 is provided as a substantially internal part (i.e. internal with respect to the more outwardly positioned cuff).

In configurations with two protrusions 280, the distance between the protrusions 280 would be less than the diameter of the threads or the distance between the outer surface of the threads, and would be more than the diameter of the outer surface of the conduit connector 400 (on which the threads are positioned). In this manner, the protrusions 280 will fit between the outer surface of the threads and the outer surface of the conduit connector 400.

As noted above, the cuff 250 may comprise of a plurality of the protrusions 280. In one embodiment, the cuff comprises two protrusions. Optionally, the protrusions may be positioned substantially opposingly from each other, or at 180° apart, or may be equally spaced about the opening 261 of the cuff 250. Alternatively, the protrusions may be spaced substantially equally apart, or may be spaced non-equally apart from each other. For each protrusion provided, there may be provided a correspondingly provided discontinuous thread region to accept the protrusion.

The protrusion or protrusions 280 may also act as an alignment mechanism for aligning of the cuff and the conduit connector together.

As noted above, the thread 403 may comprise of a plurality of the discontinuous regions 480. In one embodiment, the thread 403 may comprise of two discontinuous regions, for example as shown in FIG. 71. In another embodiment, there may be provided a single discontinuity, for example as shown in FIG. 69.

As with the previous disclosure herein, a nasal prong 200 is connectable or connected to the conduit connector 400.

The cuff 250 may abut or make contact with, or otherwise impinge upon, the nasal prong 200 when the cuff 250 is in a substantially engaged position within or upon the thread 403.

As the nasal prong 200 can be formed of a relatively soft or substantially compliant material, the cuff 250 may at least partially compress the nasal prong 200 or a portion thereof when the cuff 250 is engaged with the thread 403, or the nasal prong 200 or a portion thereof may be at least partially compressed upon engagement of the cuff 250 with the thread 403. Accordingly, a friction-fit type engagement of the cuff 250 with the nasal prong 200 may be subsequently achieved.

The cuff 250 and the conduit connector 400 may be removably attached with each other in a non-permanent manner. In this way, the cuff and the conduit connector can be detachable from each other.

Depending on the configuration of the thread 403 of the conduit connector 400, the cuff 250 may be engageable with a first thread T' of the conduit connector 400, or the cuff 250 may be engageable with a first thread portion T' and a second thread portion T" provided upon the conduit connector 400.

With respect to the protrusion 280, a protrusion may be a substantially radially inwardly extending projection. In such a configuration, such protrusion 280 may be a tab.

Figure 62:
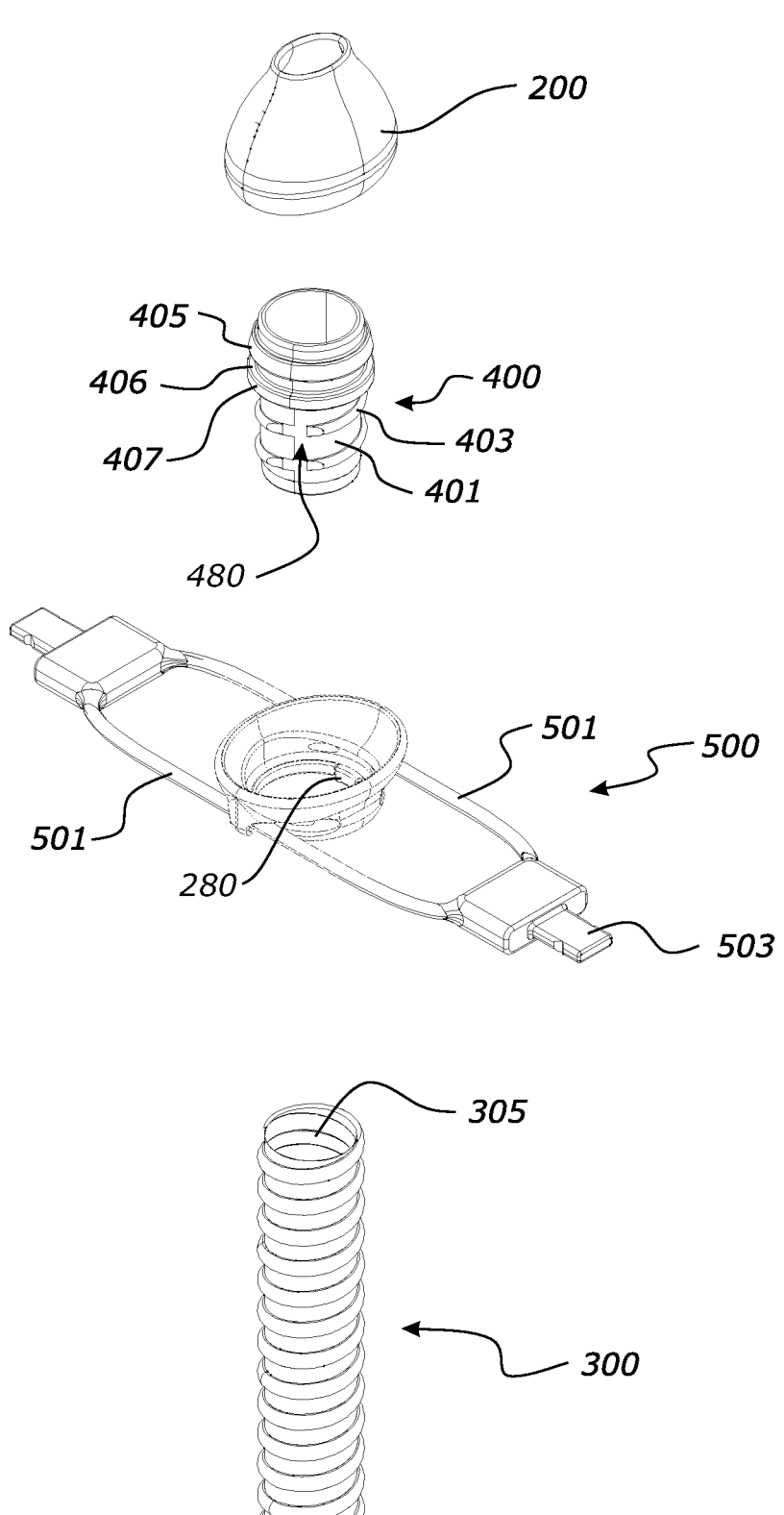
FIG. 62 illustrates an exploded set of components to be assembled together, including a prong, a conduit connector comprising of a thread with regions of discontinuity, a cuff (to be engaged with the conduit connector), and a conduit, FIG. 63A exemplifies the first direction for putting a cuff into position with a protrusion (or protrusions) to interact with the regions of discontinuity of the conduit connector thread.

As shown in FIGS. 69-71, the discontinuity region 480 provides for a predetermined width W' of discontinuity sufficient to receive or accommodate a width P' of a protrusion 280, such that the width P' of the protrusion is less than the width W' of the discontinuity region 480, In this manner, the protrusion 280 can be accepted for insertion into the discontinuity region 480, before then being moved in a second direction, A width H' of a region between adjacent turns of windings of the thread 403 or between a feature of the conduit connector such as a flange 407 (e.g. a stopping flange or the second flange 407 as for example shown in FIG. 62) and an adjacent turn or winding may also be of sufficient height dimension to receive the height dimension of the protrusion(s).

Once the protrusion(s) 280 have been successfully inserted or accommodated within the region of discontinuity, the protrusion(s) can then be brought into engagement with the thread 403 or turns or windings of the thread 403 by locating each protrusion(s) 280 to within a region A" which may be between adjacent winds of the thread (for example see FIG. 70B), or into a region A' adjacent to a wind or a turn or run of the thread 403 and a feature (such as flange 407) of the conduit connector 400. The flange 407 of the conduit connector 400 may be a ridge or a stopping flange providing for a physical structure against which the protrusion(s) 280 are unable to be wound past. Alternatively, rotation may be stopped or inhibited due to an increasing force requirement or resistance to rotation as the cuff compresses the prong with continuing rotations as the cuff is wound up upon the thread of the conduit connector 400.

The region or regions of discontinuity are to be sized so as to allow the insertion or receipt of one or more protrusions provided by a cuff. The region of discontinuity is for example a region of the conduit connector which is devoid of the thread 403, or which is at least of a substantially reduced height or depth (in a radial direction) so as to facilitate the accommodation of a protrusion therein.

In an alternative configuration, the cuff 250 can provide for a shank portion 281 upon which the protrusion(s) 280 are located radially inwardly thereof, for example of an inner wall 282 of the cuff 250. The shank portion 281 can have a longitudinal length (or height) 5' sufficient to locate the protrusion(s) 280 thereof to be suitably received by the conduit connector 400 in a region adjacent A' to a winding or turn or run of the thread or within a region A" between adjacent winds of the thread. The protrusions 280 can be located at a distance within the height 5' in order to be suitably engageable or receivable with the thread of the conduit connector 400.

The cuff 250 may also comprise a notch 283 or an indentation (being of a radially outward shape) about an inner wall 282 of an opening 261 of the cuff 250. For example, as shown in FIG. 678, a cuff 250 may be alternatively provided with a notch or a recessed region 283 instead of with protrusions 280 as shown in FIG. 67A.

The size or dimensions of the opening of the notch 261 is to be larger than the dimensions of the thread 403 which is to be received therein. One or more notches may be provided about the cuff 250 depending on the thread 403 of the conduit connector 400. The notch(es) 261 provided for a feature which can receive the thread 403, and provide a pathway through which the thread 403 may be advanced as the cuff is wound onto a conduit connector 400.

The notch 283 can be sized and/or shaped to facilitate with accommodating the thread 403, to thereby provided for an aid with initiating a rotation of the cuff 250 about the thread 403.

It will be appreciated the thread 403 may be a substantially helical thread. The pitch of the thread 403 may be constant or may vary along the thread length. The pitch of the thread 403 provided on the conduit connector 400 can be substantially the same as the pitch of conduit corrugations or other formations capable of being wound onto the thread 403 of the conduit connector. In some configurations, the pitch of the thread 403 the conduit connector 400 may be varied slightly due to the relatively flexible nature of the conduit 300 or to accommodate slight difference in pitch of the thread 403 and the features of the conduit 300 which are capable of being wound onto the thread 403.

Figure 8:
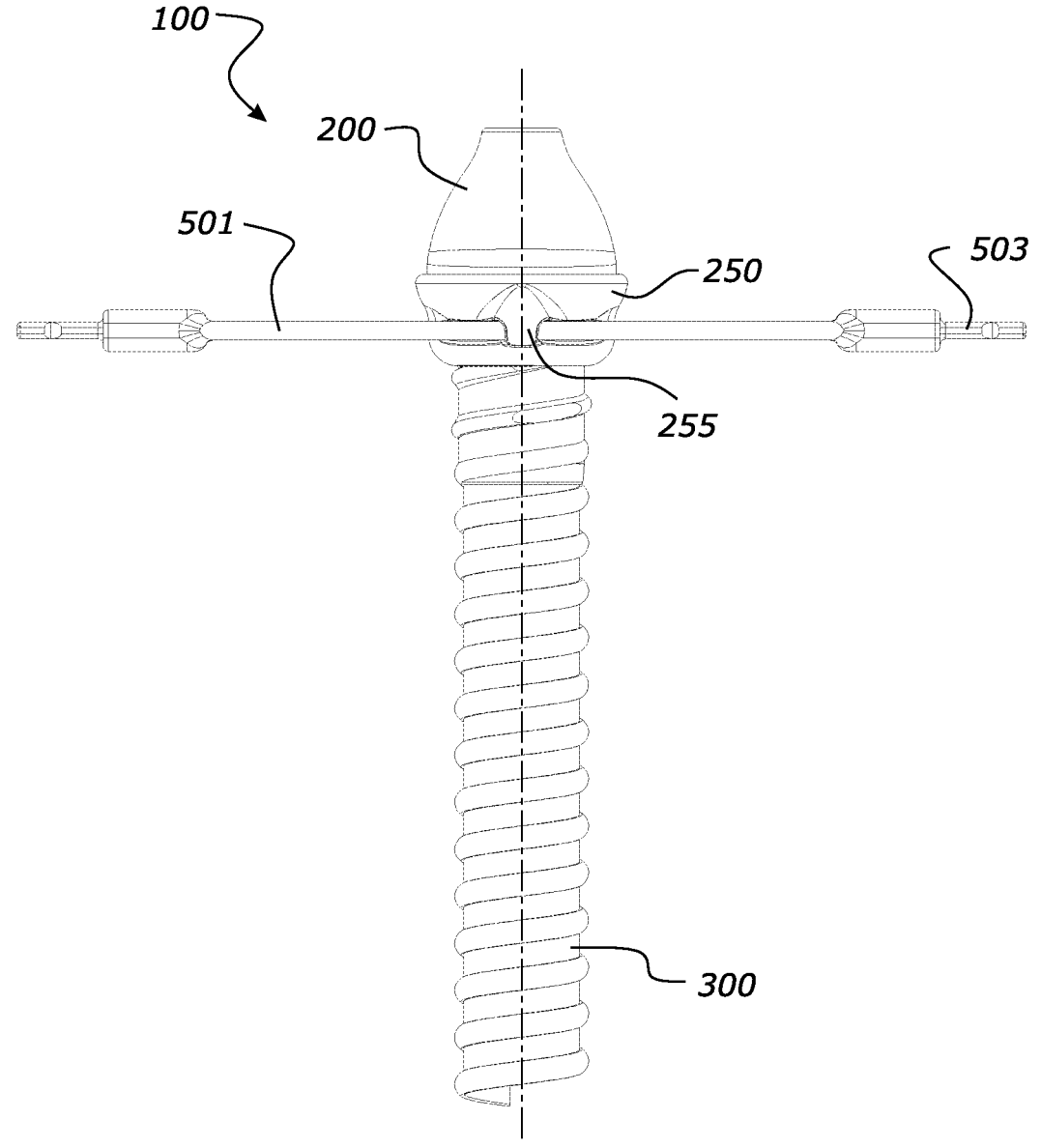
FIG. 8 is a front view of the respiratory interface of FIG. 2.

As disclosed herein, a conduit 300 can be substantially engaged with the conduit connector 400 by rotating or winding of the conduit upon the thread to thereby engage these two parts, forming an assembly of a conduit 300 and a conduit connector 400, for example to result in an assembly shown by FIG. 8.

Preferentially, the conduit 300 may be substantially engaged with the conduit connector 400 subsequent (i.e. after) the cuff 250 has been brought into engagement with the thread. In this manner, the sequential engagement of different components provides for an assembly of a cuff upon a conduit connector and a prong with a cuff. The prong can be additionally sandwiched or more securely held in place or position by the additional pressure or force of the cuff being squeezed against the prong in such an arrangement.

In a further configuration, a conduit connector 400 can be provided with a continuous thread 403, for example as shown in FIG. 76. That is, the conduit connector 400 can be provided devoid of the regions of discontinuity. In this configuration, a cuff 250 comprising of one or more protrusions 280 or one or more notches 261, can be wound on to the conduit connector in screw format, and thereby provided into a screw-fit assembly. Once the cuff has been screwed or wound into place, a conduit 300 may be additionally (but optionally) attached to the conduit connector, whether by friction fit or by winding (screwing) the conduit 300 onto the conduit connector 400 using the thread 403. In this manner, the additional (but optional) connection of the conduit to the conduit connector, after the cuff has been wound (screwed) into place provides for a more secure connection or an additional component that functions to retain the cuff in place and preferentially prevent or inhibit undesired disconnection of the cuff 250 from the conduit connector 400.

In other words, the cuff can be held in a predetermined orientation or position by a compression fit between each of:

i) a terminal end of the conduit once the conduit is substantially engaged with the thread of said conduit connector, and ii) by a base of the nasal prong once the nasal prong is substantially engaged with the cuff.

In an alternative configuration, the conduit connector 400 and the cuff 250 may be a single, integral part. In this alternative configuration, the single sealing nasal prong 200 and the conduit connector 400 may be disconnectable by a threaded connection or a friction fit or a snap fit.

In another alternative configuration, the single sealing nasal prong 200 and the cuff 250 may be a single, integral part. In this alternative configuration, the conduit connector 400 may be disconnectable from the prong/cuff component by a threaded connection or a friction fit or a snap fit.

Figure 6:
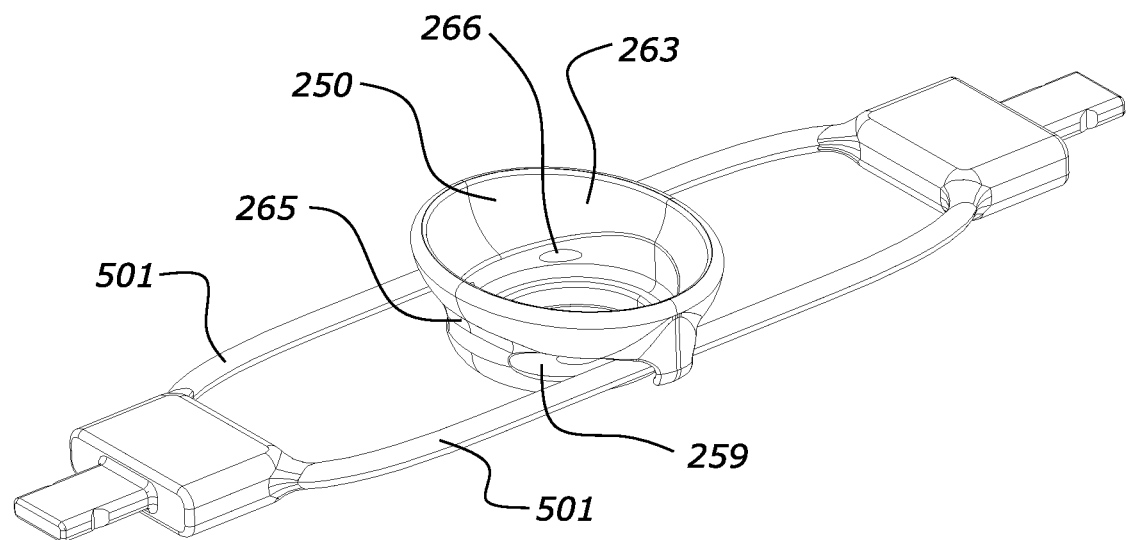
FIG. 6 is a top perspective view of the cuff and sliding members of the respiratory interface of FIG. 2.
Figure 7:
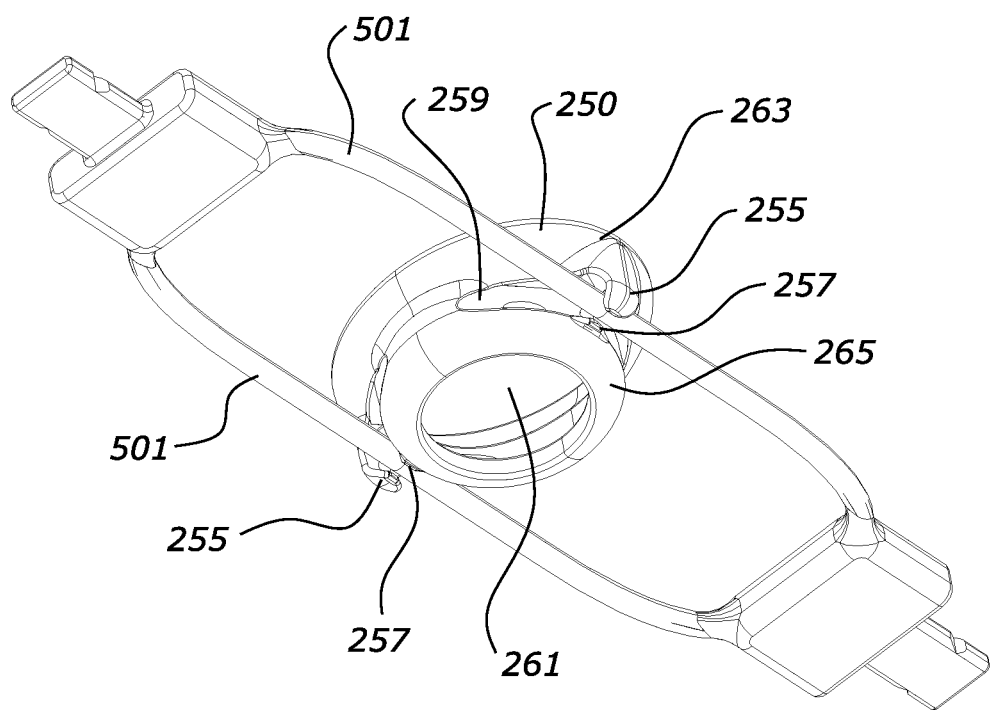
FIG. 7 is a bottom perspective view of the cuff and sliding members of FIG. 6.

The cuff may have a variety of different couplings including one or more rings, hooks, or clips for connection with the support. FIGS. 6 and 7 show the cuff 250 having hooks in the form of curved fingers 255 that couple with the members 501. The cuff includes a protrusion 257 opposing each of the fingers 255. The protrusions 257 extend outwardly from the cuff. The protrusions are located closer to the centre of the cuff 250 than the fingers 255. As shown in FIG. 6, the protrusions 257 are located adjacent the conduit entry opening 261. Each protrusion 257 forms a C-shaped clip with each of the fingers 255 to retain the sliding member 501. The c-shaped clips retain the sliding member with the cuff 250 when the strap pivots in the recess.

FIG. 7 shows the cuff 250 also includes a recess 259. The recess 259 allows the cuff to readily pivot relative to the sliding member 501. The cuff 250 can pivot relative to the sliding member 501 and slide along the member 501. As the cuff pivots relative to the sliding member 501, the recess 259 receives a portion of the member 501. This allows the cuff 250 to pivot relative to the member 501 while still being held by the member 501. The recess has a generally circular profile that complements the profile of the sliding member 501. In the illustrated configuration, the recess 259 extends around about a third of the perimeter of the cuff 250. The cuff 250 can include two recesses that are opposed to each other. The recesses are mirror images of each other. The recesses 259 are equal in shape and dimensions. In an alternative configuration, the recess 259 may extend further, including extending around the entire perimeter. In other alternative configurations, the recess 259 may extend along a shorter portion. The recesses 259 allow the cuff 250, together with the single sealing nasal prong 200, to pivot or rotate relative to the support assembly 500, including the sliding members 501. The recesses 259 provide a space to receive a portion of the sliding member to facilitate rotation of the cuff 250 and the single sealing nasal prong 200. The rotatable cuff allows the single sealing nasal prong 200 to pivot or rotate about its longitudinal axis. The sliding members allow the single sealing nasal prong to be adjusted in situ, allow the single sealing nasal prong to be moved between the user's nares without removing the interface 100, the single sealing nasal prong may be worn in any orientation relative to the sliding members. Further, it is possible to adjust the location and orientation of the single sealing nasal prong simultaneously.

As described later, there is also a configuration that does not allow pivoting of the cuff 250 and therefore does not have the recesses 259. The cuff may only slide relative to the sliding members 501 and will not pivot or rotate relative to the straps.

In the configuration shown, the sliding members 501 are removably coupled to the single sealing nasal prong 200 via the cuff 250. Each sliding member 501 can be removed by passing through the space between the finger 255 and the protrusion 257, or bending or deforming the curved fingers away from the member 501. The single sealing nasal prong 200 can be decoupled from the members 501 and replaced, readjusted or substituted for a different interface. This allows for quick and simple adjustments to be made and can allow multiple therapies to be delivered to a patient without requiring removal or adjustment of the headgear arrangement. Alternatively, the sliding members 501 are non-removably or permanently coupled to the single sealing nasal prong 200 via the cuff 250. In such configurations, a hook or clip may be used to couple the sliding members 501 with the cuff, while still allowing the sliding motion to occur.

The headgear 600 is coupled to, or couplable with the sliding member 501. In the configuration shown, the sliding member 501 comprise a headgear attachment. In other configurations, the headgear attachment may take a variety of different forms. For example, the headgear attachment may be a ring through which the sliding member 501 is inserted, a partial ring, or a hook. The sliding member 501 and/or the headgear 600 can be permanently coupled with the ring or detachably coupled with the ring. By detachably coupling the headgear to the ring, the respiratory interface can be removed while the headgear is left on the patient. Another respiratory interface can then be attached to the patient without refitting and readjusting new headgear.

The respiratory interface 100 further comprises clips 503 at end portions of support(s) 500 coupled to, or couplable with, headgear. The clips may be rectangular tabs with a pair of notches for receiving complementary protrusions of a headgear clip, or could be any other suitable configuration.

A clip component that may be used to couple a respiratory interface as described herein to a headgear is described in international patent application WO 2015 193833, which is incorporated by reference in its entirety.

In an alternative embodiment, the respiratory interface 100 may comprise a rectangular base from which the clips extended. The rectangular base may be elongated to locate the clips closer to the ears of the patient when in use. In such a configuration, the rectangular base could be a rigid member. In such a configuration, the headgear may comprise shorter straps as a result of the elongated rectangular base, Advantageously, this configuration may help stabilize the interface on the patient. Alternatively, the sliding members or supports 500 of any of the respiratory interfaces as disclosed herein may be longer to locate the clips closer to the patient's ears as described herein.

The arrangement described above allows the single sealing nasal prong 200 to be translatable relative to the support 500 to be interchangeably received by the patient's nares. During this movement, the single sealing nasal prong 200 remains coupled to the support 500, and does not need to be detached from the support 500. That is, the single sealing nasal prong 200 is coupled to the support 500 when positioned in either one of the patient's nares and also when it is being moved between the patient's nares. The headgear 600 provides tension to the single sealing nasal prong 200, and that tension is decoupled by the support 500. This arrangement allows lateral sliding or other movement of the support 500 without causing the single sealing nasal prong 200 to move relative to the patient's nare, or be dislodged from the patient's nare. The support 500 can slide relative to the prong based on tension or forces from the headgear. The support 500 is configured to decouple the single sealing nasal prong from tension when it is moved from one nare to the other while still allowing the headgear to maintain the headgear retention force.

The support allows the user to maintain a specific headgear setting by decoupling the single sealing nasal prong 200 from the headgear 600, This allows the single sealing nasal prong 200 to be moved relative to the face of the patient. For example, it is possible to move the prong from one nostril to the other nostril without the need to adjust the headgear tension i.e. without needing to adjust the headgear setting.

The single sealing nasal prong 200 can be translated in a substantially horizontal direction across the face from one nostril to the other nostril. The translation and rotation of the prong relative to the support allows for the single sealing nasal prong 200 to be swapped from one nostril to the other as well as achieve a seal with either nostril.

The arrangement of the support 500 of the illustrated configuration isolates the prong from the forces provided by the headgear. The support 500 decouples the respiratory interface from the headgear, thereby preventing the prong from being moved/dislodged due to forces on the headgear, such as patient head movement. The support 500 also decouples patient head movement from the prong so that the prong does not dislodge due to patient head movement. The strap can move/translate relative to the prong to account for headgear forces and head movement.

The single sealing nasal prong 200 may be translatable by pivoting, sliding, or pivoting and sliding relative to the support 500, FIG. 16 shows the single sealing nasal prong 200 in three different examples of pivot positions relative to the support 500, Other angles of rotation are also possible and can be chosen to better fit the patient's nares.

This arrangement allows the sliding member 501 to slide through the recess, isolating the headgear from the tension of the cuff 250. The sliding members 501 can alternatively be removably attached to the cuff 250 using clips. Another variation is clips on the sliding member.

In configurations in which the cuff 250 and prong 200 are not pivotable relative to the strap, the single sealing nasal prong 200 is angled correctly into the nose upon the initial fitting.

In some configurations, the prong 200, cuff 250 and/or interface 100 may be configured to allow the prong to interchangeably seal in or with a left or a right nare of a patient, while allowing the prong to remain attached to the support 500 or without being detached or requiring detachment from the support 500. In some configurations, the prong may be translatable relative to the support as described above. Alternatively, the prong (and/or cuff) may be located in a fixed position relative to the support 500. Accordingly, the interface may be flipped or turned around so as to position the prong in or with the other desired nare without requiring the prong to be repositioned or relocated upon the support. In such configurations, there may be two general orientations of the interface on the patient's face, those orientations can be respectively associated with a left nare and a right nare of the patient, where these two general orientations such that the single prong can remain affixed or in a static location upon the support, and the interface can be flipped or rotated through 180', such that a left hand end of the interface becomes a right hand end and a right hand end becomes a left hand end of the interface once rotated (i.e. about a plane substantially transverse to a central point of the interface). In this manner, the prong can be positioned in a left nare and the interface can then be flipped or rotated (i.e. reversed) and the prong can then be provided for positioning into the patient's right nare, all without needing adjustment of the prong upon the support. This allows for a swapping of the nare which is to receive a gases therapy, yet without an adjustment of the prong upon the support. It will be appreciated that in some instances, the headgear may be adjusted to provide for suitable comfort and fitment once the prong can be swapped from one nare to the other of the patient. Such a configuration may simplify the ease of use of such an interface and minimise the need for significant adjustment of the prong upon the support.

In alternative configurations, the single sealing nasal prong and cuff may be permanently or removable connected in other manners. Permanent connections include gluing, welding, press-fits, and one-time clips. Removable connections include clips or complementary threaded portions.

The illustrated configuration has been shown and described as having separate head straps and sliding members. In an alternative configuration, the headstrap and sliding member(s) may be integral.

The cuff has been described as a separate component to the single sealing nasal prong 200. In an alternative configuration, the cuff 250 may be part of the single sealing nasal prong 200. The conduit connector 400 and cuff 250 may be separate components. In an alternative configuration, the conduit connector 400 and cuff 250 may be a single integral component. The cuff 250 has a prong coupling portion or a prong coupler 263. The single sealing nasal prong is received by, or receivable by, the prong coupling portion 263 of the cuff 250. In an alternative configuration, the prong coupling portion 263 of the cuff 250 is received by, or receivable by, the prong coupling portion 263 of the cuff 250.

Figure 1C:
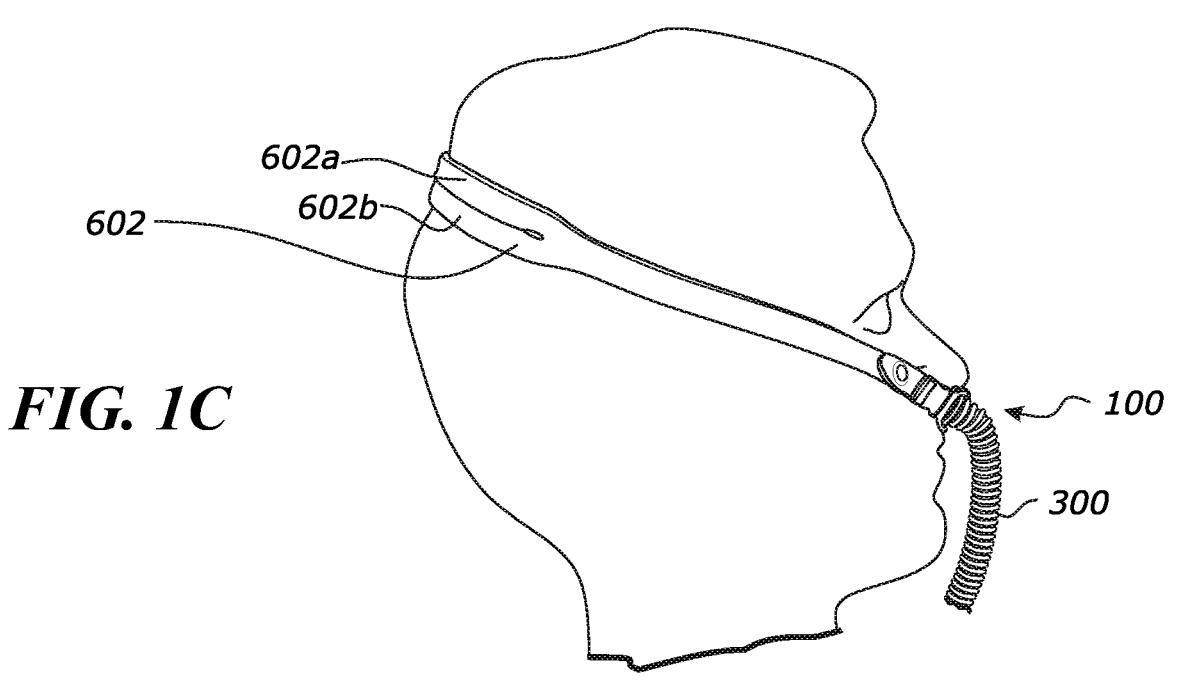
Figure 1D:
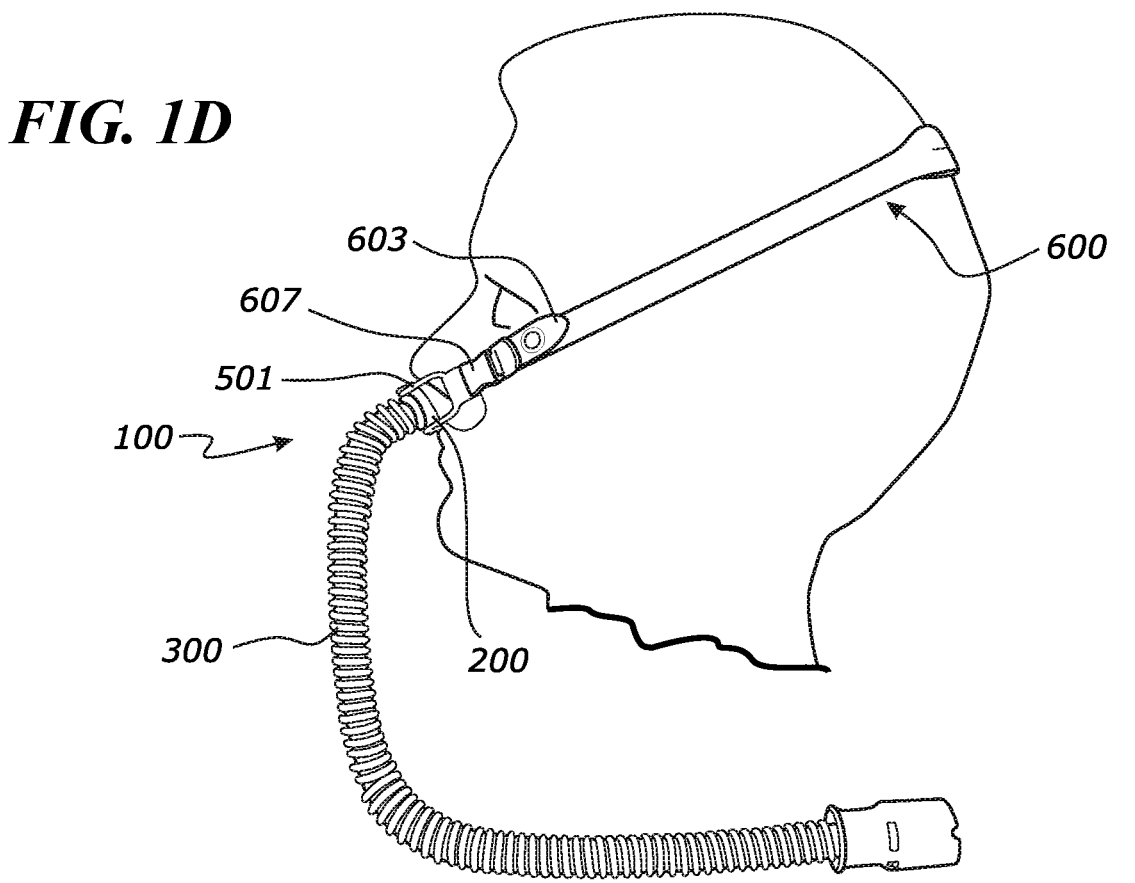

The details of headgear 600 of the respiratory interface 100 will now be described. The headgear 600 provides sufficient retention force to maintain the seal at the patients rare. In the configurations shown, the headgear is a headstrap 600. The headstrap 600 may be a single strap or a bifurcated strap. The bifurcated strap is shown in FIGS. 1B to 1D. The bifurcated strap may provide extra grip on the patient's head compared to a single strap.

In the configuration shown, the headgear 600 includes a pair of side straps 601 and a rear strap portion 602. The rear strap 602 can be separated to form a split strap headgear. The rear strap can be split to include a first intermediate strap 602a and a second intermediate strap 602b that are both coupled to the side strap portions 601. The split strap headgear can be used in the split arrangement or as a single rear strap with an enlarged area than the side straps. The split strap headgear provides a force diagonally upward at an angle between 30 deg to 80 deg from the horizontal. The upward diagonal force has an upward component and a lateral (sideward) component to create a seal with the nostril. The force pulls the single sealing nasal prong 200 into the nostril and maintains the seal. The headgear includes clips, which can be removably connected to the extensions from the support members.

The headgear may be tightened or loosened by adjusting the headstrap 600. The headgear includes headgear connectors 607 that connect to the sliding member. The headgear connectors 607 include length adjusting elements 606. The length adjusting elements 606 may be on a single side or on both sides. The length adjusting elements 606 may also be located at the back. The length adjusting elements 606 receive the free ends 603 of the strap, with a portion 605 of the strap extending through the length adjusting elements.

The length adjusting elements 606 are located adjacent or on the headgear connectors 607. The length adjusting elements 606 can adjust the operative length of the headgear strap thereby adjusting the tightness of the strap on the head of the patient.

With reference to FIG. 4, the respiratory interface 100 fits into a smaller footprint than conventional interfaces. For example, the volume taken up by the interface 100 can be determined a bounding box (shown with broken lines) placed around the respiratory interface. The bounding box is a rectangular prism that contains the interface shown in FIGS. 1 to 10. The box can have dimensions of:

A width of 110 mm or less. The illustrated configuration is 95 mm or less (including the two connecting clips). Other widths include 105 mm, 100 mm, 90 mm, 85 mm, 80 mm, or 75 mm.

A height of 40 mm or less. The height is the vertical height of the single sealing nasal prong 200 and the support 500 shown in FIG. 4, but not including the conduit 300. The illustrated configuration is 25 mm or less. Other heights include 35 mm, 30 mm, 20 mm, or 15 mm.

A depth of 50 mm car less. The depth is the dimension outwards from the patient's face. The illustrated embodiment is 30 mm or less. Other depths include 45 mm, 40 mm, 35 mm, 30 mm, or 25 mm.

The bounding box is smaller than a corresponding equivalent sized dual prong cannula. For example, a medium sized single sealing prong cannula has a smaller footprint (i.e. a smaller bounding box volume) than a medium sized dual prong cannula. The smaller footprint of the respiratory interface provides a less intrusive interface for a user and makes the interface more comfortable for the user.

FIGS. 17 to 25 show another configuration of the respiratory interface 100. The features, functionality, and options of the respiratory interface are the same as described above, unless described below. Like numbers are used to indicate like numbers with the addition of 1000.

In this configuration, the support 1500 has a single member or strap 1501, The single strap may be curved as shown, or straight. Similar to the sliding members of the earlier configuration, the single strap is relatively rigid, but flexible allowing the single strap to readily bend or flex. The single strap decouples the single sealing prong from headgear and allows the single sealing nasal prong to be moved from one nare to another. Advantages of a single strap include being lighter than two straps, having a smaller footprint than the earlier configuration, and more flexible than two straps. The cuff 250 has a single curved finger 1255 for coupling with the strap 1501, Alternatively, the cuff may have a ring or clip to removably or permanently couple the strap 1501 to the cuff 250.

Figure 27:
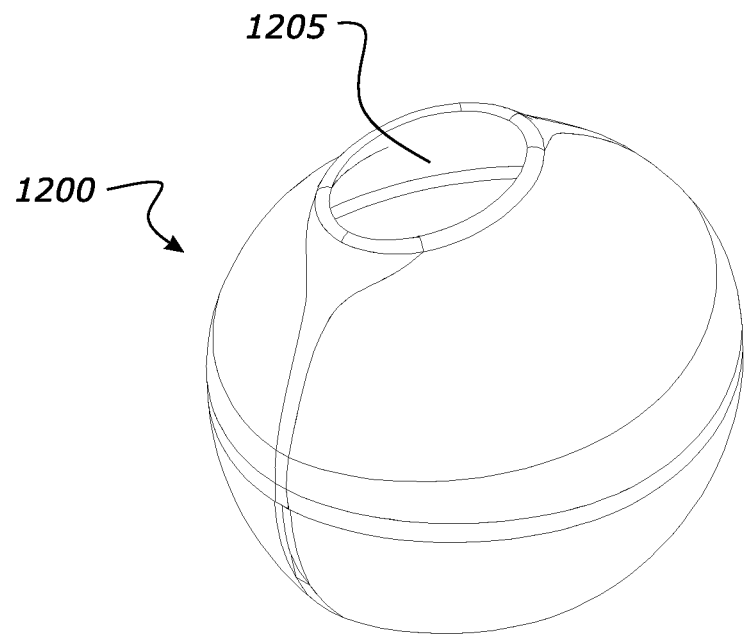
FIG. 27 is a rear perspective view of the nasal prong of FIG. 26.
Figure 28:
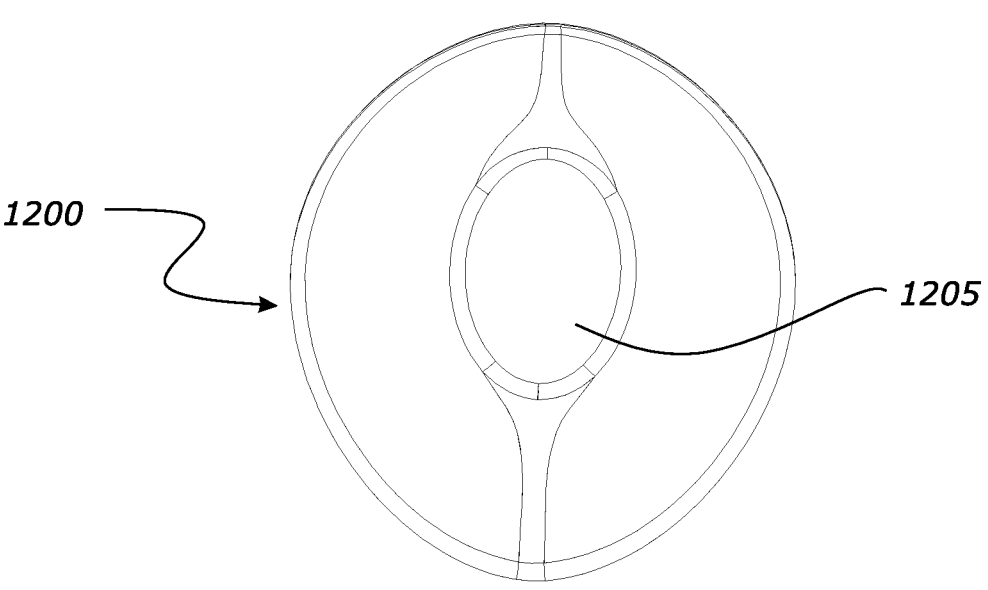
FIG. 28 is a top view of the nasal prong of FIG. 26.
Figure 29:
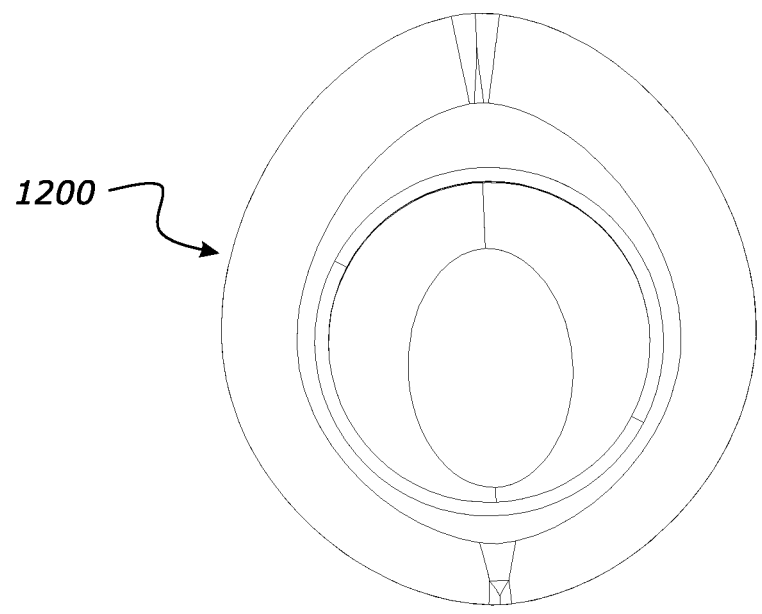
FIG. 29 is a bottom view of the nasal prong of FIG. 26.

FIGS. 26 to 32 show various views of the single sealing nasal prong 1200. Similar to the earlier described configuration, this single sealing nasal prong 1200 has an inlet 1203 and an outlet 1205. FIG. 27 shows the prong in a compressed orientation, which is what happens when the prong is engaged in nostril to seal against the nostril.

Figure 30:
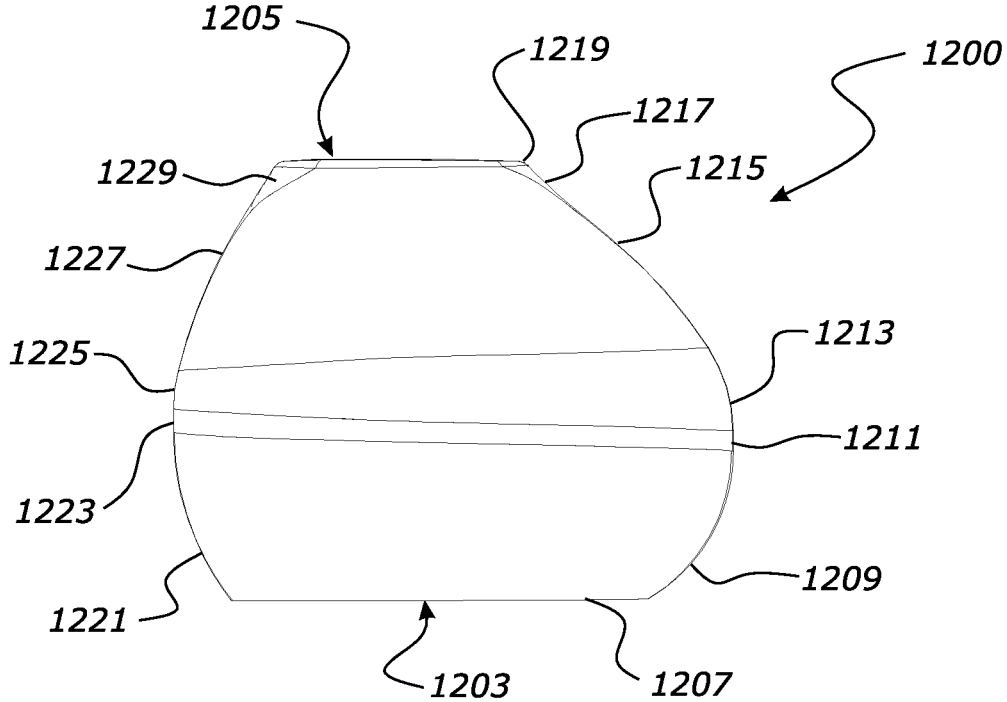
FIG. 30 is a left view of the nasal prong of FIG. 26.

FIG. 30 shows the single sealing nasal prong 200 from the left side. The right side of the single sealing nasal prong is a mirror image of the left side of the single sealing nasal prong. When viewed in the orientation of FIG. 30, the right side of FIG. 30 is the front of the prong 1200 and the left side is the rear of the prong. The radius lines shown in FIG. 30 indicate how the surfaces transition between the front and the rear of the single sealing nasal prong 1200.

Starting from the inlet 1203, the bottom surface 1207 of the single sealing nasal prong 1200 is flat. There is a relatively sharp transition to the front surface of the prong 1200. The lowermost portion 1209 of the front surface is curved outwardly. The lowermost surface 1209 also tapers outwardly. The front surface then transitions into a relatively short generally vertical surface 1211 (when viewed as a profile shown in FIG. 30), which transitions into a gentle outwardly curved surface 1213 that also tapers inwardly. The centre 1215 of the single sealing nasal prong 1200 is a gentle outwardly curved surface. In addition to being curved, the surface 1215 tapers inwardly. Between the central surface 1215 and a rim 1219 is a generally flat surface 1217. The transitions between each surface, except the transition between surfaces 1207 and 1209, are smooth transitions. The top edge 1219 of the single sealing nasal prong 200 also forms the rim of the outlet 1205.

Still referring to FIG. 30, the rear surface of the prong 1201 is different to the front surface of the prong. There is a relatively sharp transition to the rear surface of the prong 1200. The lowermost portion 1221 of the rear surface is curved outwardly. The lowermost surface 1209 also tapers 1221, but not as steep as the angle of the similar surface 1209 of the front surface. The rear surface then transitions into a relatively short generally vertical surface 1223 (when viewed as a profile shown in FIG. 30), which transitions into a gentle outwardly curved surface 1225 that also tapers inwardly. The centre 1227 of the single sealing nasal prong 1200 is a gentle outwardly curved surface. In addition to being curved, the surface 1227 tapers inwardly, but at a steeper angle than surface 1215 of the front surface. Between the central surface 1227 and a rim 1219 is a generally flat surface 1229. The transitions between each surface, except the transition between surfaces 1207 and 1221, are smooth transitions.

Figure 31:
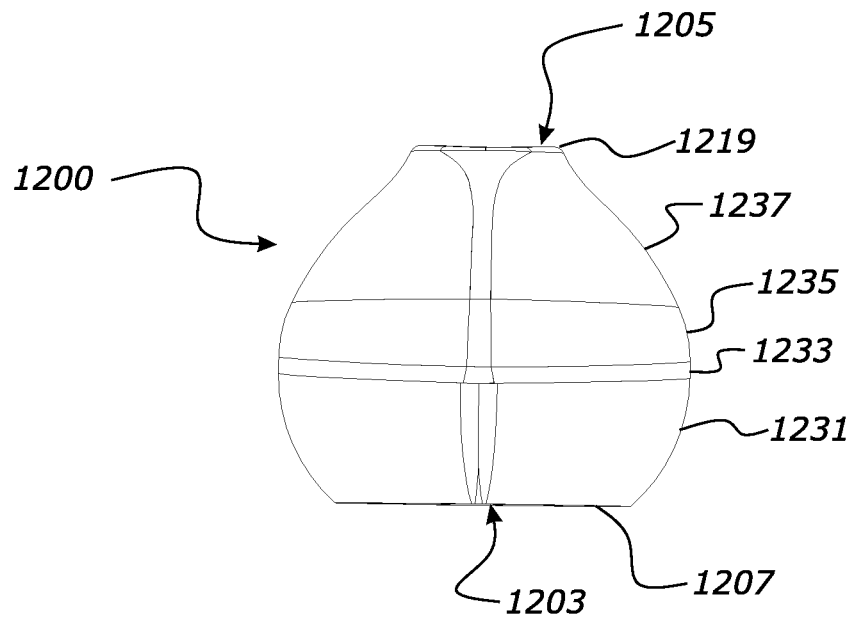
FIG. 31 is a front view of the nasal prong of FIG. 26.
Figure 32:
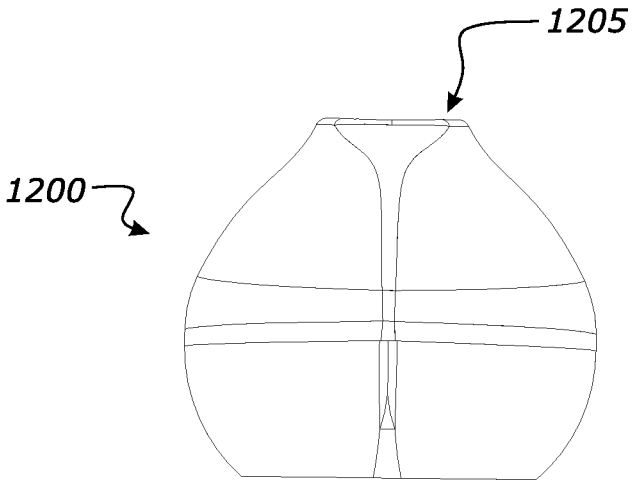
FIG. 32 is a rear view of the nasal prong of FIG. 26.
Figure 33:
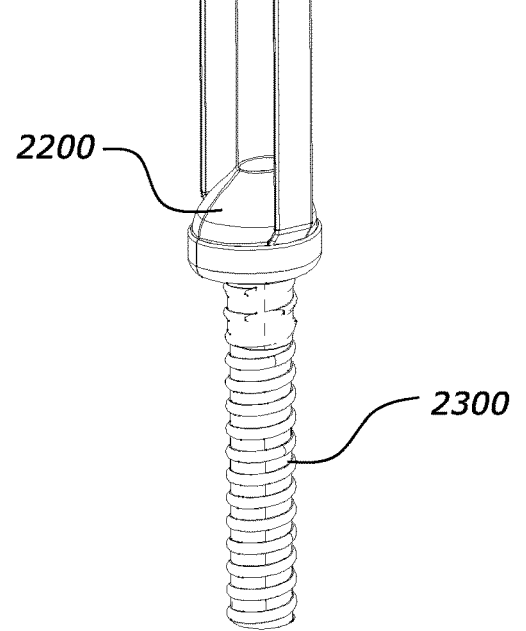
FIG. 33 is a front perspective view of another configuration of a respiratory interface.
Figure 34:
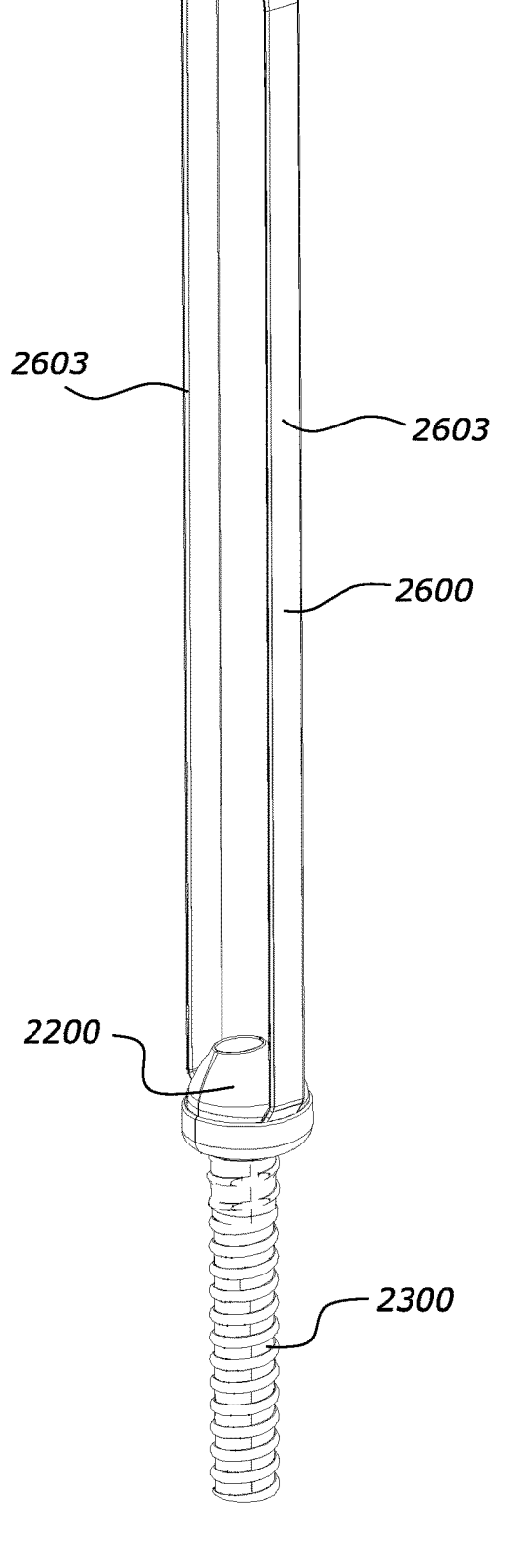
FIG. 34 is a rear perspective view of the respiratory interface of FIG. 33.
Figure 35:
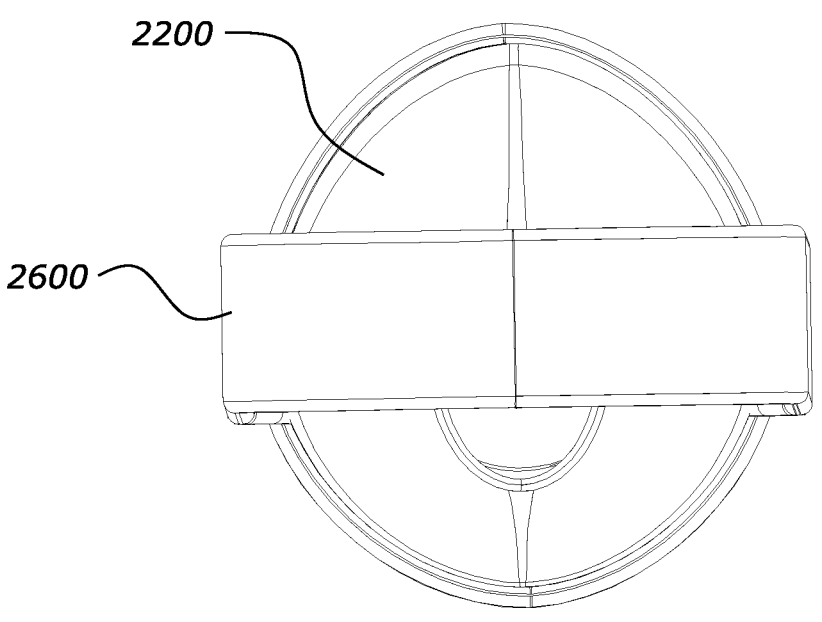
FIG. 35 is a top view of the respiratory interface of FIG. 33.
Figure 36:
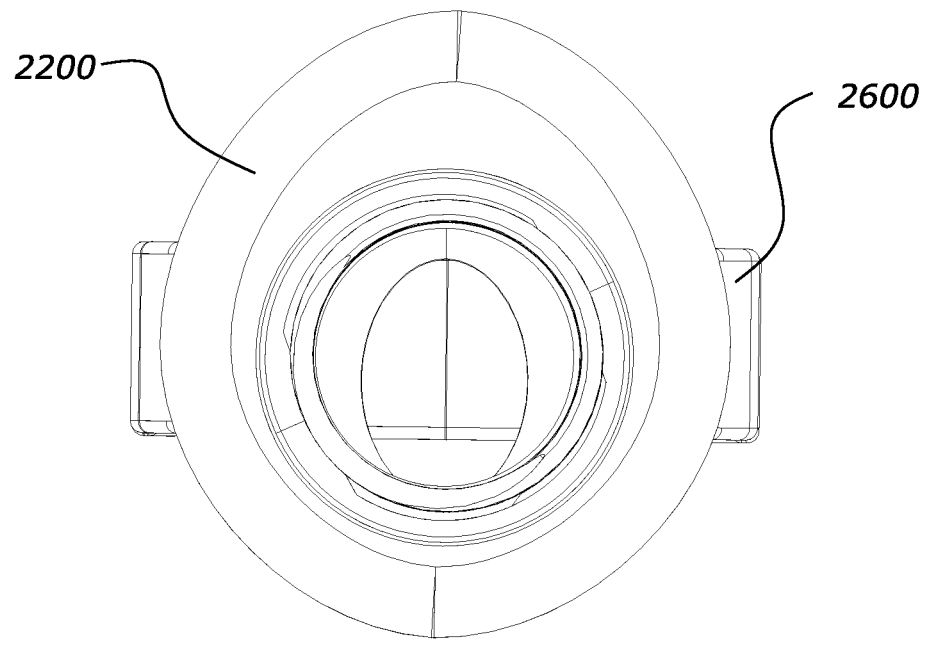
FIG. 36 is a bottom view of the respiratory interface of FIG. 33.

FIG. 31 shows the single sealing nasal prong 200 from the front. The rear of the single sealing nasal prong is identical to the front of the single sealing nasal prong. Starting from the inlet 1203, the bottom surface 1207 of the single sealing nasal prong 200 is flat. There is a relatively sharp transition to the right surface of the prong 1200. The lowermost portion 1231 of the front surface is curved outwardly. The lowermost surface 1231 also tapers outwardly. The front surface then transitions into a relatively short generally vertical surface 1233 (when viewed as a profile shown in FIG. 31), which transitions into a gentle outwardly curved surface 1235 that also tapers inwardly. The centre 1237 of the single sealing nasal prong 1200 is a gentle outwardly curved surface. In addition to being curved, the surface tapers inwardly. The transitions between each surface, except the transition between surfaces 1207 and 1209, are smooth transitions, FIG. 32 is a rear view of the nasal prong of FIG. 26. Comparing FIGS. 31 and 32, it can be seen that the exterior profile of the prong when viewed from the front is the same as the rear. The radius lines shown in FIGS. 31 and 32 indicate how the surfaces transition between the left and the right sides of the single sealing nasal prong 1200.

Figure 19:
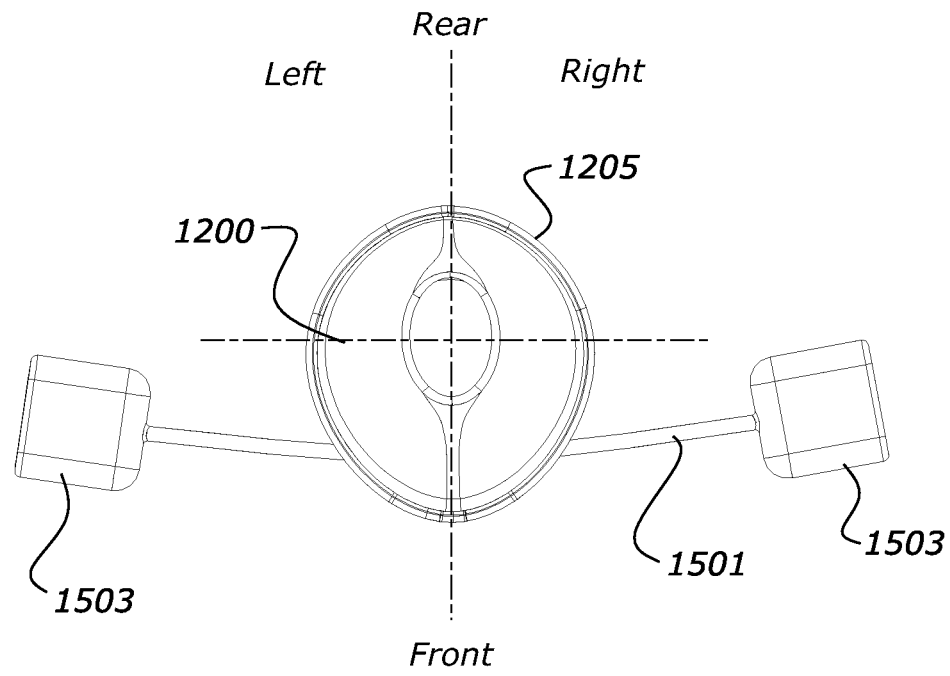
FIG. 19 is a top view of the respiratory interface of FIG. 17.
Figure 20:
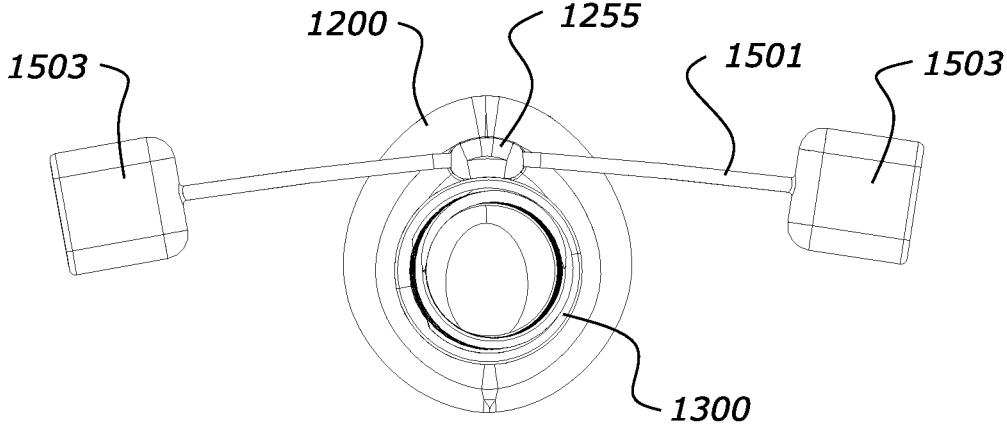
FIG. 20 is a bottom view of the respiratory interface of FIG. 17.
Figure 21:
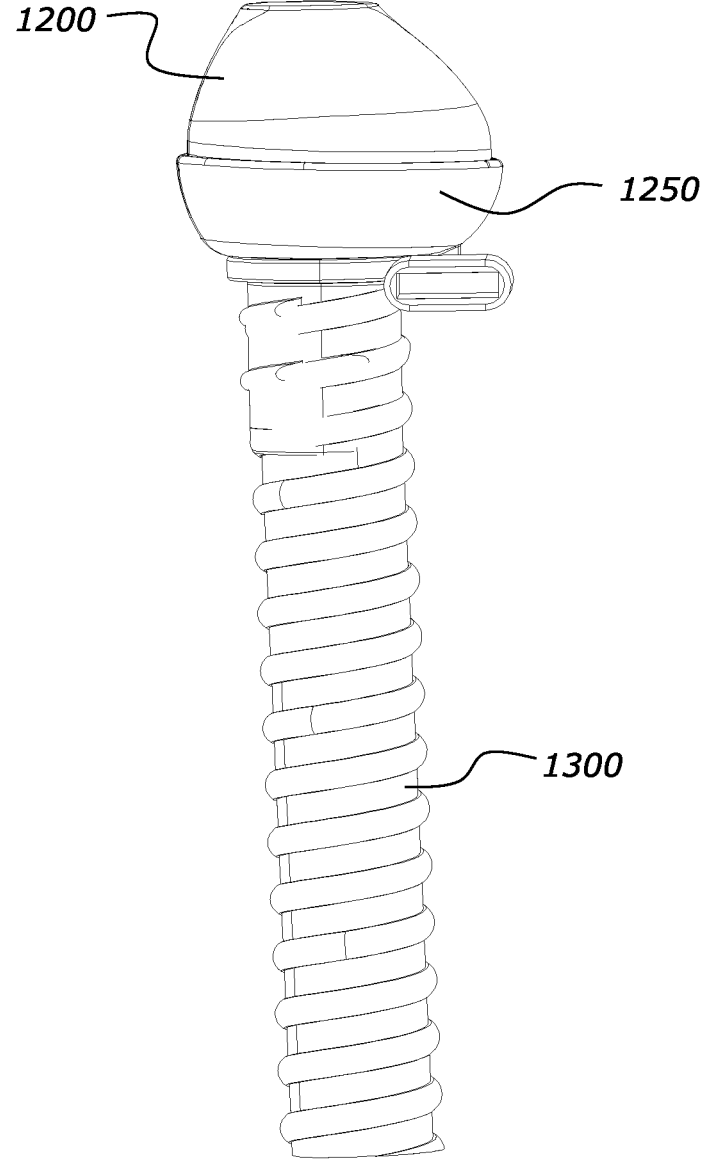
FIG. 21 is a left side view of the respiratory interface of FIG. 17.
Figure 22:
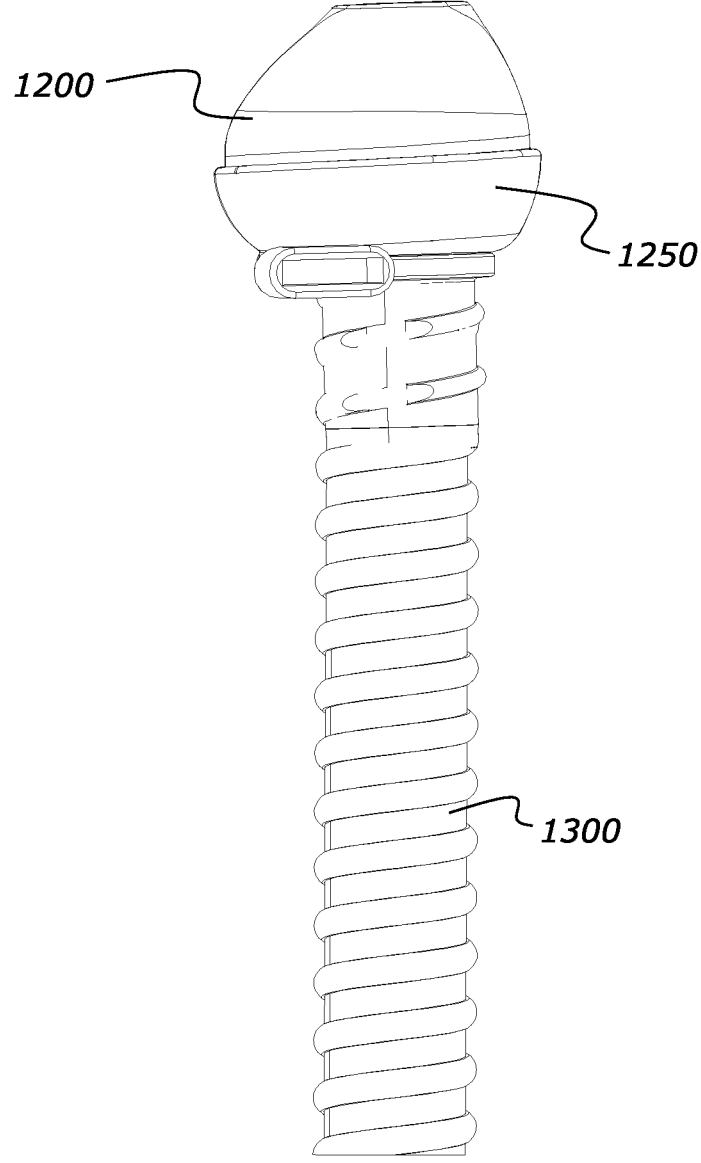
FIG. 22 is a right side view of the respiratory interface of FIG. 17.
Figure 23:
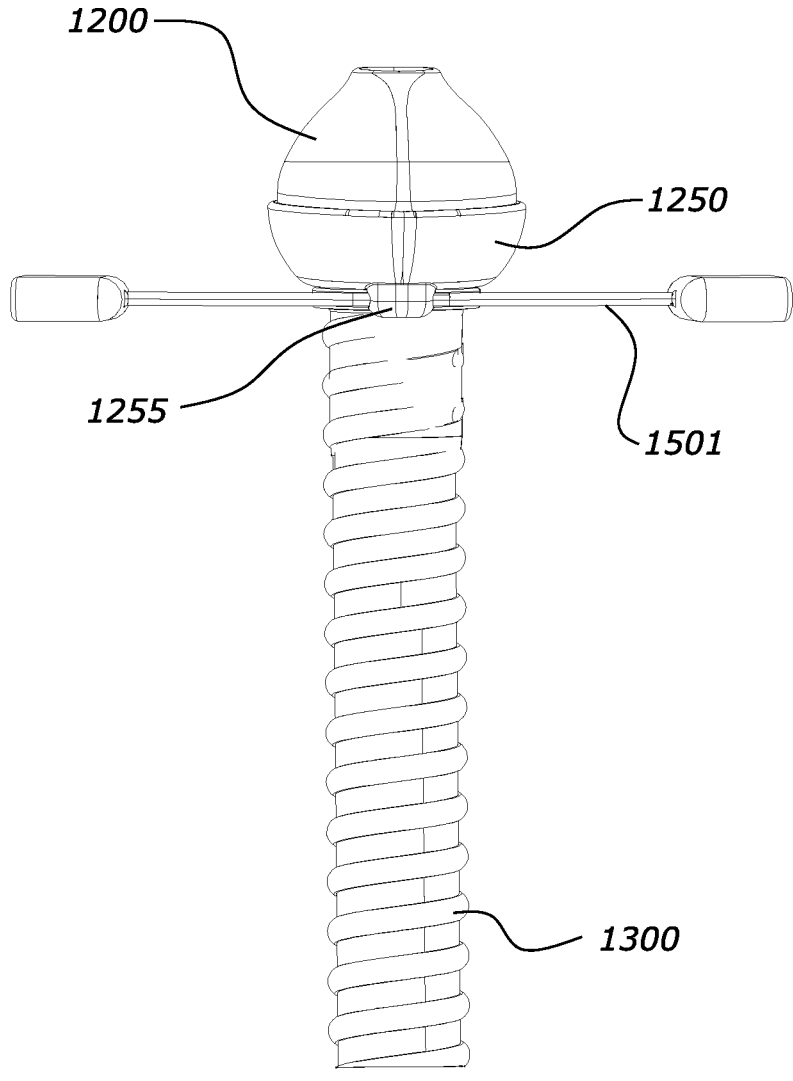
FIG. 23 is a front view of the respiratory interface of FIG. 17.
Figure 24:
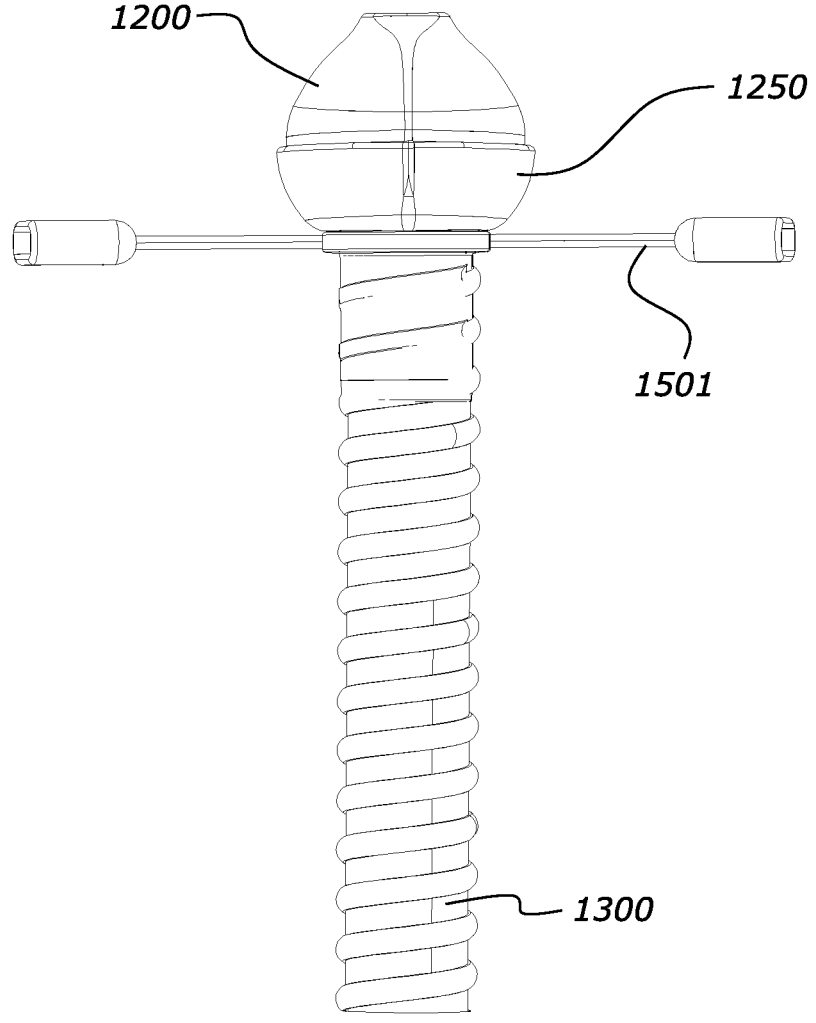
FIG. 24 is a rear view of the respiratory interface of FIG. 17.
Figure 25:
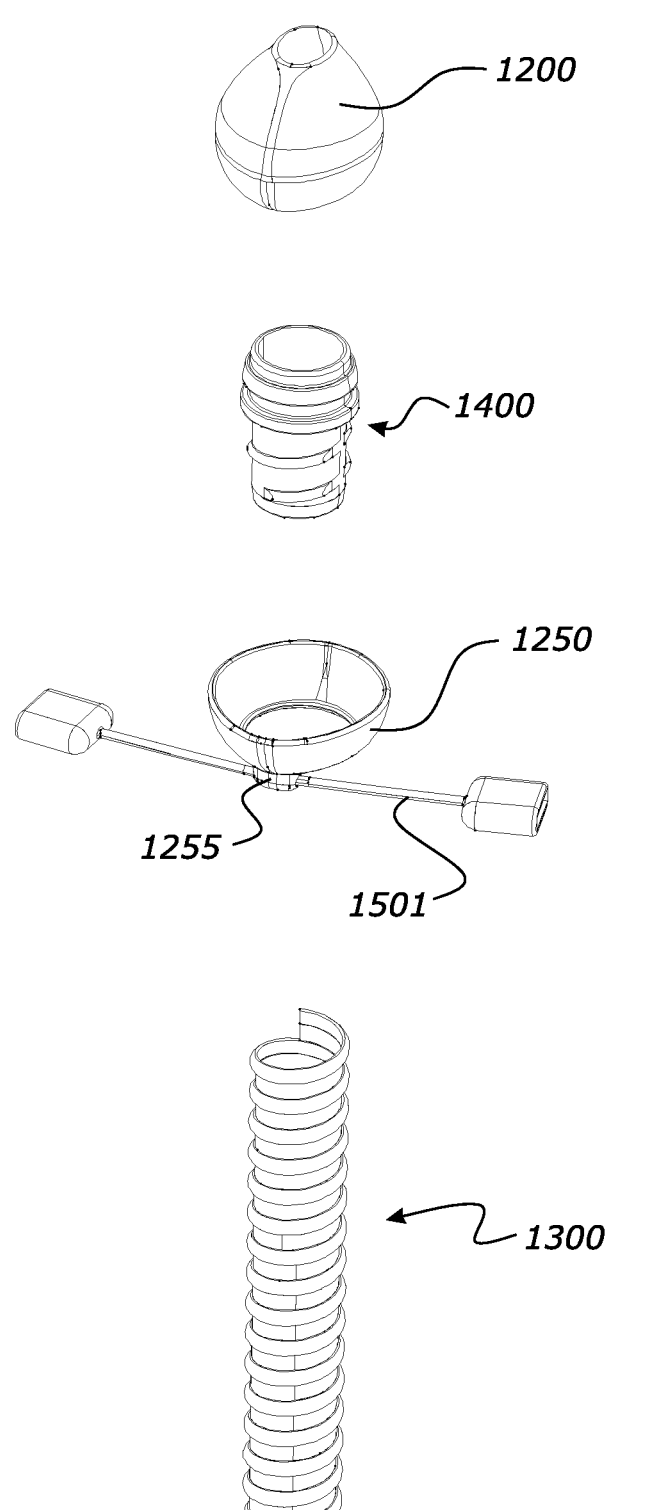
FIG. 25 is an exploded view of the respiratory interface of FIG. 17.
Figure 26:
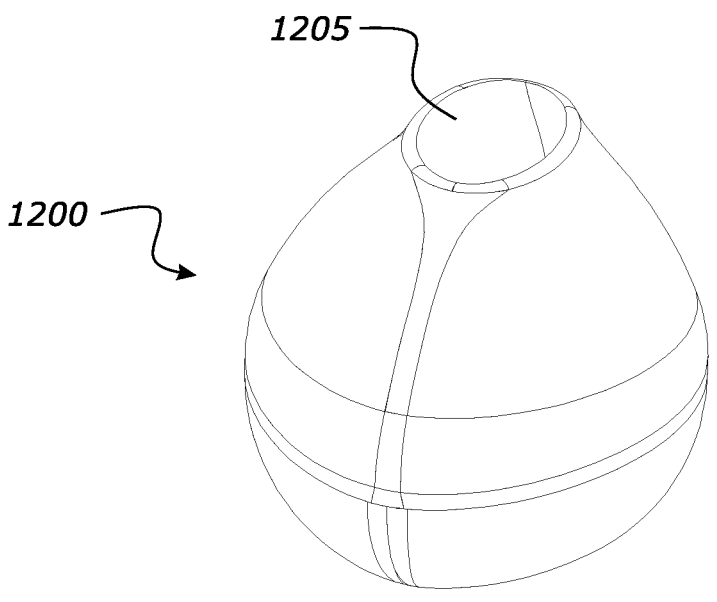
FIG. 26 is a front perspective view of the nasal prong of the respiratory interface of FIG. 17.

With reference to orientation of the single sealing nasal prong 1200 in FIG. 19, the exterior shape of the single sealing nasal prong 1200 is offset in a vertical direction—the outlet 1205 and the highest point of the single sealing nasal prong 1200 is closer to the rear surface of the prong 1200, which corresponds to the contours of the nasal cavity. The single sealing nasal prong 1200 is symmetrical between the left and right surfaces—they are mirror images of each other. This offset shape improves comfort for the patient. The offset shape also improves sealing between the single sealing nasal prong 1200 and the patient's nare. The single sealing nasal prong 1200 may have a feature, such as a logo, arrow, or other indicia to indicate the correct orientation of the single sealing nasal prong 200.

Although this asymmetrical single sealing nasal prong 1200 is shown with a support having a single strap 1501, it will be appreciated that the asymmetrical single sealing nasal prong 1200 may be used with other supports. For example, the asymmetrical single sealing nasal prong 1200 may be used with the support 500 having two straps. Further, a symmetrical single sealing nasal prong having the shape of the earlier described configuration may be used with the single strap 1501.

FIGS. 33 to 49 show another configuration of the respiratory interface 2100, The features, functionality, and options of the respiratory interface are the same as described above, unless described below, Like numbers are used to indicate like numbers with the addition of 2000.

In this configuration, the single sealing nasal prong 2200 has a rigid portion 2235. The rigid portion 2235 of the single sealing nasal prong 2200 comprises cut outs or recesses 2241 configured to receive a portion of a headgear strap 2600. The cut outs 2241 are a similar width and depth to the width and depth of the headgear strap 2600. The cut outs 2241 have a substantially rectangular shape, when the prong 2200 is viewed from the side. The recess 2241 is substantially smooth. In an alternative configuration, the recess 2241 may have surface features or teeth to increase the engagement with the strap. The single sealing nasal prong 2200 is then received within the prong coupler to couple the headgear and the interface.

The cuff 2250 functions as a hub or central component that couples to, or engages with, various components of the respiratory interface. The cuff 2250 couples to the conduit, couples to the headgear 2600, and receives the single sealing nasal prong 2200. The cuff 2250 acting as a connection hub to couple to all the components of the system reduces the number of components in the system. The respirator interface does not require a separate manifold to couple the conduit to the single sealing nasal prong 2200, nor does the interface need a separate, such as a body with side arms or other stabilisers. The cuff also reduces the footprint of the respiratory interface compared to conventional respiratory interfaces that require contact with the patient's face to be supported.

Figures 37, 38:
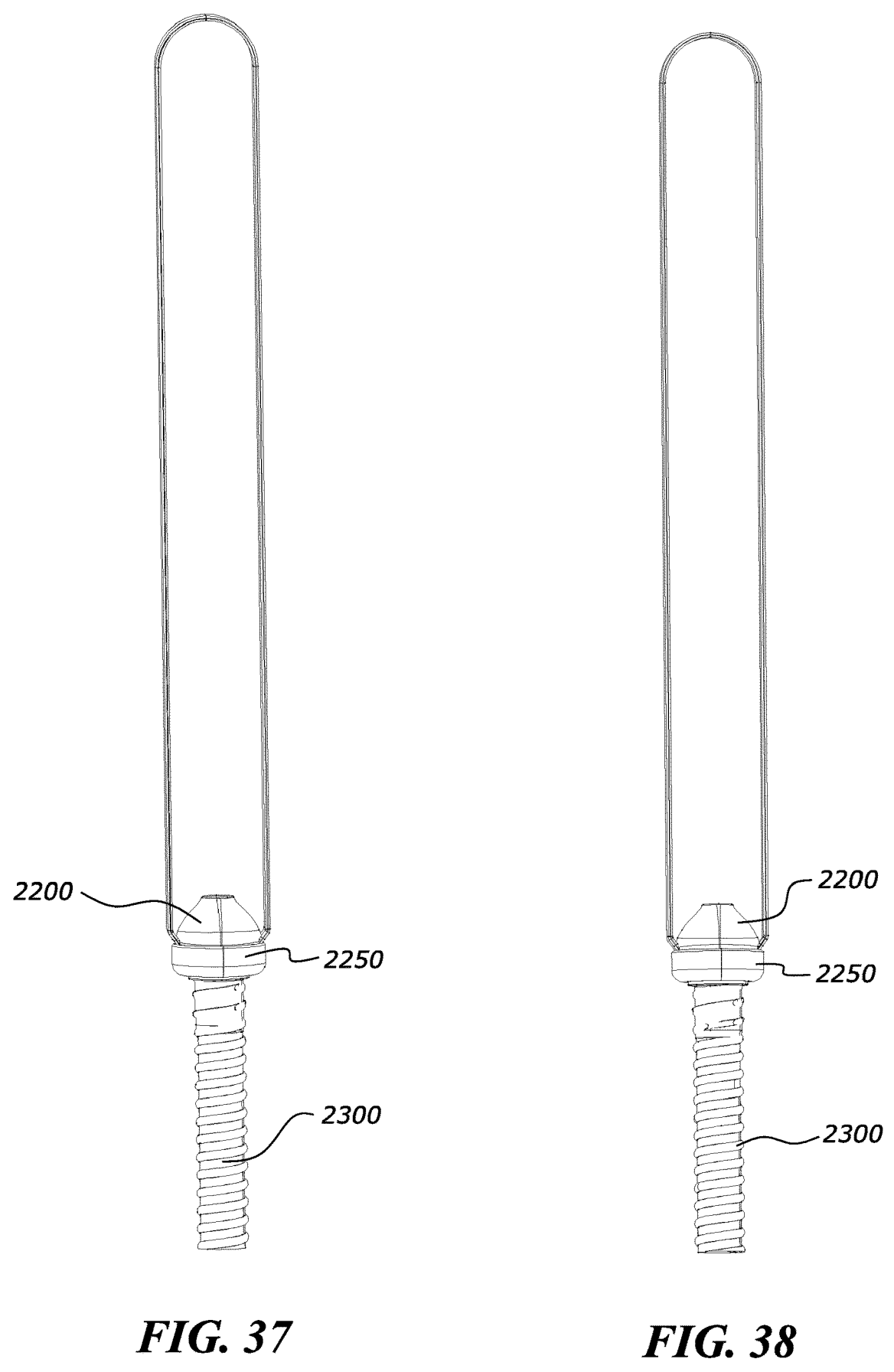
Figure 39:
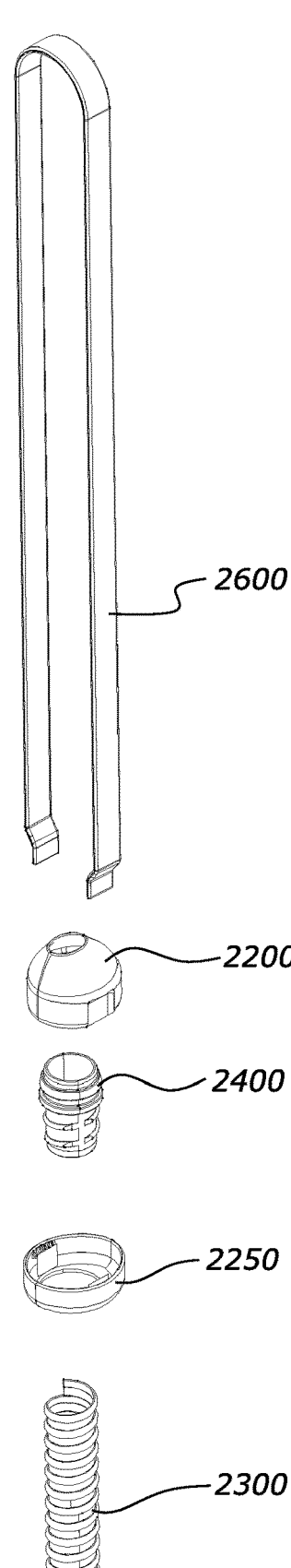
FIG. 39 is an exploded view of the respiratory interface of FIG. 33.

FIGS. 37 and 38 show the headstrap 2600 is directly connected to the gases delivery assembly. That is, the headstrap 2600 is directly connected to the single sealing nasal prong 2200. FIG. 39 shows an exploded view of the interface of FIGS. 37 and 38, In the configuration shown, the strap has two ends 2601. The ends 2601 of the strap 2600 are directly connected to the single sealing nasal prong 2200 in the orientation of FIG. 39.

The headstrap 2600 may be attached in a variety of ways. Suitable examples include gluing, welding to the prong, simple friction or press fit, protrusions, clips, or a combination. In the preferred configuration, the headstrap is attached via a combination of a friction fit and protrusions in the form of teeth. Once fitted in the cut-outs on the single sealing nasal prong 2200, the single sealing nasal prong 2200 and headstrap are assembled with the cuff 2250. The headgear shown in the figures is just an example orientation. The strap is a flexible strap.

The cuff 2250 functions as a hub that couples to various components of the system. The cuff 2250 couples to the conduit 2300, the 2600 headgear and receives the single sealing nasal prong 2200. The cuff 2250 acting as a connection hub to couple to all the components of the system reduces the number of components in the system. in this configuration, the interface does not require a separate manifold to couple the conduit 2300 to the prong 2200, nor does the interface need separate side arms. The use of the cuff 2250 as a hub reduces the footprint of the interface.

The cuff 2250 comprises teeth 2270 configured to grip and retain a portion of a headgear strap 2600. The teeth 2270 are arranged to extend partly around the cuff 2250. The teeth 2270 are provided on an inner surface of the cuff 2250 and extend inwardly. In the configuration shown, the teeth 2270 extend radially inwardly. In one configuration, the teeth 2270 may extend around substantially all of the cuff 2250 or entirely around cuff 2250. The entire inner surface may comprise teeth 2270 or other textured surfaces. The prong coupling portions of the cuff 2250 are disposed adjacent the teeth. This allows the headgear to be held onto the teeth 2270 by the prong being positioned in the cuff 2250 and engaging with the prong coupling portions.

In an alternative configuration, the headstrap held in place via friction fit. In other alternative configurations, the headstrap may be coupled to the single sealing nasal prong via glue, welding, protrusion(s), and/or clips.

In the configuration shown, the strap 2600 has a stretchable portion 2603 on each side of a non-stretchable portion 2605. In an alternative configuration, the strap 2600 may have a single stretchable portion. In another alternative configuration, the strap 2600 may be a single knitted strap. The stretchable portion 2603 enables the patient to readjust the single sealing nasal prong 2200 without exerting extra tension on the patient's face due to the adjustment. Each of these configurations allows the interface to be used on a variety of different patients having different shaped and/or sized heads. It is not necessary to provide a variety of different sized straps for different patients. The stretchable strap, and straps having stretchable portions, allows for adjustment of the single sealing nasal prong 2200 without any additional tension. Further the stretchable strap allows the prong to be swapped between nostrils.

Figure 40:
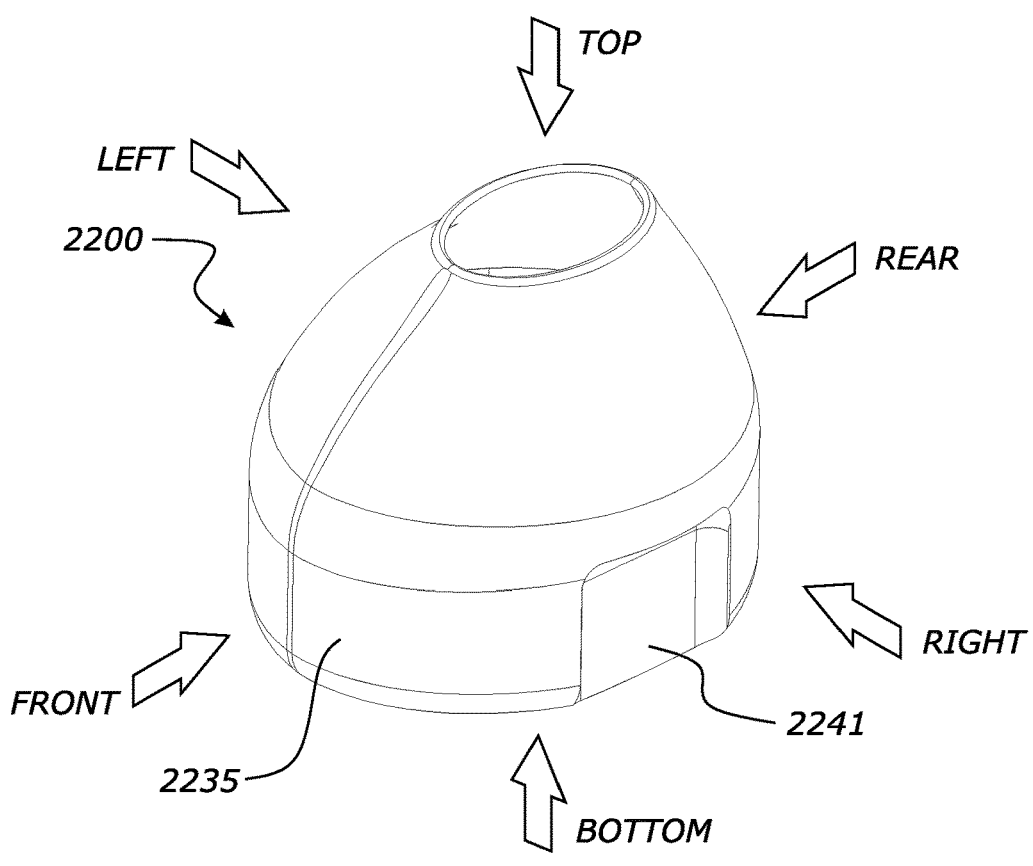
FIG. 40 is a front perspective view of the nasal prong of the respiratory interface of FIG. 33.
Figure 41:
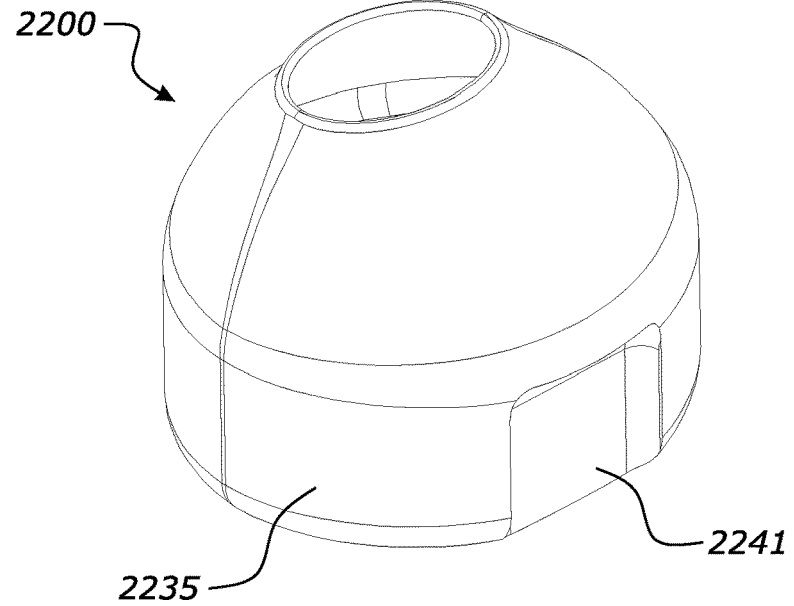
FIG. 41 is a rear perspective view of the nasal prong of FIG. 40.
Figure 42:
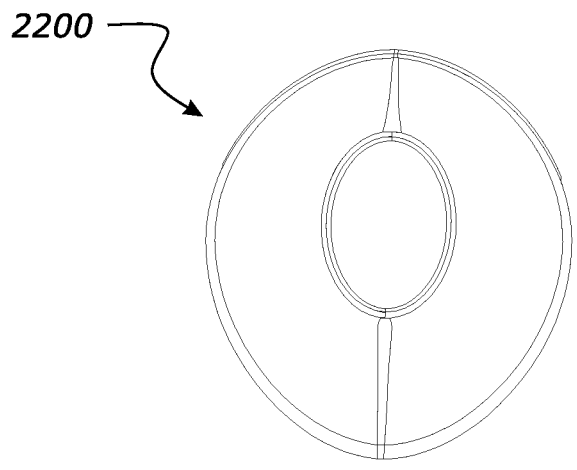
FIG. 42 is a top view of the nasal prong of FIG. 40.
Figure 43:
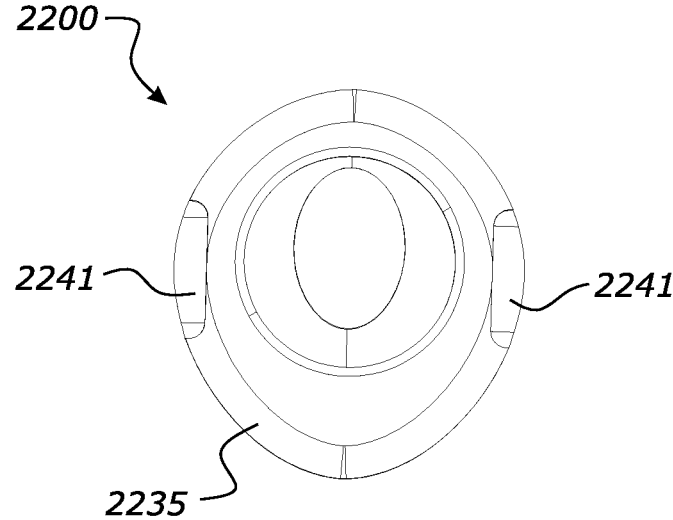
FIG. 43 is a bottom view of the nasal prong of FIG. 40.
Figure 44:
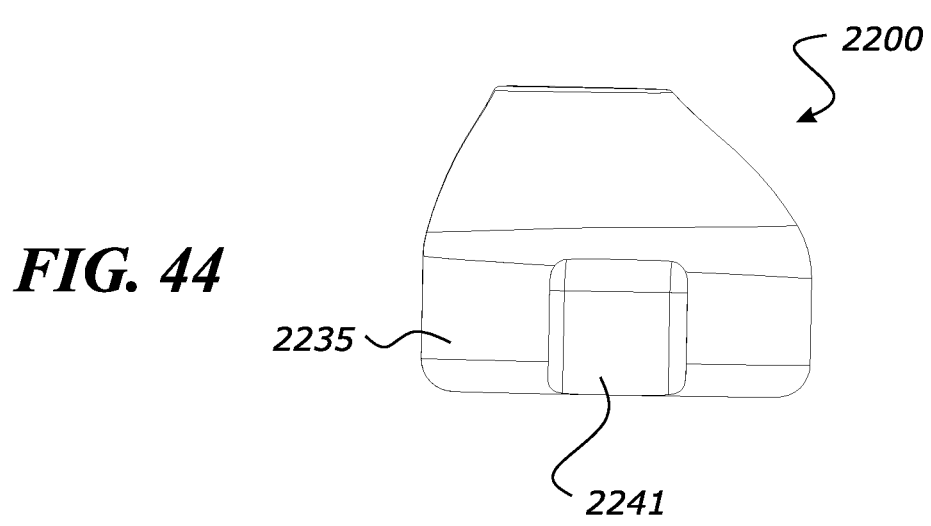
FIG. 44 is a left view of the nasal prong of FIG. 40.
Figure 45:
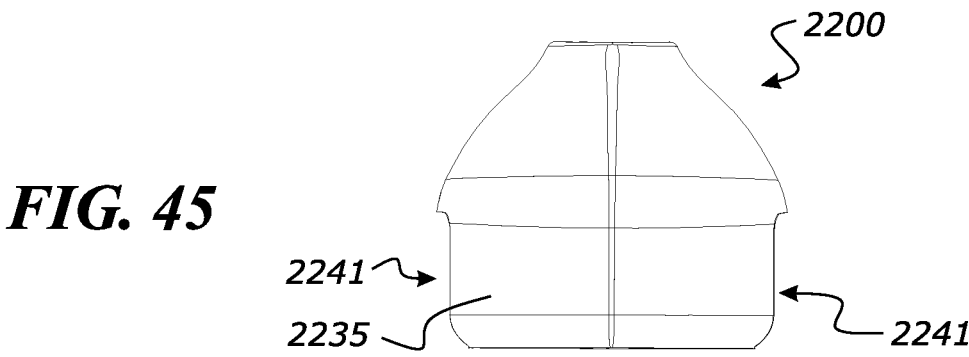
FIG. 45 is a front view of the nasal prong of FIG. 40.
Figure 46:
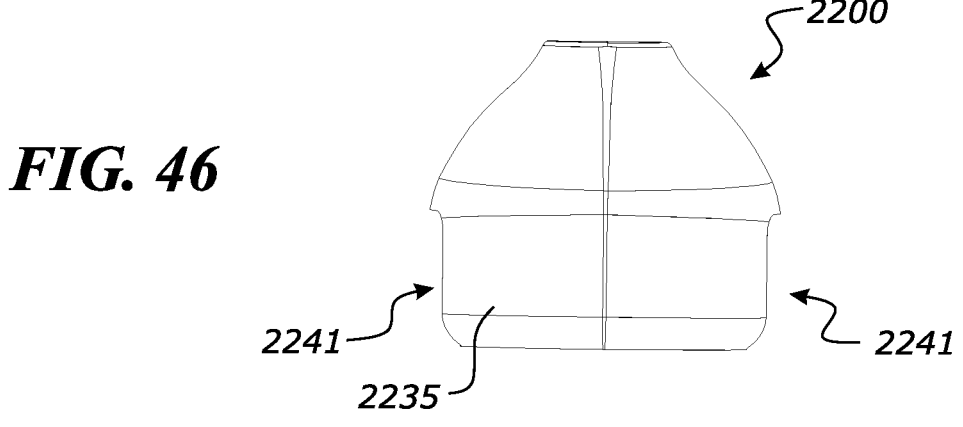
FIG. 46 is a rear view of the nasal prong of FIG. 40.

The configuration shown in FIGS. 33 to 49 include a single sealing nasal prong 2200 having an outlet 2205 that is located in a generally central location between the left and right surfaces but is closer to the rear surface than the front surface, when viewed in the orientation shown in FIG. 40.

The respiratory interface 100, 1100, 2100 may include any one or more of the features described above. For example, the respiratory interface 100, 1100, 2100 may include any one of the conduit assemblies described above, any one of the headgear assemblies described above, and/or any one of the supports described above. The single sealing nasal prong may be slidable and/or pivotable to transfer between nares.

The gases delivery causes washout of dead space gases through the unsealed nave.

In some configurations, the respiratory interface 100 may have a manifold 3700. An example of a respiratory interface 100 with a manifold is shown in FIGS. 50 to 53. The manifold respiratory interface has a pair of side arms 3701, 3702, a gases inlet on one side of the manifold, the inlet configured to receive gases from a gases supply via a conduit 3301. The manifold may be a separate part from the side arms, the side arms being couplable to, or coupled with, the manifold. The manifold 3700 is a single piece having an elongate outlet (not visible). The outlet may be oval shaped. The side arms 3701, 3702 are part of the respiratory interface and extend outwardly from a face mount part 3704. The face mount part contacts the patient's face and the prongs extend from the face mount. The manifold 3700 is received within the face mount part.

Figure 50:
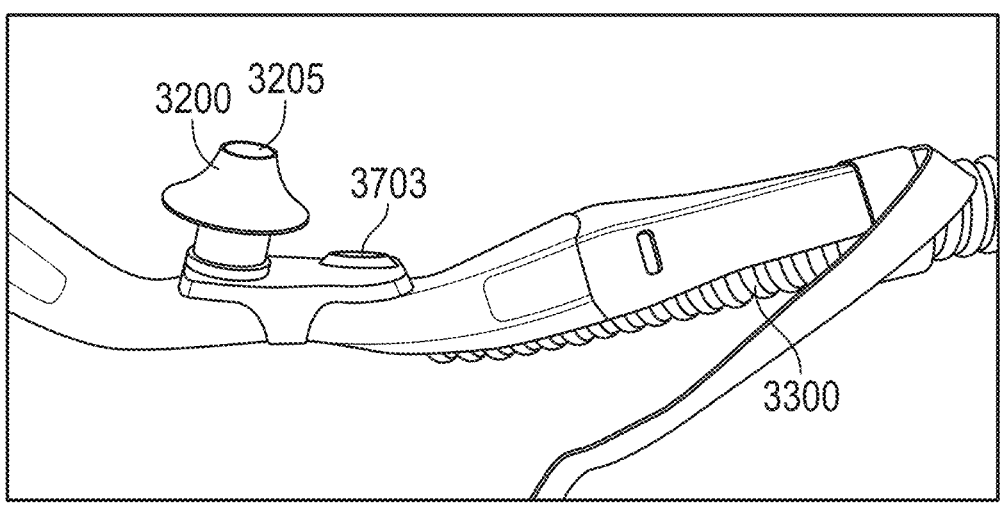
FIG. 50 is a partial front perspective view of another configuration of a respiratory interface.
Figure 51:
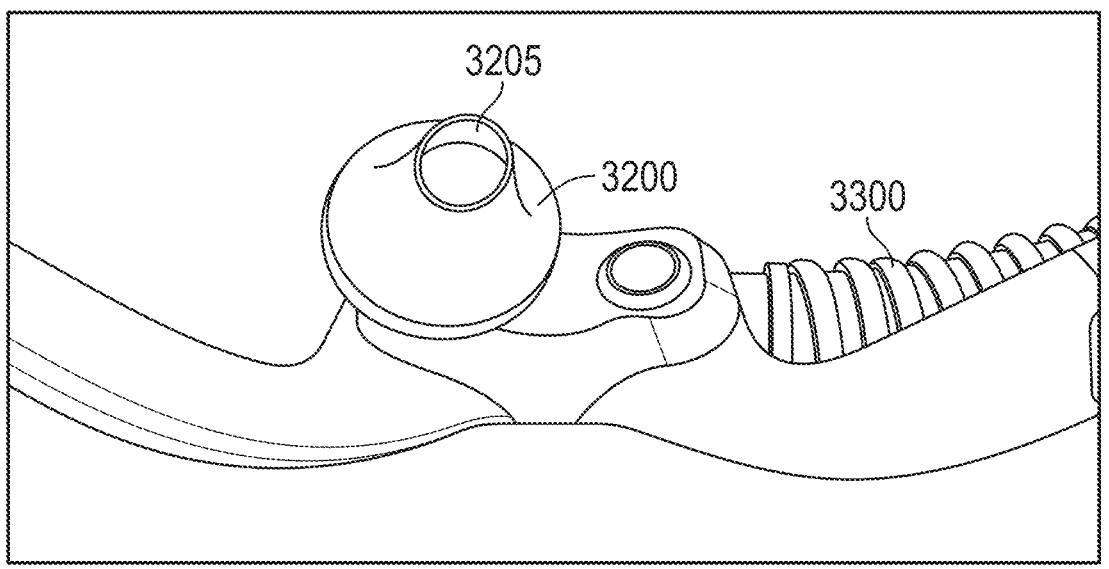
FIG. 51 is a detailed front perspective view of the respiratory interface of FIG. 50.
Figure 52:
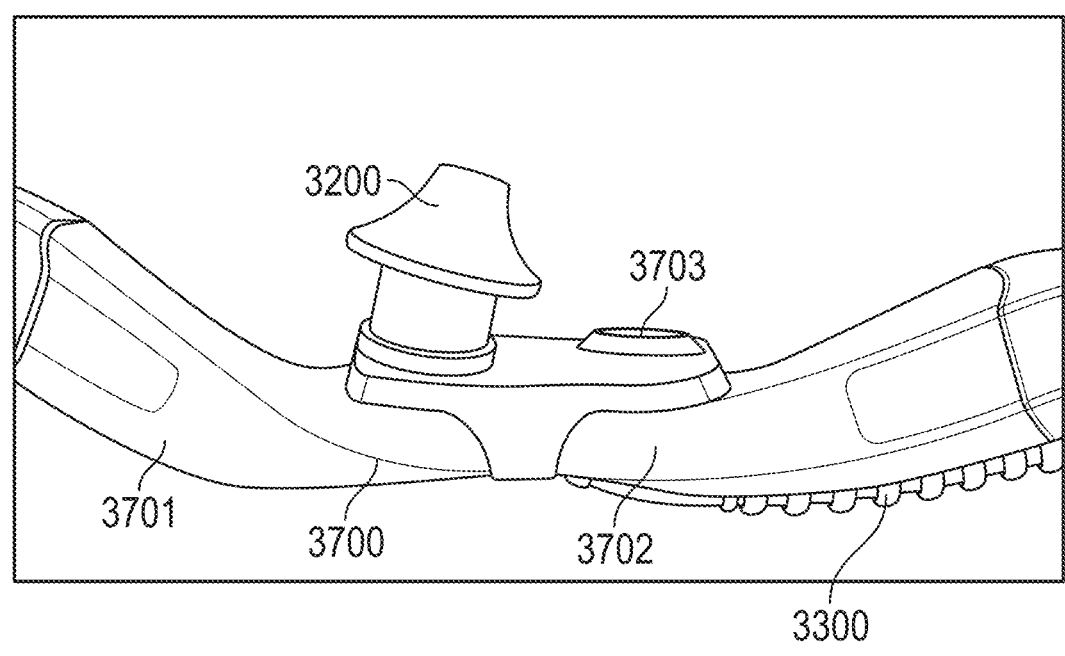
FIG. 52 is a top view of the respiratory interface of FIG. 50.
Figure 53:
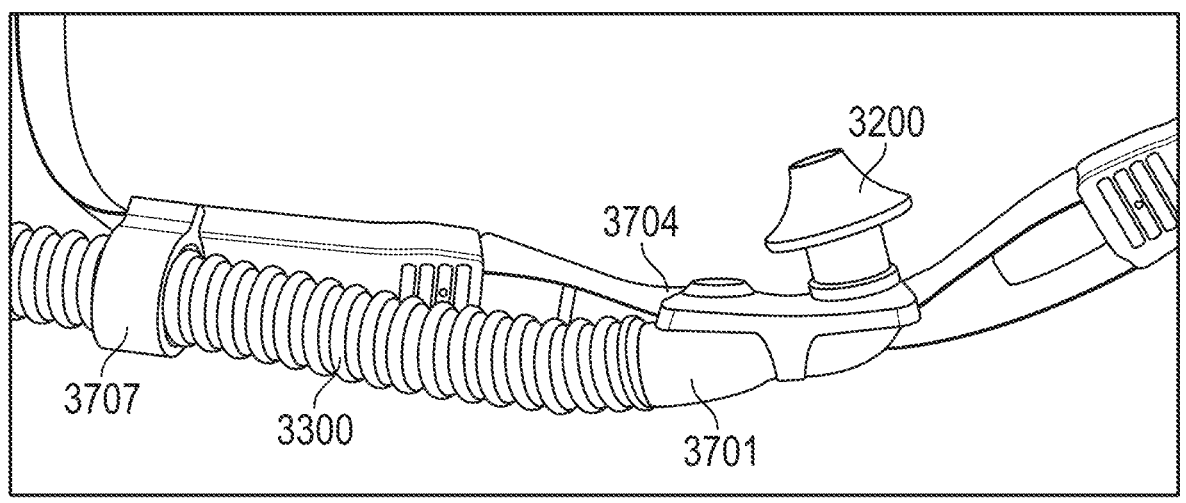
FIG. 53 is another front perspective view of the respiratory interface of FIG. 50.

In this configuration, the conduit 3300 is arranged to extend laterally across the patient's face so that the conduit outlet attaches to a side of the respiratory interface. This lateral arrangement is shown in FIG. 50.

This lateral arrangement can create a bending moment on the respiratory interface, To reduce the bending moment, the respiratory interface includes a tube clip. The tube clip reduces drag from the conduit being transferred to the respiratory interface. The tube clip also reduces the bending moment.

Each section on either side of the head strap and adjacent the respective primary end portion may include or have applied thereto a cheek support comprising at least a surface region for frictionally engaging with the patient's face to stabilise the headgear 600 on the face at the cheek, such as the cheekbone or below or a region thereof, both during coupling of the headgear to the respiratory interface and after when in use. The surface region is preferably of a relatively higher frictional surface material than the remainder of the strap.

The high friction surface material is adapted to extend over a portion of the side of a patient's face in use, preferably at or at least substantially towards the patient's cheek, to assist with retaining or stabilising of the respiratory interface upon the face of a patient. The high friction surface material, being locatable at the cheek of the patient, further assists in keeping a remainder of the head strap separated from and preferably extending below the eye or the orbit of the eye of the patient, so as to prevent obstruction of vision and/or discomfort resulting from the head strap bridging at or near the eye or eye orbit. In one example, the high friction surface material may comprise a textured material or may include adhesive dots that create a surface roughness on the headgear straps.

It will be appreciated the high friction surface material may be adapted to extend over a portion of the side of a patient's face in use, for example, extending from at or near or above the left and right outer upper lips rearwardly and upwardly across the left and right cheeks.

The sides arms 3701, 3702 comprise a headgear attachment feature and/or a conduit clip 3707 engaged with, or engageable with, the conduit 3301. The conduit clip 3707 helps to reduce conduit drag on the interface. Reducing conduit drag enhances the seal of the respiratory interface 100, Reducing conduit drag also improves patient comfort. The clip, in combination with the headgear advantageously maintain the conduit in a sealing position within the nose of the patient.

The side arm 3701, 3702 provides extra stability by bearing on the patient's cheeks. The side arms 3701, 3702 transmit loads on the interface to the patient's cheeks. The side arms 3701, 3702 may be rigid arms. The side arms 3701, 3702 may include a rigid frame and may include a soft material overmoulded onto the arms. Alternatively, the arms may comprise a semi-rigid material. The semi-rigid material is such that the side arms 3701, 3702 are soft to the touch but also can hold their shape in the absence of forces. Further the side arms 3701, 3702 can be bent along a longitudinal axis of each of the side arms 3701, 3702. The semi rigid side arms 3701, 3702 support the interface on the face but reduces pressure sores occurring on the patient's face.

The prong outlet 205 is angled along the average angle of the nares major axis such that it protrudes into but is not occluded by the internal nare surface.

Some patients may find the unevenness of having a prong in only one nare unpleasant after extended use. Accordingly, the respiratory interface 100 may allow for the patient to swap which nare is being engaged.

In some configurations, a respiratory interface 100 comprises a single sealing nasal prong and an adjuster. The nasal prong may be a sealing nasal prong or a partially sealing nasal prong. The single nasal prong comprises a body, an inlet configured to receive gases, and an outlet configured to supply the gases to the patient. Where the nasal prong is to be of a sealing type configuration, there may be a seal body. The seal body may be configured to seal with one of the nares of a patient. The seal body is substantially symmetrical about a first axis.

In an alternate configuration of the interface shown in FIGS. 50 to 56, the interface may comprise a single removable prong. The removable prong can be removed from a face mount part and may be inserted into one of two operative positions i.e. to engage with left nostril or the right nostril.

The adjuster (sliding member 501) is configured to allow the single sealing nasal prong to be removable from the first nare and positioned in the patient's other nare to seal with the other nare without the single sealing nasal prong being removable from the respiratory interface 100. That is, the single nasal prong remains in-situ with the respiratory interface 100 and does not need to be detached or decoupled from the respiratory interface 100.

Figure 55:
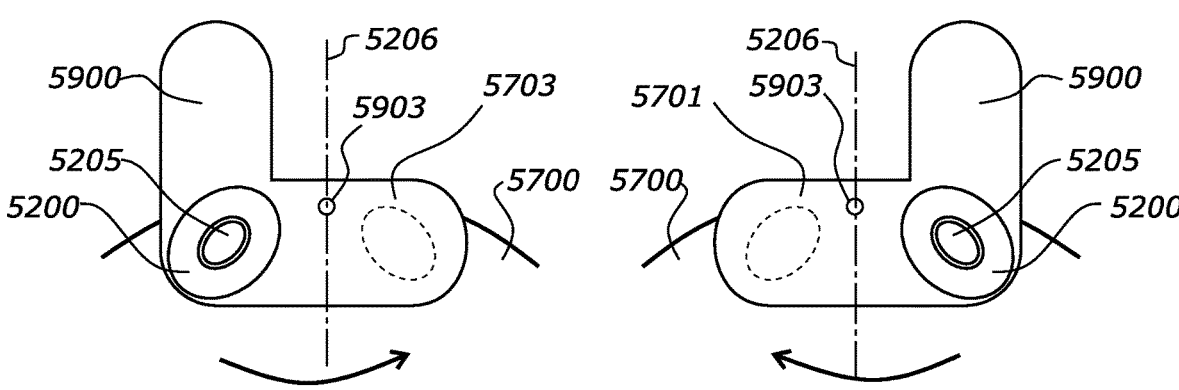
FIG. 55 shows a series of schematics of another configuration of a respiratory interface.
Figure 56:
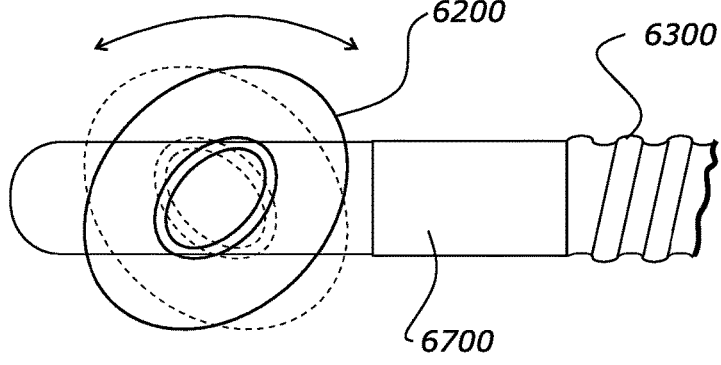
FIG. 56 is a schematic of another configuration of a respiratory interface.

With reference to FIG. 55, the single sealing nasal prong 5200 may be a movable prong. The single sealing nasal prong 5200 preferably extends from a movable support 5900. For example, the support 5900, together with the single sealing prong 5200, may be rotatable from a first location in which the prong 5200 seals with a first nare of a patient to a second location in which the prong 5200 seals with a second nare of a patient. The movable support 5900 is rotatable about a pivot point 5903. The pivot point 5903 is located between the first location and the second location.

The first location of the single sealing nasal prong 5200 is on a first region of a manifold 5700 and the second location is on a second region of the manifold. In an alternative configuration, the first location and the second location are on the same region of the manifold 5700. For example, in the case of a pivoting single sealing nasal prong that does not have a movable support as shown in FIG. 55, or if the movable support is much smaller/less obvious.

When in the first location, the prong outlet 5205 extends at a first angle relative to a central plane 5206 to correspond to the angle of the first nare. When in the second location, the prong outlet 5205 extends at a second angle relative to the central plane 5206 to correspond to the angle of the second nare. The manifold 5700 has first outlet 5701 corresponding to the first location of the prong and a second outlet 5703 corresponding to the second location of the prong. The respiratory interface 5100 further comprises a bung configured to seal the second outlet 5703 when the single sealing nasal prong is in the first location and seal the first outlet 5701 when the single sealing nasal prong is in the second location. The manifold may comprise a single opening that extends the between the prongs or at least from one prong to the other prong.

The bung (not visible) is integral with the prong 5200. The single sealing nasal prong 5200 and the bung may be integral with the support 5900, Accordingly, the bung is configured to rotate as the prong rotates. In an alternative configuration, the bung and prong may not be integral. In this configuration, the prong may be a rotatable prong and the bung can be placed to seal the second outlet when the single sealing nasal prong is in the first location and seal the first outlet when the single sealing nasal prong is in the second location. This embodiment respiratory interface may have a tether that couples the bung to the respiratory interface 100.

With reference to the orientation of the single sealing nasal prong 200 in FIG. 55, the prong outlet 5205 is located in a generally central location between the left and right surfaces and located in a generally central location between the front and rear surfaces such that the single sealing nasal prong can seal either one of the patient's nares independently of vertical orientation. In some configurations, alternatively the opening can be asymmetrical as discussed above and biased towards fitting into one nare, but upon rotation of the prong, the opening fits in the other nare.

Figures 54A, 54B, 54C:
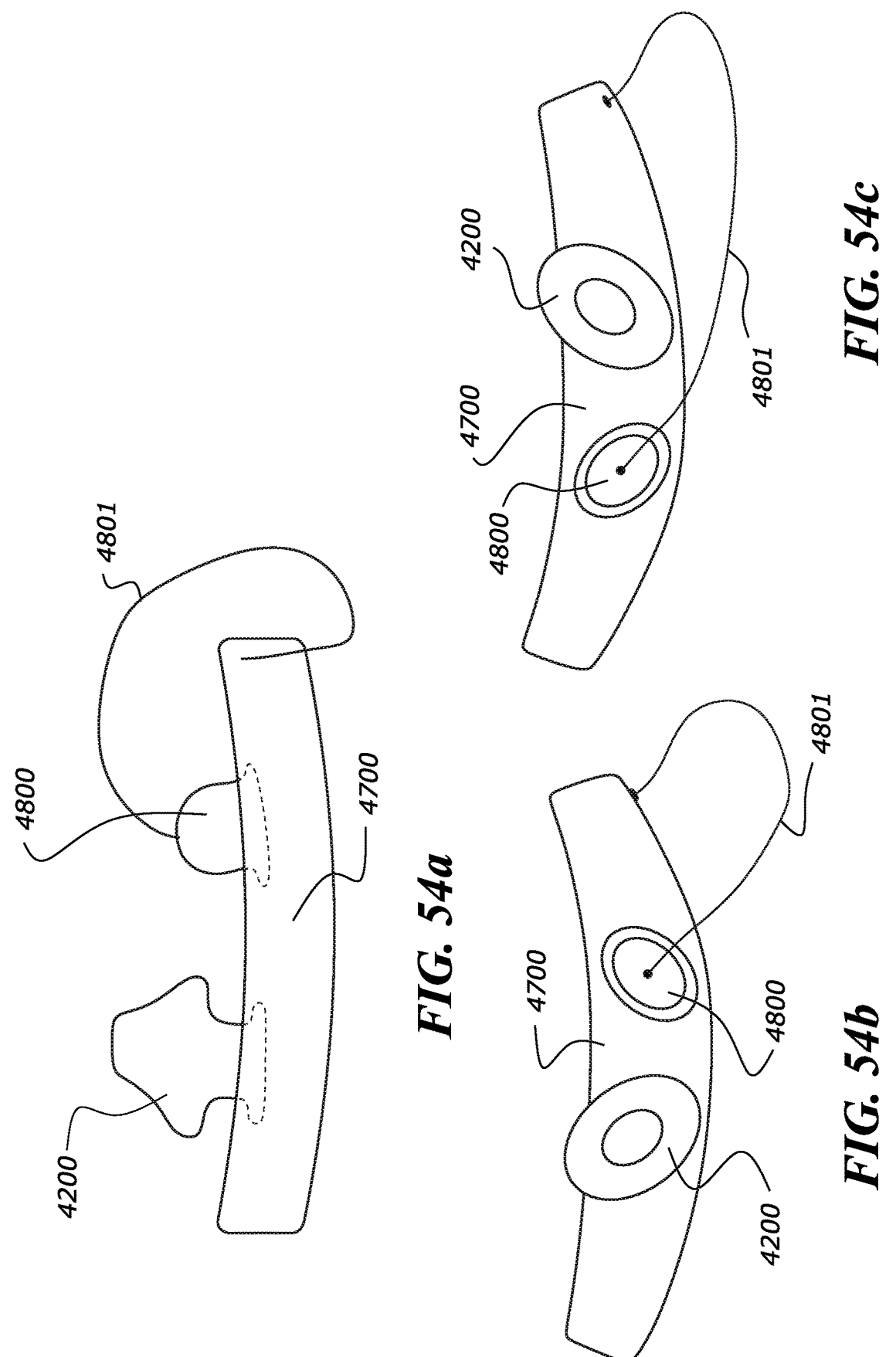
FIGS. 54a to 54c are schematics of another configuration of a respiratory interface.

In an alternative configuration, shown in FIGS. 54a to 54c the respiratory interface 100 may comprise a prong 4200 that may be removed and attached to an outlet on each side of a manifold or support. In this configuration, the unused port is sealed using a plug, bung 4800, or valve. The bung 4800 is attached to the manifold 4700 by a tether 4801.

The following configurations describe further variations that may allow for the patient to swap which nare is being engaged.

In one configuration, the respiratory interface comprises a single prong design (without a manifold) in which the single sealing nasal prong is rotatable relative to the cuff. For example, the single sealing nasal prong may rotate about a central axis between one orientation that corresponds to being used with one nare and another orientation that corresponds to being used with another nare. This embodiment has a single sealing nasal prong having the shape and features of the first described respiratory interface that is symmetrical between the front and rear surfaces and the left and right surfaces. This single sealing nasal prong has a centrally located outlet.

In one configuration, the respiratory interface comprises a single sealing nasal prong that is movable from one side and to the other. The prong may be movable by sliding, pivoting, or a combination of sliding and pivoting. For example, using the sliding member described above. In some configurations, features may be included to reduce tension of the single sealing nasal prong once it has been reinserted into the other nare.

In one configuration, the respiratory interface comprises a prong that sits centrally and may be pivoted or twisted to align with either nare. This configuration may include a barrier (i.e. a stopper) that prevents the single sealing nasal prong from being twisted beyond an appropriate angle. The respiratory interface 100 of this configuration may have a locking mechanism that holds the single sealing nasal prong in the correct alignment. An integral plug may move into place as the single sealing nasal prong moves.

Each of the configurations of the respiratory interface described herein may be provided in multiple sizes, for example, neo-natal, extra-small, small, medium, large, and extra-large. Each size will have a slightly different interaction with the therapy.

The respiratory interface 100 is configured to provide respiratory flow therapy (i.e. respiratory gases) to the patient through the single sealing nasal prong 200. Test results are described in more detail later in the specification. As described above, the wall 206 of the single sealing nasal prong 200 has an at-rest shape. The wall 206 is configured to substantially maintain the at-rest shape upon insertion into a patient's nare. The seal body 201 and the outlet 205 of the single sealing nasal prong 200 are arranged such that one of the patient's nares is substantially sealed and gases are supplied to that nare from the outlet while the other of the patient's nares is unsealed and is free from direct gases supply from the outlet. Gases flowing through the gases passage causes the exterior of the single sealing nasal prong to seal with one of the nares of a patient.

In addition to using a respiratory interface having the features described above, the flow rate is controlled to generate desired pressures on inspiration and expiration. For example, the flow rate is lowered when the patient expires to lower the expiratory pressure. In some example operations the expiratory airway pressure is about 5-10 cmH2O The occlusion level of the nostril can be adjusted by the adjusting the tightness of the headgear. For example, the level of sealing, i.e. occlusion, can be adjusted by the user tightening or loosening the headgear straps. If the headgear is pulled tighter then the prong pulled further into and against the nostril thereby increasing occlusion.

Possible discomfort may be further reduced by having a support at the side of the conduit just below the single sealing nasal prong 200 that is designed to contact the patient's upper lip. The support may include a soft and/or flexible component that is offset from the surface of the conduit. The flexible component may comprise a plastic material or any suitably soft/flexible material designed to adjust to the contours of the patient's skin. The support may be provided in a single suitable location. The single sealing nasal prong 200 may be rotatable relative to the end of the conduit. The rotatable prong allows the single sealing nasal prong 200 to be aligned with either one of the patient's nares while still having the lip support in an ideal position.

The single sealing nasal prong 200 is configured to provide expiratory airway pressure between 3.5 cmH2O and 20 cmH2O, In particular the single sealing nasal prong substantially occludes one nostril and provides gases at a flow rate that create an expiratory airway pressure of between 3.5 cmH2O and 20 cmH2O. Other expiratory pressures may be provided. For example, the expiratory pressure may be 4 cmH2O, 4.5 cmH2O, 5 cmH2O, 5.5 cmH2O, 6 cmH2O, 6.5 cmH2O, 7 cmH2O, 7.5 cmH2O, 8 cmH2O, 8.5 cmH2O, 9 cmH2O, 9.5 cmH2O, 10 cmH2O, 10.5 cmH2O, 11 cmH2O, 12 cmH2O, 12.5 cmH2O, 13 cmH2O, 13.5 cmH2O, 14 cmH2O, 14.5 cmH2O, 15 cmH2O, 15.5 cmH2O, 16 cmH2O, 16.5 cmH2O, 17 cmH2O, 17.5 cmH2O, 18 cmH2O, 18.5 cmH2O, 19 cmH2O, or 19.5 cmH2O.

Below is a description of some additional alternative configurations to those described earlier. These configurations include optional elements and elements in the below described configurations may be used in combination with the earlier described configurations.

In some configurations, the respiratory interface consists of a gases delivery assembly and headgear connected to, or connectable to, the gases delivery assembly. The gases delivery assembly has the single sealing nasal prong and the conduit directly coupled to the single sealing nasal prong and in fluid communication with the single sealing nasal prong. The single sealing nasal prong has the seal body configured to seal with one of the nares of the patient, the inlet configured to receive gases, and an outlet configured to supply the gases to the patient. In these configurations, the respiratory interface only has the gases delivery assembly and the headgear. The headgear is sufficient to maintain the seal with the patient's nare.

In some configurations the respiratory interface comprises a cuff, the cuff being a connection hub such that the cuff interconnects a prong and a tube (i.e. a conduit) to form the interface. The cuff connects directly to the prong and tube. The cuff facilitates a fluid connection between the tube and the prong. The cuff further facilitates connection with a headgear. The headgear may directly connect to the cuff. Alternatively, the cuff may connect to a support that connects to a headgear.

In some configurations, a respiratory support system or apparatus 10 (such as that shown in FIG. 1A) may comprise a gases flow source 11 configured to provide a gases flow at a high flow rate to a patient. The respiratory support system may also comprise a humidifier 12 configured to heat and humidify the gases flow to be provided to the patient, and a patient interface 100 comprising a single sealing nasal prong interface (such as any of the single sealing nasal prong configurations as described herein, for example in FIGS. 10 to 76) configured to deliver the gases flow at the high flow rate to the patient. The single sealing nasal prong interface 100 may comprise a single sealing nasal prong 200 adapted to substantially seal with a single nare of two nares of the patient. In some configurations, the humidifier 12 comprises a humidification chamber removably connected to a humidifier base unit. The humidification chamber is configured to be filled with a humidification liquid such as water for the humidification of the gases flow to the patient. In some configurations, the humidification chamber comprises a heat conductive base and the humidifier base unit comprises a heater plate, and the heat conductive base allows the heating of the humidification liquid in the chamber when in contact with the heater plate of the humidifier base unit. In some configurations, the flow source and humidifier base unit are integral.

In an example embodiment, the patient interface 100 may be configured to increase expiratory pressure in the patient's airway. This is described in more detail in the "Test results" section below.

The humidifier 12 may comprise a humidification chamber (not shown), comprising a gases inlet to receive the gases flow from the gases flow source, and a gases outlet to deliver humidified gases flow to the patient interface. The respiratory support system may comprise an inspiratory conduit located between the humidifier and the patient interface, the inspiratory conduit configured to deliver the humidified gases flow to the patient interface 100. The inspiratory conduit may be a heated inspiratory conduit.

Alternatively, or in addition, the respiratory support system may comprise a patient conduit 300 located between the inspiratory conduit and the patient interface 100. The patient conduit may be formed of breathable material.

The high flow rate may comprise a gases flow to be delivered to the patient of at least 20 L/min, and/or up to about 70 L/min. The gases flow may be a substantially set gas flow rate, for example a gas flow rate set at a particular flow rate. The flow rate may be a constant set flow rate, for example may be set to a constant flow rate for the duration of a therapy. Alternatively, multiple set flow rates may be used for a therapy, for example a first set flow rate for a particular duration, and a second, different set flow rate for a particular duration, for a particular therapy. In an example embodiment a first set flow rate may be a low flow rate, for example 15 L/min for one hour, following by a second set flow rate at a higher flow rate, for example 35 L/min for one hour.

The respiratory support system may comprise a headgear 600 to retain the patient interface 100 on the patient's face.

The respiratory support system may comprise a respiratory interface 100 for delivering gases to a single nare of a patient, the respiratory interface comprising the single sealing nasal prong interface of any of the configurations as described herein.

In some configurations a kit is provided that may comprise a humidification chamber configured to be filled with a humidification liquid such as water for the humidification of the gases flow to the patient. The humidification chamber comprises a humidification inlet, the humidification inlet configured to couple to a flow source, and a humidification outlet. In some configurations, the humidification chamber may be removably connectable to a humidifier base unit (which may be integral with the flow source), in some configurations, the humidification chamber may comprise a heat conductive base and the humidifier base unit comprises a heater plate, and the heat conductive base allows the heating of the humidification liquid in the chamber when in contact with the heater plate of the humidifier base unit. The kit may comprise an inspiratory conduit with an inspiratory conduit inlet configured to couple to the humidification outlet, and an inspiratory conduit outlet. The kit may also comprise a single sealing nasal prong interface, such as the single sealing nasal prong interface 100 of any of the configurations described herein, configured to couple to the inspiratory conduit outlet.

The single sealing nasal prong interface 100 may comprise a patient conduit 300, the patient conduit comprising an inlet configured to couple to the inspiratory conduit outlet. The patient conduit 300 may be formed of a breathable material. The inspiratory conduit may be heated.

The kit may further comprise a conduit clip (not shown) configured to secure the inspiratory conduit to a patient or the surroundings of a patient.

In some configurations, a respiratory interface comprises a single sealing nasal prong the single sealing nasal prong comprises a seal body configured to seal with one of the nares of a patient. The seal body may have opposing front and rear surfaces, and opposing left and right surfaces. The opposing front and rear surfaces may be substantially symmetrical to each other. When viewed from the top, the opposing front and rear surfaces may be symmetrical about a vertical plane. The single sealing nasal prong 2 may have the inlet configured to receive gases and the outlet configured to supply the gases to the patient. The inlet of the prong may be distal to the nostril and the outlet may be proximal when the prong is positioned in an operational position. The outlet may be located in a generally central location between the left and right surfaces such that the single sealing nasal prong can seal either one of the patient's nares. The central location of the single sealing nasal prong may be a location in which the centre of the outlet is equidistant from an outer circumferential surface of the prong. The outer circumferential surface may be considered at the widest circumferential region of the prong. Explained another way the outlet of the prong may be in the centre of the outer circumferential surface of the prong body when viewed from the top. The outlet may be positioned such that the prong may be symmetrical about at least two perpendicular vertical planes passing through the prong.

The location of the prong outlet may allow the single sealing nasal prong to be used independently of nostril orientation and may allow the prong to seal with either nostril. Human nostrils are angled toward each other and the current prong may be shaped and configured to seal with either nostril. The seal body and the outlet of the single sealing nasal prong may be arranged such that one of the patient's nares is substantially sealed and gases are supplied to that nare from the outlet while the other of the patient's nares is unsealed and is free from direct gases supply from the outlet or gases supply from a respiratory system to which the respiratory interface is part of. The outlet being centrally located helps to allow the prong to engage and seal against either the left or right nostril of the user. The prong may be shaped to fit into and substantially occlude either the right or left nostril of the user. For example, the prong can be positioned or located on the patient's face in two different orientations. That is, the interface could itself be rotated 180 degrees and still appropriately fit the patient for suitable prong engagement with a patient's nare. The central prong outlet location can also allow the interface to be suitably fitted for engagement in or with the nare when rotated about 180 degrees and as such can be considered to be orientation-independent when being positioned on the patient's face, provided the sliding member or members (e.g. item 501, 1501) extend in a substantially horizontal manner, or plane, across the face. In some configurations, the prong may be configured to allow the interface to be suitably fitted for engagement in or with the nare when rotated about 180 degrees and as such can be considered to be orientation-independent when being positioned on the patient's face while remaining attached to a support (e.g. support 500) or without being disconnected, detached or decoupled from a support (e.g. support 500). In some configurations, the prong or interface may be configured to allow the prong to be interchangeably fitted in or with a left or right nare of a patient while allowing the prong to remain attached to a support (e.g. support 500) or without being detached from a support (e.g. support 500), for example the prong is trans-latable relative to the support or if the prong is located in a fixed position relative to the support, the interface can be flipped to position the prong in or with the desired nare.

The respiratory interface as described herein may comprise a conduit to transport gases to a prong. The conduit may be an unheated, breathable conduit. The conduit may allow some water vapour to escape through the walls of the conduit. The breathable conduit may allow excess water vapour to escape from the gases flow to prevent condensation within the conduit. The conduit may comprise a breathable wall or may comprise breathable sections within the wall of the conduit.

In an alternative configuration the conduit may comprise a heater wire positioned within the conduit. The heater wire may be located in the lumen of the conduit or alternatively may be integrated into the wall of the conduit. The heater wire is configured to heat the gases within the conduit.

In some configurations a respiratory interface for delivering gases to a single nare of a patient comprises a single sealing nasal prong having a seal body configured to seal with one of the two nares of a patient, a prong inlet configured to receive gases, and a prong outlet configured to supply the gases to the patient. The respiratory interface may comprise a support for the single sealing nasal prong, and a conduit directly coupled to the single sealing nasal prong and in fluid communication with the single sealing nasal prong. The single sealing nasal prong and/or the respiratory interface may be configured to allow the prong to inter-changeably seal in or with a left or right nare of a patient.

The prong and/or respiratory interface may be configured to allow the prong to interchangeably seal in or with a left or right nare of a patient while allowing the prong to remain attached to the support or without being detached from the support. The prong may be located in a fixed position relative to the support, or may be translatable relative to the support. The support may be outside of or separate from (i.e.

does not form a part of) the conduit or gases being supplied to the single sealing nasal prong.

The conduit may be fluidly separated from the support, or the support may not form a part of a gas path of gases being supplied to the single sealing nasal prong. Put another way, the conduit may be only in fluid communication with the single sealing nasal prong, and not connected to the support. The conduit may comprise a single conduit.

The respiratory interface may further comprise a gases path from the conduit to the prong outlet, and the gases path may be substantially linear. A conduit outlet of the conduit may be directly coupled to the prong inlet of the single sealing nasal prong, and the conduit outlet and the prong outlet may share a substantially common substantially central axis.

The respiratory interface may further comprise a headgear removably connectable to the support, and a cuff, where the single sealing nasal prong may be configured to couple with the cuff as described herein. The respiratory interface may further comprise a conduit connector, where the conduit is configured to couple with the conduit connector. The conduit connector and the cuff may be separate components, or may be integral components.

The single sealing nasal prong may comprise a substantially supple or substantially compliant material, and the conduit connector and/or cuff may comprise a substantially rigid material.

Test Results

Figure 57:
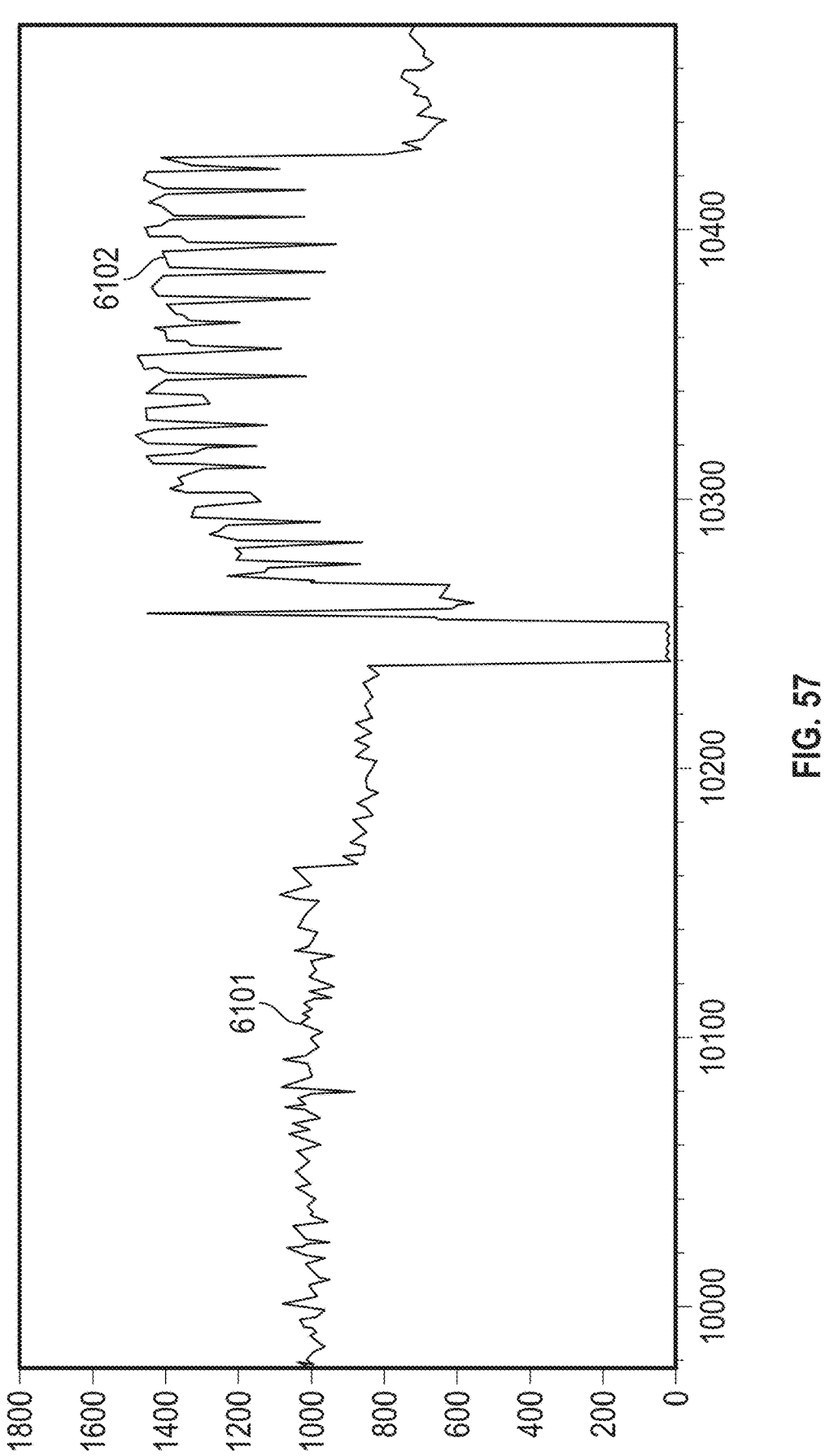
FIG. 57 is a graph with results of testing flow provided at 60 LPM comparing a standard respiratory interface having two nasal prongs and a respiratory interface according to a configuration of the invention.

FIG. 57 shows a graph with results of testing flow provided at 60 LPM. The graph shows results pressure vs time. The plot on the left 6101 is an unsealed dual prong cannula. The plot on the right 6102 of the trough is the single sealing nasal prong respiratory interface, as disclosed herein. In these test results the configurations shown in FIGS. 51 to 53 was used. A non-sealing dual prong cannula is shown on the left and a respiratory interface with a single sealing nasal prong according to the disclosure is shown on the right, each followed by periods where the respiratory interface is out of the nose. It can be seen that there is a trough in the graph that indicates a change in the respiratory interface. Higher pressures and greater pressure swings are generated using the respiratory interface with a single sealing nasal prong according to the disclosure.

The graph shows that for the same flow rate applied by a single sealing cannula a greater expiratory airway pressure is achieved. The peaks indicate expiratory airway pressure. The single sealing nasal prong is advantageous because it produces a higher expiratory airway pressure for a given flow as compared to a dual unsealed prong nasal cannula. The increased expiratory airway pressure helps to prevent the alveoli collapsing during expiration and helps to add expiratory resistance that decreases the expiration rate.

Figure 58A:
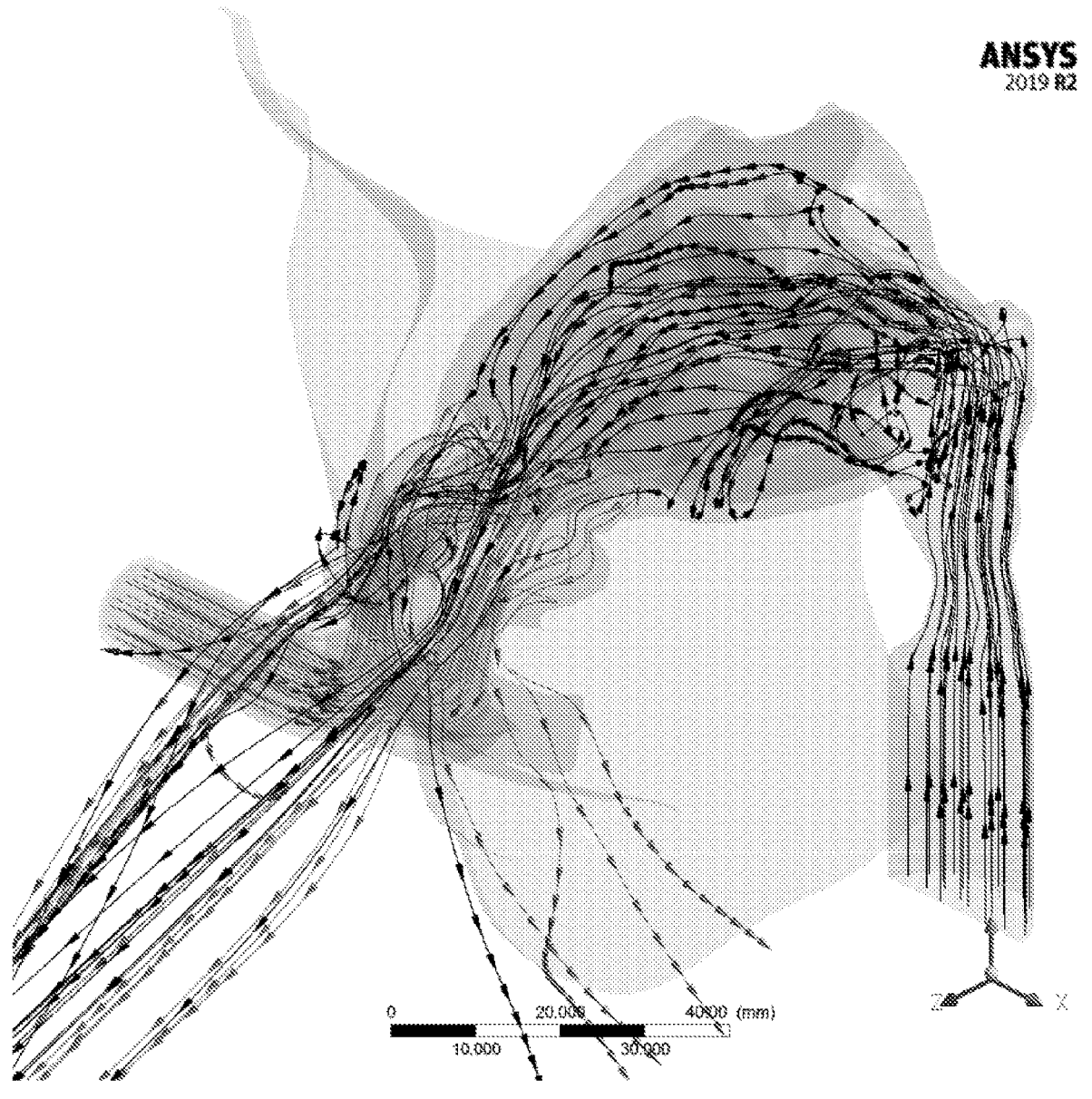
FIGS. 58A, 58B, 58C, and 58D show streamlines of flow during exhalation of a respiratory interface with two prongs providing nasal gases flow.
Figure 58B:
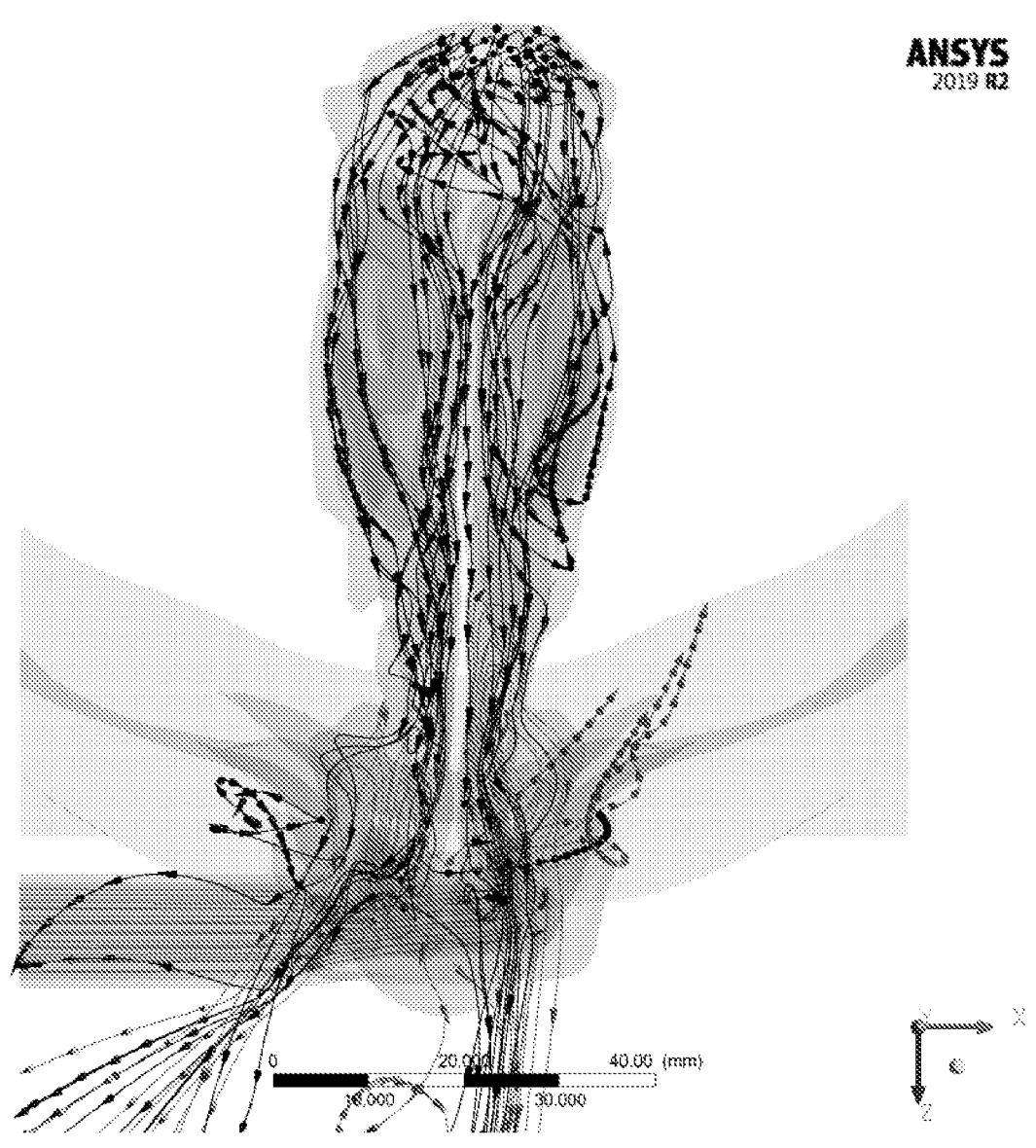
Figure 58C:
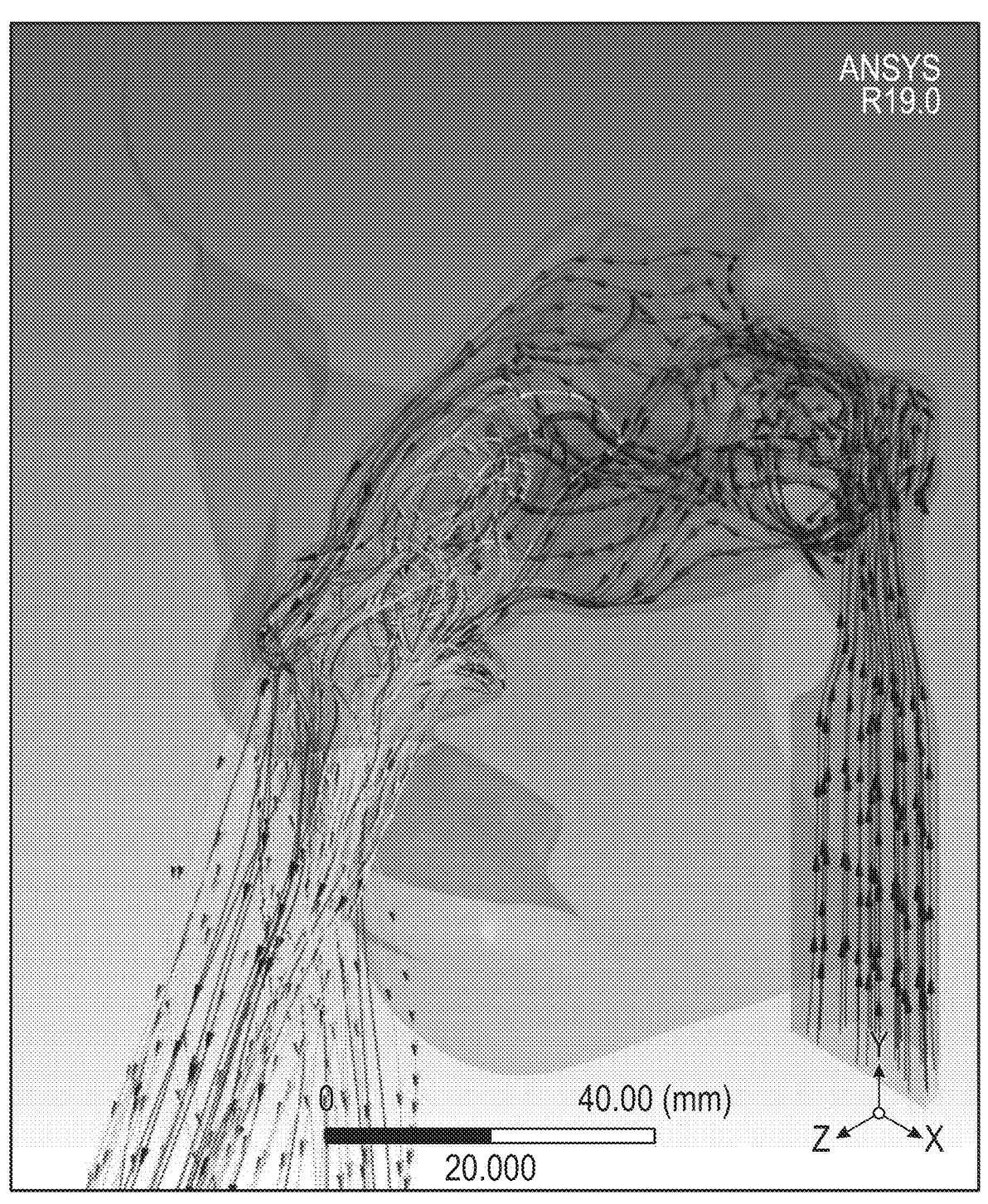
Figure 58D:
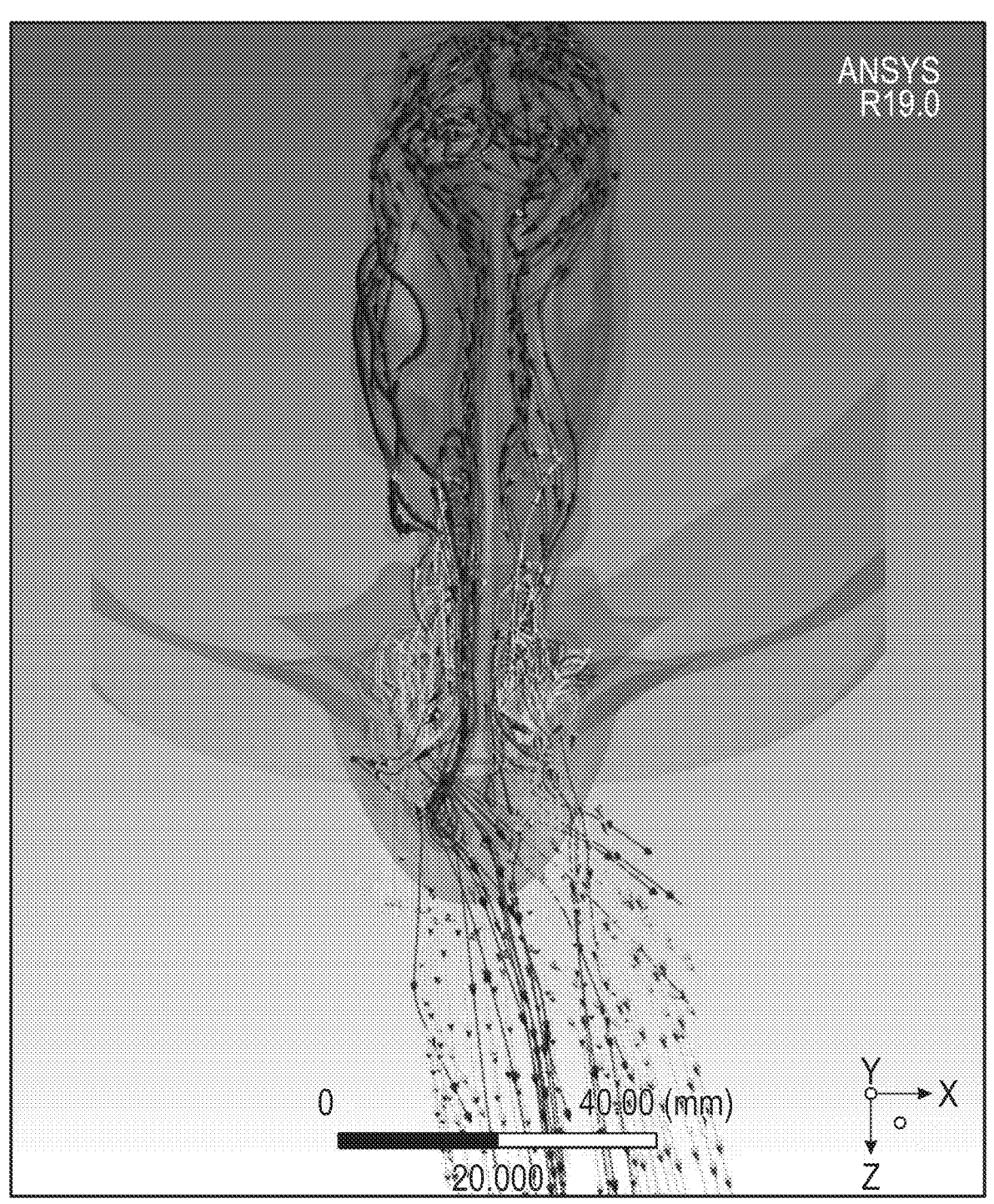
Figure 59A:
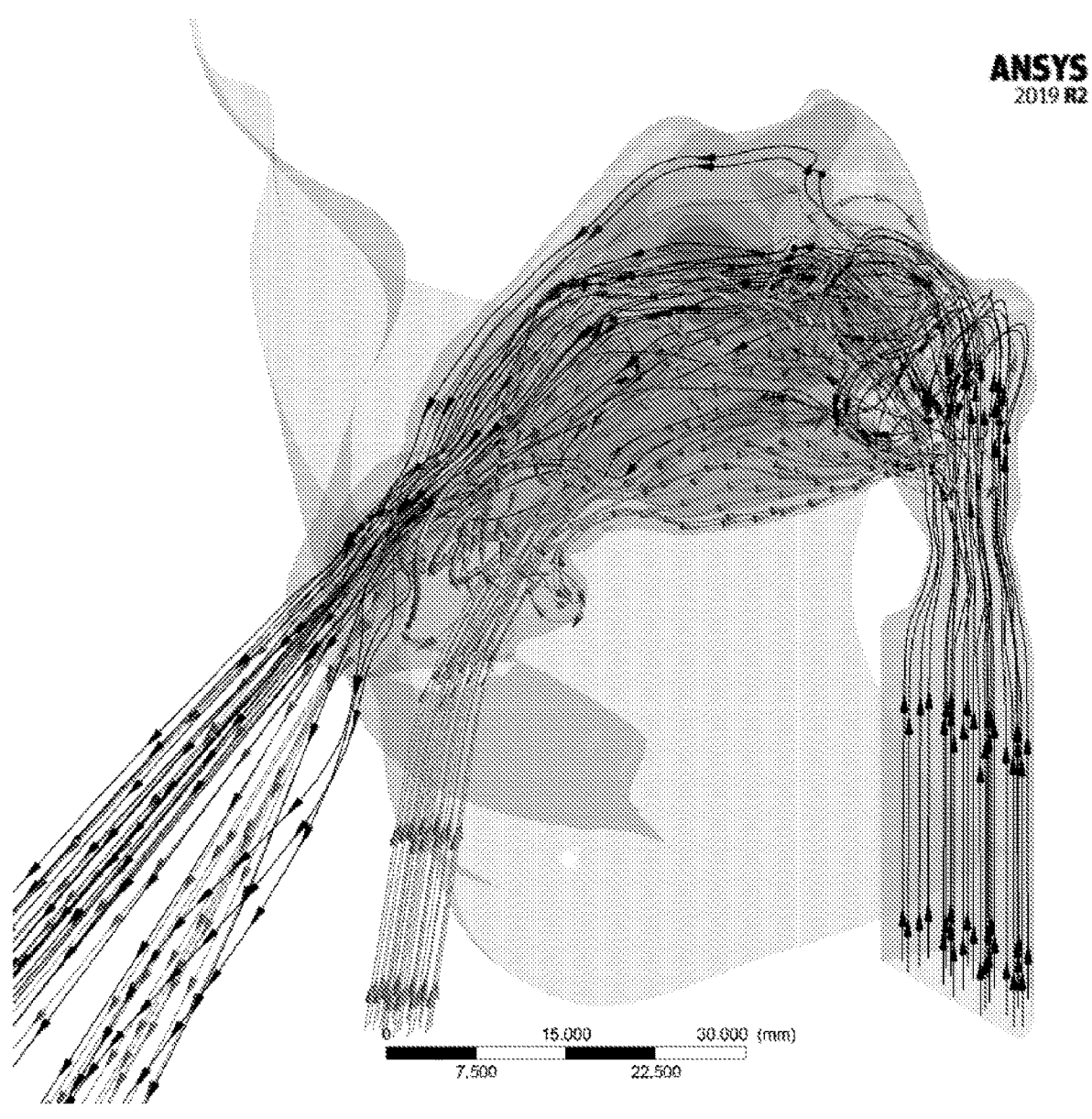
FIGS. 59A, 59B, 59C, and 59D show streamlines of flow during exhalation of a respiratory interface with a single sealing nasal prong providing nasal gases flow.
Figure 59B:
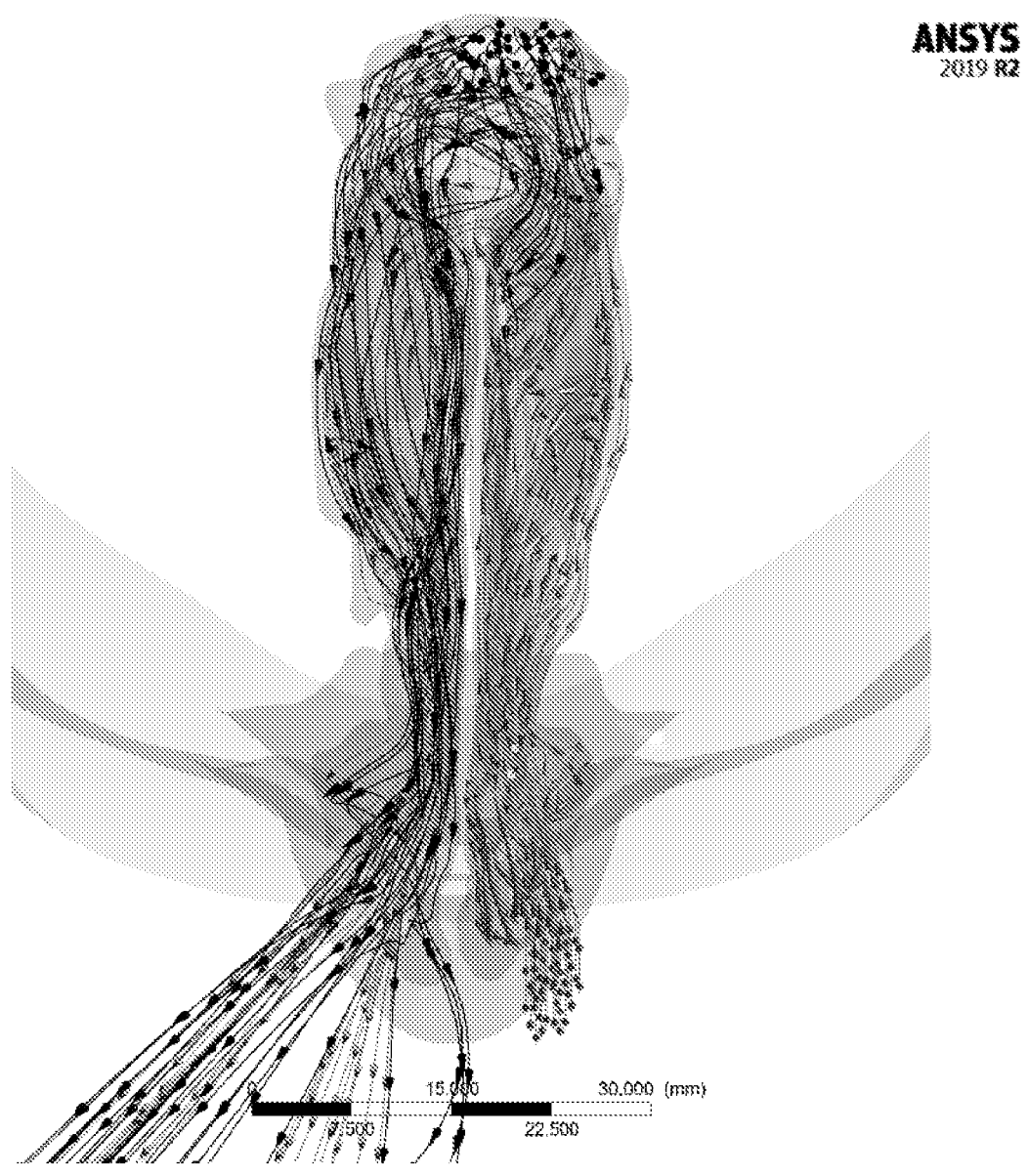
Figure 59C:
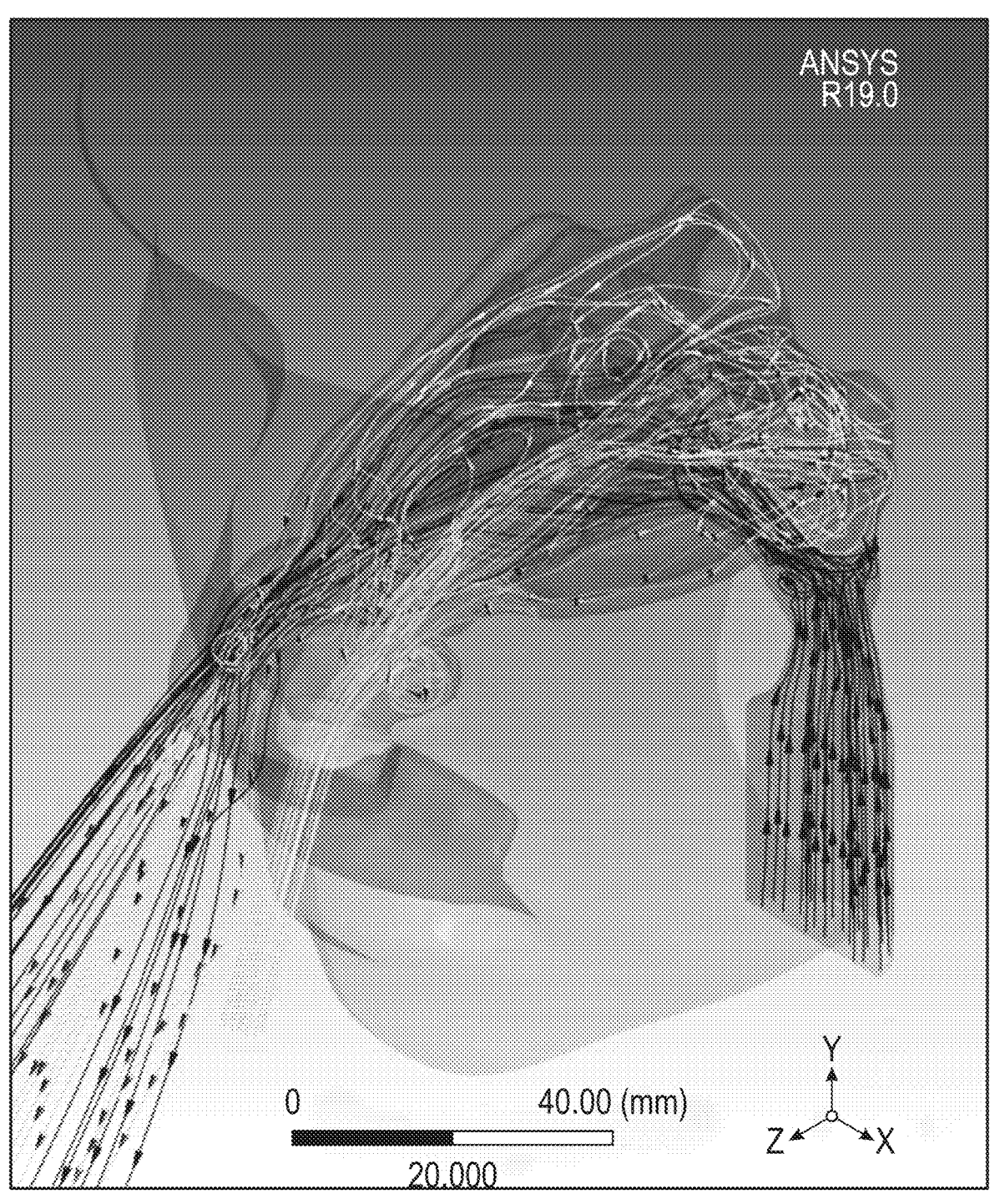
Figure 59D:
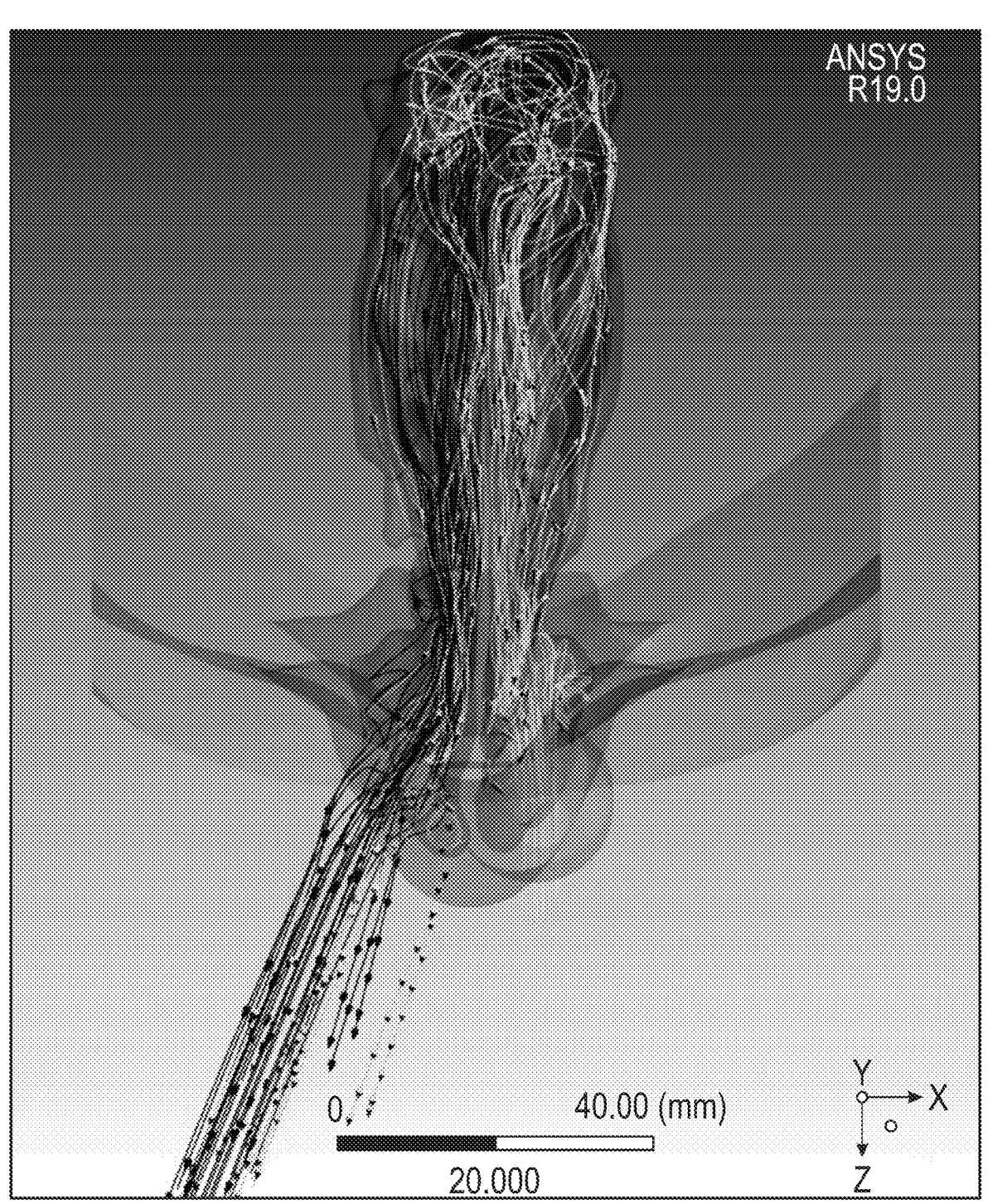

FIGS. 58A, 58B, 58C, and 58D show streamlines of flow during exhalation with two unsealed prongs using nasal high flow therapy. FIGS. 58A and 58B show a side entry interface. FIGS. 58C and 58D show a front entry interface. Pressure from exhaled gases forces the prong flow streams to reverse and exit through gaps in the prongs. Lighter grey represents the delivered flow from the nasal high flow and darker grey represents the expired respiratory flow.

FIGS. 59A, 593, 59C, and 59D show streamlines of flow during exhalation with a single sealing nasal prong providing respiratory flow. Lighter grey streamlines represent the delivered flow from the respiratory interface i.e. fresh gases and darker grey streamlines represents the expired respiratory flow i.e. mainly carbon dioxide. The delivered flows from the single sealing nasal prong increases the resistance to flow in the patient's nasal passage (of the nare that the single sealing nasal prong substantially seals with), which increases the expiratory pressure of the expired respiratory flow during exhalation. The pressure from exhaled gases forces the prong flow streams to reverse, but not before it circulates through the entire nasal cavity. Using the single sealing prong interface causes the fresh gases flow stream to extend further into the back of the airways of the patient's nares. The gases reaching deeper into the airways provides more efficient dead space clearance. The flow reaching further into the airways of the patient also improves dead space clearance and also can result in more dead space clearance.

The various configurations of the single sealing nasal prong described herein provide a respiratory interface that seals one nare and leaves the other nare free. This arrangement reduces the noise created by the expansion of the gases as it leaves the cannula as well as the shearing noise of the delivered flow from the cannula colliding with the expiratory flow from the patient. The benefits of a single sealing nasal prong include providing a unidirectional flow that increases respiratory pressures, preferably expiratory pressures in a patient. Increased expiratory pressure helps to maintain airway patency. This decreases respiration rate that reduces strain on the muscles and reduces respiratory effort. The benefits of the single sealing nasal prong also includes an increase in the clearance of deadspace. The improved dead space clearance also reduces the work of breathing since the patient is getting more fresh gases as compared to a dual unsealed prongs cannula for a given flow rate.

These test results were obtained from benchtop testing a dual unsealed prong nasal cannula as compared to the single sealing nasal prong,

| | Flow L/min | expiratory cmH2O |
|---|---|---|
| Interface with single sealed prong | 15 | 3.5 |
| | 25 | 6 |
| | 60 | 14 |
| Interface with two prongs | 25 | 3 |
| | 60 | 10.5 |

Increased expiratory resistance may increase the length of the expiratory phase, which reduces respiratory rate. The resistance is related to the amount of the patient's nare that is blocked. This reduces respiratory effort of the user.

By only engaging a single nare of the patient, the other nare is left free for the patient to breathe out from. The free nare provides an unoccluded path for expiratory gases to be expired by the user. The free nare also potentially reduces resistance to expiration out of that nare as compared to using a dual prong system. Keeping the other nare free also provides space to insert other instruments e.g. nasogastric (NG) tubes or feeding tubes into the free nostril, while still providing the benefits of increased dead space clearance, flushing and increased expiratory airway pressure.

Figure 60A:
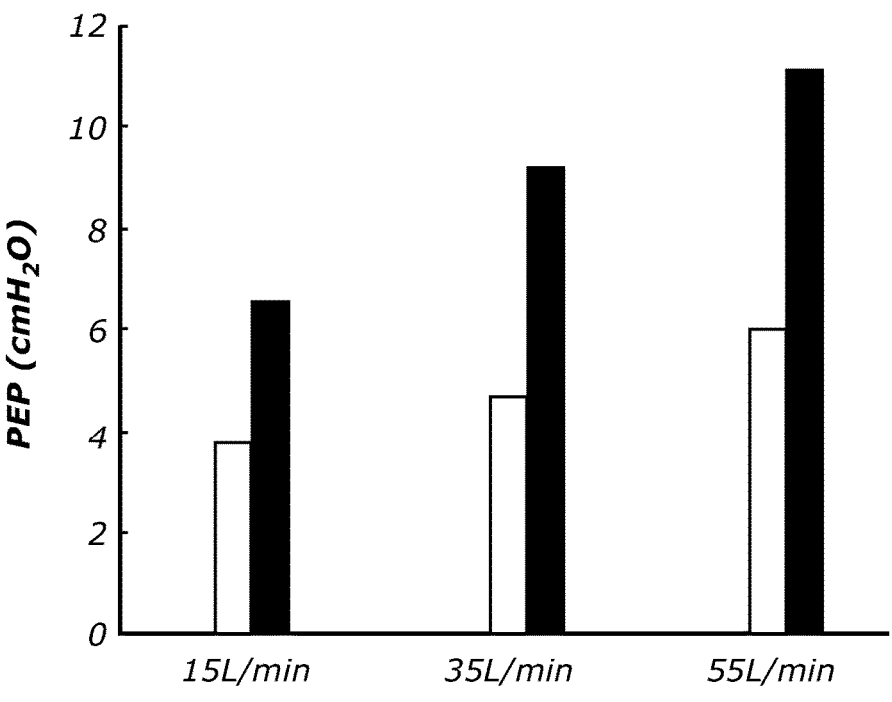
FIGS. 60A and 60B show graphs with results of testing positive expiratory, pressure comparing standard respiratory interfaces having two nasal prongs and a respiratory interface according to a configuration of the invention.
Figure 60B:
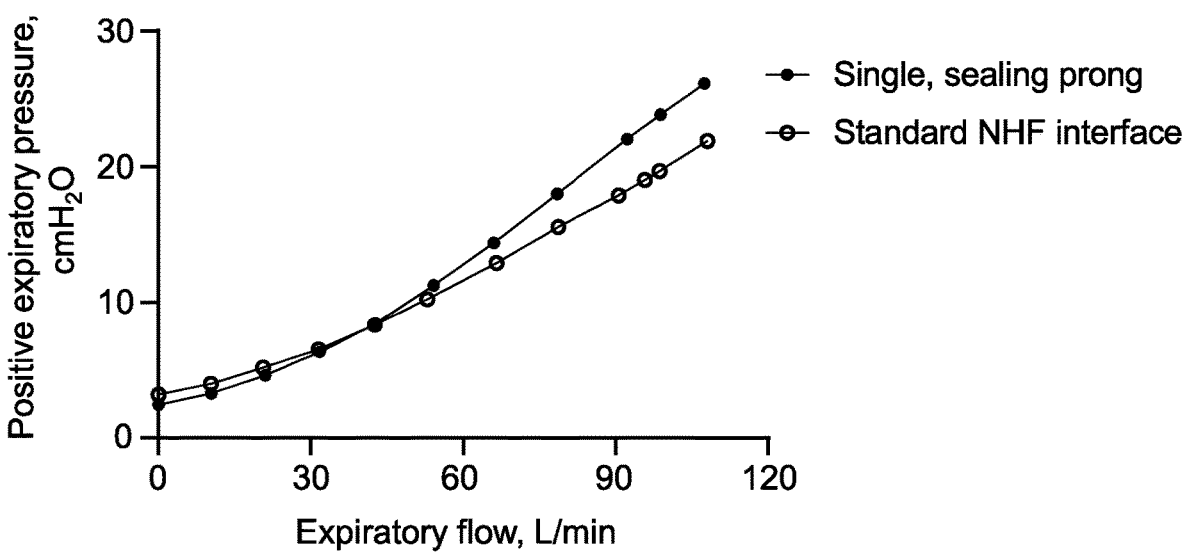

FIGS. 60A and 60B show graphs with results of testing Positive Expiratory Pressure (PEP) comparing standard respiratory interfaces having two nasal prongs and a respiratory interface according to a configuration of the invention, FIGS. 60A and B show increased PEP for a single sealed prong interface, such as that described herein, in comparison with a two prong interface.

FIG. 60A shows PEP results of testing a standard two nasal prongs non-sealing interface (white) and a single sealing prong interface according to an embodiment described herein (black) on 5 adult males for 3 minutes per interface per flow rate. Pressure is measured in the mouth. Heated and humidified flows were provided to the test subjects. The PEP was measured at set flow rates of 15, 35, and 55 L/min respectively. An increase in PEP was observed for the single sealing prong interface (black) across all flow rates compared to standard two nasal prongs non-sealing interface (white).

FIG. 60B illustrates PEP measured in the trachea of an upper airway model during an expiratory flow rate ranging between 0 L/min and 120 L/min at a delivered gas set flow rate via a single sealing nasal prong interface such as that described herein (closed circles) and a standard two nasal prongs non-sealing interface (open circles). The PEP increases at a steeper rate as the expiratory flow rate increases during the use of the single sealing nasal prong interface versus the standard two nasal prongs non-sealing interface.

FIGS. 61A and 61B show graphs with results of testing respiratory rate comparing a standard two nasal prongs non-sealing respiratory interface and a single sealing prong respiratory interface according to a configuration herein.

FIG. 61A shows respiratory rate results of testing a standard two nasal prongs non-sealing interface (white) and a single sealing prong interface according to an embodiment described herein (black) on 5 adult males for 3 minutes per interface per flow rate, Heated and humidified flows were provided to the test subjects. Respiratory rate was measured at set flow rates of 15, 35, and 55 L/min respectively. A decrease in respiratory rate was observed for the single sealing prong interface (black) across all flow rates compared to standard two nasal prongs non-sealing interface (white).

FIG. 613 shows another set of respiratory rate results of a study in healthy volunteers. Mean respiratory rate (breaths per minute, BPM) in 4 healthy volunteers receiving nasal high flow (NHF) delivered via a standard two prong non-sealing interface (white bar) or a single sealed prong interface (grey bar) such as that described herein. NHF was delivered at a set flow rate of 30 L/min of room air. The use of the single sealed prong interface to deliver nasal high flow resulted in a lower respiratory rate in 3 out of 4 participants.

By sealingly engaging the whole of a nare, the flow velocity of the gases at the outlet of the sealed prong is decreased (as compared to two non-sealing nasal prongs) for the same volumetric flow rate. That is because a single sealing nasal prong has a larger cross-sectional area than two non-sealing nasal prongs combined. Two non-sealing nasal prongs would require gaps or spaces around the edges of the prongs for the expiratory flow to escape. Lowering the speed of the flow has the advantage of lowering the noise from expansion and changes in direction of the flow.

The size of the prong outlet is about 33% larger than a conventional nasal prong. In some cases, the cross-sectional area increases within the prong and reduces again at the prong outlet. Increasing the cross-sectional area reduces gases velocity, which reduces noise at the respiratory interface, Narrowing at the prong outlet does not negate these effects as the decrease in flow resistance is offset by the increase in cross-sectional area within the prong.

A unidirectional flow increases airway pressure within the nose especially during the expiratory cycle helps to reduce the effects of nasal cycling. A unidirectional flow also improves flushing of the nasal cavity increasing the dead space clearance such that the patient inhales more therapeutic gases and less rebreathing occurs. The unidirectional flow also can help in driving the fresh gases deeper into the airways to enhance the dead space clearance i.e. flushing effect.

Configurations of the single sealing nasal prong described herein reduce the overall footprint of the cannula. The reduced footprint improves the experience of the patient.

A further advantage is that sealing/occluding a single prong reduces risk barotrauma since there is always one unsealed nostril. This can be particularly useful for use with neonates as there is a large leak due to the unsealed/unused nostril.

In one example operation a constant flow rate is delivered by a respiratory flow therapy apparatus during inspiration and expiration. The constant flow rate creates an inspiratory airway pressure and an expiratory airway pressure due to the prong sealing with one nostril i.e. occluding one nostril. At least 50% of the nostril is occluded, and preferably at least 75% or more of the nostril is occluded. This creates an expiratory airway pressure that is advantageous as it helps to open the alveoli and prevents the alveoli from collapsing. The described respiratory interface helps to decrease respiratory rate of the patient due to the increased expiratory airway pressure, as compared to expiratory airway pressure when delivering gases through a nasal cannula with a pair of unsealed prongs.

The present respiratory interface as described is shaped and configured to occlude at least 30% of the whole nose. The respiratory interface is shaped and configured to seal approximately 50% of the whole nose i.e. occlude or seal one nostril while maintaining the other nostril as unoccluded or unsealed. The occluded nostril helps to create expiratory airway pressure. The occluded nostril also can generate some airway pressure during inspiration. The unoccluded nostril prevents the risk of barotrauma and provides a pathway for expired gases to be passed out of the airways.

Another benefit of the configurations of the single sealing nasal prong describe herein is that any nebulized medicament added to the flow would be more efficiently delivered to the patient. That is because substantially all, preferably all, of the flow would be forced into the patient's airways without any chance for gases to escape between the single sealing nasal prong and the nare opening.

A further benefit of the configurations of the single sealing nasal prong describe herein is that the single sealing nasal prong allows for a more standardized leak across populations because one nostril is occluded. With a dual prong unsealed system, there is a risk of incorrect sizing and over occlusion due to the prongs being fitted into the nostrils. Having one nostril unsealed reduces variation in the overall amount of occlusion.

The nasal cycle is a continuous cycle of each side of the nasal cavity of a patient partially closing and opening over time. The nasal cycle is thought to be a natural mechanism of alternating congestion and decongestion for each side of the nose. The nasal cycle creates a difference between the resistance to flow through the left and right portions of the nose. The proportion of the total inspiratory and/or expiratory flow through each nasal passage can therefore differ substantially. Inevitable inter-personal nostril geometry variation and breathing device interface placement can compound to bias flow through one or the other nasal passage.

The asymmetry in nasal resistance due to the nasal cycling can affect the positive airway pressures that are generated by a single sealing nasal prong as described herein, depending on which nare the prong is substantially sealed with. This provides a further benefit due to the configurations of the single sealing nasal prong as described herein.

FIG. 61C shows test data of the above described asymmetry. FIG. 61C shows graphs with results of testing peak expiratory flow rate comparing a left and right nare of a user with a respiratory interface according to a configuration of the invention. Pressure (cmH2O) is measured in the trachea of an upper airway model during peak expiratory flow of 30 L/min (A) or 60 L/min (B) at delivered gas flow rates of 20-70 L/min via the single sealing nasal prong interface such as that described herein. At the two peak expiratory flows (shown in the two graphs), the peak expiratory pressure is greater when the gas flow is delivered via the left nostril versus the right nostril. The results indicate that the positive airway pressures that are generated during the use of the single sealing nasal prong interface can be adjusted by switching the nare that the prong seals with.

Another benefit of the configurations of the single sealing nasal prong describe herein is that the single sealing nasal prong also helps to reduce variation of dead space clearance since there is less variation of prong placement in the nostrils. The single sealing nasal prong is more repeatable in use since it is large enough to cause occlusion.

A further benefit of the configurations of the single sealing nasal prong describe herein is that the single sealing nasal prong provides dead space clearance at the end of expiration. The single sealing nasal prong may allow for substantially similar dead space clearance as compared to a dual unsealed prong system.

FIGS. 77A, 77B and 77C illustrate perspective, front, and side views of an example embodiment of a strap attachment or ferrule. The strap attachment may be configured to terminate a headgear strap, and may advantageously secure or retain an end of a headgear strap.

The strap attachment may advantageously reduce a fraying or splitting of a headgear strap or portion of a headgear strap located within the strap attachment.

The strap attachment may advantageously provide for a grip portion of a headgear strap for a user to grip or hold onto when adjusting the tightness of a patient interface, such as when placed on the patient.

Figure 78A:
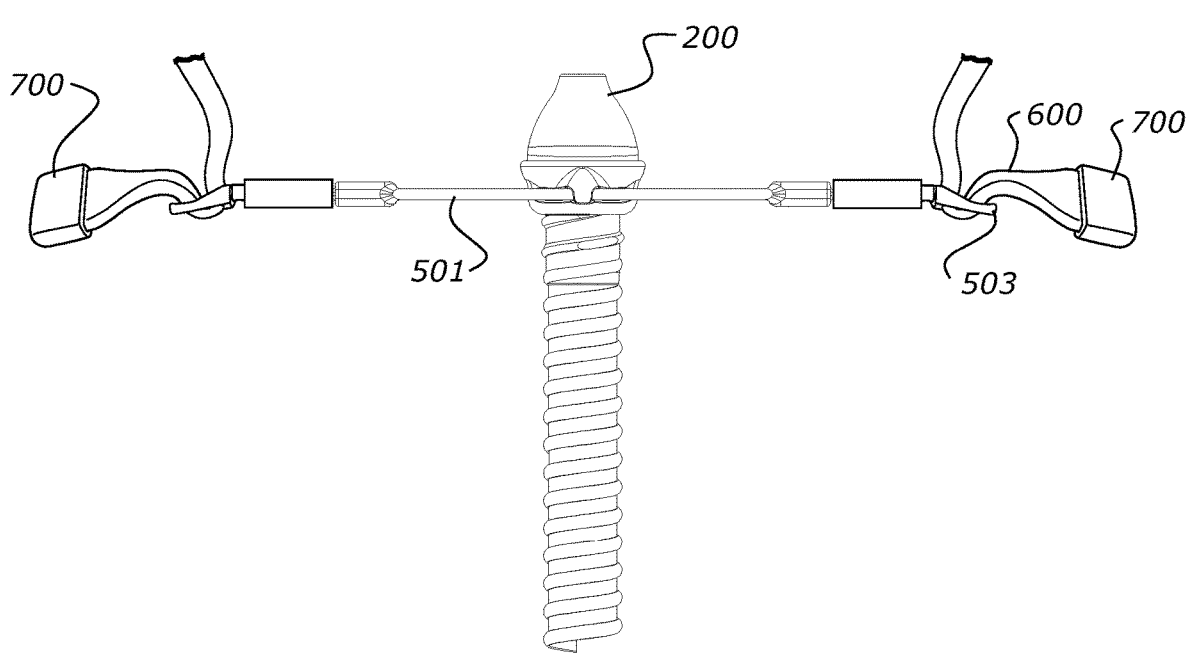
FIG. 78A illustrates an example embodiment of a respiratory interface with a strap attachment.
Figure 78B:
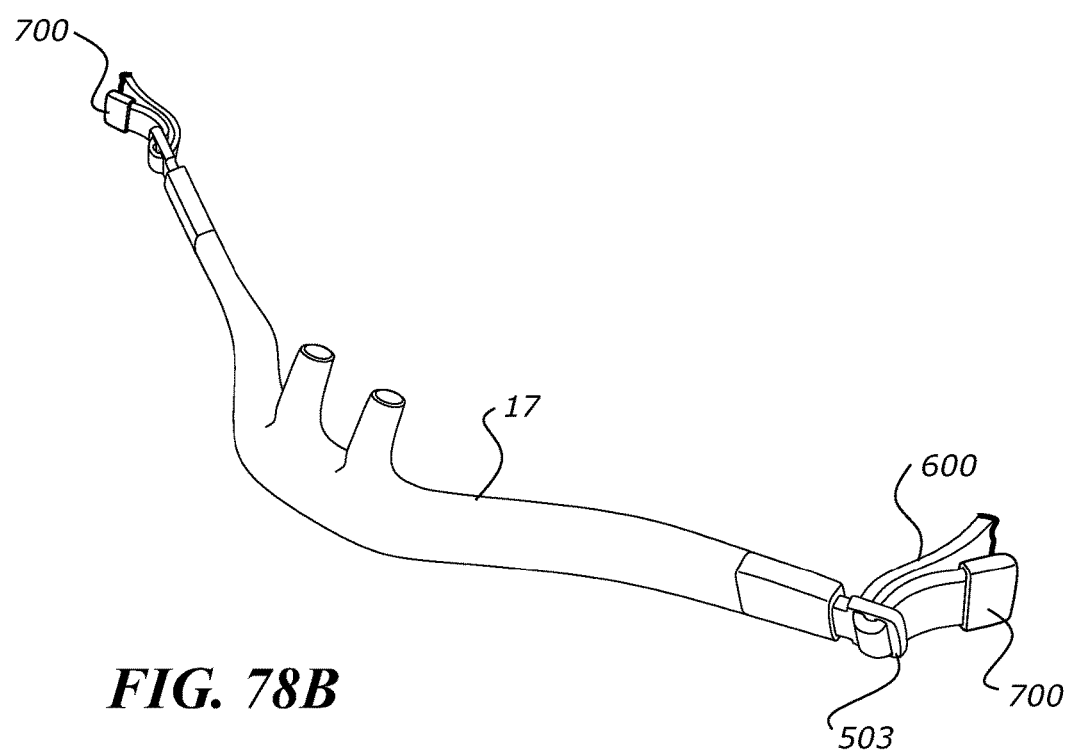
FIG. 78B illustrates a second example embodiment of a respiratory interface with a strap attachment.

In an example embodiment, a strap attachment 700 may be configured to terminate a headgear strap 600 as shown in FIGS. 78A and 78B.

FIG. 78A illustrates a single sealing nasal prong 200 as outlined in embodiments herein, comprising sliding member 501, and clip 503 connectable to headgear 600. Two strap attachments 700 are shown terminating a headstrap on both sides of the headgear 600 in FIGS. 78A and 78B.

FIG. 78B illustrates a second example embodiment, comprising a patient interface 17 with two nasal prongs as described herein, a clip 503 connected to headgear 600, and a strap attachment 700 terminating a free end of the headgear 600. In the embodiment of FIG. 78B, the patient interface 17 is a nasal cannula. The nasal cannula may be a sealing or a non-sealing cannula. In certain configurations, the nasal cannula comprises a cannula body from which the two nasal prongs extend, and a supply tube for delivering gases from a flow source to the patient via cannula body and prongs. In certain configurations, the nasal cannula comprises a manifold for coupling the supply tube to the cannula body. The manifold may be removably attached to the cannula body. In certain configurations, the supply tube may extend from one side of the nasal cannula. An exemplary nasal cannula is described in US2004/0261797. The contents of that specification are incorporated herein in their entirety by way of reference.

Figure 79:
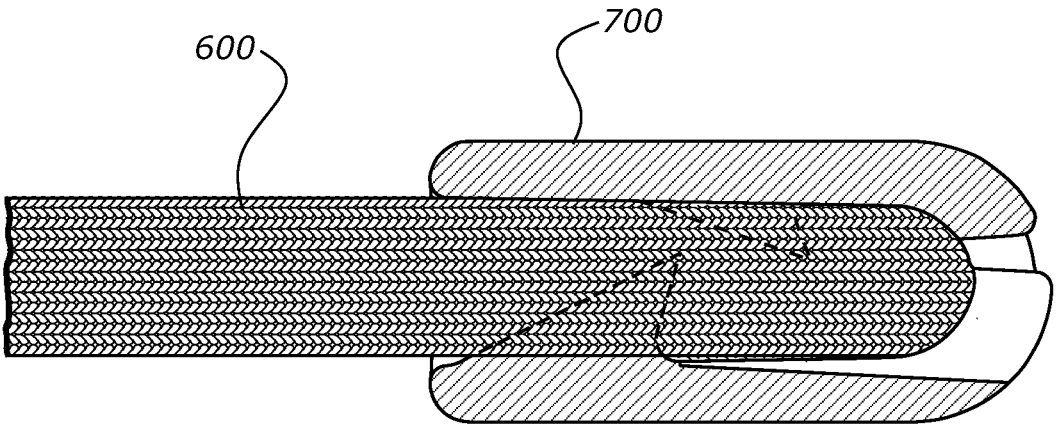
FIG. 79 illustrates a cross section view of a strap attachment and a headstrap of a respiratory interface.

FIG. 79 illustrates a cross section view of a strap attachment 700 and a headgear strap 600 of a respiratory interface, where the projections are engaged with and/or embedded in fabric of the headgear strap 600. The headgear strap 600 is shown inserted within strap attachment 700.

Figure 80A:
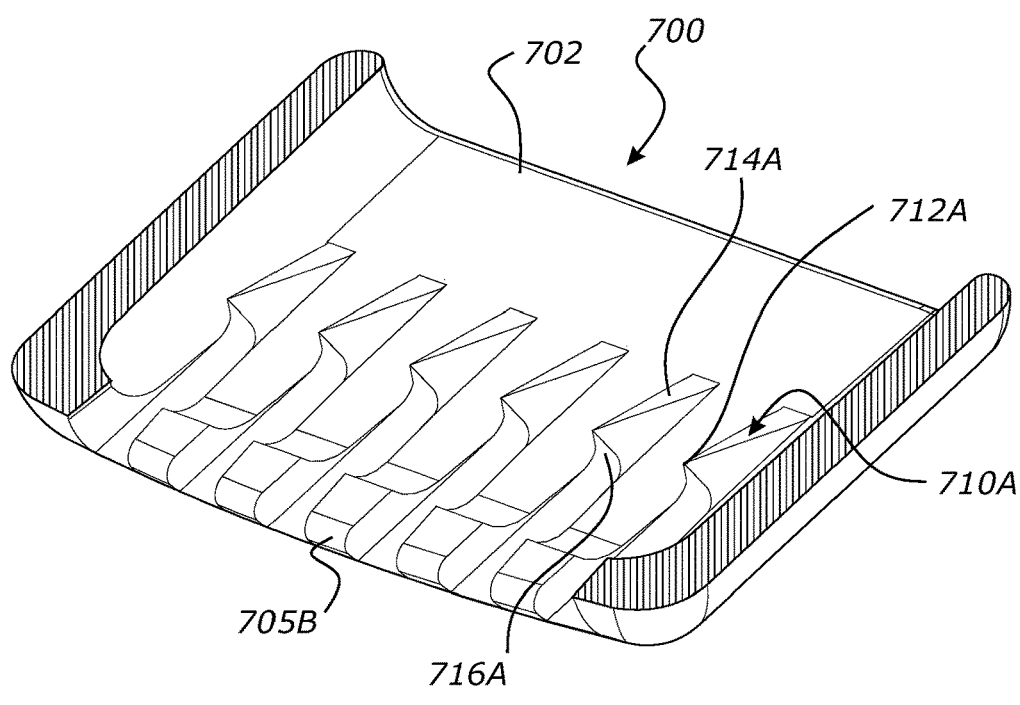
FIGS. 80A and 80B illustrate perspective sectional views of an example embodiment of a strap attachment.
Figure 80B:
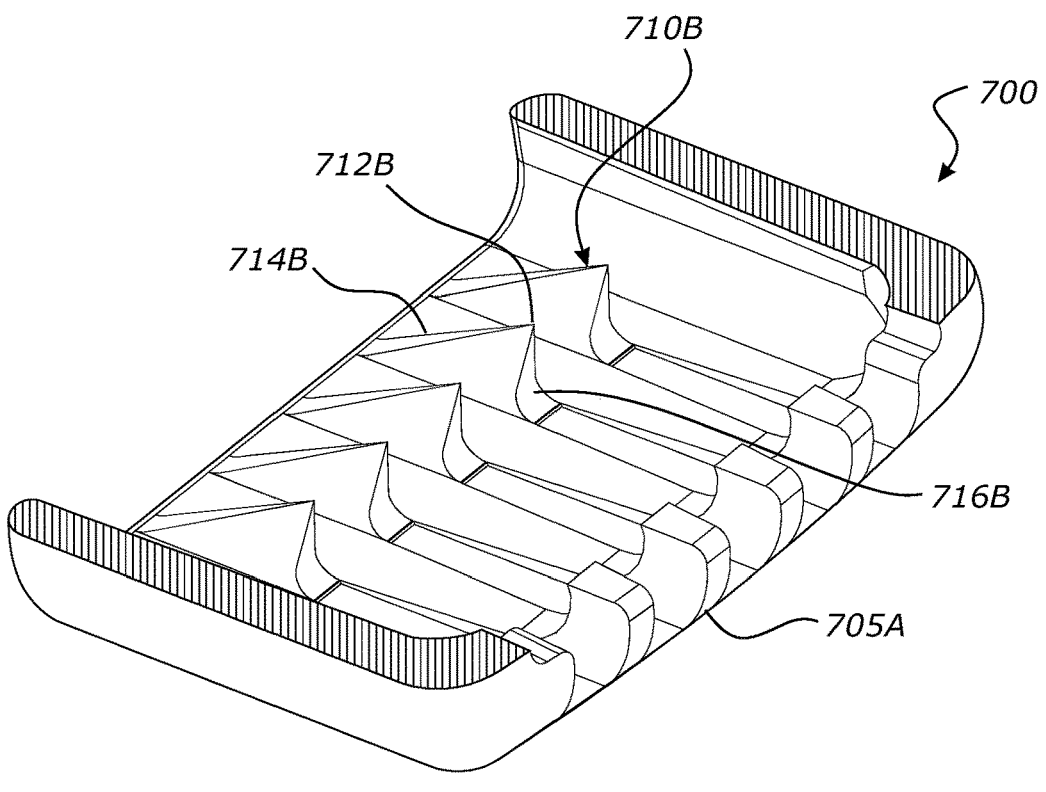

FIGS. 80A and 80B illustrate perspective sectional views of an example embodiment of a strap attachment with a channel 702.

FIG. 80A illustrates a first section of strap attachment 700 comprising a first set of projections 710A extending into channel 702. The first set of projections 710A may comprise a distal end comprising a point or apex 712A, a leading side 714A, and a trailing side 716A.

In an example embodiment, the leading side 714A is configured to be longer than the trailing side 716A in a direction along which the strap attachment is configured to receive a strap.

FIG. 80B illustrates a second section of strap attachment 700 comprising a second set of projections 7103 extending into channel 702. In an example embodiment, the second set of projections 7103 are configured to be interleaved with and higher than the first set of projections 710A in a distance perpendicular to that along which the strap attachment is to receive a headgear strap, or a height above a channel sidewall from which the projections extend.

In an example embodiment, the projections 710A and 710B are configured to receive and retain a headgear strap inserted into channel 702. The leading sides 714A, B and trailing sides 716A, B, may advantageously result in a point or apex 712A, B facing substantially away from an entrance to the channel 702 to receive a headgear strap 600. In such an example embodiment, the point or apex may advantageously grip and secure a headgear strap inserted into channel 702 beyond the point or apex 712A, B.

In an example embodiment, leading sides 714A, B and trailing sides 716A, B may form a substantially hook shaped projection. In an example embodiment, the combination of the leading and trailing sides 714A, B and 716A, B may result in a form that is analogous to a hook, configured to engage a fabric of a headgear strap. In such an embodiment, the engagement of the resulting projection with the headgear strap may retain the headgear strap within the strap attachment 700. The resulting hook shaped projections, exemplified as opposing projections 710A, B in FIGS. 80A and 80B, may resist a pull out force vector that can act or is applied to the headgear strap in a direction substantially opposing a direction said headgear strap is to enter the strap attachment 700.

In an example embodiment, the projections 710A and 710B may be configured to oppose and interleave such that the apex or point 712A, B of each projection may create a curved or tortuous path for a headgear strap inserted into channel 702 beyond the point or apex 712A, B of the projections.

In an example embodiment, projections 710B are formed closer to an entrance to channel 702 than projections 710A. Such a configuration may advantageously facilitate easier threading of the headgear strap 600 into strap attachment 700. In an example embodiment, the tortuous path formed by the projections results in a pathway for the strap to move through as it is inserted into strap attachment 700, However, the tortuous path and projections may result in a retention such that it is difficult to remove an assembled strap from the strap attachment. The multiple projections and resulting tortuous path may create multiple points of engagement with the strap 600 that retain the strap within the strap attachment 700.

In an example embodiment as shown in FIGS. 80A and 80B, protrusions 705B and 705A are provided at or towards a terminal end of the strap attachment 700 opposite a mouth end to which the strap attachment 700 is configured to receive a headgear strap 600, In an example embodiment, protrusions 705B and 705A are substantially aligned with opposing projections 710B and 710A, respectively. In an example embodiment, the protrusions 705B and 705A are configured to be of same or similar height to projections 710A and 710B, respectively, located on the same side of channel 702, where a height is in reference to a distance above a sidewall of the channel from which the projection or protrusion extends to a distal end of said projection or protrusion.

In an example embodiment, the protrusions 705A, B may advantageously partially or fully close or obscure an end of channel 702 such that a headgear strap 600 inserted into channel 702 is restrained from exiting channel 702 at the opposing terminal end of strap attachment 700 to the mouth end which is to receive a headstrap 600.

Additionally, protrusions 705A, B may advantageously reduce access to the interior of the strap attachment 700 at the terminal end of the strap attachment, for example into channel 702.

Figure 81A:
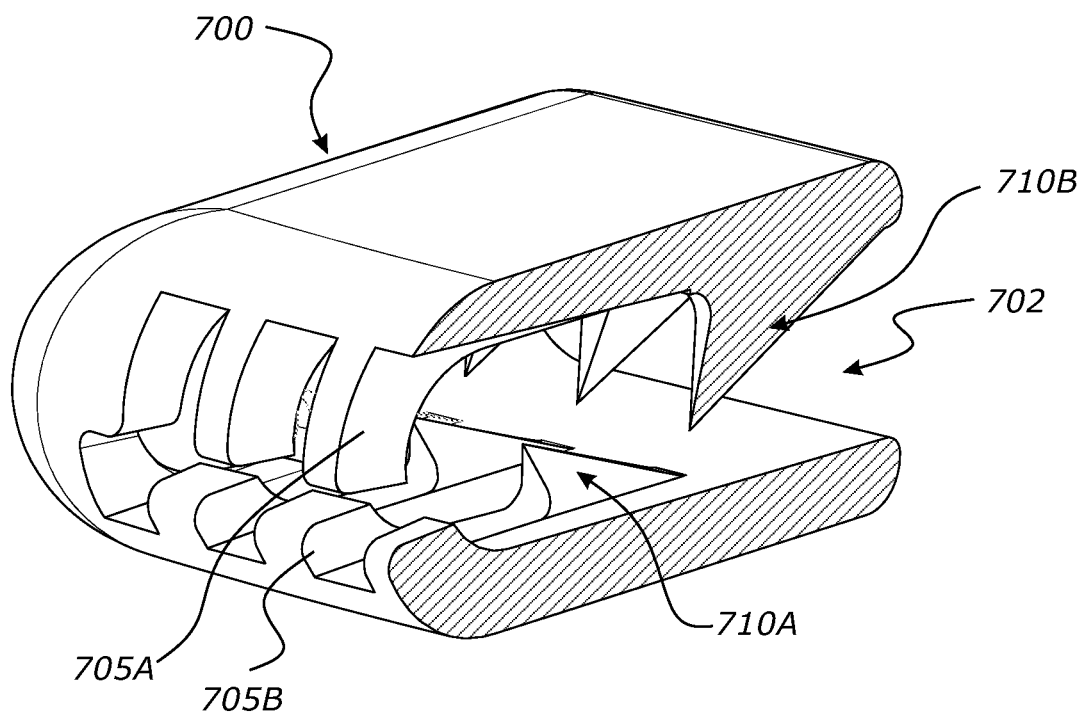
FIGS. 81A and 81B illustrate perspective sectional views of an example embodiment of a strap attachment.
Figure 81B:
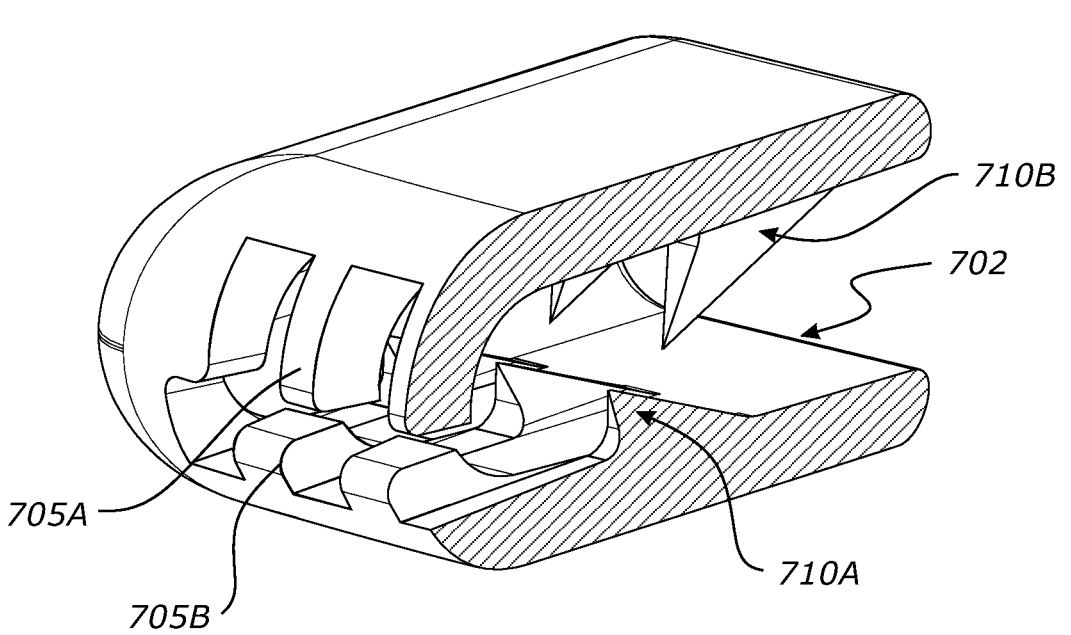

FIGS. 81A and 81B illustrate perspective sectional views of an example embodiment of a strap attachment. In the example embodiment of FIG. 81A, projection 7106 and protrusion 7056, are shown to be aligned in plane in a direction to which the channel 702 is to receive a headgear strap. However, it will be understood that protrusions 705A and 705B may be aligned or offset with projections 710A and 7103.

Similarly, FIG. 81B shows the alignment of projection 710A in a lower part of strap attachment 700 with protrusion 705A in an upper part of strap attachment 700 along a single plane in a direction to which channel 702 is to receive a headgear strap.

In an example embodiment as shown in FIGS. 81A and 81B channel 702 comprises an entrance or mouth at an end of the channel 702 configured to receive a headgear strap 600. The entrance or mouth may comprise lead in features to enable easier insertion of the headgear strap into the channel 702. In an example embodiment, the lead in features may comprise rounded or smooth lips, or a substantially rounded or curved profile.

Figure 82A:
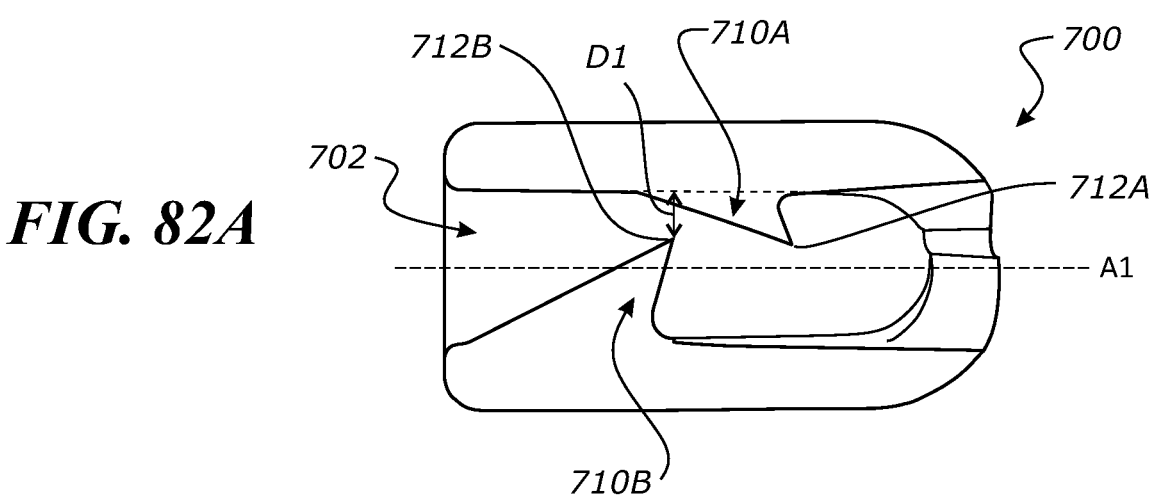
FIGS. 82A, 82B, and 82C illustrate cross sectional views of an example embodiment of a strap attachment.

FIG. 82A illustrate a cross sectional view of an example embodiment of a strap attachment 700 showing distance D1, between a point or apex 712B of projection 7103 and an upper opposing wall of channel 702 (onto which projections 710A are disposed). FIG. 82A also illustrates a mid-plane A1 of channel 702 illustrating that both point or apex 712B of projection set 7106 and point or apex 712A of projection set 710A are located beyond a mid-way point of channel 702, and on the same half of said channel. Put another way, projections 710B are longer than projections 710A. However, in an example embodiment (not shown), projection 710B may be of a shorter height than projection 710A, such that apex 712A and 7126 are below mid plane A1 of channel 702.

In an example embodiment, the apices of projections 710A and/or 710B may be on alternative sides of mid-plane A1 of channel 702, such that either the projections 710A, B are shorter than a half width of said channel 702, or that projections 710A, B are longer than a half width of said channel 702 (i.e. they overlap in a vertical direction).

The distance D1 may advantageously be varied depending on a thickness, material and/or compressibility of headgear strap to be received into strap attachment 700. In some example embodiments, distance D1 is provided as a function of a thickness of the headstrap 600, such as a ratio of distance D1 to thickness of the headstrap is in the range from about 1:4 to about 1:1.

In an example embodiment, the distance between the apex 7123 of projection 7103 to a plane joining the leading sides 714A of projection set 710A, may be function of the headgear strap thickness, material and/or compressibility. This may advantageously provide for a path for the threading of the headgear strap 600 into the strap attachment, (with the use of a tool if required).

Figure 82B:
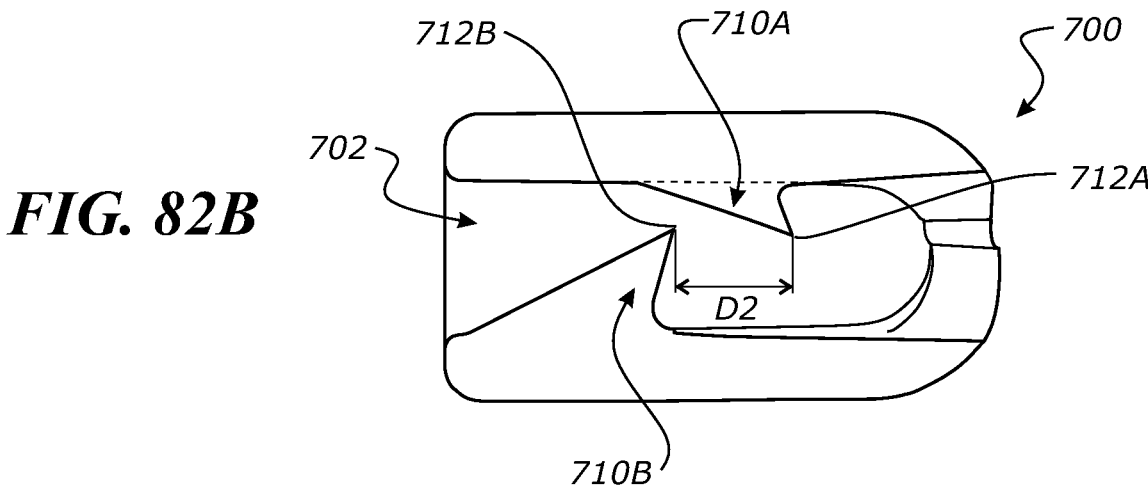

FIG. 82B illustrates a distance D2 between point or apex 712A and 712B of projection sets 710A and 7103, respectively. Such a distance D2 may similar be varied and provided as a function of a thickness of the headstrap 600 to which the strap attachment 700 is to receive.

Figure 82C:
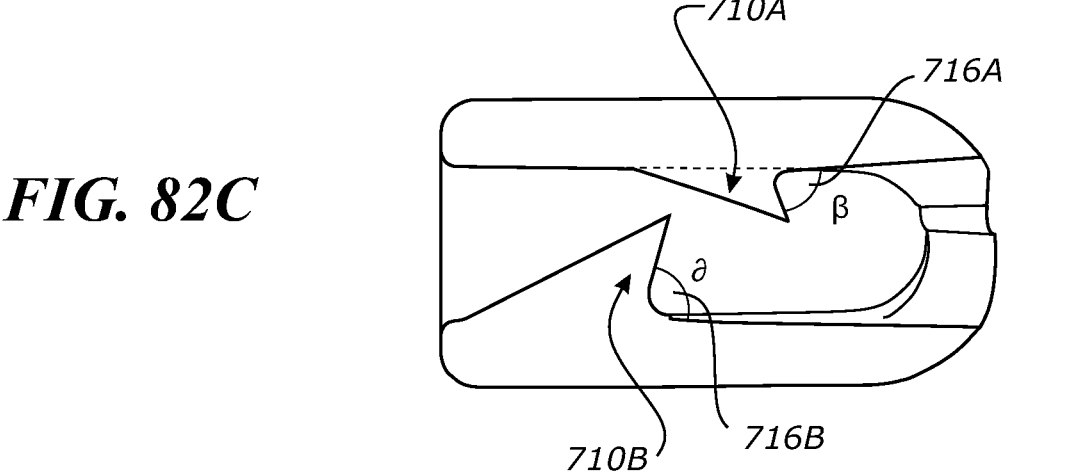

FIG. 82C illustrates projection sets 710A and 710B comprising an acute angle β on trailing edge 716A and an acute angle α on trailing edge 716B, respectively. In an example embodiment, acute angles β and α may be about 40 degrees to about 80 degrees.

In an example embodiment, the acute angles β and α may provide for a direction or lean of projections 710A and 710B, and a position of point or apex 712A, 712B in a direction substantially in line with a direction of channel 702 to receive a headgear strap 600. Advantageously, angles and a may facilitate projections 710A and 710B that are configured to retain a headgear strap inserted into channel 702.

In an example embodiment as shown in FIGS. 82A, B and C, projections 710A, B comprise trailing edges 716A, B and leading edges 714A, B. In the example embodiment shown, leading edges 714A, B are substantially straight, and trailing edges 716A, B comprise straight and curved sections. In this embodiment, the curved sections of trailing edges 716A, B of each projection are set towards the base of said projection, such that a transition from a wall of channel 702 to the trailing edge of each projection is gradual. This may advantageously provide additional strength to the projections 710A, B, however it will be understood that this transition could be a less gradual transition, or a corner of two planes forming said angles 3 and a. In either embodiment, the acute nature of angles β and α result in a projection forming a hook like apex 712A, B, resulting in the retention of a headgear strap 600 as described herein.

Figure 83:
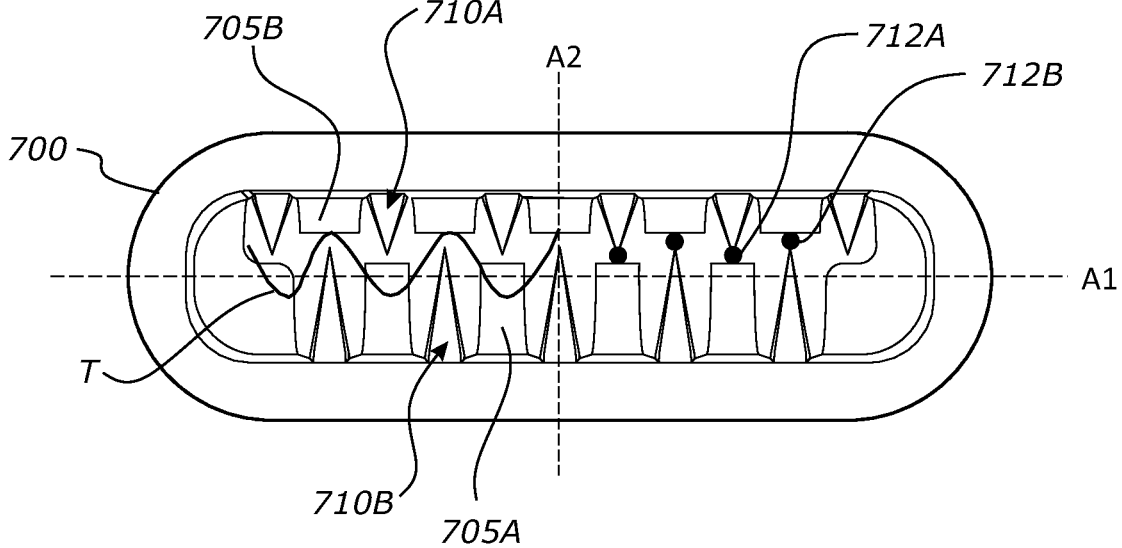
FIG. 83 illustrates a front view of an example embodiment of a strap attachment.

FIG. 83 illustrates a front view of an example embodiment of a strap attachment 700 as described herein. This figure illustrates the interleaving and opposing configuration of points or apices 712A and 712B of projection sets 710A and 710B, respectively.

FIG. 83 illustrates an approximate central horizontal plane A1 of the channel 702, and an approximate central vertical plane A2 of the channel 702.

In an illustrated embodiment, projections 710B are shown to extend over the central horizontal plane A1, whilst projections 710A are shown under the central horizontal plane A1. However, it will be understood that the distance or extension of each of projections 710A and 710B relative to plane A1 and/or an opposing wall in the channel 702 may be a function of the strap thickness, material and/or compressibility of the strap.

The plane A1 as illustrated in FIG. 83 is shown as a dashed horizontal line perpendicular to a direction of channel 702 (i.e. across channel 702). However, it will be understood that this plane extends as a surface through the strap attachment. This is shown in FIG. 82A, where dashed line A1 represents the same plane, but shown in a direction parallel to the direction of channel 702. In an example embodiment, the projections 710A and 710B may be offset from each other in one or both of these plane directions (i.e. parallel and perpendicular to a direction of channel 702). As outlined above, and illustrated in FIG. 82B, projections 710A and 710B may be offset in a direction of the channel 702 by distance D2. Additionally, or alternatively, projections 710A and 7108 may be offset in a direction perpendicular to a direction of the channel, as shown in FIG. 83.

In an illustrated embodiment, projection sets 710A and 710B are shown symmetrically arranged on either side of central vertical plane A2, with the projection sets 710A and 710B offset such that a central projection of the projection set 710B is bisected by vertical plane A2, and central projections of projection set 710A are separated by vertical plane A2. The offset position of the projection sets 710A and 710B along plane A1 provides a tortuous path (illustrated as a wavy line T) along which a strap is retained. The offset position of the projection sets 710A and 710B may also create more points of loading (as shown as dots at apices of the projection sets 710A, B in FIG. 83) on a strap retained in the channel 702 compared to projection sets which are arranged such that opposing apices are aligned along the same plane. Nevertheless, it will be understood that the projection sets 710A and 710B may be arranged to directly oppose each other, or arranged in any suitable pattern to provide a retention of a strap inserted into channel 702, and the tortuous path as described herein.

Reference to any prior art in this specification is not, and should not be taken as, an acknowledgement or any form of suggestion that the prior art forms part of the common general knowledge in the field of endeavour in any country in the world.

Where reference is used herein to directional terms such as 'up', 'down', 'forward', 'rearward', 'horizontal', 'vertical' etc, those terms refer to the position and orientation of the interface shown in the figures, and are used to show and/or describe relative directions or orientations. Those positions and orientations may be different when the interface is in-use.

Although the present disclosure has been described in terms of certain configurations, other configurations apparent to those of ordinary skill in the art also are within the scope of this disclosure. Thus, various changes and modifications may be made without departing from the spirit and scope of the disclosure. For instance, various components may be repositioned as desired. Features from any of the described configurations may be combined with each other and/or an apparatus may comprise one, more, or all of the features of the above described configurations. Moreover, not all of the features, aspects and advantages are necessarily required to practice the present disclosure. Accordingly, the scope of the present disclosure is intended to be defined only by the claims that follow.

The invention claimed is:

1. A respiratory interface for delivering gases to a single nare of a patient, the respiratory interface comprising:
   a single sealing nasal prong having a seal body configured to seal with one of two nares of the patient, a prong inlet configured to receive gases, and a prong outlet configured to supply the gases to the patient,
   a support for the single sealing nasal prong, and a conduit in fluid communication with the single sealing nasal prong to form a substantially linear gases path from the conduit to the prong outlet, wherein the single sealing nasal prong and/or the respiratory interface is configured to allow the single sealing nasal prong to interchangeably seal in or with a left or right nare of the patient while allowing the single sealing nasal prong to remain attached to the support or without being detached from the support;

wherein the single sealing nasal prong is configured to engage only one of the two nares of the patient.

2. The respiratory interface according to claim 1, wherein the single sealing nasal prong is located in a fixed position relative to the support.

3. The respiratory interface according to claim 1, wherein the single sealing nasal prong is translatable relative to the support.

4. The respiratory interface according to claim 1, wherein the support is outside of or separate from or does not form a part of the conduit or gases being supplied to the single sealing nasal prong.

5. The respiratory interface according to claim 1, wherein the conduit is fluidly separated from the support, or wherein the support does not form a part of the substantially linear gases path being supplied to the single sealing nasal prong.

6. The respiratory interface according to claim 1, wherein the conduit comprises a single conduit.

7. A respiratory interface for delivering gases to a single nare of a patient, the respiratory interface comprising:

a single sealing nasal prong having a seal body configured to seal with one of two nares of the patient, a prong inlet configured to receive gases, and a prong outlet configured to supply the gases to the patient, a support for the single sealing nasal prong, and a conduit in fluid communication with the single sealing nasal prong to form a substantially linear gases path from the conduit to the prong outlet, wherein the single sealing nasal prong and/or the respiratory interface is configured to allow the single sealing nasal prong to interchangeably seal in or with a left or right nare of the patient while allowing the single sealing nasal prong to remain attached to the support or without being detached from the support;

wherein the single sealing nasal prong is configured to engage only one of two nares of the patient, and wherein a conduit outlet of the conduit is coupled to the prong inlet of the single sealing nasal prong, and wherein the conduit outlet and the prong outlet share a common substantially central axis.

8. The respiratory interface according to claim 7, wherein a ratio of a cross sectional area of the prong outlet to a cross sectional area of the conduit outlet is about 0.2 to about 1.

9. The respiratory interface according to claim 1, further comprising a headgear removably connectable to the support.

10. The respiratory interface according to claim 1, further comprising a cuff, the single sealing nasal prong configured to couple with the cuff.

11. The respiratory interface according to claim 10, wherein the single sealing nasal prong comprises a substantially supple or substantially compliant material and the cuff comprises a substantially rigid material.

12. The respiratory interface according to claim 1, wherein the prong outlet comprises a width and a length, wherein a ratio of the width to the length is about 0.4 to about 0.9.

13. The respiratory interface according to claim 1, wherein the single sealing nasal prong is bulbous shaped or globular shaped.

14. The respiratory interface according to claim 13, wherein the seal body tapers inwardly from the prong inlet towards the prong outlet.

15. The respiratory interface according to claim 1, wherein the prong inlet is larger than the prong outlet.

16. The respiratory interface according to claim 1, wherein a cross-section of the prong outlet is elliptical.

17. The respiratory interface according to claim 1, wherein the prong inlet is generally circular and a cross section of the prong inlet is substantially similar to a cross section of a conduit outlet of the conduit.

18. The respiratory interface according to claim 1, wherein the conduit comprises an end portion, wherein the end portion and the single sealing nasal prong form the substantially linear gases path from the end portion to the prong outlet.

* * * * *